(12) United States Patent
Or et al.

(10) Patent No.: US 10,689,391 B2
(45) Date of Patent: Jun. 23, 2020

(54) ISOXAZOLE ANALOGS AS FXR AGONISTS AND METHODS OF USE THEREOF

(71) Applicant: Enanta Pharmaceuticals, Inc., Watertown, MA (US)

(72) Inventors: Yat Sun Or, Waltham, MA (US); Jun Ma, Belmont, MA (US); Guoqiang Wang, Belmont, MA (US); Xuechao Xing, Wilmington, MA (US); Ruichao Shen, Belmont, MA (US); Bin Wang, Brighton, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 16/217,749

(22) Filed: Dec. 12, 2018

(65) Prior Publication Data

US 2019/0194216 A1    Jun. 27, 2019

Related U.S. Application Data

(60) Provisional application No. 62/597,730, filed on Dec. 12, 2017.

(51) Int. Cl.

| C07D 491/048 | (2006.01) |
|---|---|
| C07D 493/04 | (2006.01) |
| C07D 487/04 | (2006.01) |
| C07D 417/14 | (2006.01) |

(52) U.S. Cl.
CPC ....... C07D 491/048 (2013.01); C07D 417/14 (2013.01); C07D 487/04 (2013.01); C07D 493/04 (2013.01)

(58) Field of Classification Search
CPC .............................. C07D 491/048; C07D 493/04; C07D 487/04; C07D 417/14
See application file for complete search history.

(56) References Cited

U.S. PATENT DOCUMENTS

| 5,571,809 A | 11/1996 | Hargrave et al. |
|---|---|---|
| 6,974,830 B2 | 12/2005 | Giegrich et al. |
| 7,319,109 B2 | 1/2008 | Boggs et al. |
| 7,846,960 B2 | 12/2010 | Bell et al. |
| 7,863,302 B2 | 1/2011 | Bell et al. |
| 7,897,773 B2 | 3/2011 | Aletru et al. |
| 7,902,373 B2 | 3/2011 | Blake et al. |
| 8,952,042 B2 | 2/2015 | Kremoser et al. |
| 9,751,874 B2 | 9/2017 | Gege et al. |
| 2004/0048316 A1 | 3/2004 | Haffner et al. |
| 2007/0054902 A1 | 3/2007 | Fukui et al. |
| 2007/0142340 A1* | 6/2007 | Pellicciari ............... C07J 9/00 514/169 |
| 2008/0167356 A1 | 7/2008 | Caldwell et al. |
| 2009/0163474 A1 | 6/2009 | Zhang et al. |
| 2010/0063697 A1 | 3/2010 | Lindgren et al. |
| 2010/0099703 A1 | 4/2010 | Garcia-López et al. |
| 2010/0120775 A1 | 5/2010 | Bass, III et al. |
| 2010/0152166 A1 | 6/2010 | Genin et al. |
| 2010/0184809 A1 | 7/2010 | Kremoser et al. |
| 2010/0210660 A1 | 8/2010 | Kremoser et al. |
| 2010/0249179 A1 | 9/2010 | Deaton et al. |
| 2010/0292212 A1 | 11/2010 | Ackermann et al. |
| 2011/0034507 A1 | 2/2011 | Akwabi-Ameyaw et al. |
| 2011/0275595 A1 | 11/2011 | Eckhardt et al. |
| 2012/0004164 A1 | 1/2012 | Dales et al. |
| 2013/0261108 A1 | 10/2013 | Tully et al. |
| 2014/0038947 A1 | 2/2014 | Glick et al. |
| 2014/0221659 A1 | 8/2014 | Kinzel et al. |
| 2015/0299210 A1 | 10/2015 | Bailey et al. |
| 2015/0366856 A1 | 12/2015 | Mutnick et al. |
| 2016/0130297 A1 | 5/2016 | Xing et al. |
| 2017/0298068 A1 | 10/2017 | Gege et al. |
| 2017/0304270 A1 | 10/2017 | Or et al. |
| 2017/0304271 A1 | 10/2017 | Or et al. |

(Continued)

FOREIGN PATENT DOCUMENTS

| CN | 106588804 A | 4/2017 |
|---|---|---|
| CN | 106632294 A | 5/2017 |

(Continued)

OTHER PUBLICATIONS

"Pubchem CID 123486225" Create Date: Jan. 25, 2017 (Jan. 25, 2017) Date Accessed: Apr. 1, 2019 (Jan. 4, 2019).
Medline Plus. Hardening of the Arteries. (2018). Web: http://www.nlm.nih.gov/medlineplus/ency/article/000171.htm.
Merck Manual, Diabetes Mellitus. (2017. Web: http://www.merck.com/mmpe/print/sec12/ch_158/ch_158b.html.
Ali, et al., "Recent advances in the development of farnesoid X receptor agonists", Ann Transl Med, 3(1), 2015, 1-16.
Buijsman, et al., "Non-Steroidal Steroid Receptor Modulators", Current Medicinal Chemistry, 12, 2005, 1017-1075.

(Continued)

*Primary Examiner* — Alexander R Pagano
*Assistant Examiner* — Ebenezer O Sackey
(74) *Attorney, Agent, or Firm* — Edgar W. Harlan; Carolyn S. Elmore; Elmore Patent Law Group, P.C.

(57) ABSTRACT

The present invention provides compounds of Formula (I),

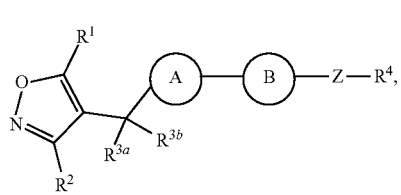

and pharmaceutically acceptable salts thereof, as well as pharmaceutical compositions comprising these compounds and methods of using these compounds to prevent or treat FXR-mediated or TGR5-mediated diseases or conditions.

22 Claims, No Drawings

(56) References Cited

U.S. PATENT DOCUMENTS

| | | |
|---|---|---|
| 2017/0304272 A1 | 10/2017 | Or et al. |
| 2017/0333399 A1 | 11/2017 | Or et al. |
| 2017/0334893 A1 | 11/2017 | Or et al. |
| 2017/0334894 A1 | 11/2017 | Or et al. |
| 2017/0355685 A1 | 12/2017 | Blomgren et al. |
| 2017/0355693 A1 | 12/2017 | Blomgren et al. |
| 2017/0355694 A1 | 12/2017 | Gege |
| 2017/0368038 A1 | 12/2017 | Badman et al. |
| 2018/0030003 A1 | 2/2018 | Wang et al. |
| 2018/0099957 A1 | 4/2018 | Ma et al. |
| 2018/0141941 A1 | 5/2018 | He et al. |
| 2019/0248777 A1* | 8/2019 | Shen ................ A61P 3/10 |

FOREIGN PATENT DOCUMENTS

| | | | |
|---|---|---|---|
| CN | 106946867 A | | 7/2017 |
| CN | 106995416 A | | 8/2017 |
| CN | 107021957 A | | 8/2017 |
| CN | 108017636 A | | 5/2018 |
| CN | 108341822 A | | 7/2018 |
| CN | 109053751 A | | 12/2018 |
| WO | WO2004/046162 A2 | | 6/2004 |
| WO | WO2009/149795 A1 | | 12/2009 |
| WO | WO2011/020615 A1 | | 2/2011 |
| WO | WO2011/021645 A1 | | 2/2011 |
| WO | WO2012/087519 A1 | | 6/2012 |
| WO | WO2012/087520 A1 | | 6/2012 |
| WO | WO2012/087521 A1 | | 6/2012 |
| WO | WO2013/007387 A1 | | 1/2013 |
| WO | WO2013/037482 A1 | | 3/2013 |
| WO | 2013166176 A1 | | 11/2013 |
| WO | WO2015/036442 A1 | | 3/2015 |
| WO | WO2017/118294 A1 | | 7/2017 |
| WO | WO2017/128896 A1 | | 8/2017 |
| WO | WO2017/145041 A1 | | 8/2017 |
| WO | WO2017/133521 A1 | | 10/2017 |
| WO | 2018024224 A1 | | 2/2018 |
| WO | 2018039386 A1 | | 3/2018 |
| WO | 2018075207 A1 | | 4/2018 |
| WO | 2018085148 A1 | | 5/2018 |
| WO | 2018133730 A1 | | 7/2018 |
| WO | 2018170173 A1 | | 9/2018 |
| WO | 2018190643 A1 | | 10/2018 |
| WO | 2018214959 A1 | | 11/2018 |
| WO | 2019007418 A1 | | 1/2019 |

OTHER PUBLICATIONS

Crawley, , "Farnesoid X Receptor Modulators: a patent review", Expert Opinion on Therapeutic Patents, 20(8), 2010, 1047-1057.

Ruano, J.L. G. et al., "4-(diethoxymethyl)-3-pyridin-3-ylisoxazole-5-carboxylates: useful scaffold for highly functionalised 3-(pyridin-3-yl)isoxazole", Tetrahedron, 61(18), 2005, 4363-4371.

Sepe, et al., "Farnesoid X receptor modulators (2011-2014): a patent review", Expert Opinion on Therapeutic Patents, 25:8, 2015, 885-896.

* cited by examiner

ISOXAZOLE ANALOGS AS FXR AGONISTS AND METHODS OF USE THEREOF

RELATED APPLICATIONS

This application claims the benefit of U.S. Provisional Application No. 62/597,730, filed on Dec. 12, 2017. The entire teachings of the above application are incorporated herein by reference.

TECHNICAL FIELD

The present invention relates generally to compounds and pharmaceutical compositions useful as FXR modulators. Specifically, the present invention relates to isoxazole derivatives useful as agonists for FXR, and methods for their preparation and use.

BACKGROUND OF THE INVENTION

Farnesoid X Receptor (FXR) is an orphan nuclear receptor initially identified from a rat liver cDNA library (B M. Forman, et al., Cell, 1995, 81(5), 687-693) that is most closely related to the insect ecdysone receptor. FXR is a member of the nuclear receptor family of ligand-activated transcription factors that includes receptors for the steroid, retinoid, and thyroid hormones (D J. Mangelsdorf, et al., Cell, 1995, 83(6), 841-850). The relevant physiological ligands of FXR are bile acids (D. Parks et al., Science, 1999, 284(5418), 1362-1365). The most potent one is chenodeoxycholic acid (CDCA), which regulates the expression of several genes that participate in bile acid homeostasis. Farnesol and derivatives, together called farnesoids, are originally described to activate the rat orthologue at high concentration but they do not activate the human or mouse receptor. FXR is expressed in the liver, throughout the entire gastrointestinal tract including the esophagus, stomach, duodenum, small intestine, colon, ovary, adrenal gland and kidney. Beyond controlling intracellular gene expression, FXR seems to be also involved in paracrine and endocrine signaling by upregulating the expression of the cytokine Fibroblast Growth Factor (J. Holt et al., Genes Dev., 2003, 17(13), 1581-1591; T. Inagaki et al., Cell Metab., 2005, 2(4), 217-225).

Small molecule compounds which act as FXR modulators have been disclosed in the following publications: WO 2000/037077, WO 2002/072598, WO 2003/015771, WO 2003/099821, WO 2004/00752, WO 2004/048349, WO 2005/009387, WO 2005/082925, US 2005/0054634, WO 2007/052843, WO 2007/070796, WO 2007/076260, WO 2007/092751, WO 2007/095174, WO 2007/140174, WO 2007/140183, US 2007/0142340, WO 2008/000643, WO 2008/002573, WO 2008/025539, WO 2008/025540, WO 2008/051942, WO 2008/073825, WO 2008/157270, US 2008/0299118, US 2008/0300235, WO 2009/005998, WO 2009/012125, WO 2009/027264, WO 2009/062874, WO 2009/127321, WO 2009/149795, US 2009/0131409, US 2009/0137554, US 2009/0163474, US 2009/0163552, US 2009/0215748, WO 2010/043513, WO 2011/020615, WO 2011/117163, WO 2012/087519, WO 2012/087520, WO 2012/087521, WO 2013/007387, WO 2013/037482, WO 2013/166176, WO 2013/192097, WO 2014/184271, US 2014/0186438, US 2014/0187633, WO 2015/017813, WO 2015/069666, WO 2016/073767, WO 2016/116054, WO 2016/103037, WO 2016/096116, WO 2016/096115, WO 2016/097933, WO 2016/081918, WO 2016/127924, WO 2016/130809, WO 2016/145295, WO 2016/173524, CN 106632294, CN 106588804, US 2017/0196893, WO 2017/062763, WO 2017/053826, CN 106518708, CN 106518946, CN 106478759, CN 106478447, CN 106478453, WO 2017/027396, WO 2017/049172, WO 2017/049173, WO 2017/049176, WO 2017/049177, WO 2017/118294, WO 2017/128896, WO 2017/129125, WO 2017/133521, WO 2017/147174, WO 2017/156024 A1. Further small molecule FXR modulators have been recently reviewed (R. C. Buijsman, et al., Curr. Med. Chem. 2005, 12(9), 1017-1075; Crawley, M. L. Expert Opin. Ther. Patents 2010, 20(8), 1047-1057; V. Sepe, et al., Expert Opin. Ther. Patents 2015, 25(8), 885-896).

There is a need for the development of FXR modulators for the treatment and prevention of disease. The present invention has identified compounds which modulate FXR as well as methods of using these compounds to treat disease.

SUMMARY OF THE INVENTION

In one aspect, the invention provides compounds represented by Formula I and pharmaceutically acceptable salts thereof:

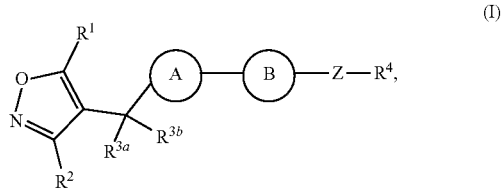

wherein:
$R^1$ is hydrogen, halogen, cyano, optionally substituted —$C_1$-$C_6$ alkyl, optionally substituted —$C_2$-$C_6$ alkenyl, optionally substituted —$C_2$-$C_6$ alkynyl, optionally substituted —$C_3$-$C_6$ cycloalkyl or optionally substituted 3- to 6-membered heterocycloalkyl. Preferably, $R^1$ is isopropyl, tert-butyl, or cyclopropyl.
$R^2$ is optionally substituted aryl, optionally substituted heteroaryl, optionally substituted —$C_3$-$C_{12}$ cycloalkyl or optionally substituted 3- to 12-membered heterocycloalkyl; $R^{3a}$, $R^{3b}$ are each independently selected from groups consisting of hydrogen, halogen, optionally substituted —$C_1$-$C_6$ alkyl, optionally substituted —$C_1$-$C_6$ alkoxy and optionally substituted —$C_3$-$C_6$ cycloalkyl. Preferably, $R^{3a}$ and $R^{3b}$ are both hydrogen. Alternatively, $R^{3a}$ and $R^{3b}$ are taken together with the carbon atom to which they are attached to form a cyclic moiety selected from optionally substituted —$C_3$-$C_6$ cycloalkyl, optionally substituted 3- to 6-membered heterocycloalkyl, and optionally substituted —$C_3$-$C_6$ cycloalkenyl.
Ⓐ is

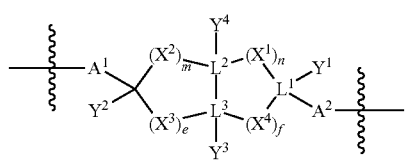

$L^1$, $L^2$, $L^3$ are each independently C or N;
e, f, m, and n are each independently 0, 1, 2, 3, or 4;
$A^1$ is O, $NR^{3c}$, S, S(O) or S(O)$_2$;
$A^2$ is absent, O, $NR^{3c}$, S, S(O) or S(O)$_2$;
$A^1$ is attached to —$CR^{3a}R^{3b}$—, and $A^2$ is attached to Ⓑ;

each $X^1$, $X^2$, $X^3$ and $X^4$ is independently selected from group consisting of: O, C(O), S, S(O), S(O)$_2$, NR$^{3c}$, and CR$^{3d}$R$^{3e}$; wherein R$^{3d}$ and R$^{3e}$ are each independently selected from hydrogen, halogen, optionally substituted —C$_1$-C$_6$ alkyl, optionally substituted —C$_3$-C$_6$ cycloalkyl, and optionally substituted —O—C$_1$-C$_6$ alkyl; alternatively, R$^{3d}$ and R$^{3e}$ are taken together with the carbon atom to which they are attached to form a optionally substituted —C$_3$-C$_6$ cycloalkyl or optionally substituted 3- to 6-membered heterocycloalkyl. R$^{3c}$ is hydrogen, optionally substituted —C$_1$-C$_6$ alkyl, optionally substituted —C$_3$-C$_6$ cycloalkyl, formyl, or acetyl; Y$^1$ is absent when L$^1$ is N, and hydrogen, hydroxyl, halogen, optionally substituted —C$_1$-C$_6$ alkyl, optionally substituted —C$_3$-C$_6$ cycloalkyl, or optionally substituted —O—C$_1$-C$_6$ alkyl when L$^1$ is C; Y$^3$ is absent when L$^3$ is N, and hydrogen, hydroxyl, halogen, optionally substituted —C$_1$-C$_6$ alkyl, optionally substituted —C$_3$-C$_6$ cycloalkyl, or optionally substituted —O—C$_1$-C$_6$ alkyl when L$^3$ is C; Y$^4$ is absent when L$^4$ is N, and hydrogen, hydroxyl, halogen, optionally substituted —C$_1$-C$_6$ alkyl, optionally substituted —C$_3$-C$_6$ cycloalkyl, or optionally substituted —O—C$_1$-C$_6$ alkyl when L$^4$ is C; Y$^2$ is hydrogen, hydroxyl, halogen, optionally substituted —C$_1$-C$_6$ alkyl, optionally substituted —C$_3$-C$_6$ cycloalkyl, or optionally substituted —O—C$_1$-C$_6$ alkyl; provided that Ⓐ is not

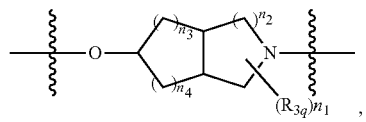

wherein $n_1$, $n_2$, $n_3$, $n_4$ is 0, 1, 2 or 3; $R_{3q}$ is selected from hydrogen, halogen, optionally substituted —C$_1$-C$_3$ alkyl, optionally substituted —C$_3$-C$_6$ cycloalkyl, optionally substituted —O—C$_1$-C$_3$ alkyl; alternatively two $R_{3q}$ groups are linked together to form a —C$_3$-C$_6$ cycloalkyl, aryl, heteroaryl or 3- to 6-membered heterocycloalkyl.

Ⓑ is optionally substituted aryl, optionally substituted heteroaryl, optionally substituted 3-12 membered heterocycloalkyl. Preferably, the substituents are selected from group consisting of OH, halogen, CN, optionally substituted —O—C$_1$-C$_6$ alkyl, optionally substituted —C$_1$-C$_6$-alkyl, optionally substituted 3- to 6-membered-heterocycloalkyl and optionally substituted —C$_3$-C$_6$-cycloalkyl, optionally substituted aryl and optionally substituted heteroaryl;

Z is selected from the group consisting of:
1) Absent;
2) Optionally substituted —C$_1$-C$_6$ alkyl;
3) Optionally substituted —C$_2$-C$_6$ alkenyl;
4) Optionally substituted —C$_2$-C$_6$ alkynyl;
5) Optionally substituted —C$_3$-C$_8$ cycloalkyl;
6) Optionally substituted 3- to 8-membered heterocycloalkyl;
7) Optionally substituted —C$_3$-C$_8$ cycloalkenyl;
8) Optionally substituted aryl; and
9) Optionally substituted heteroaryl; and R$^4$ is hydroxy, protected hydroxy, —O-(hydroxy prodrug group), tetrazolyl, cyano, —CO$_2$R$^5$, —O—Y—CO$_2$R$^5$, —NR$^{4b}$—Y—CO$_2$R$^5$, —CONR$^{4a}$R$^{4b}$,

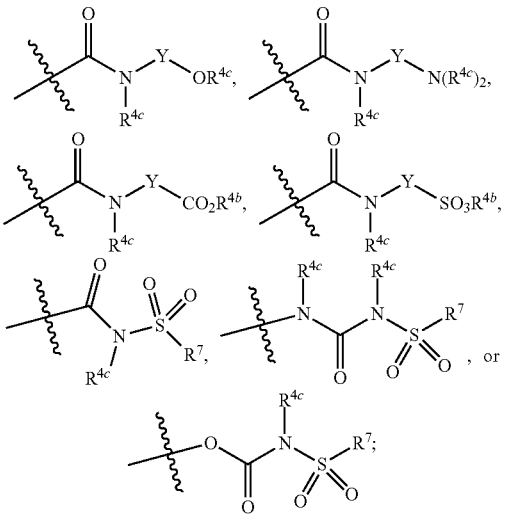

wherein
Y is absent or optionally substituted —C$_1$-C$_6$ alkyl;
R$^{4a}$ and R$^{4b}$ are independently selected from the groups consisting of:
1) Hydrogen;
2) Optionally substituted —C$_1$-C$_8$ alkyl;
3) Optionally substituted —C$_2$-C$_8$ alkenyl;
4) Optionally substituted —C$_2$-C$_8$ alkynyl; and
5) Optionally substituted —C$_3$-C$_8$ cycloalkyl;
R$^{4c}$ is hydrogen or optionally substituted —C$_1$-C$_6$ alkyl; preferably R$^{4c}$ is hydrogen or —CH$_3$;
R$^5$ is selected from the groups consisting of:
1) Hydrogen;
2)

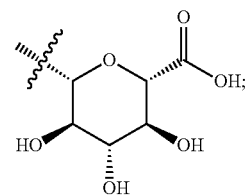

3) Optionally substituted —C$_1$-C$_8$ alkyl;
4) Optionally substituted —C$_2$-C$_8$ alkenyl;
5) Optionally substituted —C$_2$-C$_8$ alkynyl; and
6) Optionally substituted —C$_3$-C$_8$ cycloalkyl;
R$^7$ is selected from the groups consisting of:
1) Optionally substituted —C$_1$-C$_8$ alkyl;
2) Optionally substituted —C$_2$-C$_8$ alkenyl;
3) Optionally substituted —C$_2$-C$_8$ alkynyl;
4) Optionally substituted —C$_3$-C$_8$ cycloalkyl;
5) Optionally substituted —C$_3$-C$_8$ cycloalkenyl;
6) Optionally substituted 3- to 8-membered heterocycloalkyl;
7) Optionally substituted 3- to 8-membered heterocycloalkenyl;
8) Optionally substituted aryl;
9) Optionally substituted —C$_1$-C$_8$ arylalkyl;
10) Optionally substituted heteroaryl;
11) Optionally substituted —C$_1$-C$_8$ heteroarylalkyl; and
12) NR$^9$R$^{10}$; wherein R$^9$ and R$^{10}$ are each independently selected from hydrogen, optionally substituted —C$_1$-

C₈ alkyl, optionally substituted —C₂-C₈ alkenyl, optionally substituted —C₂-C₈ alkynyl, optionally substituted —C₃-C₈ cycloalkyl, optionally substituted aryl, optionally substituted alkylaryl, optionally substituted 3- to 8-membered heterocycloalkyl, optionally substituted heteroaryl, optionally substituted alkylheteroaryl; alternatively, $R^9$ and $R^{10}$ are taken together with the nitrogen atom to which they are attached to form a heterocyclic ring.

In certain embodiments, the hydroxy prodrug group is phosphate or sulfamate. In certain embodiments, the hydroxy prodrug group is an acyl group derived from an amino acid, preferably an α-amino acid.

In another embodiment, the present invention provides a pharmaceutical composition comprising a therapeutically effective amount of a compound or combination of compounds of the present invention, or a pharmaceutically acceptable salt form, stereoisomer, solvate, hydrate or combination thereof, in combination with a pharmaceutically acceptable carrier or excipient.

In another embodiment, the present invention provides a method for the prevention or treatment of an FXR mediated disease or condition. The method comprises administering a therapeutically effective amount of a compound of Formula (I). The present invention also provides the use of a compound of Formula (I) for the preparation of a medicament for the prevention or treatment of an FXR mediated disease or condition.

DETAILED DESCRIPTION OF THE INVENTION

In one embodiment, the present invention provides a compound of Formula (I) as described above, or a pharmaceutically acceptable salt thereof.

In certain embodiments, the present invention relates to compounds of Formula (I), and pharmaceutically acceptable salts thereof, wherein $R^1$ is optionally substituted isopropyl, cyclopropyl, or tert-butyl.

In certain embodiments, the present invention relates to compounds of Formula (I), and pharmaceutically acceptable salts thereof, wherein $R^2$ is optionally substituted cyclohexyl, cyclopentyl, or cyclopropyl.

In certain embodiments, the present invention relates to compounds of Formula (I), and pharmaceutically acceptable salts thereof, wherein $R^2$ is cyclohexyl or cyclopentyl, each of which is optionally substituted with up to 3 groups which are independently selected from halogen, optionally substituted —C₁-C₆ alkyl, optionally substituted —C₁-C₆ alkoxy, optionally substituted —C₃-C₆ cycloalkyl, optionally substituted, —C₃-C₆ cycloalkenyl, optionally substituted aryl, and optionally substituted heteroaryl.

In certain embodiments, the present invention relates to compounds of Formula (I), and pharmaceutically acceptable salts thereof, wherein $R^2$ is cyclopropyl which is optionally substituted with up to 2 groups which are independently selected from of halogen, optionally substituted —C₁-C₆ alkyl, optionally substituted —C₁-C₆ alkoxy, optionally substituted —C₃-C₆ cycloalkyl, optionally substituted —C₃-C₆ cycloalkenyl, optionally substituted aryl, and optionally substituted heteroaryl.

In certain embodiments, the present invention relates to compounds of Formula (I), and pharmaceutically acceptable salts thereof, wherein $R^2$ is optionally substituted phenyl.

In certain embodiments, the present invention relates to compounds of Formula (I), and pharmaceutically acceptable salts thereof, wherein $R^2$ is optionally substituted heteroaryl.

In certain embodiments, the present invention relates to compounds of Formula (I), and pharmaceutically acceptable salts thereof, wherein $R^2$ is selected from the groups set forth below:

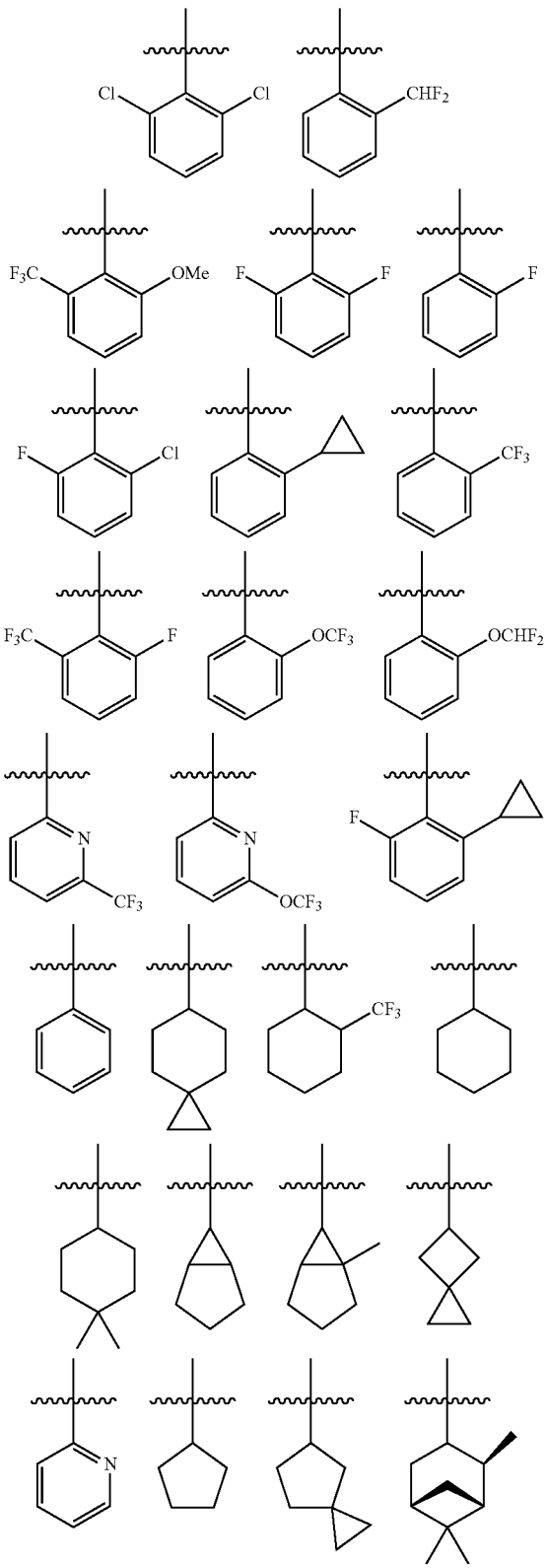

-continued

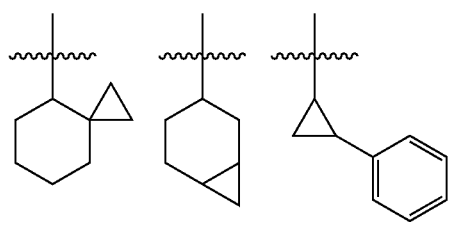

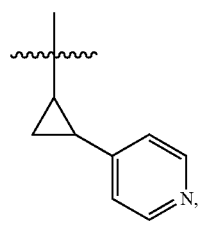

wherein each of the above groups is optionally further substituted. The preferred substituents are halogen, optionally substituted $C_1$-$C_6$ alkyl, optionally substituted $C_1$-$C_6$ alkoxy, optionally substituted $C_3$-$C_6$ cycloalkyl, optionally substituted $C_3$-$C_6$ cycloalkenyl, optionally substituted aryl, and optionally substituted heteroaryl.

In certain embodiments, the present invention relates to compounds of Formula (I), and pharmaceutically acceptable salts thereof, wherein at least one of $R^{3a}$ and $R^{3b}$ is hydrogen or halogen. In certain embodiments, the present invention relates to compounds of Formula (I), and pharmaceutically acceptable salts thereof, wherein both $R^{3a}$ and $R^{3b}$ are independently hydrogen or halogen.

In certain embodiments, the present invention relates to compounds of Formula (I), and pharmaceutically acceptable salts thereof, wherein Ⓐ is

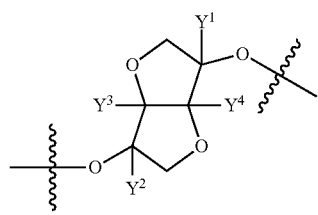

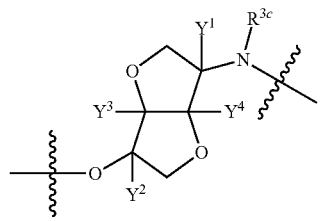

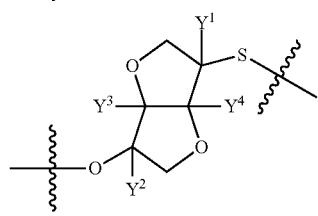

-continued

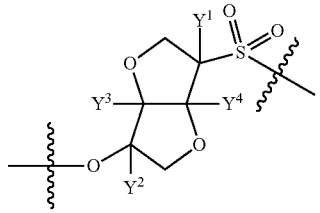

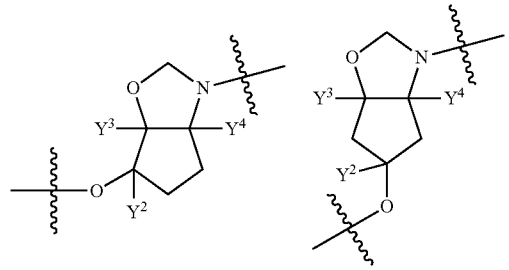

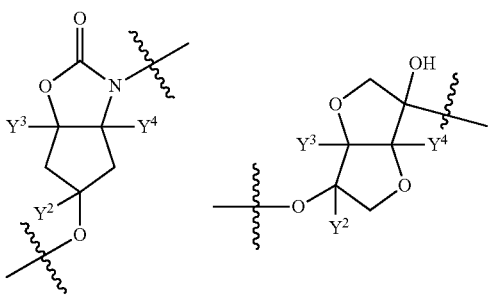

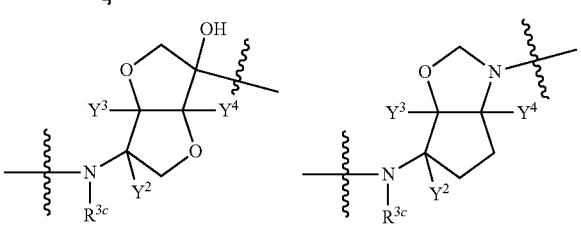

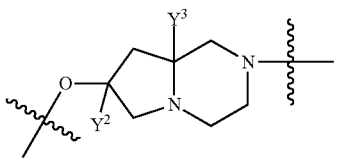

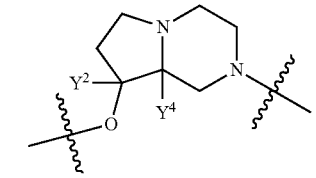

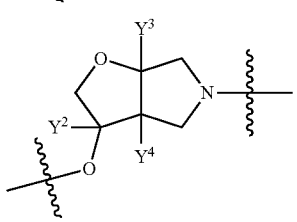

-continued

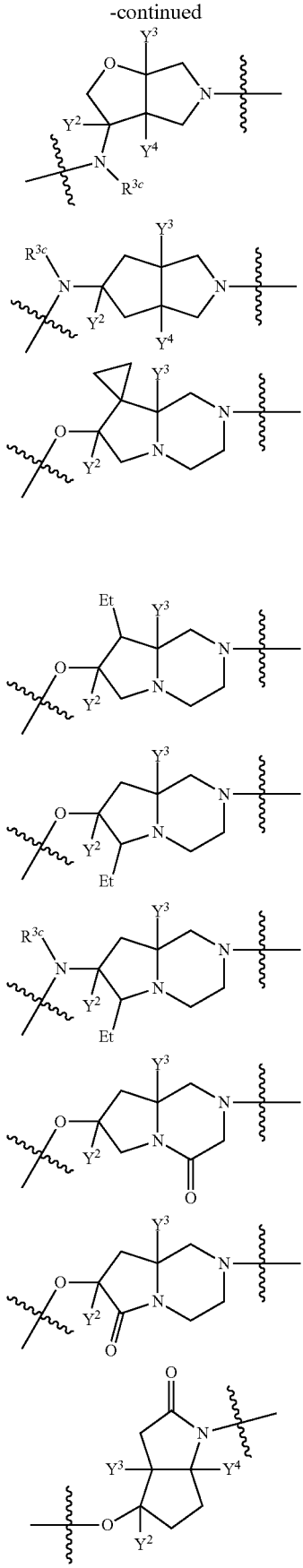

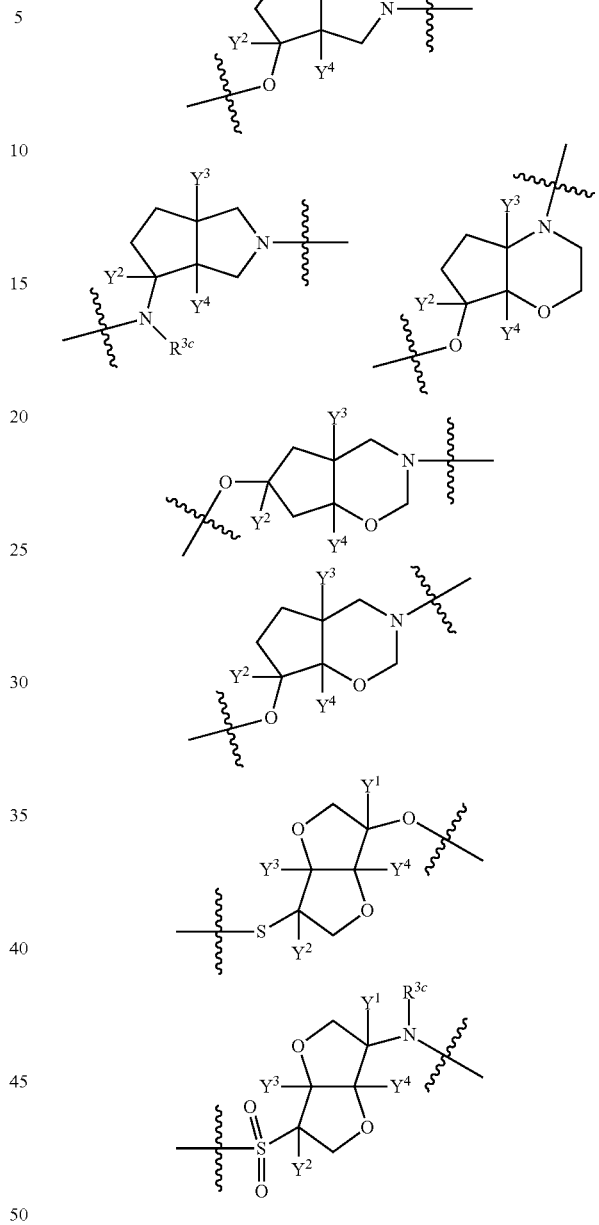

where $R^{3c}$ is previously defined; preferably, $R^{3c}$ is hydrogen, methyl, isopropyl or formyl; $Y^1$, $Y^2$, $Y^3$, and $Y^4$ are as previously defined; preferably, $Y^1$, $Y^2$, $Y^3$ and $Y^4$ are each independently hydrogen, methyl, hydroxyl, or halogen.

In certain embodiments, the present invention relates to compounds of Formula (I), and pharmaceutically acceptable salts thereof, wherein Ⓑ is optionally substituted fused aryl, optionally substituted fused heteroaryl or optionally substituted fused 3-12 membered heterocycloalkyl.

In certain embodiments, the present invention relates to compounds of Formula (I), and pharmaceutically acceptable salts thereof, wherein Ⓑ is optionally substituted phenyl, pyridyl, pyrimidinyl, pyrazolyl, thienyl, thiazolyl, triazolyl, isothiazolyl, pyrrolyl, pyrazolyl, oxazolyl, oxadiazolyl, imidazolyl, furanyl, indolyl, benzothienyl, naphthyl, quinolyl, naphthyridyl, quinoxalinyl, pyridopyrazolyl, pyridooxazolyl, pyridothiazolyl, isoquinolyl, pyridofuranyl, indazolyl, benzisoxazolyl, benzofuranyl, benzotriazolyl, or benzothiazolyl. Preferred substituents include halogen, —CN, —NO$_2$, —NH$_2$, optionally substituted C$_1$-C$_6$ alkyl, optionally substituted C$_1$-C$_6$ alkoxy, optionally substituted C$_3$-C$_6$ cycloalkyl, optionally substituted C$_3$-C$_6$ cycloalkenyl, optionally substituted aryl, and optionally substituted heteroaryl.

In certain embodiments, the present invention relates to compounds of Formula (I), and pharmaceutically acceptable salts thereof, wherein (B) is selected from the groups set forth below:

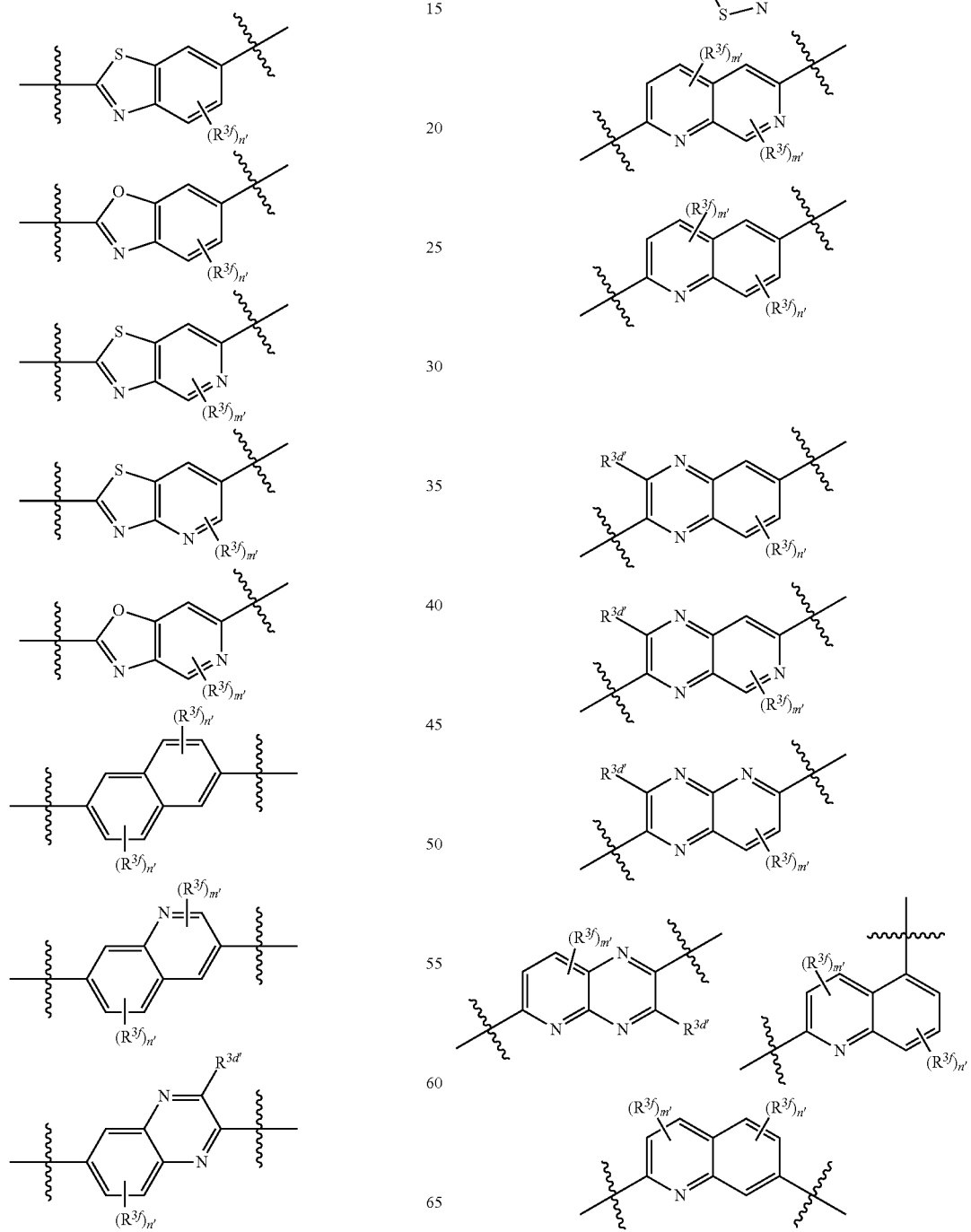

-continued

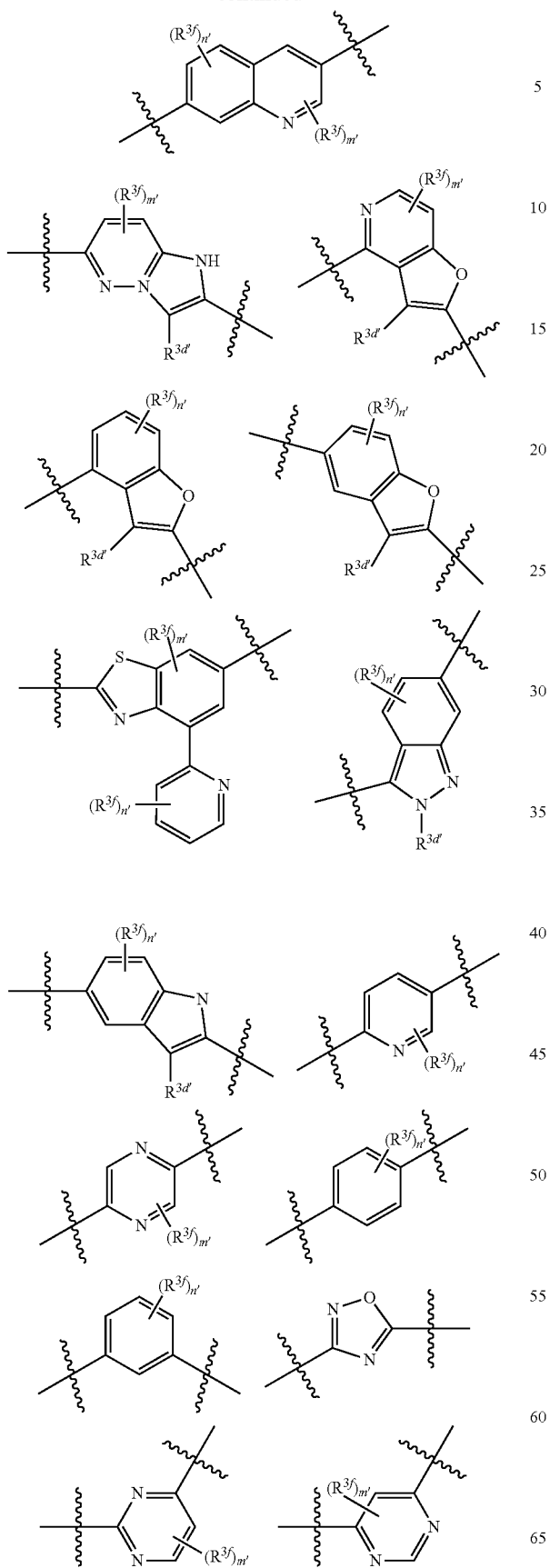

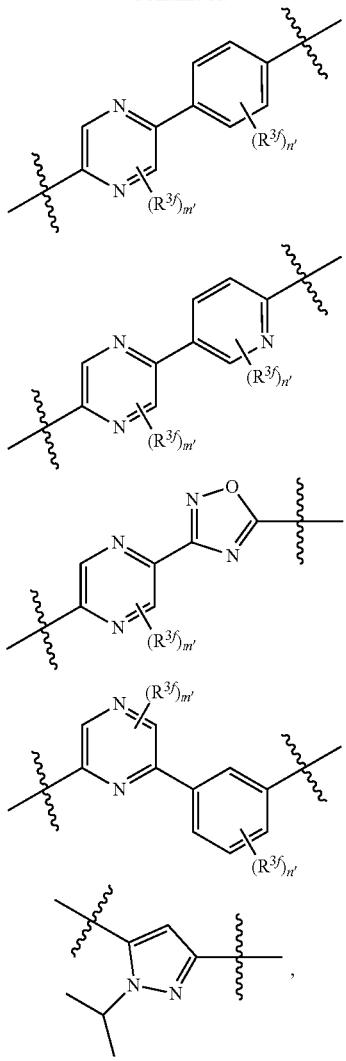

wherein one of the indicated valences is the point of attachment to A and the other is the point of attachment to Z; $R^{3f}$ is selected from a group consisting of halogen, —CN, —NO$_2$, —NH$_2$, optionally substituted $C_1$-$C_6$ alkyl, optionally substituted $C_1$-$C_6$ alkoxy, optionally substituted $C_3$-$C_6$ cycloalkyl, optionally substituted $C_3$-$C_6$ cycloalkenyl, optionally substituted aryl, and optionally substituted heteroaryl; $R^{3d'}$ is selected from a group consisting of hydrogen, halogen, —CN, —NO$_2$, —NH$_2$, optionally substituted $C_1$-$C_6$ alkyl, optionally substituted $C_1$-$C_6$ alkoxy, optionally substituted $C_3$-$C_6$ cycloalkyl, optionally substituted $C_3$-$C_6$ cycloalkenyl, optionally substituted aryl, and optionally substituted heteroaryl; m' is 0, 1 or 2; and n' is 0, 1, 2 or 3; preferably, m' and n' are each independently 0 or 1.

In certain embodiments, the present invention relates to compounds of Formula (I), and pharmaceutically acceptable salts thereof, wherein Z is absent. In certain embodiments, the present invention relates to compounds of Formula (I), and pharmaceutically acceptable salts thereof, wherein Z is optionally substituted —CH$_2$; preferably, Z is —CH$_2$, —CHF, or —CF$_2$. In certain embodiments, the present invention relates to compounds of Formula (I), and pharmaceutically acceptable salts thereof, wherein Z is optionally substituted —CH$_2$CH$_2$—. In certain embodiments, the present invention relates to compounds of Formula (I), and pharmaceutically acceptable salts thereof, wherein Z is optionally substituted cyclopropyl.

In certain embodiments, the present invention relates to compounds of Formula (I), and pharmaceutically acceptable salts thereof, wherein Z is optionally substituted

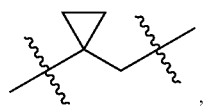

wherein, one of the indicated valences is the point of attachment to B and the other is the point of attachment to $R^4$.

In certain embodiments, the present invention relates to compounds of Formula (I), and pharmaceutically acceptable salts thereof, wherein Z is optionally substituted aryl; preferably Z is optionally substituted phenyl. In certain embodiments, the present invention relates to compounds of Formula (I), and pharmaceutically acceptable salts thereof, wherein Z is optionally substituted heteroaryl; preferably Z is optionally substituted pyridyl.

In certain embodiments, the present invention relates to compounds of Formula (I), and pharmaceutically acceptable salts thereof, wherein $R^4$ is —$CO_2R^5$, and $R^5$ is previously defined. Preferably $R^5$ is hydrogen, methyl, ethyl, t-butyl, or

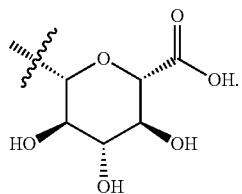

In certain embodiments, the present invention relates to compounds of Formula (I), and pharmaceutically acceptable salts thereof, wherein $R^4$ is

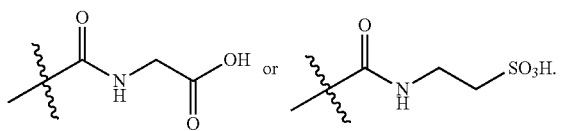 [SMILES: *C(=O)NCC(=O)O ; *C(=O)NCCS(=O)(=O)O]

In certain embodiments, the present invention relates to compounds of Formula (I), and pharmaceutically acceptable salts thereof, wherein $R^4$ is

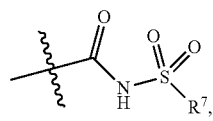

and $R^7$ is previously defined.

In certain embodiments, the present invention relates to compounds of Formula (I), and pharmaceutically acceptable salts thereof, wherein $R^1$ is optionally substituted cyclopropyl; $R^2$ is selected from

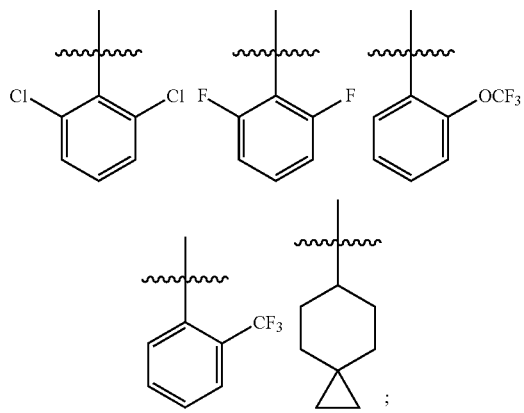

$R^{3a}$ is hydrogen; $R^{3b}$ is hydrogen; Ⓐ is optionally substituted

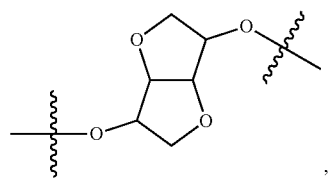

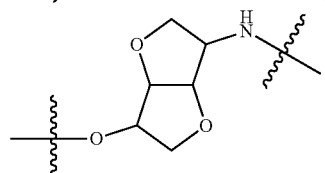

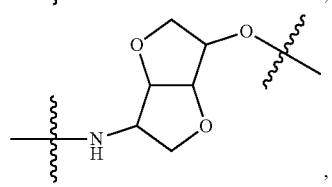

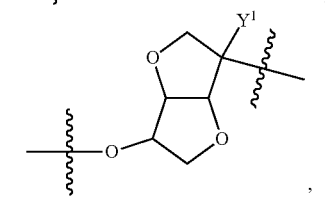

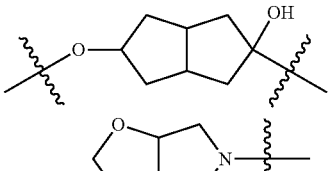

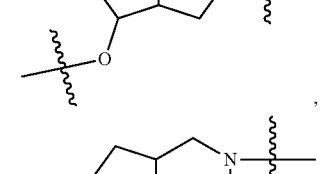

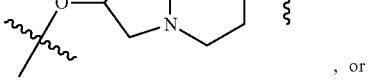

, or

-continued

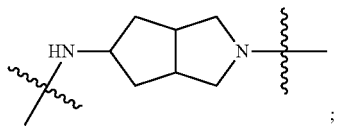

(B) is optionally substituted and selected from:

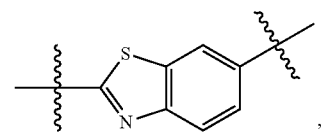

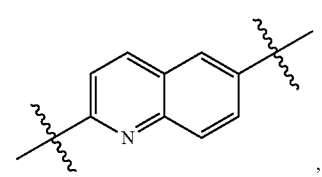

, and

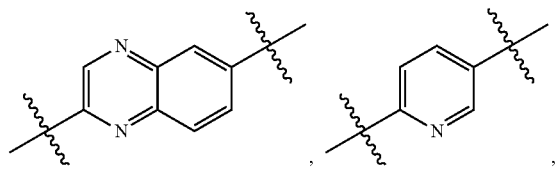

;

Z is absent; and $R^4$ is

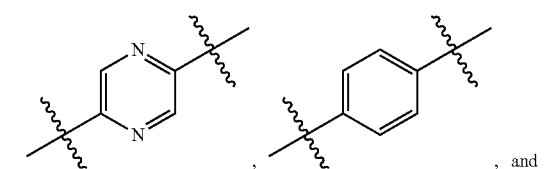

,

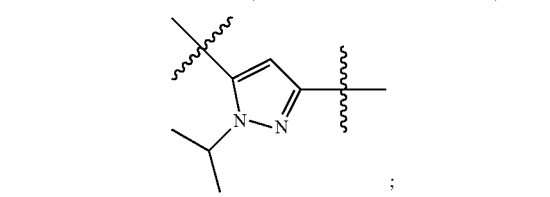

or $-CO_2R^5$; $R^7$ is as previously defined and $R^5$ is hydrogen, methyl, ethyl, t-butyl, or

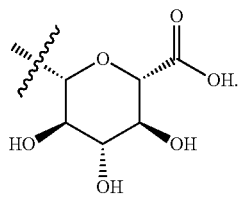

In another embodiment, the compound of Formula (I) is represented by Formula (IIa), Formula (IIb), or a pharmaceutically acceptable salt thereof:

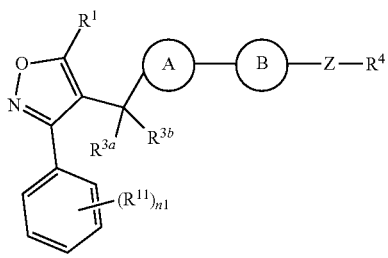
(IIa)

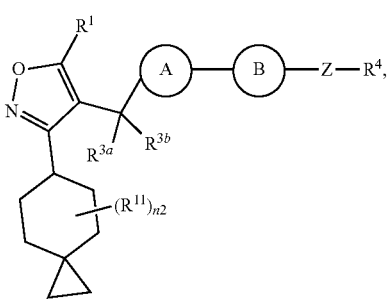
(IIb)

wherein $R^1$, $R^{3a}$, $R^{3b}$, (A), (B), Z and $R^4$ are as previously defined; $R^{11}$ at each occurrence is independently selected from the group consisting of halogen, optionally substituted $-C_1-C_6$ alkyl, optionally substituted $-C_1-C_6$ alkoxy, optionally substituted $-C_3-C_6$ cycloalkyl, optionally substituted $-C_3-C_6$ cycloalkenyl, optionally substituted aryl, and optionally substituted heteroaryl; n1 is 0, 1, 2, 3, 4, or 5; and n2 is 0, 1, 2 or 3.

In another embodiment, the compound of Formula (I) is represented by Formula (IIa-1), (IIa-2), (IIa-3), (IIb-1), (IIb-2), or (IIb-3), or a pharmaceutically acceptable salt thereof:

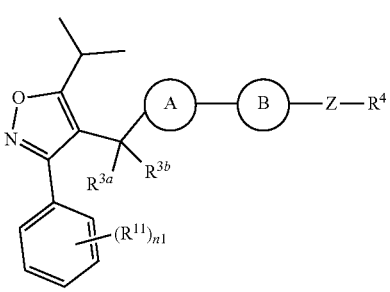
(IIa-1)

-continued (IIa-2)
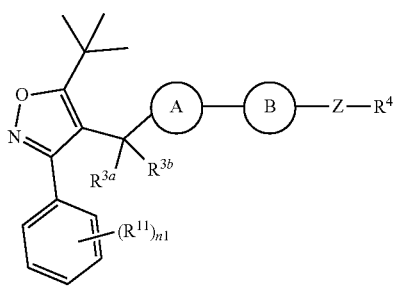

(IIa-3)
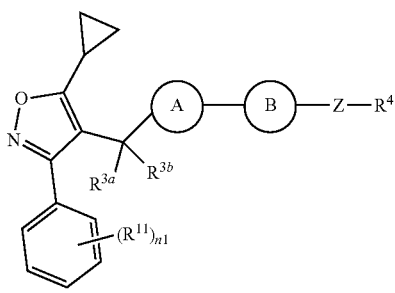

(IIb-1)
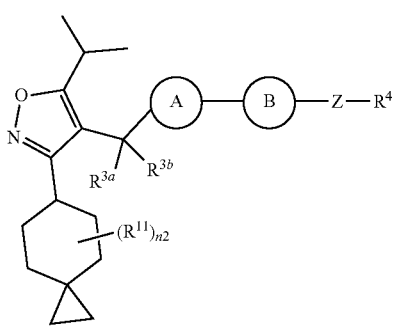

(IIb-2)
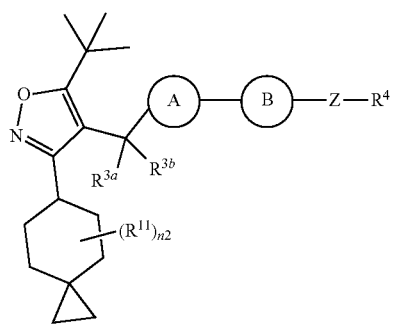

(IIb-3)
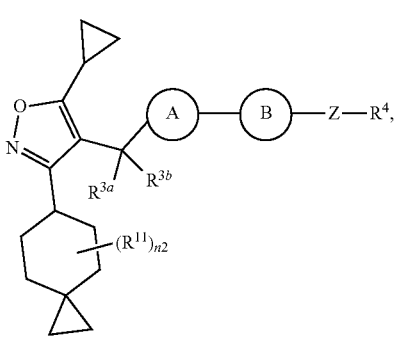

wherein $R^{3a}$, $R^{3b}$, Ⓐ, Ⓑ, Z, $R^4$, $R^{11}$, n1 and n2 are as previously defined.

In another embodiment, the compound of Formula (I) is represented by Formula (IIIa) or (IIIb), or a pharmaceutically acceptable salt thereof:

(IIIa)
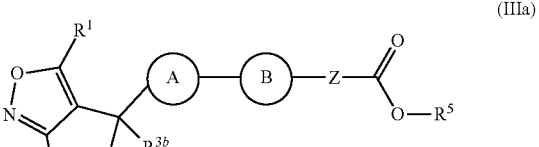

(IIIb)
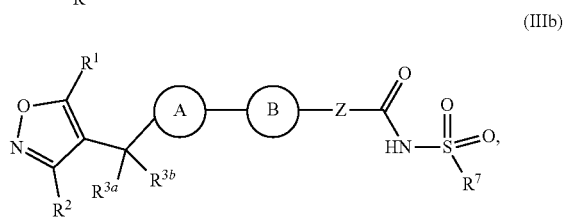

wherein Ⓐ, Ⓑ, Z, $R^1$, $R^2$, $R^{3a}$, $R^{3b}$, $R^5$, and $R^7$ are as previously defined.

In another embodiment, the compound of Formula (I) is represented by Formula (IVa) or (IVb), or a pharmaceutically acceptable salt thereof:

(IVa)
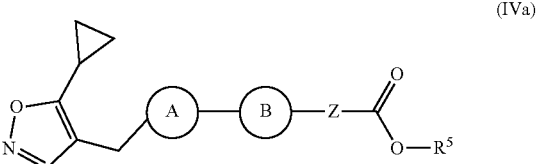

(IVb)
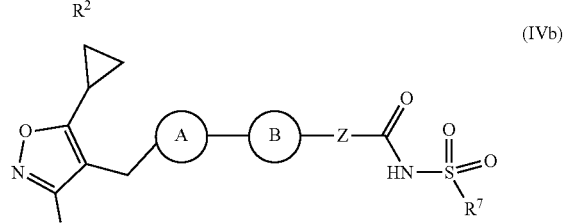

wherein Ⓐ, Ⓑ, Z, $R^2$, $R^5$, and $R^7$ are as previously defined.

In another embodiment, the compound of Formula (I) is represented by Formula (Va), (Vb), (Vc), or (Vd), or a pharmaceutically acceptable salt thereof:

(Va)
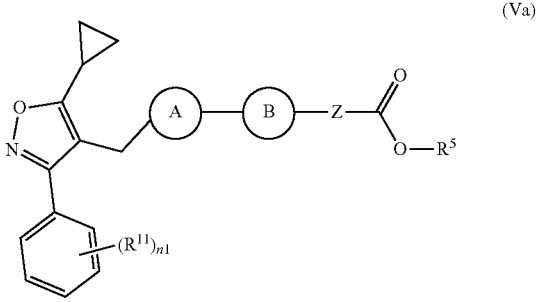

-continued (Vb)
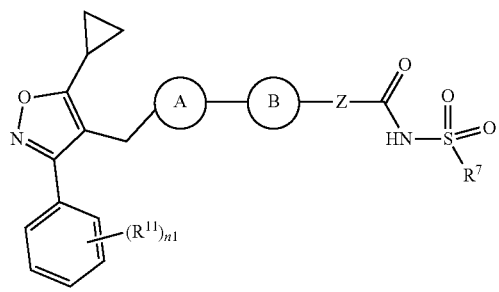

(Vc)
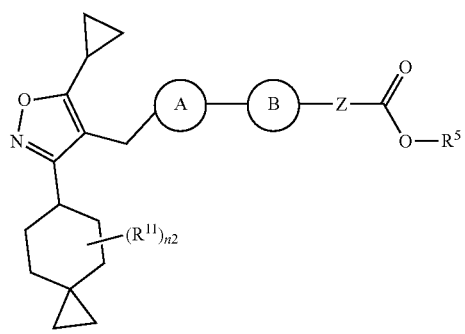

(Vd)
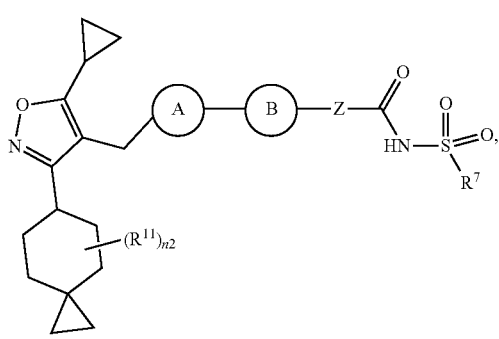

wherein Ⓐ, Ⓑ, Z, $R^5$, $R^7$, $R^{11}$, n1 and n2 are as previously defined.

In another embodiment, the compound of Formula (I) is represented by Formula (VIa), or (VIb), or a pharmaceutically acceptable salt thereof:

(VIa)
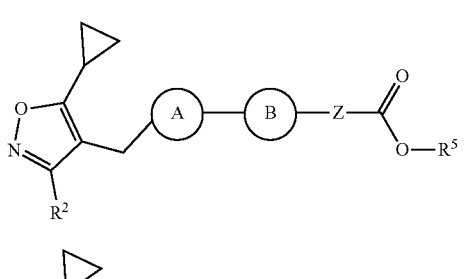

(VIb)
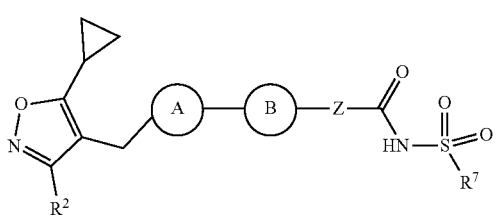

wherein Ⓐ, Ⓑ, $R^2$, $R^5$, and $R^7$ are as previously defined.

In another embodiment, the compound of Formula (I) is represented by Formula (VIIa), (VIIb), (VIIc), or (VIId), or a pharmaceutically acceptable salt thereof:

(VIIa)
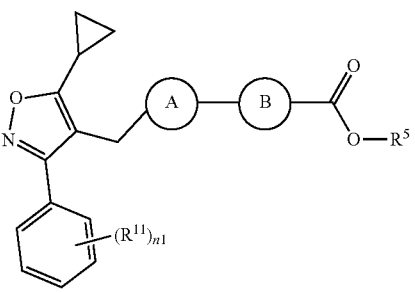

(VIIb)
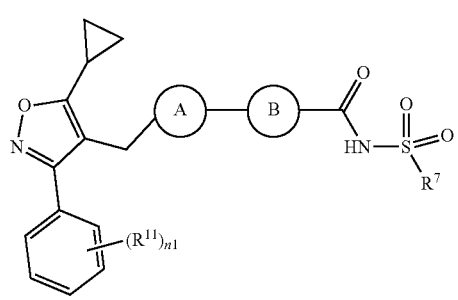

(VIIc)
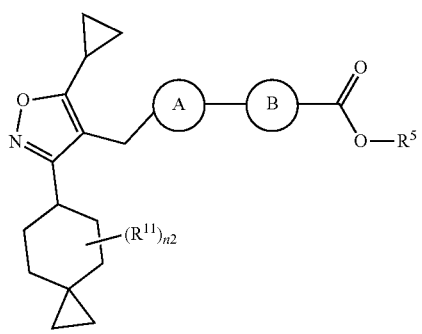

(VIId)
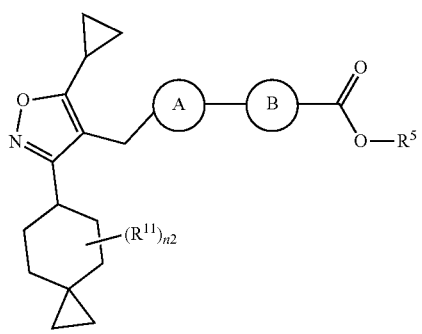

wherein Ⓐ, Ⓑ, $R^5$, $R^7$, $R^{11}$, n1 and n2 are as previously defined.

In another embodiment, the compound of Formula (I) is represented by Formula (VIIa-1), (VIIa-2), (VIIa-3), (VIIa-4), (VIIa-5), or (VIIa-6), or a pharmaceutically acceptable salt thereof:

(VIIa-1)
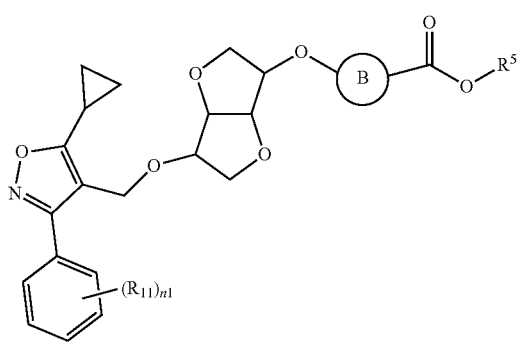
(VIIa-2)
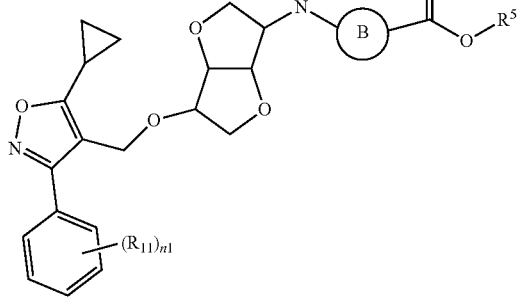
(VIIa-3)
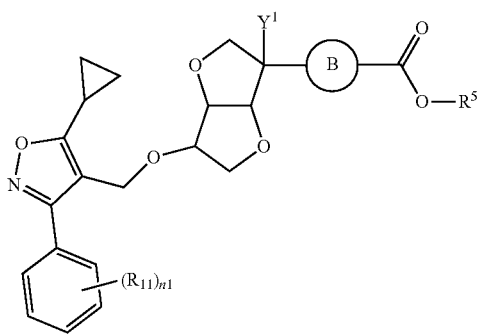
(VIIa-4)
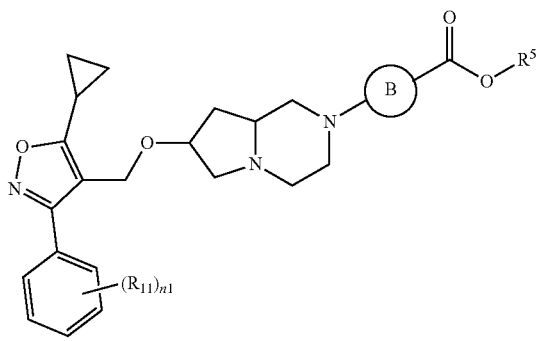
(VIIa-5)
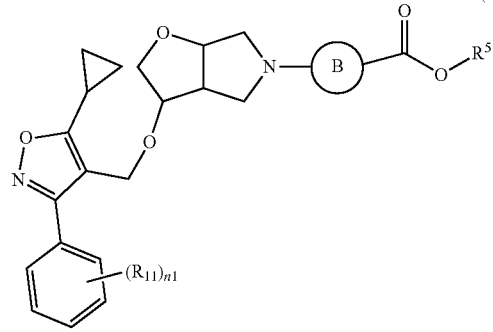
(VIIa-6)
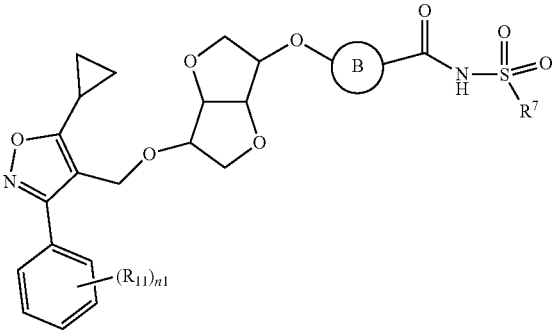
wherein Ⓑ, $R^5$, $R^{11}$, $Y^1$ and n1 are as previously defined.
In another embodiment, the compound of Formula (I) is represented by Formula (VIIb-1), (VIIb-2), (VIIb-3), (VIIb-4), (VIIb-5), or (VIIb-6), or a pharmaceutically acceptable salt thereof:
(VIIb-1)
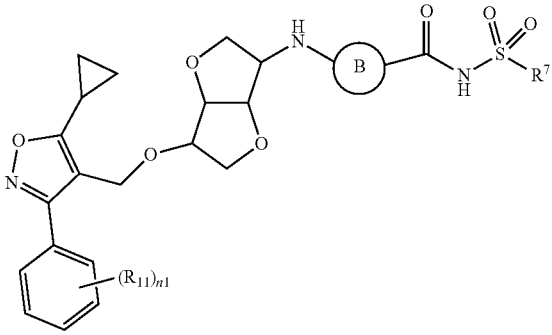
(VIIb-2)

(VIIb-3)

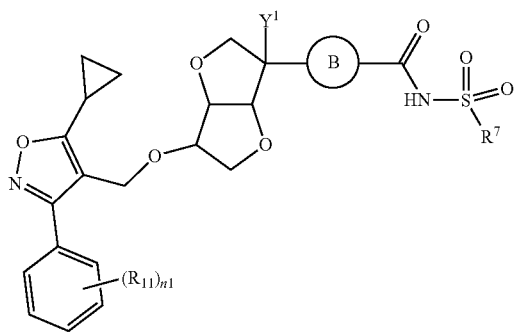

(VIIb-4)

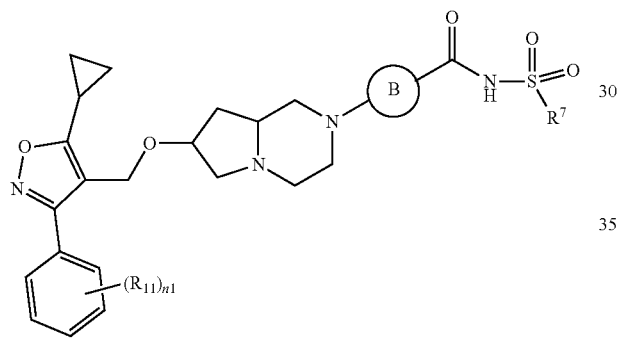

(VIIb-5)

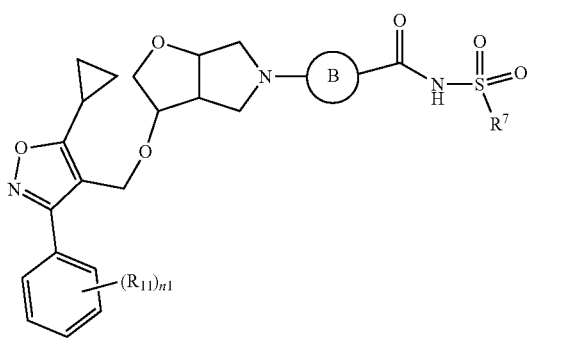

(VIIb-6)

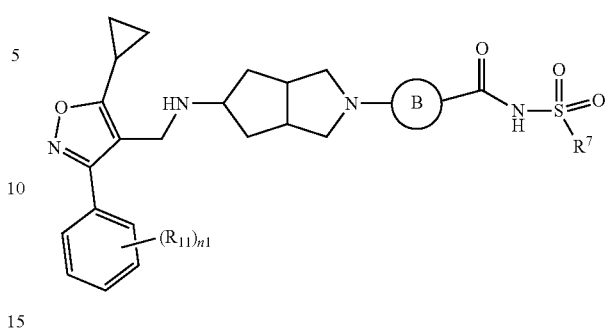

wherein ⒷⒷ, $R^7$, $R^{11}$, $Y^1$ and n1 are as previously defined.

In another embodiment, the compound of Formula (I) is represented by Formula (VIII) or a pharmaceutically acceptable salt thereof:

(VIII)

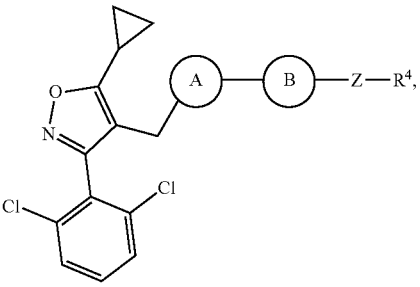

wherein Ⓐ, Ⓑ, Z and $R^4$ are as previously defined.

Representative compounds of the invention include, but are not limited to, the following compounds in Table 1 according to Formula (VIII), and pharmaceutically acceptable salts thereof, wherein, Ⓐ, Ⓑ, and Z—$R^4$ are delineated for each example in Table 1.

(VIII)

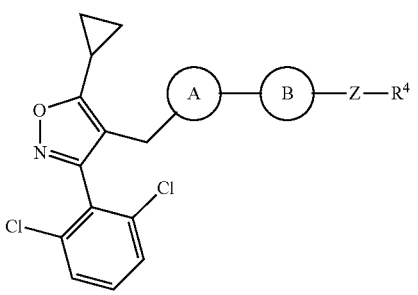

TABLE 1

| Compound | Ⓐ | Ⓑ | ⎯ξ⎯Z⎯R⁴ |
|---|---|---|---|
| 1 | isosorbide-like bicyclic diether (stereoisomer 1) | benzothiazole with OiPr at 4-position | C(CH₃)₂COOH |
| 2 | isosorbide-like bicyclic diether (stereoisomer 2) | benzothiazole with OiPr at 4-position | C(CH₃)₂COOH |
| 3 | isosorbide-like bicyclic diether (stereoisomer 3) | benzothiazole with OiPr at 4-position | C(CH₃)₂COOH |
| 4 | isosorbide-like bicyclic diether (stereoisomer 4) | benzothiazole with OiPr at 4-position | C(CH₃)₂COOH |
| 5 | isosorbide-like bicyclic diether | benzothiazole with F at 4-position | C(CH₃)₂COOH |
| 6 | isosorbide-like bicyclic diether | benzothiazole with F at 4-position | C(CH₃)₂COOH |

TABLE 1-continued

| Compound | Ⓐ | Ⓑ | —Z—R⁴ |
|---|---|---|---|
| 7 | isosorbide-type bicyclic diether (3R,6S) | 4-fluorobenzothiazole-2,6-diyl | 2-hydroxy-2-methylpropanoic acid linker (C(CH₃)₂COOH) |
| 8 | isosorbide-type bicyclic diether | 4-fluorobenzothiazole-2,6-diyl | C(CH₃)₂COOH |
| 9 | isosorbide-type bicyclic diether | 4-methoxybenzothiazole-2,6-diyl | C(CH₃)₂COOH |
| 10 | isosorbide-type bicyclic diether | 4-methoxybenzothiazole-2,6-diyl | C(CH₃)₂COOH |
| 11 | isosorbide-type bicyclic diether | 4-methoxybenzothiazole-2,6-diyl | C(CH₃)₂COOH |
| 12 | isosorbide-type bicyclic diether | 4-methoxybenzothiazole-2,6-diyl | C(CH₃)₂COOH |

TABLE 1-continued

| Compound | Ⓐ | Ⓑ | —⸺Z—R⁴ |
|---|---|---|---|
| 13 | [bicyclic diether with two O-linkages, both H shown] | [benzothiazole, 2,6-disubstituted] | C(CH₃)₂COOH |
| 14 | [bicyclic diether, different stereochemistry] | [benzothiazole, 2,6-disubstituted] | C(CH₃)₂COOH |
| 15 | [bicyclic diether, different stereochemistry] | [benzothiazole, 2,6-disubstituted] | C(CH₃)₂COOH |
| 16 | [bicyclic diether, different stereochemistry] | [benzothiazole, 2,6-disubstituted] | C(CH₃)₂COOH |
| 17 | [bicyclic diether] | [benzothiazole, 2,6-disubstituted, with OCHF₂] | C(CH₃)₂COOH |
| 18 | [bicyclic diether] | [benzothiazole, 2,6-disubstituted, with OCF₃] | C(CH₃)₂COOH |

TABLE 1-continued

| Compound | Ⓐ | Ⓑ | ⸝⸝⸝—Z—R⁴ |
|---|---|---|---|
| 19 | isosorbide-like bicyclic diether with two O-attachment points | benzothiazole, 2,6-disubstituted, 7-OCH₂F | 2-methylpropanoic acid (C(CH₃)₂COOH) |
| 20 | isosorbide-like bicyclic diether with two O-attachment points | benzothiazole, 2,6-disubstituted, 7-CF₃ | 2-methylpropanoic acid |
| 21 | isosorbide-like bicyclic diether with two O-attachment points | benzothiazole, 2,6-disubstituted, 7-CH₃ | 2-methylpropanoic acid |
| 22 | isosorbide-like bicyclic diether with two O-attachment points | benzothiazole, 2,6-disubstituted, 7-Br | 2-methylpropanoic acid |
| 23 | isosorbide-like bicyclic diether with two O-attachment points | benzothiazole, 2,6-disubstituted, 7-Cl | 2-methylpropanoic acid |
| 24 | isosorbide-like bicyclic diether with two O-attachment points | benzothiazole, 2,6-disubstituted, 7-cyclopropyl | 2-methylpropanoic acid |

TABLE 1-continued

| Compound | (A) | (B) | ⸺Z—R⁴ |
|---|---|---|---|
| 25 | isosorbide-like bicyclic diether | 5-Me-benzothiazole-2,6-diyl | 2-methyl-2-carboxyethyl (C(Me)₂COOH) |
| 26 | isosorbide-like bicyclic diether | 7-Me-benzothiazole-2,6-diyl | C(Me)₂COOH |
| 27 | isosorbide-like bicyclic diether | benzoxazole-2,6-diyl | C(Me)₂COOH |
| 28 | isosorbide-like bicyclic diether | 4-F-benzoxazole-2,6-diyl | C(Me)₂COOH |
| 29 | isosorbide-like bicyclic diether | 4-OMe-benzoxazole-2,6-diyl | C(Me)₂COOH |
| 30 | isosorbide-like bicyclic diether | 4-OiPr-benzoxazole-2,6-diyl | C(Me)₂COOH |

TABLE 1-continued

| Compound | Ⓐ | Ⓑ | ⸺Z—R⁴ |
|---|---|---|---|
| 31 | isosorbide-type bicyclic diether | 5-fluoroquinoline (2,6-linked) | C(CH₃)₂COOH |
| 32 | isosorbide-type bicyclic diether | 7-fluoroquinoline (2,6-linked) | C(CH₃)₂COOH |
| 33 | isosorbide-type bicyclic diether | quinoline (2,6-linked) | C(CH₃)₂COOH |
| 34 | isosorbide-type bicyclic diether | quinoline (3,7-linked) | C(CH₃)₂COOH |
| 35 | isosorbide-type bicyclic diether | 3-fluoroquinoline (2,6-linked) | C(CH₃)₂COOH |
| 36 | isosorbide-type bicyclic diether | 3-methoxyquinoline (2,6-linked) | C(CH₃)₂COOH |

TABLE 1-continued

| Compound | Ⓐ | Ⓑ | —Z—R⁴ |
|---|---|---|---|
| 37 | isosorbide diyl | quinoxaline-2,6-diyl | 2-methylpropanoic acid |
| 38 | isosorbide diyl | 3-methoxyquinoxaline-2,6-diyl | 2-methylpropanoic acid |
| 39 | isosorbide diyl | 3-chloroquinoxaline-2,6-diyl | 2-methylpropanoic acid |
| 40 | isosorbide diyl | 8-isopropoxyquinoxaline-2,6-diyl | 2-methylpropanoic acid |
| 41 | isosorbide diyl | naphthalene-2,6-diyl | 2-methylpropanoic acid |
| 42 | isosorbide diyl | 8-fluoronaphthalene-2,6-diyl | 2-methylpropanoic acid |

TABLE 1-continued

| Compound | Ⓐ | Ⓑ | —Z—R⁴ |
|---|---|---|---|
| 43 | isosorbide-type bicyclic diether | 3-fluoronaphthalene-2,6-diyl | 2-methyl-2-carboxy (C(CH₃)₂COOH) |
| 44 | isosorbide-type bicyclic diether | 8-methoxynaphthalene-2,6-diyl | 2-methyl-2-carboxy |
| 45 | isosorbide-type bicyclic diether | naphthalene-2,6-diyl | 2-methyl-2-carboxy |
| 46 | isosorbide-type bicyclic diether | 4-methoxynaphthalene-2,6-diyl | 2-methyl-2-carboxy |
| 47 | isosorbide-type bicyclic diether | isoquinoline-3,7-diyl | 2-methyl-2-carboxy |
| 48 | isosorbide-type bicyclic diether | quinoline-2,5-diyl | 2-methyl-2-carboxy |

TABLE 1-continued

| Compound | Ⓐ | Ⓑ | —Z—R⁴ |
|---|---|---|---|
| 49 | isosorbide | quinoline-2,5-diyl | 2-methylpropanoic acid |
| 50 | isosorbide | 8-fluoroquinoline-2,6-diyl | 2-methylpropanoic acid |
| 51 | isosorbide | quinoxaline-2,6-diyl | 2-methylpropanoic acid |
| 52 | isosorbide | quinazoline-2,6-diyl | 2-methylpropanoic acid |
| 53 | isosorbide | quinazoline-4,7-diyl | 2-methylpropanoic acid |
| 54 | isosorbide | 4-methylbenzofuran-2,5-diyl | 2-methylpropanoic acid |

TABLE 1-continued

| Compound | Ⓐ | Ⓑ | —⟋Z—R⁴ |
|---|---|---|---|
| 55 | hexahydrofuro[3,2-b]furan-3,6-diyl bis(oxy) | pyrazolo[1,5-a]pyrimidine-2,5-diyl | 2-methyl-2-carboxyethyl (C(CH₃)₂COOH) |
| 56 | hexahydrofuro[3,2-b]furan-3,6-diyl bis(oxy) | imidazo[1,2-a]pyridine-3,6-diyl | C(CH₃)₂COOH |
| 57 | hexahydrofuro[3,2-b]furan-3,6-diyl bis(oxy) | 5-fluoro-benzo[d]isothiazole-3,6-diyl | C(CH₃)₂COOH |
| 58 | hexahydrofuro[3,2-b]furan-3,6-diyl bis(oxy) | benzo[d]isothiazole-3,6-diyl | C(CH₃)₂COOH |
| 59 | hexahydrofuro[3,2-b]furan-3,6-diyl bis(oxy) | pyrazine-2,5-diyl | C(CH₃)₂COOH |
| 60 | hexahydrofuro[3,2-b]furan-3,6-diyl bis(oxy) | 3-fluoropyrazine-2,5-diyl | C(CH₃)₂COOH |

TABLE 1-continued

| Compound | Ⓐ | Ⓑ | ⸺Z—R⁴ |
|---|---|---|---|
| 61 | isosorbide-type bicyclic diether | 3-fluoro-1,4-phenylene | 2-methylpropanoic acid |
| 62 | isosorbide-type bicyclic diether | 2-fluoro-1,4-phenylene | 2-methylpropanoic acid |
| 63 | isosorbide-type bicyclic diether | pyrazine-2,5-diyl | 2-methylpropanoic acid |
| 64 | isosorbide-type bicyclic diether | pyridine-2,6-diyl | 2-methylpropanoic acid |
| 65 | isosorbide-type bicyclic diether | 6-methylpyrimidine-2,4-diyl | 2-methylpropanoic acid |
| 66 | isosorbide-type bicyclic diether | 4-fluoropyridine-2,5-diyl | 2-methylpropanoic acid |

TABLE 1-continued

| Compound | Ⓐ | Ⓑ | —Z—R⁴ |
|---|---|---|---|
| 67 | isosorbide diether | pyridine-2,5-diyl | C(CH₃)₂COOH |
| 68 | isosorbide diether | thiazole-2,5-diyl | C(CH₃)₂COOH |
| 69 | isosorbide diether | thiazole-2,4-diyl | C(CH₃)₂COOH |
| 70 | isosorbide diether | pyridine-2,6-diyl | C(CH₃)₂COOH |
| 71 | isosorbide diether | 4-methylpyridine-2,5-diyl | C(CH₃)₂COOH |
| 72 | isosorbide diether | 3-fluoropyridine-2,5-diyl | C(CH₃)₂COOH |

TABLE 1-continued

| Compound | (A) | (B) | —ξ—Z—R⁴ |
|---|---|---|---|
| 73 | isosorbide-type bicyclic diether | 3-methyl-pyridine-2,5-diyl | 2-methylpropanoic acid (α,α-dimethyl CH₂COOH) |
| 74 | isosorbide-type bicyclic diether | 3-(trifluoromethyl)pyridine-2,5-diyl | 2-methylpropanoic acid |
| 75 | isosorbide-type bicyclic diether | 3-cyclopropylpyridine-2,5-diyl | 2-methylpropanoic acid |
| 76 | isosorbide-type bicyclic diether | 2,6-difluoro-1,4-phenylene | 2-methylpropanoic acid |
| 77 | isosorbide-type bicyclic diether | 1,2,4-oxadiazole-3,5-diyl | 2-methylpropanoic acid |
| 78 | isosorbide-type bicyclic diether | 1,2,4-oxadiazole-3,5-diyl | 3-carboxyphenyl (benzoic acid) |

TABLE 1-continued

| Compound | Ⓐ | Ⓑ | —Z—R⁴ |
|---|---|---|---|
| 79 | isosorbide-diyl ether | 1,2,4-oxadiazole-3,5-diyl | 6-carboxypyridin-2-yl |
| 80 | isosorbide-diyl ether | 1,2,4-oxadiazole-3,5-diyl | 3-carboxy-4-fluorophenyl |
| 81 | isosorbide-diyl ether | 1,2,4-oxadiazole-3,5-diyl | 4-carboxyphenyl |
| 82 | isosorbide-diyl ether | 1,2,4-oxadiazole-3,5-diyl | 3-carboxycyclohexyl |
| 83 | isosorbide-diyl ether | 4-(OiPr)-benzothiazole-2,6-diyl | CN |
| 84 | isosorbide-diyl ether | 4-(OiPr)-benzothiazole-2,6-diyl | tetrazol-5-yl |

TABLE 1-continued

| Compound | (A) | (B) | —Z—R⁴ |
|---|---|---|---|
| 85 | isosorbide-type bis-ether | 2,5-pyrazinyl | CN |
| 86 | isosorbide-type bis-ether | 2,5-pyrazinyl | tetrazole (NH) |
| 87 | isosorbide-type bis-ether | 2-fluoro-1,4-phenylene | CN |
| 88 | isosorbide-type bis-ether | 2-fluoro-1,4-phenylene | tetrazole (NH) |
| 89 | isosorbide-type bis-ether | 2-methoxy-1,4-phenylene | CN |
| 90 | isosorbide-type bis-ether | 2-methoxy-1,4-phenylene | tetrazole (NH) |

TABLE 1-continued

| Compound | Ⓐ | Ⓑ | —Z—R⁴ |
|---|---|---|---|
| 91 | isosorbide diether | 6-benzothiazolyl | carbamate-SO₂-C₆H₄-OiPr |
| 92 | isosorbide diether (isomer) | 6-benzothiazolyl | carbamate-SO₂-C₆H₄-OiPr |
| 93 | isosorbide diether | 6-benzothiazolyl, 4-OiPr | carbamate-SO₂-C₆H₄-OiPr |
| 94 | isosorbide diether (isomer) | 6-benzothiazolyl, 4-OiPr | carbamate-SO₂-C₆H₄-OiPr |
| 95 | isosorbide diether | 6-benzothiazolyl | carbamate-SO₂-C₆H₄-OtBu |
| 96 | isosorbide diether (isomer) | 6-benzothiazolyl | carbamate-SO₂-C₆H₄-OtBu |

TABLE 1-continued

| Compound | Ⓐ | Ⓑ | $-\xi-Z-R^4$ |
|---|---|---|---|
| 97 | isosorbide-like bicyclic diether | 7-OiPr-benzothiazole (2,6-linked) | carbamoyl sulfonyl 4-tert-butoxyphenyl |
| 98 | isosorbide-like bicyclic diether (alt. stereo) | 7-OiPr-benzothiazole (2,6-linked) | carbamoyl sulfonyl 4-tert-butoxyphenyl |
| 99 | isosorbide-like bicyclic diether | benzothiazole (2,6-linked) | carbamoyl sulfonyl 6-piperidinyl-pyridin-3-yl |
| 100 | isosorbide-like bicyclic diether | 7-F-benzothiazole (2,6-linked) | carbamoyl sulfonyl 6-piperidinyl-pyridin-3-yl |
| 101 | isosorbide-like bicyclic diether | 7-OiPr-benzothiazole (2,6-linked) | carbamoyl sulfonyl 6-piperidinyl-pyridin-3-yl |
| 102 | isosorbide-like bicyclic diether | 7-cyclopropyl-benzothiazole (2,6-linked) | carbamoyl sulfonyl 6-piperidinyl-pyridin-3-yl |

TABLE 1-continued

| Compound | Ⓐ | Ⓑ | —Z—R⁴ |
|---|---|---|---|
| 103 | isosorbide-like bicyclic diether | 6-benzothiazolyl | -CH₂-O-C(O)-NH-SO₂-C₆H₄-O-tBu |
| 104 | isosorbide-like bicyclic diether | 4-F-6-benzothiazolyl | -CH₂-O-C(O)-NH-SO₂-C₆H₄-O-tBu |
| 105 | isosorbide-like bicyclic diether | 4-OiPr-6-benzothiazolyl | -CH₂-O-C(O)-NH-SO₂-C₆H₄-O-tBu |
| 106 | isosorbide-like bicyclic diether | 4-cyclopropyl-6-benzothiazolyl | -CH₂-O-C(O)-NH-SO₂-C₆H₄-O-tBu |
| 107 | isosorbide-like bicyclic diether | 6-benzothiazolyl | -NH-C(O)-NH-SO₂-C₆H₄-tBu |
| 108 | isosorbide-like bicyclic diether | 4-F-6-benzothiazolyl | -NH-C(O)-NH-SO₂-C₆H₄-tBu |

TABLE 1-continued

| Compound | Ⓐ | Ⓑ | —Z—R⁴ |
|---|---|---|---|
| 109 | isosorbide-type bicyclic diether | benzothiazole with OiPr | urea-sulfonyl-4-tert-butylphenyl |
| 110 | isosorbide-type bicyclic diether | benzothiazole with cyclopropyl | urea-sulfonyl-4-tert-butylphenyl |
| 111 | isosorbide-type bicyclic diether | benzothiazole | CH₂-urea-sulfonyl-4-tert-butylphenyl |
| 112 | isosorbide-type bicyclic diether | benzothiazole with F | CH₂-urea-sulfonyl-4-tert-butylphenyl |
| 113 | isosorbide-type bicyclic diether | benzothiazole with OiPr | CH₂-urea-sulfonyl-4-tert-butylphenyl |
| 114 | isosorbide-type bicyclic diether | benzothiazole with cyclopropyl | CH₂-urea-sulfonyl-4-tert-butylphenyl |

TABLE 1-continued

| Compound | Ⓐ | Ⓑ | —ʒ—Z—R⁴ |
|---|---|---|---|
| 115 | isosorbide-di-O | 2-yl-7-OiPr-benzothiazol-6-yl | —CO₂Me |
| 116 | isosorbide-di-O | 2-yl-7-OiPr-benzothiazol-6-yl | —CO₂t-Bu |
| 117 | isosorbide-di-O | 2-yl-7-OiPr-benzothiazol-6-yl | —CH₂CO₂Me |
| 118 | isosorbide-di-O | 2-yl-7-OiPr-benzothiazol-6-yl | —CH₂CO₂H |
| 119 | isosorbide-di-O | 2-yl-7-OiPr-benzothiazol-6-yl | —CH₂CH₂C(O)OMe |
| 120 | isosorbide-di-O | 2-yl-7-OiPr-benzothiazol-6-yl | —CH₂CH₂C(O)OH |

TABLE 1-continued

| Compound | Ⓐ | Ⓑ | —Z—R⁴ |
|---|---|---|---|
| 121 | isosorbide-like bicyclic diether | benzothiazole with OiPr | —CH₂—O—CH₂—C(=O)OMe |
| 122 | isosorbide-like bicyclic diether | benzothiazole with OiPr | —CH₂—O—CH₂—C(=O)OH |
| 123 | isosorbide-like bicyclic diether | benzothiazole with OiPr | —CH₂—NH—CH₂—C(=O)OMe |
| 124 | isosorbide-like bicyclic diether | benzothiazole with OiPr | —CH₂—NH—CH₂—C(=O)OH |
| 125 | isosorbide-like bicyclic diether | benzothiazole with OiPr | —CH₂—N(Me)—CH₂—C(=O)OMe |
| 126 | isosorbide-like bicyclic diether | benzothiazole with OiPr | —CH₂—N(Me)—CH₂—C(=O)OH |

TABLE 1-continued

| Compound | Ⓐ | Ⓑ | ⸺Z—R⁴ |
|---|---|---|---|
| 127 | isosorbide-diyl | 2-yl-6-yl-4-OiPr-benzothiazole | -C(CH₃)₂-CH₂OH |
| 128 | isosorbide-diyl | 2-yl-6-yl-4-OiPr-benzothiazole | -C(CH₃)₂-CH₂CH₂OH |
| 129 | isosorbide-diyl | 2-yl-6-yl-4-OiPr-benzothiazole | -C(CH₃)(cyclopropyl-CO₂Me) |
| 130 | isosorbide-diyl | 2-yl-6-yl-4-OiPr-benzothiazole | -C(CH₃)(cyclopropyl-CO₂H) |
| 131 | isosorbide-diyl | 2-yl-6-yl-4-OiPr-benzothiazole | -C(CH₃)(cyclopropyl-CH₂CO₂Me) |
| 132 | isosorbide-diyl | 2-yl-6-yl-4-OiPr-benzothiazole | -C(CH₃)(cyclopropyl-CH₂CO₂H) |

TABLE 1-continued

| Compound | Ⓐ | Ⓑ | —Z—R⁴ |
|---|---|---|---|
| 133 | isosorbide-diyl dioxy | 4-OiPr-benzothiazol-2,6-diyl | C(CF₂)(Me)CO₂Me |
| 134 | isosorbide-diyl dioxy | 4-OiPr-benzothiazol-2,6-diyl | C(CF₂)(Me)CO₂H |
| 135 | isosorbide-diyl dioxy | 4-OiPr-benzothiazol-2,6-diyl | CN |
| 136 | isosorbide-diyl dioxy | 4-OiPr-benzothiazol-2,6-diyl | 1H-tetrazol-5-yl |
| 137 | isosorbide-diyl dioxy | 4-OiPr-benzothiazol-2,6-diyl | C(Me)₂C(O)NHCH₂CO₂tBu |
| 138 | isosorbide-diyl dioxy | 4-OiPr-benzothiazol-2,6-diyl | C(Me)₂C(O)NHCH₂CO₂H |

TABLE 1-continued

| Compound | Ⓐ | Ⓑ | —Z—R⁴ |
|---|---|---|---|
| 139 | isosorbide-diyl | 4-OiPr-benzothiazole-2,6-diyl | C(=O)-NH-C(CH₃)₂-COOH |
| 140 | isosorbide-diyl | 4-OiPr-benzothiazole-2,6-diyl | C(=O)-NH-CH(CH₃)-COOH |
| 141 | isosorbide-diyl | 4-OiPr-benzothiazole-2,6-diyl | C(=O)-NH-CH₂CH₂-SO₂Me |
| 142 | isosorbide-diyl | 4-OiPr-benzothiazole-2,6-diyl | C(=O)-NH-CH₂CH₂-SO₃H |
| 143 | isosorbide-diyl | 4-OiPr-benzothiazole-2,6-diyl | C(=O)-NH-C(cyclopropyl)-CH₂-SO₃H |
| 144 | isosorbide-diyl | 4-OiPr-benzothiazole-2,6-diyl | C(=O)-NH-C(CH₃)₂-CH₂-SO₃H |

TABLE 1-continued

| Compound | Ⓐ | Ⓑ | 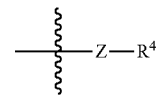 |
|---|---|---|---|
| 145 | (isosorbide-like bicyclic diether) | 2-substituted-4-OiPr-benzothiazole-6-yl | -C(=O)-NH-CH₂-O-CH₂-OSO₃H |
| 146 | (isosorbide-like bicyclic diether) | 2-substituted-4-OiPr-benzothiazole-6-yl | -C(=O)-NH-CH₂-NH-CH₂-OSO₃H |
| 147 | (isosorbide-like bicyclic diether) | 2-substituted-benzothiazole-6-yl | glucuronide ester |
| 148 | (isosorbide-like bicyclic diether) | 2-substituted-4-OMe-benzothiazole-6-yl | glucuronide ester |
| 149 | (isosorbide-like bicyclic diether) | 2-substituted-4-F-benzothiazole-6-yl | glucuronide ester |
| 150 | (isosorbide-like bicyclic diether) | 2-substituted-4-OiPr-benzothiazole-6-yl | glucuronide ester |

TABLE 1-continued

| Compound | A | B | —Z—R⁴ |
|---|---|---|---|
| 151 | [structure] | [benzothiazole-OiPr] | [C(CH₃)₂COOH] |
| 152 | [structure] | [benzothiazole-OiPr] | [C(CH₃)₂COOH] |
| 153 | [structure] | [benzothiazole-OiPr] | [C(CH₃)₂COOH] |
| 154 | [structure] | [benzothiazole-OiPr] | [C(CH₃)₂COOH] |
| 155 | [structure] | [benzothiazole-OiPr] | [C(CH₃)₂COOH] |
| 156 | [structure] | [benzothiazole-OiPr] | [C(CH₃)₂COOH] |
| 157 | [structure] | [benzothiazole-OiPr] | [C(CH₃)₂COOH] |

TABLE 1-continued
| Compound | Ⓐ | Ⓑ | —Z—R⁴ |
|---|---|---|---|
| 158 | 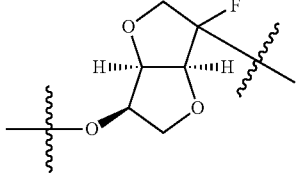 [SMILES: *O[C@@H]1CO[C@H]2[C@@H]1OCC2(*)F] | 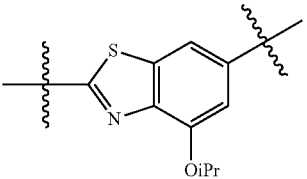 | 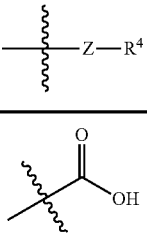 |
| 159 | 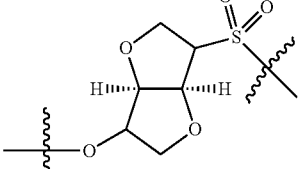 | 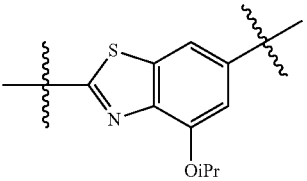 | 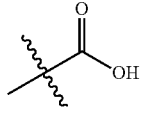 [SMILES: *C(=O)O] |
| 160 | 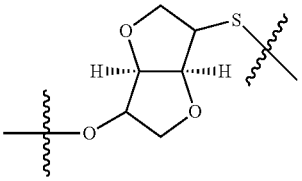 [SMILES: *OC1CO[C@@H]2C(S*)CO[C@H]12] | 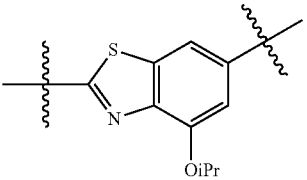 | 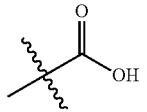 [SMILES: *C(=O)O] |
| 161 | 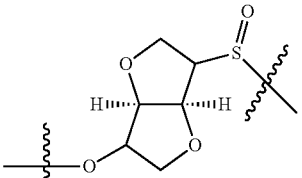 | 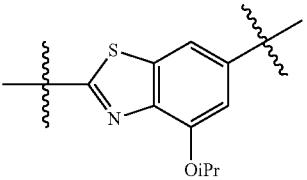 | 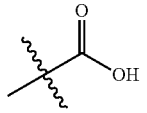 [SMILES: *C(=O)O] |
| 162 | 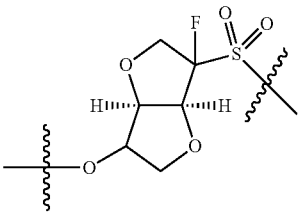 [SMILES: *OC1CO[C@H]2[C@@H]1OCC2(F)S(*)(=O)=O] | 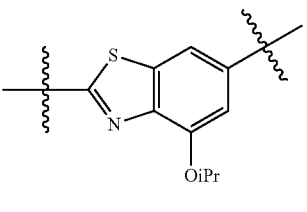 | 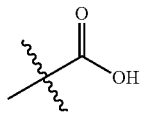 [SMILES: *C(=O)O] |
| 163 | 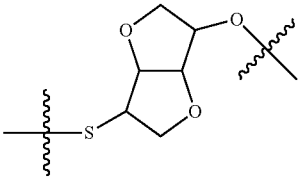 [SMILES: *OC1COC2C(S*)COC12] | 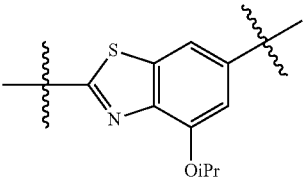 | 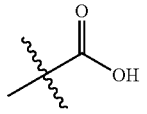 |
| 164 | 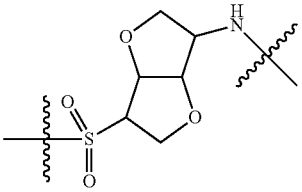 [SMILES: *NC1COC2C1OCC2S(*)(=O)=O] | 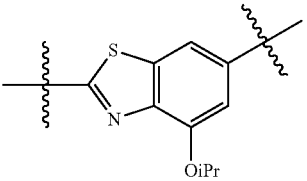 | 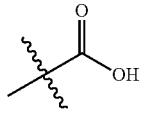 [SMILES: *C(=O)O] |

TABLE 1-continued

| Compound | A | B | —Z—R⁴ |
|---|---|---|---|
| 165 | (bicyclic oxazolidine with O-linker on cyclopentane, N-attached) | 2-linked-7-OiPr-benzothiazole-5-yl | –C(CH₃)₂–COOH |
| 166 | (bicyclic oxazolidine with NH-linker on cyclopentane, N-attached) | 2-linked-7-OiPr-benzothiazole-5-yl | –C(CH₃)₂–COOH |
| 167 | (bicyclic oxazolidine with O-linker on cyclopentane, N-attached) | 2-linked-7-OiPr-benzothiazole-5-yl | –C(CH₃)₂–COOH |
| 168 | (bicyclic oxazolidinone with O-linker on cyclopentane, N-attached) | 2-linked-7-OiPr-benzothiazole-5-yl | –C(CH₃)₂–COOH |
| 169 | (bicyclic diaminooctahydropentalene, both NH linkers) | 2-linked-7-OiPr-benzothiazole-5-yl | –C(CH₃)₂–COOH |
| 170 | (bicyclic octahydropentalene with O and NH linkers) | 2-linked-7-OiPr-benzothiazole-5-yl | –C(CH₃)₂–COOH |

TABLE 1-continued

| Compound | Ⓐ | Ⓑ | —Z—R⁴ |
|---|---|---|---|
| 171 | | | |
| 172 | | | |
| 173 | | | |
| 174 | | | |
| 175 | | | |
| 176 | | | |
| 177 | | | |

TABLE 1-continued

| Compound | Ⓐ | Ⓑ | —Z—R⁴ |
|---|---|---|---|
| 178 | | | |
| 179 | | | |
| 180 | | | |
| 181 | | | |
| 182 | | | |
| 183 | | | |
| 184 | | | |
| 185 | | | |

TABLE 1-continued

| Compound | A | B | —Z—R⁴ |
|---|---|---|---|
| 186 | | | |
| 187 | | | |
| 188 | | | |
| 189 | | | |
| 190 | | | |
| 191 | | | |

TABLE 1-continued

| Compound | Ⓐ | Ⓑ | ⸗Z—R⁴ |
|---|---|---|---|
| 192 | 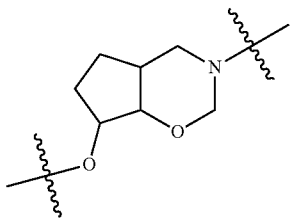 [SMILES: *OC1CCC2CN(*)COC21] | 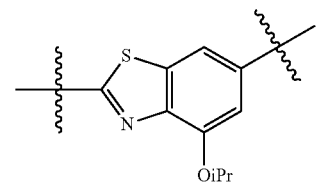 | 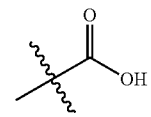 |

In another embodiment, the compound of Formula (I) is represented by Formula (IX), or a pharmaceutically acceptable salt thereof:

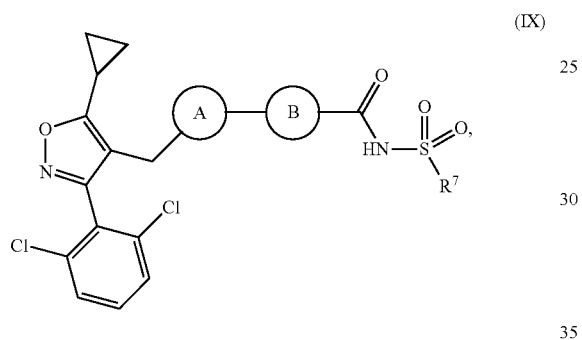

(IX)

wherein Ⓐ, Ⓑ, and $R^7$ are as previously defined.

Representative compounds of the invention include, but are not limited to, the following compounds in Table 2 according to Formula (IX), and pharmaceutically acceptable salts thereof, wherein Ⓐ, Ⓑ, and $R^7$ are delineated for each example in Table 2.

TABLE 2

| compound | Ⓐ | Ⓑ | $R^7$ |
|---|---|---|---|
| 201 | 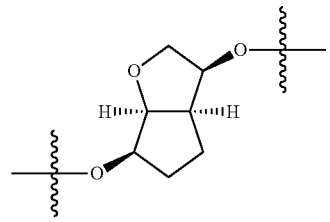 | 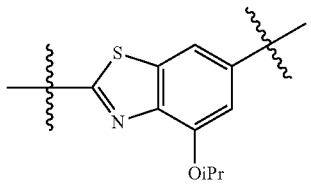 [SMILES: *c1cc(OC(C)C)c2nc(*)sc2c1] | 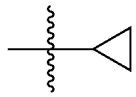 [SMILES: *C1CC1] |
| 202 | 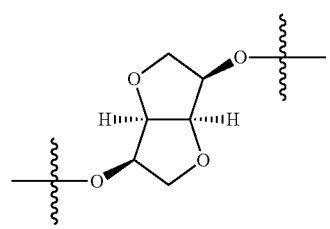 [SMILES: *O[C@@H]1CO[C@H]2[C@@H]1OC[C@H]2O*] | 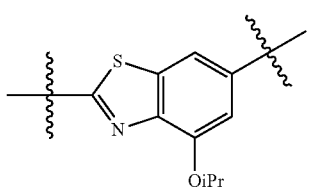 [SMILES: *c1cc(OC(C)C)c2nc(*)sc2c1] | 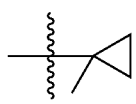 [SMILES: *C1(C)CC1] |

TABLE 2-continued

| compound | Ⓐ | Ⓑ | R⁷ |
|---|---|---|---|
| 203 | isosorbide-type bicyclic diether linker | 4-OiPr-benzothiazole-2,6-diyl | cyclopropyl-CHO |
| 204 | isosorbide-type bicyclic diether linker | 4-OiPr-benzothiazole-2,6-diyl | cyclopropyl-CD₃ |
| 205 | isosorbide-type bicyclic diether linker | 4-OiPr-benzothiazole-2,6-diyl | cyclopropyl-CH₂OH |
| 206 | isosorbide-type bicyclic diether linker | 4-OiPr-benzothiazole-2,6-diyl | cyclopropyl-CHF₂ |
| 207 | isosorbide-type bicyclic diether linker | 4-OiPr-benzothiazole-2,6-diyl | cyclopropyl-CF₃ |
| 208 | isosorbide-type bicyclic diether linker | 4-OiPr-benzothiazole-2,6-diyl | cyclopropyl-F |
| 209 | isosorbide-type bicyclic diether linker | 4-OiPr-benzothiazole-2,6-diyl | cyclopropyl-Cl |

TABLE 2-continued

| compound | Ⓐ | Ⓑ | R⁷ |
|---|---|---|---|
| 210 | isosorbide-diyl | 4-OiPr-benzothiazole-2,6-diyl | 1-(fluoromethyl)cyclopropyl |
| 211 | isosorbide-diyl | 4-OiPr-benzothiazole-2,6-diyl | 1-(methoxymethyl)cyclopropyl |
| 212 | isosorbide-diyl | 4-OiPr-benzothiazole-2,6-diyl | 1-cyanocyclopropyl |
| 213 | isosorbide-diyl | 4-OiPr-benzothiazole-2,6-diyl | 1-carboxycyclopropyl |
| 214 | isosorbide-diyl | 4-OiPr-benzothiazole-2,6-diyl | 1-(methoxycarbonyl)cyclopropyl |
| 215 | isosorbide-diyl | 4-OiPr-benzothiazole-2,6-diyl | 1-(pyrrolidin-1-ylsulfonylaminocarbonyl)cyclopropyl |

TABLE 2-continued

| compound | Ⓐ | Ⓑ | R⁷ |
|---|---|---|---|
| 216 | isosorbide-like bicyclic diether | 4-OiPr-benzothiazole-2,6-diyl | 1-carbamoylcyclopropyl |
| 217 | isosorbide-like bicyclic diether | 4-OiPr-benzothiazole-2,6-diyl | 2,2-difluoro-1-methylcyclopropyl |
| 218 | isosorbide-like bicyclic diether | 4-OiPr-benzothiazole-2,6-diyl | 2,2-difluorocyclopropyl |
| 219 | isosorbide-like bicyclic diether | 4-OiPr-benzothiazole-2,6-diyl | azetidin-1-yl |
| 220 | isosorbide-like bicyclic diether | 4-OiPr-benzothiazole-2,6-diyl | pyrrolidin-1-yl |
| 221 | isosorbide-like bicyclic diether | 4-OiPr-benzothiazole-2,6-diyl | piperidin-1-yl |
| 222 | isosorbide-like bicyclic diether | 4-OiPr-benzothiazole-2,6-diyl | 4,4-difluoropiperidin-1-yl |

TABLE 2-continued
| compound | Ⓐ | Ⓑ | R⁷ |
|---|---|---|---|
| 223 | 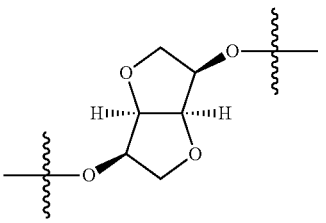 | 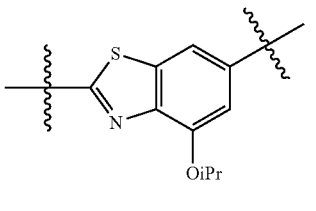 | 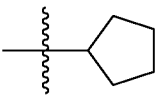 |
| 224 | 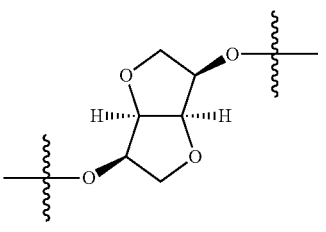 | 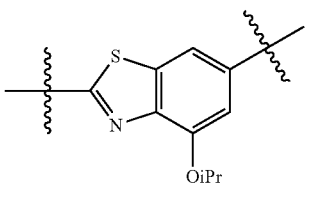 | 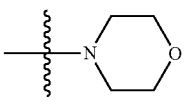 |
| 225 | 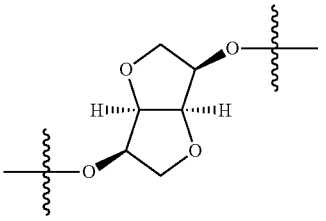 [SMILES: *O[C@@H]1CO[C@H]2[C@@H]1OC[C@H]2O*] | 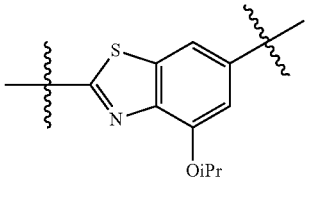 | 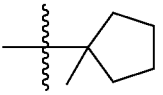 [SMILES: *C1(C)CCCC1] |
| 226 | 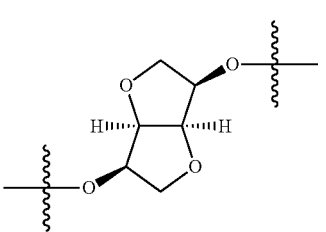 [SMILES: *O[C@@H]1CO[C@H]2[C@@H]1OC[C@H]2O*] | 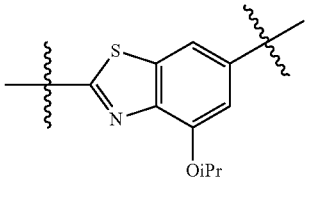 | 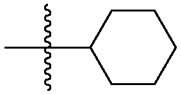 |
| 227 | 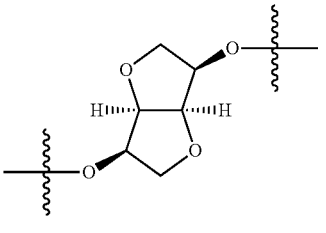 [SMILES: *O[C@@H]1CO[C@H]2[C@@H]1OC[C@H]2O*] | 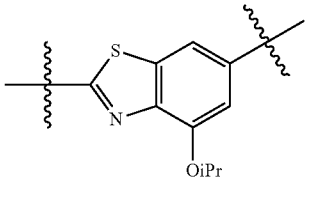 | 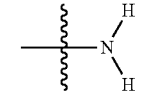 |
| 228 | 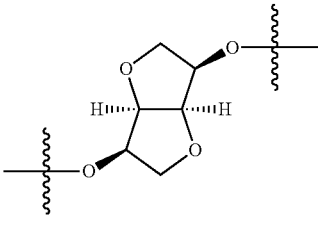 | 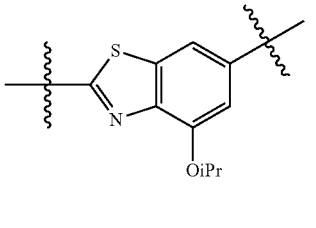 | 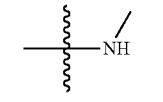 |

TABLE 2-continued

| compound | Ⓐ | Ⓑ | R⁷ |
| --- | --- | --- | --- |
| 229 | isosorbide-type bicyclic diether | 2-linked-7-OiPr-benzothiazol-6-yl | -N(CH₃)₂ |
| 230 | isosorbide-type bicyclic diether | 2-linked-7-OiPr-benzothiazol-6-yl | -NH-iPr |
| 231 | isosorbide-type bicyclic diether | 2-linked-7-OiPr-benzothiazol-6-yl | -NH-cyclopropyl |
| 232 | isosorbide-type bicyclic diether | 2-linked-7-OiPr-benzothiazol-6-yl | -NH-cyclobutyl |
| 233 | isosorbide-type bicyclic diether | 2-linked-7-OiPr-benzothiazol-6-yl | -NH-cyclopentyl |
| 234 | isosorbide-type bicyclic diether | 2-linked-7-OiPr-benzothiazol-6-yl | -NH-cyclohexyl |
| 235 | isosorbide-type bicyclic diether | 2-linked-7-OiPr-benzothiazol-6-yl | -NH-phenyl |

TABLE 2-continued

| compound | Ⓐ | Ⓑ | R⁷ |
|---|---|---|---|
| 236 | isosorbide-type bicyclic diether | 4-OiPr-benzothiazole-2,6-diyl | NH-C₆H₄-4-F |
| 237 | isosorbide-type bicyclic diether | 4-OiPr-benzothiazole-2,6-diyl | NH-C₆H₄-2-OCF₃ |
| 238 | isosorbide-type bicyclic diether | 4-OiPr-benzothiazole-2,6-diyl | NH-(pyridin-4-yl) |
| 239 | isosorbide-type bicyclic diether | 4-OiPr-benzothiazole-2,6-diyl | Me |
| 240 | isosorbide-type bicyclic diether | 4-OiPr-benzothiazole-2,6-diyl | CF₃ |
| 241 | isosorbide-type bicyclic diether | 4-OiPr-benzothiazole-2,6-diyl | iPr |

TABLE 2-continued
| compound | Ⓐ | Ⓑ | R⁷ |
|---|---|---|---|
| 242 | 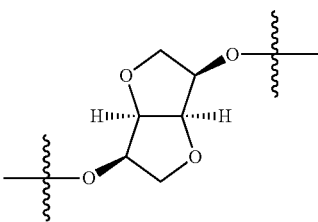 [SMILES: *O[C@@H]1CO[C@H]2[C@@H]1OC[C@H]2O*] | 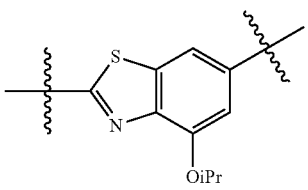 | 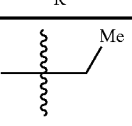 |
| 243 | 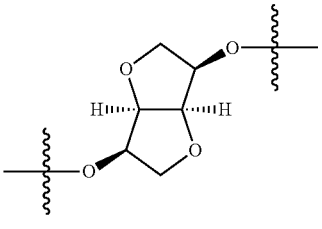 | 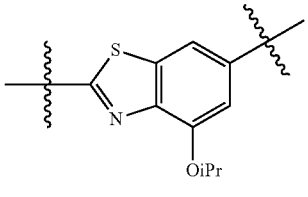 | 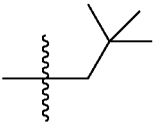 [SMILES: *CC(C)(C)C] |
| 244 | 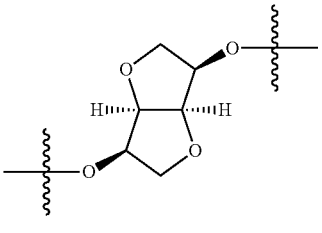 [SMILES: *O[C@@H]1CO[C@H]2[C@@H]1OC[C@H]2O*] | 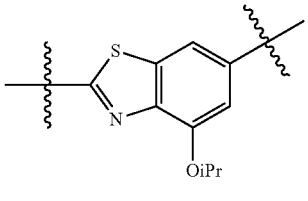 [SMILES: *c1cc(OC(C)C)c2nc(*)sc2c1] | 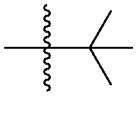 [SMILES: *C(C)(C)C] |
| 245 | 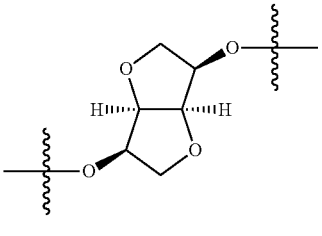 | 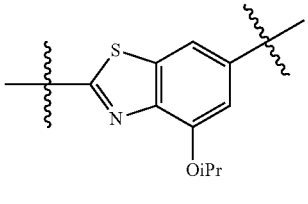 | 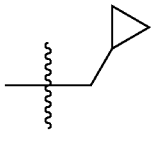 [SMILES: *CC1CC1] |
| 246 | 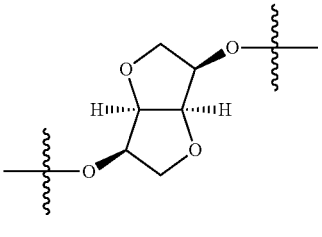 [SMILES: *O[C@@H]1CO[C@H]2[C@@H]1OC[C@H]2O*] | 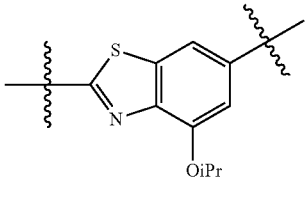 [SMILES: *c1cc(OC(C)C)c2nc(*)sc2c1] | 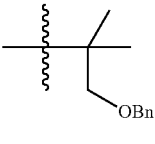 [SMILES: *C(C)(C)COCc1ccccc1] |
| 247 | 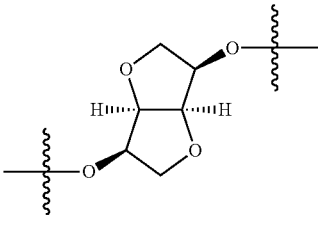 [SMILES: *O[C@@H]1CO[C@H]2[C@@H]1OC[C@H]2O*] | 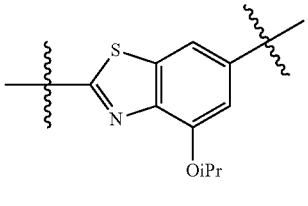 | 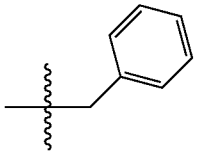 [SMILES: *Cc1ccccc1] |
| 248 | 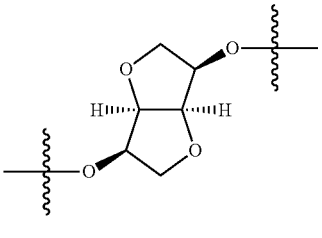 [SMILES: *O[C@@H]1CO[C@H]2[C@@H]1OC[C@H]2O*] | 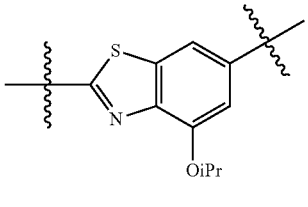 | 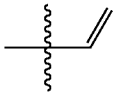 |

TABLE 2-continued

| compound | Ⓐ | Ⓑ | R⁷ |
|---|---|---|---|
| 249 | isosorbide-type bicyclic diether | 2-OiPr-benzothiazole-6-yl | -Bu |
| 250 | isosorbide-type bicyclic diether | 2-OiPr-benzothiazole-6-yl | -CH₂CH₂CH₃ (n-propyl) |
| 251 | isosorbide-type bicyclic diether | 2-OiPr-benzothiazole-6-yl | phenyl |
| 252 | isosorbide-type bicyclic diether | 2-OiPr-benzothiazole-6-yl | 4-fluorophenyl |
| 253 | isosorbide-type bicyclic diether | 2-OiPr-benzothiazole-6-yl | 2-pyridyl |
| 254 | isosorbide-type bicyclic diether | 2-OiPr-benzothiazole-6-yl | 4-tert-butylphenyl |

TABLE 2-continued

| compound | Ⓐ | Ⓑ | R⁷ |
|---|---|---|---|
| 255 | isosorbide-like bicyclic diether | benzothiazole with OiPr | 4-pyridyl |
| 256 | isosorbide-like bicyclic diether | benzothiazole with OiPr | 3-pyridyl |
| 257 | isosorbide-like bicyclic diether | benzothiazole with OiPr | 5-thiazolyl |
| 258 | isosorbide-like bicyclic diether | benzothiazole with OiPr | 5-fluoro-2-pyridyl |
| 259 | isosorbide-like bicyclic diether | benzothiazole with OiPr | 2-(1H-imidazolyl) |
| 260 | isosorbide-like bicyclic diether | benzothiazole with OiPr | 2-thiazolyl |
| 261 | isosorbide-like bicyclic diether | benzothiazole with OiPr | 2-(trifluoromethoxy)phenyl |

TABLE 2-continued

| compound | Ⓐ | Ⓑ | R⁷ |
|---|---|---|---|
| 262 | isosorbide-type bicyclic diether | benzothiazole with OiPr | N-methylimidazol-2-yl |
| 263 | isosorbide-type bicyclic diether | benzothiazole with OiPr | 2-naphthyl |
| 264 | isosorbide-type bicyclic diether | benzothiazole with OiPr | 2-methoxyphenyl |
| 265 | isosorbide-type bicyclic diether | benzothiazole with OiPr | biphenyl-4-yl |
| 266 | isosorbide-type bicyclic diether | benzothiazole with OiPr | 2,4'-bipyridyl |
| 267 | isosorbide-type bicyclic diether | benzothiazole with OiPr | 4-(pyridin-4-yl)phenyl |

TABLE 2-continued

| compound | Ⓐ | Ⓑ | R[7] |
|---|---|---|---|
| 268 | isosorbide-type bicyclic diether (O-linked both ends) | 2-yl-6-yl-4-OiPr-benzothiazole | 2,3-dihydro-1,4-benzodioxin-6-yl |
| 269 | isosorbide-type bicyclic diether (O-linked both ends) | 2-yl-6-yl-4-OiPr-benzothiazole | 1,3-benzodioxol-5-yl |
| 270 | isosorbide-type bicyclic diether (O-linked both ends) | 2-yl-6-yl-4-OiPr-benzothiazole | 2,3-dihydro-1H-inden-5-yl |
| 271 | isosorbide-type bicyclic diether (O-linked both ends) | 2-yl-6-yl-4-F-benzothiazole | cyclopropyl |
| 272 | isosorbide-type bicyclic diether (O-linked both ends) | 2-yl-6-yl-4-F-benzothiazole | 1-methylcyclopropyl |
| 273 | isosorbide-type bicyclic diether (O-linked both ends) | 2-yl-6-yl-benzothiazole | cyclopropyl |
| 274 | isosorbide-type bicyclic diether (O-linked both ends) | 2-yl-6-yl-benzothiazole | 1-methylcyclopropyl |

TABLE 2-continued
| compound | Ⓐ | Ⓑ | R⁷ |
|---|---|---|---|
| 275 | 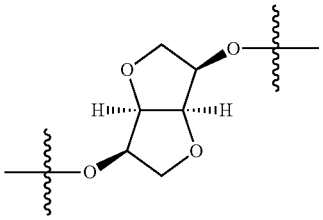 [SMILES: *O[C@@H]1CO[C@H]2[C@@H]1OC[C@H]2O*] | 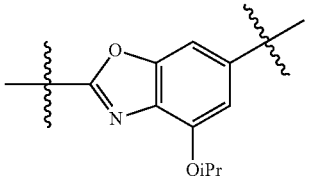 [SMILES: *c1cc(OC(C)C)c2nc(*)oc2c1] | 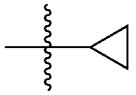 [SMILES: *C1CC1] |
| 276 | 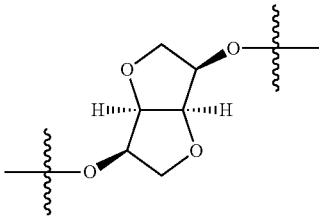 [SMILES: *O[C@@H]1CO[C@H]2[C@@H]1OC[C@H]2O*] | 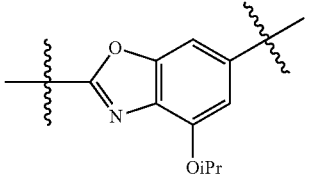 | 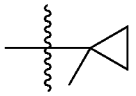 [SMILES: *C1(C)CC1] |
| 277 | 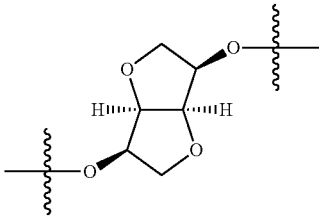 [SMILES: *O[C@@H]1CO[C@H]2[C@@H]1OC[C@H]2O*] | 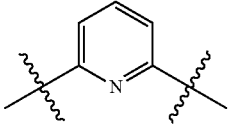 [SMILES: *c1cccc(*)n1] | 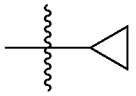 [SMILES: *C1CC1] |
| 278 | 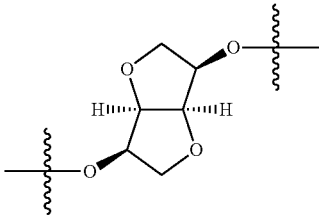 [SMILES: *O[C@@H]1CO[C@H]2[C@@H]1OC[C@H]2O*] | 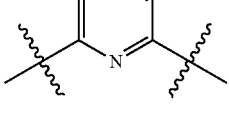 | 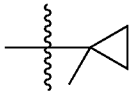 |
| 279 | 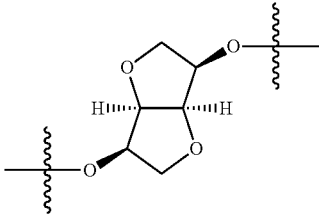 [SMILES: *O[C@@H]1CO[C@H]2[C@@H]1OC[C@H]2O*] | 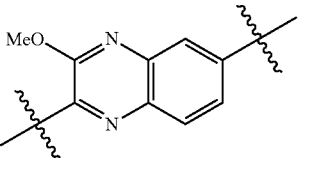 [SMILES: *c1ccc2nc(*)c(OC)nc2c1] | 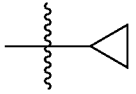 [SMILES: *C1CC1] |
| 280 | 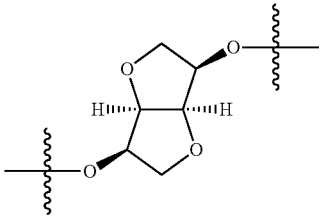 [SMILES: *O[C@@H]1CO[C@H]2[C@@H]1OC[C@H]2O*] | 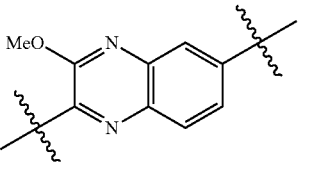 [SMILES: *c1ccc2nc(*)c(OC)nc2c1] | 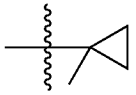 [SMILES: *C1(C)CC1] |

TABLE 2-continued
| compound | Ⓐ | Ⓑ | R⁷ |
|---|---|---|---|
| 281 | 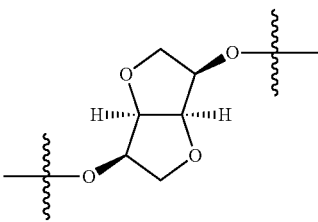 [SMILES: *O[C@@H]1CO[C@H]2[C@@H]1OC[C@H]2O*] | 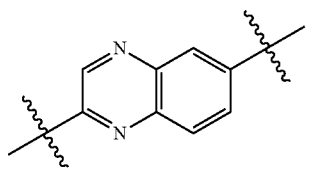 [SMILES: *c1ccc2nc(*)cnc2c1] | 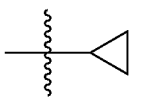 [SMILES: *C1CC1] |
| 282 | 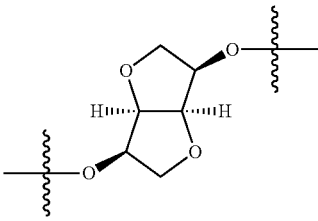 [SMILES: *O[C@@H]1CO[C@H]2[C@@H]1OC[C@H]2O*] | 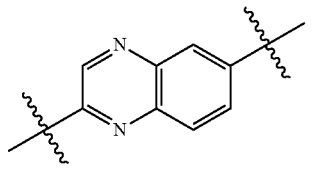 [SMILES: *c1ccc2nc(*)cnc2c1] | 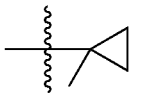 [SMILES: *C1(C)CC1] |
| 283 | 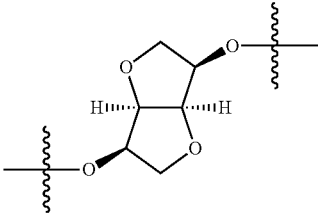 [SMILES: *O[C@@H]1CO[C@H]2[C@@H]1OC[C@H]2O*] | 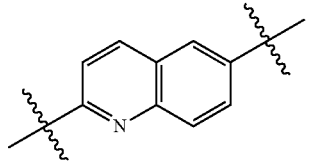 [SMILES: *c1ccc2nc(*)ccc2c1] | 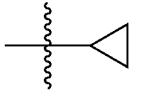 [SMILES: *C1CC1] |
| 284 | 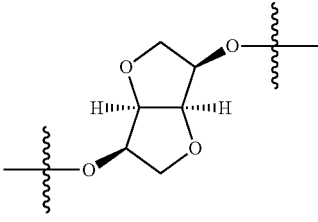 [SMILES: *O[C@@H]1CO[C@H]2[C@@H]1OC[C@H]2O*] | 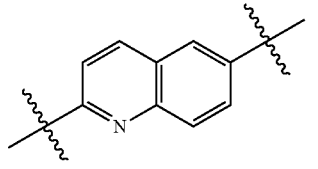 [SMILES: *c1ccc2nc(*)ccc2c1] | 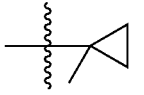 |
| 285 | 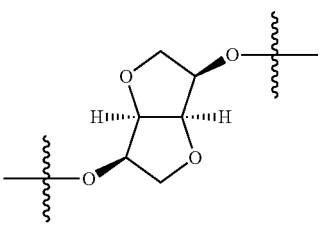 [SMILES: *O[C@@H]1CO[C@H]2[C@@H]1OC[C@H]2O*] | 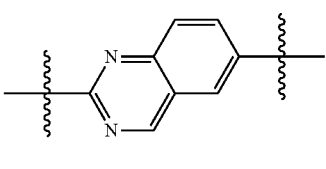 [SMILES: *c1ccc2nc(*)ncc2c1] | 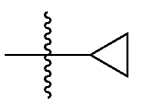 [SMILES: *C1CC1] |
| 286 | 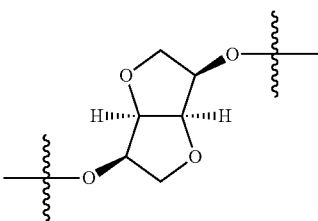 [SMILES: *O[C@@H]1CO[C@H]2[C@@H]1OC[C@H]2O*] | 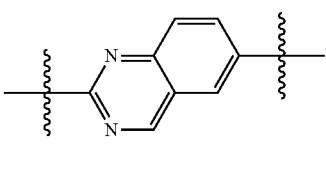 | 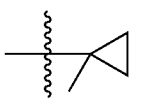 [SMILES: *C1(C)CC1] |
| 287 | 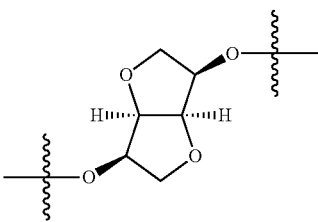 | 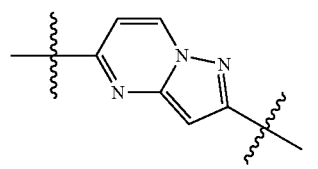 [SMILES: *c1ccn2nc(*)cc2n1] | 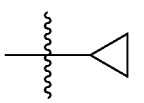 [SMILES: *C1CC1] |

TABLE 2-continued
| compound | Ⓐ | Ⓑ | R⁷ |
|---|---|---|---|
| 288 | 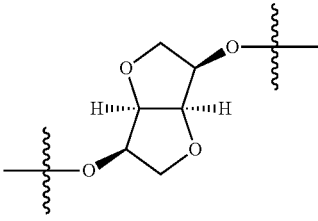 | 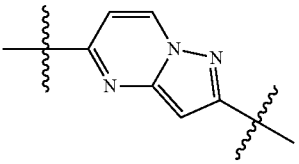 | 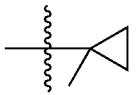 |
| 289 | 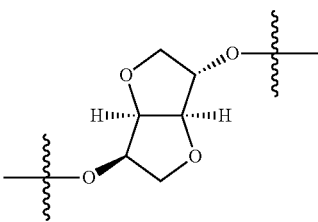 [SMILES: *O[C@H]1CO[C@H]2[C@@H]1OC[C@H]2O*] | 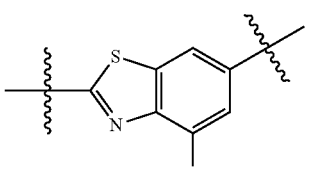 | 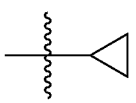 |
| 290 | 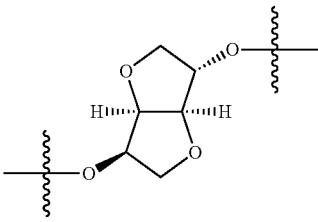 [SMILES: *O[C@H]1CO[C@H]2[C@@H]1OC[C@H]2O*] | 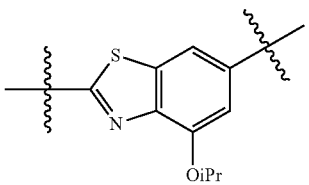 [SMILES: *c1cc(OC(C)C)c2nc(*)sc2c1] | 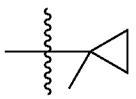 [SMILES: *C1(C)CC1] |
| 291 | 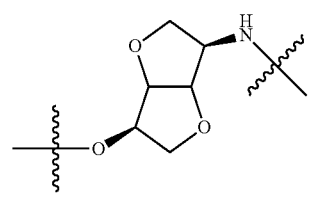 [SMILES: *N[C@@H]1COC2C1OC[C@H]2O*] | 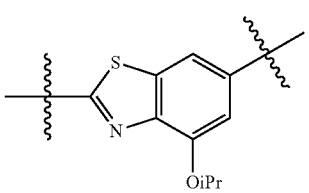 | 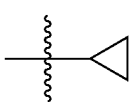 [SMILES: *C1CC1] |
| 292 | 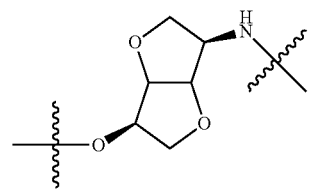 [SMILES: *N[C@@H]1COC2C1OC[C@H]2O*] | 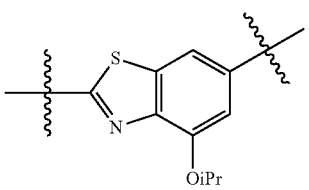 | 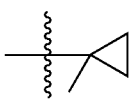 [SMILES: *C1(C)CC1] |
| 293 | 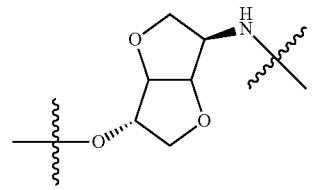 [SMILES: *N[C@@H]1COC2C1OC[C@@H]2O*] | 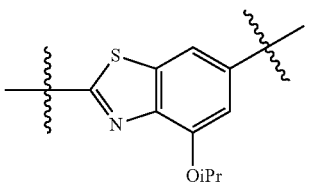 | 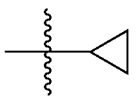 [SMILES: *C1CC1] |
| 294 | 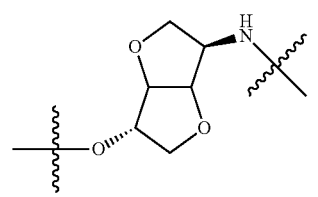 [SMILES: *N[C@@H]1COC2C1OC[C@@H]2O*] | 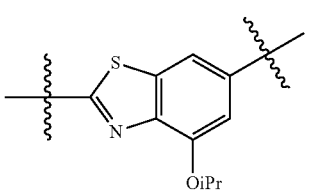 [SMILES: *c1cc(OC(C)C)c2nc(*)sc2c1] | 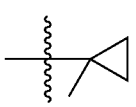 [SMILES: *C1(C)CC1] |

TABLE 2-continued

| compound | (A) | (B) | R⁷ |
|---|---|---|---|
| 295 | [isohexide diamine] | [2-linked-7-OiPr-benzothiazol-6-yl] | cyclopropyl |
| 296 | [isohexide diamine] | [2-linked-7-OiPr-benzothiazol-6-yl] | 1-methylcyclopropyl |
| 297 | [F-substituted isohexide amine] | [2-linked-7-OiPr-benzothiazol-6-yl] | cyclopropyl |
| 298 | [F-substituted isohexide amine] | [2-linked-7-OiPr-benzothiazol-6-yl] | 1-methylcyclopropyl |
| 299 | [F-substituted isohexide ether] | [2-linked-7-OiPr-benzothiazol-6-yl] | cyclopropyl |
| 300 | [F-substituted isohexide ether] | [2-linked-7-OiPr-benzothiazol-6-yl] | 1-methylcyclopropyl |
| 301 | [OH-substituted isohexide ether] | [2-linked-7-OiPr-benzothiazol-6-yl] | cyclopropyl |

TABLE 2-continued

| compound | Ⓐ | Ⓑ | R⁷ |
|---|---|---|---|
| 302 | | | |
| 303 | | | |
| 304 | | | |
| 305 | | | |
| 306 | | | |
| 307 | | | |
| 308 | | | |

TABLE 2-continued

| compound | Ⓐ | Ⓑ | R⁷ |
|---|---|---|---|
| 309 | | | |
| 310 | | | |
| 311 | | | |
| 312 | | | |
| 313 | | | |
| 314 | | | |
| 315 | | | |

TABLE 2-continued

| compound | Ⓐ | Ⓑ | R⁷ |
|---|---|---|---|
| 316 | aminofluoro-octahydrocyclopenta[c]pyrrole | 2-yl-4-OiPr-benzothiazole-6-yl | 1-methylcyclopropyl |
| 317 | hydroxy-oxa-octahydropentalene | 2-yl-4-OiPr-benzothiazole-6-yl | cyclopropyl |
| 318 | fluoro-oxa-octahydropentalene | 2-yl-4-OiPr-benzothiazole-6-yl | 1-methylcyclopropyl |
| 319 | oxa-octahydrofuro[2,3-c]pyrrole with O-linker | 2-yl-4-OiPr-benzothiazole-6-yl | cyclopropyl |
| 320 | thia-octahydrothieno[2,3-c]pyrrole with O-linker | 2-yl-4-OiPr-benzothiazole-6-yl | 1-methylcyclopropyl |
| 321 | oxa-octahydrofuro[2,3-c]pyrrole with NH-linker | 2-yl-4-OiPr-benzothiazole-6-yl | cyclopropyl |
| 322 | thia-octahydrothieno[2,3-c]pyrrole with NH-linker | 2-yl-4-OiPr-benzothiazole-6-yl | 1-methylcyclopropyl |
| 323 | octahydropyrrolo[1,2-a]pyrazine with O-linker | 2-yl-4-OiPr-benzothiazole-6-yl | cyclopropyl |

TABLE 2-continued

| compound | Ⓐ | Ⓑ | R⁷ |
|---|---|---|---|
| 324 | pyrrolo-piperazine with NH substituent | 4-OiPr-benzothiazole | 1-methylcyclopropyl |
| 325 | (S)-O-pyrrolo-piperazine | 4-OiPr-benzothiazole | cyclopropyl |
| 326 | (R)-O-pyrrolo-piperazine | 4-OiPr-benzothiazole | 1-methylcyclopropyl |
| 327 | (S)-O-pyrrolo-piperazine | 4-OiPr-benzothiazole | cyclopropyl |
| 328 | (R)-O-pyrrolo-piperazine | 4-OiPr-benzothiazole | 1-methylcyclopropyl |
| 329 | HN-pyrrolo-piperazine | 4-OiPr-benzothiazole | cyclopropyl |
| 330 | spirocyclopropyl-O-pyrrolo-piperazine | 4-OiPr-benzothiazole | 1-methylcyclopropyl |
| 331 | O-pyrrolo-piperazinone | 4-OiPr-benzothiazole | cyclopropyl |

TABLE 2-continued

| compound | Ⓐ | Ⓑ | R⁷ |
| --- | --- | --- | --- |
| 332 | (hexahydrocyclopenta-oxazine with N-attachment, O-attachment at cyclopentane) | 2-(linker),6-(linker)-4-OiPr-benzothiazole | 1-methylcyclopropyl |
| 333 | (hexahydrocyclopenta-oxazine with N-attachment, O-attachment at cyclopentane) | 2-(linker),6-(linker)-4-OiPr-benzothiazole | cyclopropyl |
| 334 | (hexahydrocyclopenta-oxazine with N-attachment, NH-attachment at cyclopentane) | 2-(linker),6-(linker)-4-OiPr-benzothiazole | 1-methylcyclopropyl |
| 335 | (hexahydrocyclopenta-1,3-oxazine with N-attachment, O-attachment at cyclopentane) | 2-(linker),6-(linker)-4-OiPr-benzothiazole | cyclopropyl |
| 336 | (hexahydrocyclopenta-1,3-oxazine with N-attachment, O-attachment at cyclopentane) | 2-(linker),6-(linker)-4-OiPr-benzothiazole | 1-methylcyclopropyl |

In another embodiment, the compound of Formula (I) is represented by Formula (X) or a pharmaceutically acceptable salt thereof:

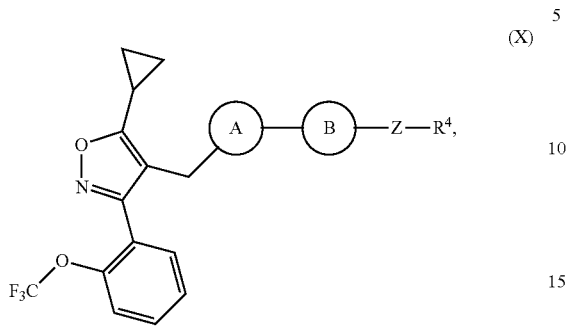

(X)

wherein Ⓐ, Ⓑ, Z, and $R^4$ are as previously defined.

Representative compounds of the invention include, but are not limited to, the following compounds in Table 3 according to Formula (X), and pharmaceutically acceptable salts thereof, wherein Ⓐ, Ⓑ, and Z—$R^4$ are delineated for each example in Table 3.

TABLE 3

| compound | Ⓐ | Ⓑ | —Z—$R^4$ |
|---|---|---|---|
| 401 | | | |
| 402 | | | |
| 403 | | | |
| 404 | | | |

TABLE 3-continued

| compound | Ⓐ | Ⓑ | —Z—R⁴ |
|---|---|---|---|
| 405 | isosorbide-like bicyclic diether | 4-F-benzothiazole (2,6-linked) | -C(CH₃)₂COOH |
| 406 | isosorbide-like bicyclic diether | 4-F-benzothiazole (2,6-linked) | -C(CH₃)₂COOH |
| 407 | isosorbide-like bicyclic diether | 4-F-benzothiazole (2,6-linked) | -C(CH₃)₂COOH |
| 408 | isosorbide-like bicyclic diether | 4-F-benzothiazole (2,6-linked) | -C(CH₃)₂COOH |
| 409 | isosorbide-like bicyclic diether | 4-OMe-benzothiazole (2,6-linked) | -C(CH₃)₂COOH |
| 410 | isosorbide-like bicyclic diether | 4-OMe-benzothiazole (2,6-linked) | -C(CH₃)₂COOH |

TABLE 3-continued

| compound | Ⓐ | Ⓑ | -Z-R⁴ |
|---|---|---|---|
| 411 | isosorbide-type bicyclic diether | 4-OMe-benzothiazol-2,6-diyl | 2-methyl-2-yl propanoic acid |
| 412 | isosorbide-type bicyclic diether | 4-OMe-benzothiazol-2,6-diyl | 2-methyl-2-yl propanoic acid |
| 413 | isosorbide-type bicyclic diether | benzothiazol-2,6-diyl | 2-methyl-2-yl propanoic acid |
| 414 | isosorbide-type bicyclic diether | benzothiazol-2,6-diyl | 2-methyl-2-yl propanoic acid |
| 415 | isosorbide-type bicyclic diether | benzothiazol-2,6-diyl | 2-methyl-2-yl propanoic acid |
| 416 | isosorbide-type bicyclic diether | benzothiazol-2,6-diyl | 2-methyl-2-yl propanoic acid |

TABLE 3-continued

| compound | Ⓐ | Ⓑ | -Z-R⁴ |
|---|---|---|---|
| 417 | isosorbide-type bicyclic diether | benzothiazole with OCHF₂ | 2-methylpropanoic acid |
| 418 | isosorbide-type bicyclic diether | benzothiazole with OCF₃ | 2-methylpropanoic acid |
| 419 | isosorbide-type bicyclic diether | benzothiazole with OCH₂F | 2-methylpropanoic acid |
| 420 | isosorbide-type bicyclic diether | benzothiazole with CF₃ | 2-methylpropanoic acid |
| 421 | isosorbide-type bicyclic diether | benzothiazole with CH₃ | 2-methylpropanoic acid |
| 422 | isosorbide-type bicyclic diether | benzothiazole with Br | 2-methylpropanoic acid |

TABLE 3-continued

| compound | Ⓐ | Ⓑ | ⸏—Z—R⁴ |
|---|---|---|---|
| 423 | isosorbide-like bicyclic diether | benzothiazole with Cl | 2-methylpropanoic acid |
| 424 | isosorbide-like bicyclic diether | benzothiazole with cyclopropyl | 2-methylpropanoic acid |
| 425 | isosorbide-like bicyclic diether | benzothiazole with Me | 2-methylpropanoic acid |
| 426 | isosorbide-like bicyclic diether | benzothiazole with Me | 2-methylpropanoic acid |
| 427 | isosorbide-like bicyclic diether | benzoxazole | 2-methylpropanoic acid |
| 428 | isosorbide-like bicyclic diether | benzoxazole with F | 2-methylpropanoic acid |

TABLE 3-continued

| compound | Ⓐ | Ⓑ | —Z—R⁴ |
|---|---|---|---|
| 429 | isosorbide linker | 2-yl-4-methoxy-benzoxazol-6-yl | 2-methylpropanoic acid |
| 430 | isosorbide linker | 2-yl-4-isopropoxy-benzoxazol-6-yl | 2-methylpropanoic acid |
| 431 | isosorbide linker | 5-fluoroquinolin-2,6-diyl | 2-methylpropanoic acid |
| 432 | isosorbide linker | 7-fluoroquinolin-2,6-diyl | 2-methylpropanoic acid |
| 433 | isosorbide linker | quinolin-2,6-diyl | 2-methylpropanoic acid |
| 434 | isosorbide linker | quinolin-3,7-diyl | 2-methylpropanoic acid |

TABLE 3-continued

| compound | Ⓐ | Ⓑ | —Z—R⁴ |
|---|---|---|---|
| 435 | isosorbide-like bicyclic diether | 3-fluoroquinoline (2,6-linked) | -C(CH₃)₂-COOH |
| 436 | isosorbide-like bicyclic diether | 3-methoxyquinoline (2,6-linked) | -C(CH₃)₂-COOH |
| 437 | isosorbide-like bicyclic diether | quinoxaline (2,6-linked) | -C(CH₃)₂-COOH |
| 438 | isosorbide-like bicyclic diether | 2-methoxyquinoxaline (3,6-linked) | -C(CH₃)₂-COOH |
| 439 | isosorbide-like bicyclic diether | 2-chloroquinoxaline (3,6-linked) | -C(CH₃)₂-COOH |
| 440 | isosorbide-like bicyclic diether | 5-isopropoxyquinoxaline (2,6-linked) | -C(CH₃)₂-COOH |

TABLE 3-continued

| compound | Ⓐ | Ⓑ | 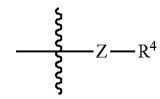 |
|---|---|---|---|
| 441 | isosorbide diyl | naphthalene-2,6-diyl | 2-methylpropanoic acid |
| 442 | isosorbide diyl | 5-fluoronaphthalene-2,7-diyl | 2-methylpropanoic acid |
| 443 | isosorbide diyl | 3-fluoronaphthalene-2,6-diyl | 2-methylpropanoic acid |
| 444 | isosorbide diyl | 5-methoxynaphthalene-2,7-diyl | 2-methylpropanoic acid |
| 445 | isosorbide diyl | naphthalene-2,6-diyl | 2-methylpropanoic acid |
| 446 | isosorbide diyl | 4-methoxynaphthalene-2,6-diyl | 2-methylpropanoic acid |

TABLE 3-continued

| compound | Ⓐ | Ⓑ | -Z-R⁴ |
|---|---|---|---|
| 447 | isosorbide | naphthalene-2,6-diyl | C(CH₃)₂COOH |
| 448 | isosorbide | quinoline-2,5-diyl | C(CH₃)₂COOH |
| 449 | isosorbide | quinoline-2,5-diyl | C(CH₃)₂COOH |
| 450 | isosorbide | 8-fluoroquinoline-2,6-diyl | C(CH₃)₂COOH |
| 451 | isosorbide | quinoxaline-2,6-diyl | C(CH₃)₂COOH |
| 452 | isosorbide | quinazoline-2,6-diyl | C(CH₃)₂COOH |

TABLE 3-continued

| compound | Ⓐ | Ⓑ | ⸺Z—R⁴ |
|---|---|---|---|
| 453 | isosorbide linker | quinazoline | 2-methylpropanoic acid |
| 454 | isosorbide linker | methylbenzofuran | 2-methylpropanoic acid |
| 455 | isosorbide linker | pyrazolo[1,5-a]pyrimidine | 2-methylpropanoic acid |
| 456 | isosorbide linker | imidazo[1,2-a]pyridine | 2-methylpropanoic acid |
| 457 | isosorbide linker | fluoro-benzisothiazole | 2-methylpropanoic acid |
| 458 | isosorbide linker | benzisothiazole | 2-methylpropanoic acid |

TABLE 3-continued

| compound | Ⓐ | Ⓑ | —⸺Z—R⁴ |
|---|---|---|---|
| 459 | isosorbide-type bicyclic diether | pyrazine-2,5-diyl | —C(CH₃)(H)—COOH |
| 460 | isosorbide-type bicyclic diether | 3-fluoropyrazine-2,5-diyl | —C(CH₃)(H)—COOH |
| 461 | isosorbide-type bicyclic diether | 2-fluoro-1,4-phenylene | —C(CH₃)(H)—COOH |
| 462 | isosorbide-type bicyclic diether | 2-fluoro-1,4-phenylene | —C(CH₃)(H)—COOH |
| 463 | isosorbide-type bicyclic diether | pyrazine-2,5-diyl | —C(CH₃)(H)—COOH |
| 464 | isosorbide-type bicyclic diether | pyridine-2,6-diyl | —C(CH₃)(H)—COOH |

TABLE 3-continued

| compound | Ⓐ | Ⓑ | —Z—R⁴ |
|---|---|---|---|
| 465 | isosorbide diether | 4-methylpyrimidine-2,6-diyl | C(CH₃)COOH |
| 466 | isosorbide diether | 4-fluoropyridine-2,5-diyl | C(CH₃)COOH |
| 467 | isosorbide diether | pyridine-2,5-diyl | C(CH₃)COOH |
| 468 | isosorbide diether | thiazole-2,5-diyl | C(CH₃)COOH |
| 469 | isosorbide diether | thiazole-2,4-diyl | C(CH₃)COOH |
| 470 | isosorbide diether | pyridine-2,6-diyl | C(CH₃)COOH |

TABLE 3-continued

| compound | Ⓐ | Ⓑ | —⌇Z—R⁴ |
|---|---|---|---|
| 471 | [isosorbide-type bicyclic diether] | [4-methylpyridine-2,5-diyl] | [−C(CH₃)₂−COOH] |
| 472 | [isosorbide-type bicyclic diether] | [3-fluoropyridine-2,5-diyl] | [−C(CH₃)₂−COOH] |
| 473 | [isosorbide-type bicyclic diether] | [3-methylpyridine-2,5-diyl] | [−C(CH₃)₂−COOH] |
| 474 | [isosorbide-type bicyclic diether] | [3-trifluoromethylpyridine-2,5-diyl] | [−C(CH₃)₂−COOH] |
| 475 | [isosorbide-type bicyclic diether] | [3-cyclopropylpyridine-2,5-diyl] | [−C(CH₃)₂−COOH] |
| 476 | [isosorbide-type bicyclic diether] | [2,6-difluorophenylene-1,4-diyl] | [−C(CH₃)₂−COOH] |

TABLE 3-continued

| compound | Ⓐ | Ⓑ | ⧸⧸⧸—Z—R⁴ |
|---|---|---|---|
| 477 | isosorbide-type bicyclic diether | 1,2,4-oxadiazole | C(CH₃)₂COOH |
| 478 | isosorbide-type bicyclic diether | 1,2,4-oxadiazole | 3-carboxyphenyl |
| 479 | isosorbide-type bicyclic diether | 1,2,4-oxadiazole | 6-carboxypyridin-2-yl |
| 480 | isosorbide-type bicyclic diether | 1,2,4-oxadiazole | 4-fluoro-3-carboxyphenyl |
| 481 | isosorbide-type bicyclic diether | 1,2,4-oxadiazole | 4-carboxyphenyl |
| 482 | isosorbide-type bicyclic diether | 1,2,4-oxadiazole | 3-carboxycyclohexyl |

TABLE 3-continued

| compound | (A) | (B) | —Z—R⁴ |
|---|---|---|---|
| 483 | isosorbide | 4-OiPr-benzothiazole-2,6-diyl | —CN |
| 484 | isosorbide | 4-OiPr-benzothiazole-2,6-diyl | 1H-tetrazol-5-yl |
| 485 | isosorbide | pyrazine-2,5-diyl | —CN |
| 486 | isosorbide | pyrazine-2,5-diyl | 1H-tetrazol-5-yl |
| 487 | isosorbide | 2-fluoro-1,4-phenylene | —CN |
| 488 | isosorbide | 2-fluoro-1,4-phenylene | 1H-tetrazol-5-yl |

TABLE 3-continued

| compound | Ⓐ | Ⓑ | —Z—R⁴ |
|---|---|---|---|
| 489 | | | CN |
| 490 | | | tetrazole |
| 491 | | | |
| 492 | | | |
| 493 | | | |
| 494 | | | |

TABLE 3-continued

| compound | Ⓐ | Ⓑ | —ξ—Z—R⁴ |
|---|---|---|---|
| 495 | isosorbide-like bicyclic diether | benzothiazole-2,6-diyl | tert-butyl (4-tert-butoxyphenylsulfonyl)carbamate |
| 496 | isosorbide-like bicyclic diether (stereoisomer) | benzothiazole-2,6-diyl | tert-butyl (4-tert-butoxyphenylsulfonyl)carbamate |
| 497 | isosorbide-like bicyclic diether | 7-OiPr-benzothiazole-2,6-diyl | tert-butyl (4-tert-butoxyphenylsulfonyl)carbamate |
| 498 | isosorbide-like bicyclic diether | 7-OiPr-benzothiazole-2,6-diyl | tert-butyl (4-tert-butoxyphenylsulfonyl)carbamate |
| 499 | isosorbide-like bicyclic diether | benzothiazole-2,6-diyl | tert-butyl (6-piperidin-1-ylpyridin-3-ylsulfonyl)carbamate |
| 500 | isosorbide-like bicyclic diether | 7-F-benzothiazole-2,6-diyl | tert-butyl (6-piperidin-1-ylpyridin-3-ylsulfonyl)carbamate |

TABLE 3-continued

| compound | Ⓐ | Ⓑ | —⸾⸾⸾Z—R⁴ |
|---|---|---|---|
| 501 | isosorbide-like bicyclic diether | benzothiazole with OiPr | tBu-O-C(O)-NH-S(O)₂-pyridyl-piperidine |
| 502 | isosorbide-like bicyclic diether | benzothiazole with cyclopropyl | tBu-O-C(O)-NH-S(O)₂-pyridyl-piperidine |
| 503 | isosorbide-like bicyclic diether | benzothiazole | tBu-O-C(O)-NH-S(O)₂-C₆H₄-OtBu |
| 504 | isosorbide-like bicyclic diether | benzothiazole with F | tBu-O-C(O)-NH-S(O)₂-C₆H₄-OtBu |
| 505 | isosorbide-like bicyclic diether | benzothiazole with OiPr | tBu-O-C(O)-NH-S(O)₂-C₆H₄-OtBu |
| 506 | isosorbide-like bicyclic diether | benzothiazole with cyclopropyl | tBu-O-C(O)-NH-S(O)₂-C₆H₄-OtBu |

TABLE 3-continued

| compound | Ⓐ | Ⓑ | ↯—Z—R⁴ |
|---|---|---|---|
| 507 | | | |
| 508 | | | |
| 509 | | | |
| 510 | | | |
| 511 | | | |
| 512 | | | |

TABLE 3-continued

| compound | Ⓐ | Ⓑ | ⸻Z—R⁴ |
|---|---|---|---|
| 513 | | | |
| 514 | | | |
| 515 | | | CO₂Me |
| 516 | | | CO₂t-Bu |
| 517 | | | CO₂Me |
| 518 | | | CO₂H |

TABLE 3-continued

| compound | Ⓐ | Ⓑ | —Z—R⁴ |
|---|---|---|---|
| 519 | isosorbide-diyl | 7-OiPr-benzothiazole-2,6-diyl | —C(Me)₂CH₂C(O)OMe |
| 520 | isosorbide-diyl | 7-OiPr-benzothiazole-2,6-diyl | —C(Me)₂CH₂C(O)OH |
| 521 | isosorbide-diyl | 7-OiPr-benzothiazole-2,6-diyl | —C(Me)₂CH₂OCH₂C(O)OMe |
| 522 | isosorbide-diyl | 7-OiPr-benzothiazole-2,6-diyl | —C(Me)₂CH₂OCH₂C(O)OH |
| 523 | isosorbide-diyl | 7-OiPr-benzothiazole-2,6-diyl | —C(Me)₂CH₂NHCH₂C(O)OMe |
| 524 | isosorbide-diyl | 7-OiPr-benzothiazole-2,6-diyl | —C(Me)₂CH₂NHCH₂C(O)OH |

TABLE 3-continued

| compound | Ⓐ | Ⓑ | —Z—R⁴ |
|---|---|---|---|
| 525 | isosorbide-type bicyclic diether | benzothiazole, OiPr | —CH₂—N(Me)—CH₂—C(O)OMe |
| 526 | isosorbide-type bicyclic diether | benzothiazole, OiPr | —CH₂—N(Me)—CH₂—C(O)OH |
| 527 | isosorbide-type bicyclic diether | benzothiazole, OiPr | —CH₂OH |
| 528 | isosorbide-type bicyclic diether | benzothiazole, OiPr | —CH₂CH₂OH |
| 529 | isosorbide-type bicyclic diether | benzothiazole, OiPr | cyclopropyl-CO₂Me |
| 530 | isosorbide-type bicyclic diether | benzothiazole, OiPr | cyclopropyl-CO₂H |

TABLE 3-continued

| compound | Ⓐ | Ⓑ | ⟋⟋⟋Z—R⁴ |
|---|---|---|---|
| 531 | isosorbide-type bicyclic diether | 4-OiPr-benzothiazole-2,6-diyl | methyl 1-(cyclopropyl)acetate |
| 532 | isosorbide-type bicyclic diether | 4-OiPr-benzothiazole-2,6-diyl | 1-(cyclopropyl)acetic acid |
| 533 | isosorbide-type bicyclic diether | 4-OiPr-benzothiazole-2,6-diyl | C(CF₂)CO₂Me |
| 534 | isosorbide-type bicyclic diether | 4-OiPr-benzothiazole-2,6-diyl | C(CF₂)CO₂H |
| 535 | isosorbide-type bicyclic diether | 4-OiPr-benzothiazole-2,6-diyl | CN |
| 536 | isosorbide-type bicyclic diether | 4-OiPr-benzothiazole-2,6-diyl | 1H-tetrazol-5-yl |

TABLE 3-continued

| compound | Ⓐ | Ⓑ | —Z—R⁴ |
|---|---|---|---|
| 537 | isosorbide linker | 7-OiPr-benzothiazole-2,6-diyl | C(=O)NH-CH₂-C(=O)O-tBu |
| 538 | isosorbide linker | 7-OiPr-benzothiazole-2,6-diyl | C(=O)NH-CH₂-COOH |
| 539 | isosorbide linker | 7-OiPr-benzothiazole-2,6-diyl | C(=O)NH-C(CH₃)₂-COOH |
| 540 | isosorbide linker | 7-OiPr-benzothiazole-2,6-diyl | C(=O)NH-CH(CH₃)-COOH |
| 541 | isosorbide linker | 7-OiPr-benzothiazole-2,6-diyl | C(=O)NH-CH₂CH₂-SO₃Me |
| 542 | isosorbide linker | 7-OiPr-benzothiazole-2,6-diyl | C(=O)NH-CH₂CH₂-SO₃H |

TABLE 3-continued

| compound | Ⓐ | Ⓑ | ⸺Z—R⁴ |
|---|---|---|---|
| 543 | isosorbide linker | 2-yl-7-OiPr-benzothiazol-6-yl | -C(O)NH-C(cyclopropyl)(CH₂SO₃H)- |
| 544 | isosorbide linker | 2-yl-7-OiPr-benzothiazol-6-yl | -C(O)NH-C(CH₃)₂-CH₂SO₃H |
| 545 | isosorbide linker | 2-yl-7-OiPr-benzothiazol-6-yl | -C(O)NH-CH₂-O-CH₂-OSO₃H |
| 546 | isosorbide linker | 2-yl-7-OiPr-benzothiazol-6-yl | -C(O)NH-CH₂-NH-CH₂-OSO₃H |
| 547 | isosorbide linker | 2-yl-benzothiazol-6-yl | glucuronate ester |
| 548 | isosorbide linker | 2-yl-7-OMe-benzothiazol-6-yl | glucuronate ester |

TABLE 3-continued
| compound | Ⓐ | Ⓑ | ⌇—Z—R⁴ |
|---|---|---|---|
| 549 | 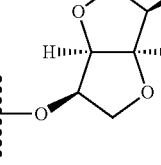 | 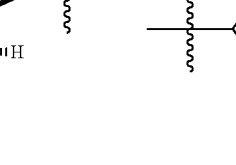 | 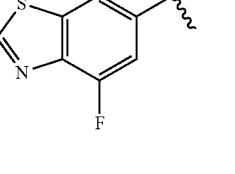 |
| 550 | 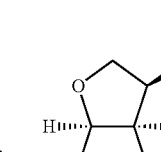 | 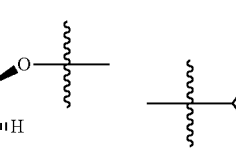 | 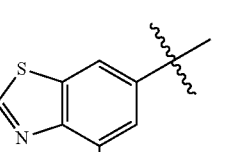 |
| 551 | 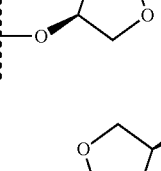 | 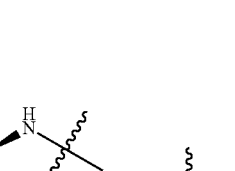 | 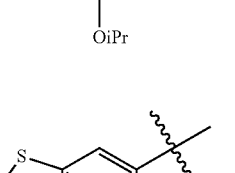 |
| 552 | 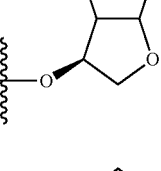 | 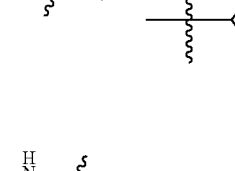 | 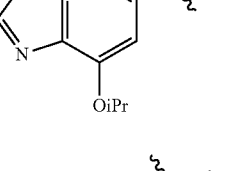 |
| 553 | 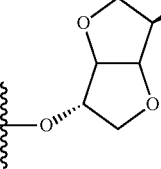 | 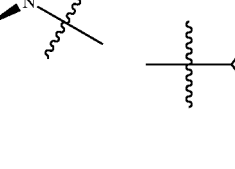 | 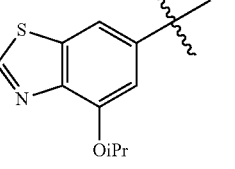 |
| 554 | 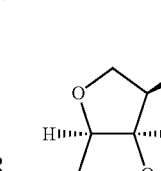 | 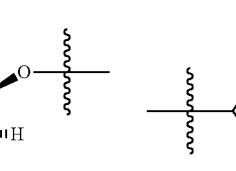 | 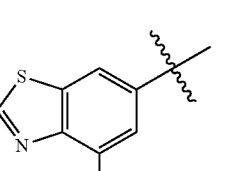 |
| 555 | 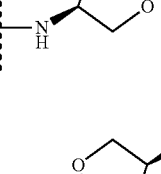 | 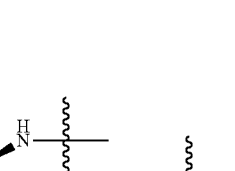 | 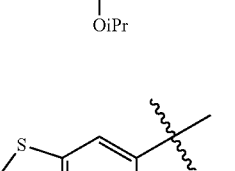 |

TABLE 3-continued

| compound | Ⓐ | Ⓑ | ⋮⋮—Z—R⁴ |
|---|---|---|---|
| 556 | [2,6-dioxabicyclo[3.3.0] with F and NH, stereochemistry H,H] | 2-yl-6-yl-benzothiazole, 7-OiPr | –C(CH₃)–COOH |
| 557 | [2,6-dioxabicyclo[3.3.0] with OH and O-linker] | 2-yl-6-yl-benzothiazole, 7-OiPr | –C(CH₃)–COOH |
| 558 | [2,6-dioxabicyclo[3.3.0] with F and NH, stereochemistry H,H] | 2-yl-6-yl-benzothiazole, 7-OiPr | –C(CH₃)–COOH |
| 559 | [2,6-dioxabicyclo[3.3.0] with SO₂ and O-linker] | 2-yl-6-yl-benzothiazole, 7-OiPr | –C(CH₃)–COOH |
| 560 | [2,6-dioxabicyclo[3.3.0] with S and O-linker] | 2-yl-6-yl-benzothiazole, 7-OiPr | –C(CH₃)–COOH |
| 561 | [2,6-dioxabicyclo[3.3.0] with S(O) and O-linker] | 2-yl-6-yl-benzothiazole, 7-OiPr | –C(CH₃)–COOH |
| 562 | [2,6-dioxabicyclo[3.3.0] with F, SO₂ and O-linker] | 2-yl-6-yl-benzothiazole, 7-OiPr | –C(CH₃)–COOH |

TABLE 3-continued

| compound | Ⓐ | Ⓑ | ⸻Z—R⁴ |
|---|---|---|---|
| 563 | tetrahydrofuro[3,2-b]furan with S-linker and O-linker | benzothiazole with OiPr | 2-methylpropanoic acid |
| 564 | tetrahydrofuro[3,2-b]furan with sulfonyl linker and NH-linker | benzothiazole with OiPr | 2-methylpropanoic acid |
| 565 | hexahydrocyclopenta[d]oxazole with N-linker and O-linker | benzothiazole with OiPr | 2-methylpropanoic acid |
| 566 | hexahydrocyclopenta[d]oxazole with N-linker and NH-linker | benzothiazole with OiPr | 2-methylpropanoic acid |
| 567 | hexahydrocyclopenta[d]oxazole with N-linker and O-linker | benzothiazole with OiPr | 2-methylpropanoic acid |
| 568 | hexahydrocyclopenta[d]oxazol-2(3H)-one with N-linker and O-linker | benzothiazole with OiPr | 2-methylpropanoic acid |

TABLE 3-continued

| compound | Ⓐ | Ⓑ | —Z—R⁴ |
|---|---|---|---|
| 569 | bicyclic diamine (octahydropentalene-2,5-diyl bis-NH) | benzothiazole with OiPr | C(CH₃)₂COOH |
| 570 | octahydropentalene with O and NH substituents | benzothiazole with OiPr | C(CH₃)₂COOH |
| 571 | octahydrocyclopenta[c]pyrrole with NH | benzothiazole with OiPr | C(CH₃)₂COOH |
| 572 | octahydrocyclopenta[c]pyrrole with NH and F | benzothiazole with OiPr | C(CH₃)₂COOH |
| 573 | octahydropentalene with O and OH | benzothiazole with OiPr | C(CH₃)₂COOH |
| 574 | octahydropentalene with O and F | benzothiazole with OiPr | C(CH₃)₂COOH |
| 575 | hexahydrofuro[3,2-c]pyrrole with O-linker | benzothiazole with OiPr | C(CH₃)₂COOH |

TABLE 3-continued

| compound | Ⓐ | Ⓑ | —Z—R⁴ |
|---|---|---|---|
| 576 | thiophene-fused pyrrolidine with O substituent | benzothiazole with OiPr | C(CH₃)₂COOH |
| 577 | furan-fused pyrrolidine with NH substituent | benzothiazole with OiPr | C(CH₃)₂COOH |
| 578 | thiophene-fused pyrrolidine with NH substituent | benzothiazole with OiPr | C(CH₃)₂COOH |
| 579 | pyrrolopiperazine with O substituent | benzothiazole with OiPr | C(CH₃)₂COOH |
| 580 | pyrrolopiperazine with NH substituent | benzothiazole with OiPr | C(CH₃)₂COOH |
| 581 | hexahydropyrrolo[1,2-a]pyrazine with O (stereo) | benzothiazole with OiPr | C(CH₃)₂COOH |
| 582 | hexahydropyrrolo[1,2-a]pyrazine with O (stereo) | benzothiazole with OiPr | C(CH₃)₂COOH |

TABLE 3-continued

TABLE 3-continued

| compound | Ⓐ | Ⓑ | ─Z─R⁴ |
|---|---|---|---|
| 590 | cyclopenta-fused morpholine with HN- and -N attachments | 2-linked-6-yl benzothiazole, 7-OiPr | -C(CH₃)₂-C(O)OH |
| 591 | cyclopenta-fused 1,3-oxazinane with HN- and -N attachments | 2-linked-6-yl benzothiazole, 7-OiPr | -C(CH₃)₂-C(O)OH |
| 592 | cyclopenta-fused 1,3-oxazinane with -O- and -N attachments | 2-linked-6-yl benzothiazole, 7-OiPr | -C(CH₃)₂-C(O)OH |

In another embodiment, the compound of Formula (I) is represented by Formula (XI) or a pharmaceutically acceptable salt thereof:

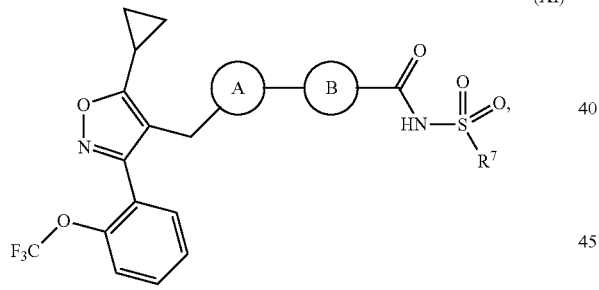

(XI)

wherein Ⓐ, Ⓑ, and R⁷ are as previously defined.

Representative compounds of the invention include, but are not limited to, the following compounds in Table 4 according to Formula (XI), and pharmaceutically acceptable salts thereof, wherein, Ⓐ, Ⓑ, and R⁷ are delineated for each example in Table 4.

TABLE 4

| compound | Ⓐ | Ⓑ | R⁷ |
|---|---|---|---|
| 701 | bis-tetrahydrofuran diol di-O- linker (isomannide-type) | 2-linked-6-yl benzothiazole, 7-OiPr | cyclopropyl |

TABLE 4-continued

| compound | Ⓐ | Ⓑ | R⁷ |
|---|---|---|---|
| 702 | isosorbide linker | 2-yl-4-OiPr-benzothiazol-6-yl | 1-methylcyclopropyl |
| 703 | isosorbide linker | 2-yl-4-OiPr-benzothiazol-6-yl | 1-(CHO)cyclopropyl |
| 704 | isosorbide linker | 2-yl-4-OiPr-benzothiazol-6-yl | 1-(CD₃)cyclopropyl |
| 705 | isosorbide linker | 2-yl-4-OiPr-benzothiazol-6-yl | 1-(CH₂OH)cyclopropyl |
| 706 | isosorbide linker | 2-yl-4-OiPr-benzothiazol-6-yl | 1-(CHF₂)cyclopropyl |
| 707 | isosorbide linker | 2-yl-4-OiPr-benzothiazol-6-yl | 1-(CF₃)cyclopropyl |
| 708 | isosorbide linker | 2-yl-4-OiPr-benzothiazol-6-yl | 1-(F)cyclopropyl |

TABLE 4-continued

| compound | Ⓐ | Ⓑ | R⁷ |
| --- | --- | --- | --- |
| 709 | hexahydrofuro[3,2-b]furan-3,6-diyl bis-O | 2-,6-disubstituted-7-OiPr-benzothiazole | 1-chlorocyclopropyl |
| 710 | hexahydrofuro[3,2-b]furan-3,6-diyl bis-O | 2-,6-disubstituted-7-OiPr-benzothiazole | 1-(fluoromethyl)cyclopropyl |
| 711 | hexahydrofuro[3,2-b]furan-3,6-diyl bis-O (alt stereo) | 2-,6-disubstituted-7-OiPr-benzothiazole | 1-(methoxymethyl)cyclopropyl |
| 712 | hexahydrofuro[3,2-b]furan-3,6-diyl bis-O | 2-,6-disubstituted-7-OiPr-benzothiazole | 1-cyanocyclopropyl |
| 713 | hexahydrofuro[3,2-b]furan-3,6-diyl bis-O | 2-,6-disubstituted-7-OiPr-benzothiazole | 1-carboxycyclopropyl |
| 714 | hexahydrofuro[3,2-b]furan-3,6-diyl bis-O | 2-,6-disubstituted-7-OiPr-benzothiazole | 1-(methoxycarbonyl)cyclopropyl |

TABLE 4-continued

| compound | Ⓐ | Ⓑ | R⁷ |
|---|---|---|---|
| 715 | isosorbide-like bicyclic diether | 4-OiPr benzothiazole | cyclopropyl-C(O)NH-S(O)₂-pyrrolidine |
| 216 | isosorbide-like bicyclic diether | 4-OiPr benzothiazole | cyclopropyl-C(O)NH₂ |
| 717 | isosorbide-like bicyclic diether | 4-OiPr benzothiazole | 2,2-difluoro-1-methylcyclopropyl |
| 718 | isosorbide-like bicyclic diether | 4-OiPr benzothiazole | 2,2-difluorocyclopropyl |
| 719 | isosorbide-like bicyclic diether | 4-OiPr benzothiazole | azetidinyl |
| 720 | isosorbide-like bicyclic diether | 4-OiPr benzothiazole | pyrrolidinyl |
| 721 | isosorbide-like bicyclic diether | 4-OiPr benzothiazole | piperidinyl |

TABLE 4-continued

| compound | Ⓐ | Ⓑ | R⁷ |
|---|---|---|---|
| 722 | isosorbide-like bicyclic diether (O-linked both sides) | 2-linked-6-yl benzothiazole with OiPr at 7 | 4,4-difluoropiperidin-1-yl |
| 723 | isosorbide-like bicyclic diether | 2-linked-6-yl benzothiazole with OiPr at 7 | cyclopentyl |
| 724 | isosorbide-like bicyclic diether (alt stereo) | 2-linked-6-yl benzothiazole with OiPr at 7 | morpholin-4-yl |
| 725 | isosorbide-like bicyclic diether | 2-linked-6-yl benzothiazole with OiPr at 4 | 1-methylcyclopentyl |
| 726 | isosorbide-like bicyclic diether | 2-linked-6-yl benzothiazole with OiPr at 4 | cyclohexyl |
| 727 | isosorbide-like bicyclic diether | 2-linked-6-yl benzothiazole with OiPr at 4 | NH₂ |

TABLE 4-continued

| compound | Ⓐ | Ⓑ | R⁷ |
|---|---|---|---|
| 728 | isosorbide-like bicyclic diether | 7-OiPr-benzothiazole-2,6-diyl | —NH—CH₃ |
| 729 | isosorbide-like bicyclic diether | 7-OiPr-benzothiazole-2,6-diyl | —N(CH₃)₂ |
| 730 | isosorbide-like bicyclic diether | 7-OiPr-benzothiazole-2,6-diyl | —NH-iPr |
| 731 | isosorbide-like bicyclic diether | 7-OiPr-benzothiazole-2,6-diyl | —NH-cyclopropyl |
| 732 | isosorbide-like bicyclic diether | 7-OiPr-benzothiazole-2,6-diyl | —NH-cyclobutyl |
| 733 | isosorbide-like bicyclic diether | 7-OiPr-benzothiazole-2,6-diyl | —NH-cyclopentyl |
| 734 | isosorbide-like bicyclic diether | 7-OiPr-benzothiazole-2,6-diyl | —NH-cyclohexyl |

TABLE 4-continued

| compound | Ⓐ | Ⓑ | R⁷ |
|---|---|---|---|
| 735 | isosorbide-type bicyclic diether | 2-linked-6-linked-7-OiPr-benzothiazole | —NH—Ph |
| 736 | isosorbide-type bicyclic diether | 2-linked-6-linked-7-OiPr-benzothiazole | —NH—C₆H₄-4-F |
| 737 | isosorbide-type bicyclic diether | 2-linked-6-linked-7-OiPr-benzothiazole | —NH—C₆H₄-2-OCF₃ |
| 738 | isosorbide-type bicyclic diether | 2-linked-6-linked-7-OiPr-benzothiazole | —NH-(pyridin-4-yl) |
| 739 | isosorbide-type bicyclic diether | 2-linked-6-linked-7-OiPr-benzothiazole | —Me |
| 740 | isosorbide-type bicyclic diether | 2-linked-6-linked-7-OiPr-benzothiazole | —CF₃ |

TABLE 4-continued
| compound | Ⓐ | Ⓑ | R⁷ |
|---|---|---|---|
| 741 | 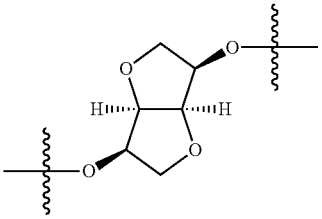 | 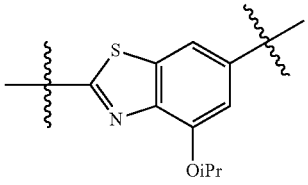 | 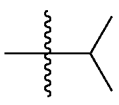 [SMILES: *C(C)C] |
| 742 | 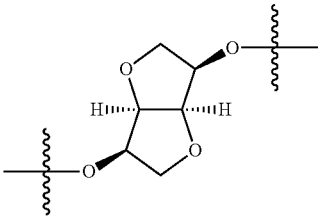 [SMILES: *O[C@@H]1CO[C@H]2[C@@H]1OC[C@H]2O*] | 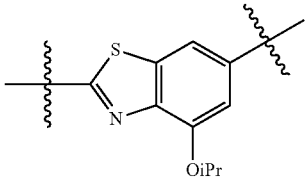 | 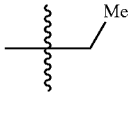 |
| 743 | 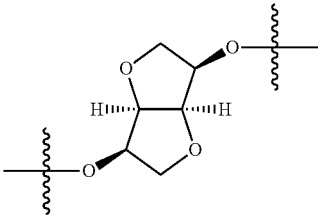 [SMILES: *O[C@@H]1CO[C@H]2[C@@H]1OC[C@H]2O*] | 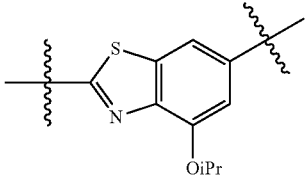 | 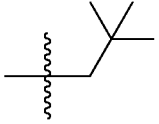 [SMILES: *CC(C)(C)C] |
| 744 | 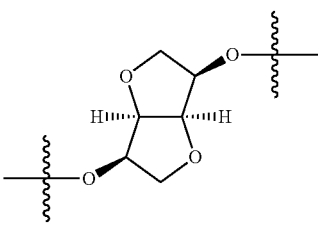 [SMILES: *O[C@@H]1CO[C@H]2[C@@H]1OC[C@H]2O*] | 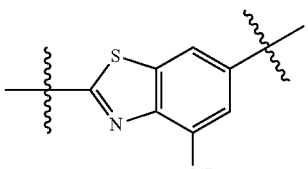 | 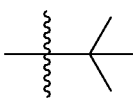 [SMILES: *C(C)(C)C] |
| 745 | 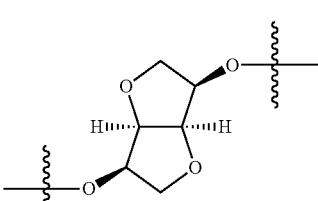 | 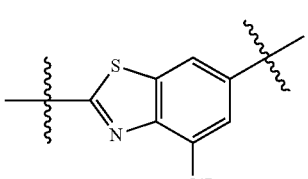 | 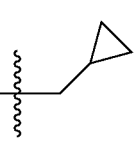 |
| 746 | 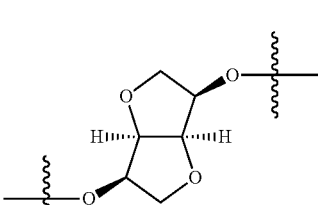 | 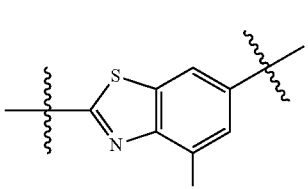 | 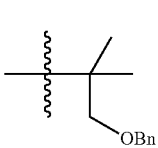 [SMILES: *C(C)(C)COCc1ccccc1] |
| 747 | 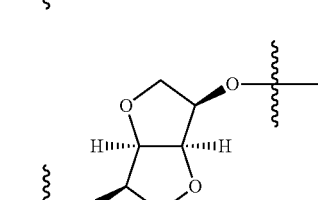 | 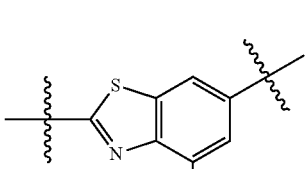 | 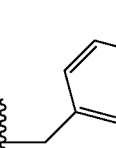 |

TABLE 4-continued

| compound | Ⓐ | Ⓑ | R⁷ |
|---|---|---|---|
| 748 | isosorbide-like bicyclic diether | 2-yl-7-OiPr-benzothiazol-6-yl | vinyl |
| 749 | isosorbide-like bicyclic diether | 2-yl-7-OiPr-benzothiazol-6-yl | -Bu |
| 750 | isosorbide-like bicyclic diether | 2-yl-7-OiPr-benzothiazol-6-yl | propyl |
| 751 | isosorbide-like bicyclic diether | 2-yl-7-OiPr-benzothiazol-6-yl | phenyl |
| 752 | isosorbide-like bicyclic diether | 2-yl-7-OiPr-benzothiazol-6-yl | 4-fluorophenyl |
| 753 | isosorbide-like bicyclic diether | 2-yl-7-OiPr-benzothiazol-6-yl | pyridin-2-yl |

TABLE 4-continued

| compound | Ⓐ | Ⓑ | R⁷ |
|---|---|---|---|
| 754 | isosorbide-like bicyclic diether | 4-OiPr-benzothiazole-2,6-diyl | 4-tert-butylphenyl |
| 755 | isosorbide-like bicyclic diether | 4-OiPr-benzothiazole-2,6-diyl | pyridin-4-yl |
| 756 | isosorbide-like bicyclic diether | 4-OiPr-benzothiazole-2,6-diyl | pyridin-3-yl |
| 757 | isosorbide-like bicyclic diether | 4-OiPr-benzothiazole-2,6-diyl | thiazol-5-yl |
| 758 | isosorbide-like bicyclic diether | 4-OiPr-benzothiazole-2,6-diyl | 5-fluoropyridin-2-yl |
| 759 | isosorbide-like bicyclic diether | 4-OiPr-benzothiazole-2,6-diyl | 1H-imidazol-2-yl |
| 760 | isosorbide-like bicyclic diether | 4-OiPr-benzothiazole-2,6-diyl | thiazol-2-yl |

TABLE 4-continued

| compound | Ⓐ | Ⓑ | R⁷ |
|---|---|---|---|
| 761 | isosorbide-type bicyclic diether (H,H stereo) | 2-yl-4-OiPr-benzothiazol-6-yl | 2-(F₃CO)phenyl |
| 762 | isosorbide-type bicyclic diether (H,H stereo) | 2-yl-4-OiPr-benzothiazol-6-yl | 1-Me-imidazol-2-yl |
| 763 | isosorbide-type bicyclic diether (H,H stereo) | 2-yl-4-OiPr-benzothiazol-6-yl | naphthalen-2-yl |
| 764 | isosorbide-type bicyclic diether (H,H stereo) | 2-yl-4-OiPr-benzothiazol-6-yl | 2-(MeO)phenyl |
| 765 | isosorbide-type bicyclic diether (H,H stereo) | 2-yl-4-OiPr-benzothiazol-6-yl | biphenyl-4-yl |
| 766 | isosorbide-type bicyclic diether (H,H stereo) | 2-yl-4-OiPr-benzothiazol-6-yl | 2,4'-bipyridin-5-yl |

TABLE 4-continued

| compound | Ⓐ | Ⓑ | R⁷ |
|---|---|---|---|
| 767 | isosorbide diyl | 2-(benzothiazol-6-yl), 4-OiPr | 4-(pyridin-4-yl)phenyl |
| 768 | isosorbide diyl | 2-(benzothiazol-6-yl), 4-OiPr | 2,3-dihydro-1,4-benzodioxin-6-yl |
| 769 | isosorbide diyl | 2-(benzothiazol-6-yl), 4-OiPr | 1,3-benzodioxol-5-yl |
| 770 | isosorbide diyl | 2-(benzothiazol-6-yl), 4-OiPr | 2,3-dihydro-1H-inden-5-yl |
| 771 | isosorbide diyl | 2-(benzothiazol-6-yl), 4-F | cyclopropyl |
| 772 | isosorbide diyl | 2-(benzothiazol-6-yl), 4-F | 1-methylcyclopropyl |
| 773 | isosorbide diyl | 2-(benzothiazol-6-yl) | cyclopropyl |

TABLE 4-continued
| compound | Ⓐ | Ⓑ | R⁷ |
|---|---|---|---|
| 774 | 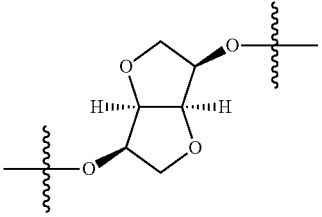 [SMILES: *O[C@@H]1CO[C@H]2[C@@H]1OC[C@H]2O*] | 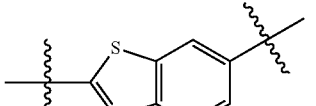 | 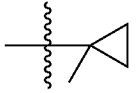 [SMILES: *C1(C)CC1] |
| 775 | 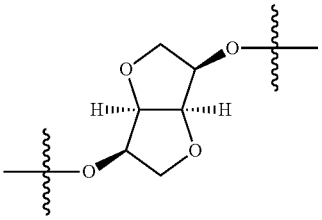 [SMILES: *O[C@@H]1CO[C@H]2[C@@H]1OC[C@H]2O*] | 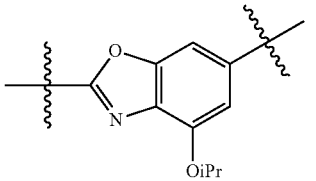 | 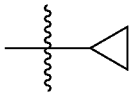 [SMILES: *C1CC1] |
| 776 | 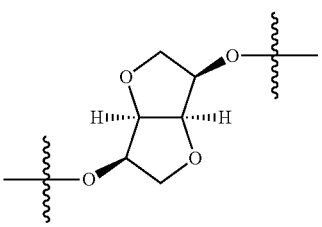 [SMILES: *O[C@@H]1CO[C@H]2[C@@H]1OC[C@H]2O*] | 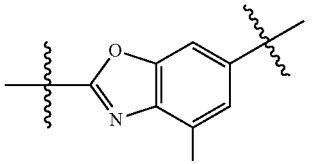 | 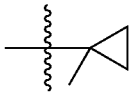 [SMILES: *C1(C)CC1] |
| 777 | 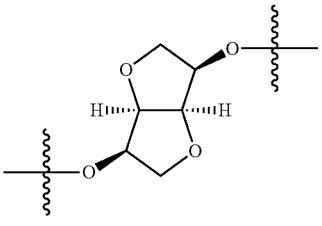 | 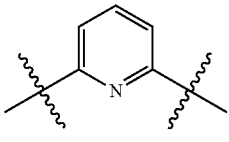 [SMILES: *c1cccc(*)n1] | 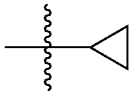 [SMILES: *C1CC1] |
| 778 | 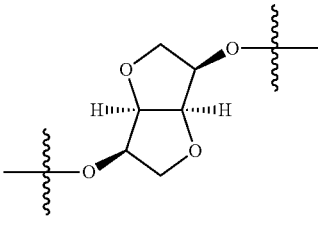 [SMILES: *O[C@@H]1CO[C@H]2[C@@H]1OC[C@H]2O*] | 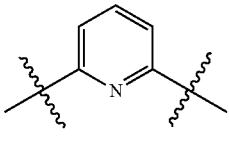 [SMILES: *c1cccc(*)n1] | 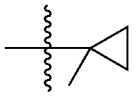 [SMILES: *C1(C)CC1] |
| 779 | 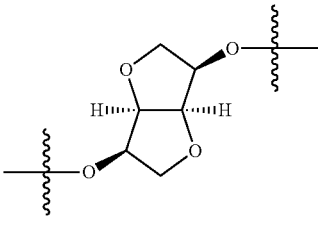 [SMILES: *O[C@@H]1CO[C@H]2[C@@H]1OC[C@H]2O*] | 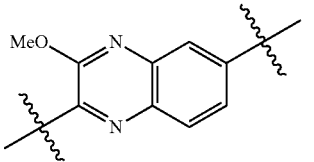 | 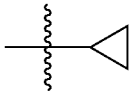 [SMILES: *C1CC1] |

TABLE 4-continued
| compound | Ⓐ | Ⓑ | R⁷ |
|---|---|---|---|
| 780 | 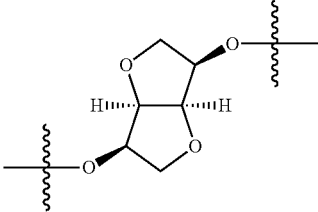 [SMILES: *O[C@@H]1CO[C@H]2[C@@H]1OC[C@H]2O*] | 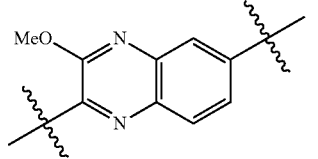 | 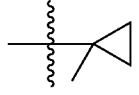 [SMILES: *C1(C)CC1] |
| 781 | 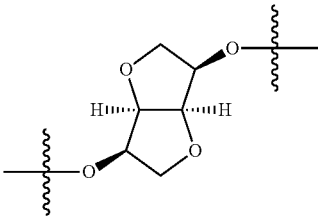 [SMILES: *O[C@@H]1CO[C@H]2[C@@H]1OC[C@H]2O*] | 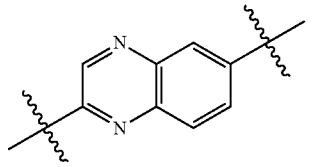 | 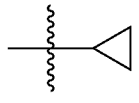 |
| 782 | 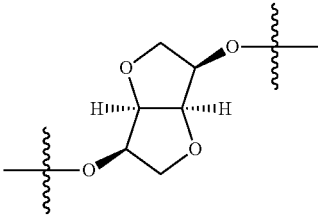 [SMILES: *O[C@@H]1CO[C@H]2[C@@H]1OC[C@H]2O*] | 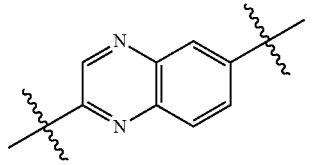 | 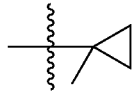 [SMILES: *C1(C)CC1] |
| 783 | 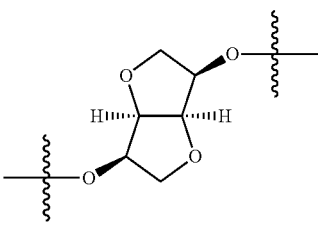 [SMILES: *O[C@@H]1CO[C@H]2[C@@H]1OC[C@H]2O*] | 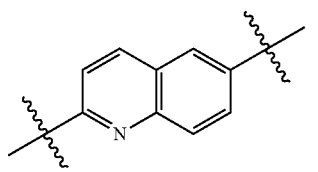 | 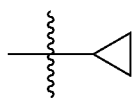 [SMILES: *C1CC1] |
| 784 | 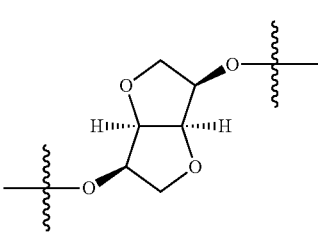 [SMILES: *O[C@@H]1CO[C@H]2[C@@H]1OC[C@H]2O*] | 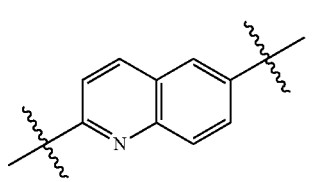 | 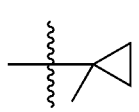 |
| 785 | 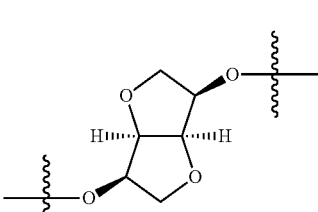 | 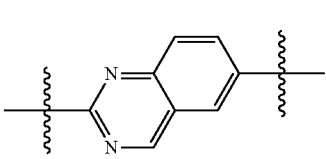 | 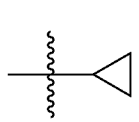 [SMILES: *C1CC1] |
| 786 | 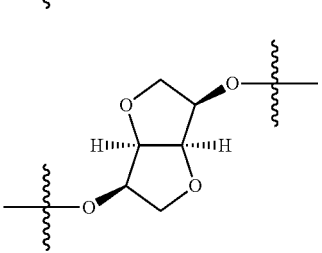 | 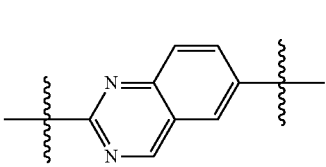 | 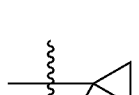 |

TABLE 4-continued
| compound | Ⓐ | Ⓑ | R[7] |
|---|---|---|---|
| 787 | 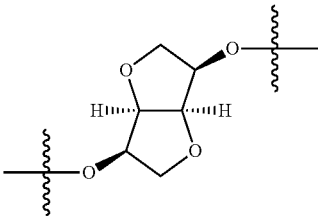 [SMILES: *O[C@@H]1CO[C@H]2[C@@H]1OC[C@H]2O*] | 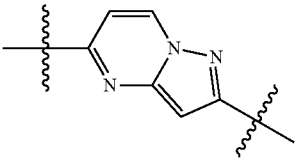 [SMILES: *c1ccn2nc(*)cc2n1] | 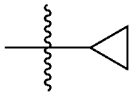 |
| 788 | 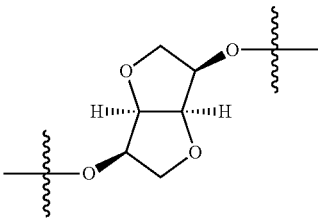 [SMILES: *O[C@@H]1CO[C@H]2[C@@H]1OC[C@H]2O*] | 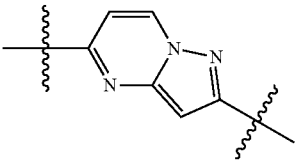 [SMILES: *c1ccn2nc(*)cc2n1] | 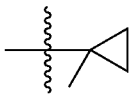 [SMILES: *C1(C)CC1] |
| 789 | 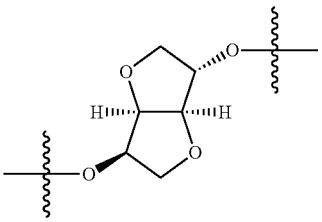 [SMILES: *O[C@H]1CO[C@H]2[C@@H]1OC[C@H]2O*] | 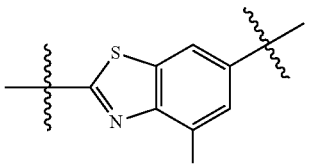 | 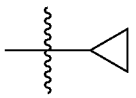 |
| 790 | 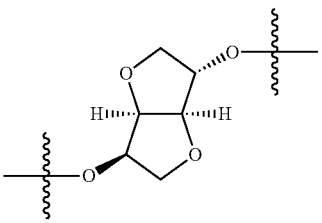 [SMILES: *O[C@H]1CO[C@H]2[C@@H]1OC[C@H]2O*] | 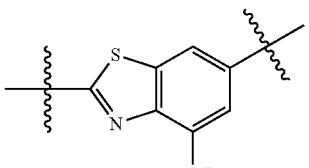 | 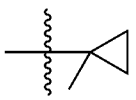 [SMILES: *C1(C)CC1] |
| 791 | 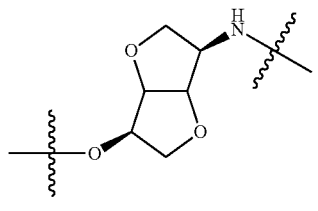 [SMILES: *N[C@@H]1COC2C1OC[C@H]2O*] | 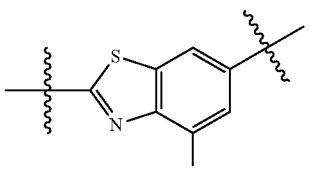 | 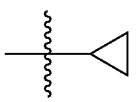 [SMILES: *C1CC1] |
| 792 | 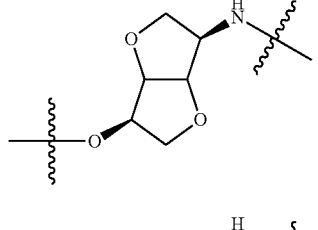 | 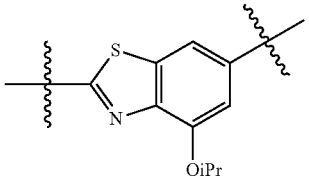 | 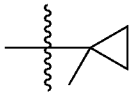 [SMILES: *C1(C)CC1] |
| 793 | 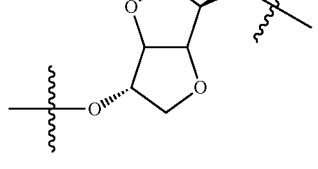 | 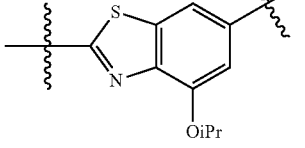 | 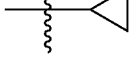 |

TABLE 4-continued

| compound | Ⓐ | Ⓑ | R⁷ |
|---|---|---|---|
| 794 | [bicyclic furan-ether/amine] | [benzothiazole with OiPr] | [1-methylcyclopropyl] |
| 795 | [bicyclic furan-diamine] | [benzothiazole with OiPr] | [cyclopropyl] |
| 796 | [bicyclic furan-diamine] | [benzothiazole with OiPr] | [1-methylcyclopropyl] |
| 797 | [fluoro bicyclic furan-amine] | [benzothiazole with OiPr] | [cyclopropyl] |
| 798 | [fluoro bicyclic furan-amine] | [benzothiazole with OiPr] | [1-methylcyclopropyl] |
| 799 | [fluoro bicyclic furan-ether] | [benzothiazole with OiPr] | [cyclopropyl] |
| 800 | [fluoro bicyclic furan-ether] | [benzothiazole with OiPr] | [1-methylcyclopropyl] |

TABLE 4-continued

| compound | Ⓐ | Ⓑ | R⁷ |
|---|---|---|---|
| 801 | | | |
| 802 | | | |
| 803 | | | |
| 804 | | | |
| 805 | | | |
| 806 | | | |
| 807 | | | |

TABLE 4-continued

| compound | Ⓐ | Ⓑ | R⁷ |
|---|---|---|---|
| 808 | [bicyclic furan-sulfonyl with NH] | [benzothiazole with OiPr] | [1-methylcyclopropyl] |
| 809 | [bicyclic oxazolidine with O] | [benzothiazole with OiPr] | [cyclopropyl] |
| 810 | [bicyclic oxazolidine with NH] | [benzothiazole with OiPr] | [1-methylcyclopropyl] |
| 811 | [bicyclic oxazolidine with O] | [benzothiazole with OiPr] | [cyclopropyl] |
| 812 | [bicyclic oxazolidinone with O] | [benzothiazole with OiPr] | [1-methylcyclopropyl] |
| 813 | [bicyclic diamine] | [benzothiazole with OiPr] | [1-methylcyclopropyl] |

TABLE 4-continued

| compound | Ⓐ | Ⓑ | R⁷ |
|---|---|---|---|
| 814 | | | |
| 815 | | | |
| 816 | | | |
| 817 | | | |
| 818 | | | |
| 819 | | | |
| 820 | | | |
| 821 | | | |

TABLE 4-continued

| compound | Ⓐ | Ⓑ | R⁷ |
| --- | --- | --- | --- |
| 822 | (thienopyrrolidine with NH and N attachment points) | (benzothiazole with OiPr) | (1-methylcyclopropyl) |
| 823 | (octahydropyrrolopyrazine with O attachment) | (benzothiazole with OiPr) | (cyclopropyl) |
| 824 | (octahydropyrrolopyrazine with NH attachment) | (benzothiazole with OiPr) | (1-methylcyclopropyl) |
| 825 | (octahydropyrrolopyrazine with O, defined stereo) | (benzothiazole with OiPr) | (cyclopropyl) |
| 826 | (octahydropyrrolopyrazine with O, defined stereo) | (benzothiazole with OiPr) | (1-methylcyclopropyl) |
| 827 | (octahydropyrrolopyrazine with O, defined stereo) | (benzothiazole with OiPr) | (cyclopropyl) |
| 828 | (octahydropyrrolopyrazine with O, defined stereo) | (benzothiazole with OiPr) | (1-methylcyclopropyl) |
| 829 | (octahydropyrrolopyrazine with NH) | (benzothiazole with OiPr) | (cyclopropyl) |

TABLE 4-continued

| compound | Ⓐ | Ⓑ | R⁷ |
|---|---|---|---|
| 830 | | | |
| 831 | | | |
| 832 | | | |
| 833 | | | |
| 834 | | | |
| 835 | | | |
| 836 | | | |

It will be appreciated that the description of the present invention herein should be construed in congruity with the laws and principles of chemical bonding. In some instances, it may be necessary to remove a hydrogen atom in order to accommodate a substituent at any given location.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of an FXR mediated disease or condition. The method comprises administering a therapeutically effective amount of a compound of Formula (I). The present invention also provides the use of a compound of Formula (I) for the preparation of a medicament for the prevention or treatment of an FXR mediated disease or condition.

In certain embodiments, the FXR-mediated disease or condition is cardiovascular disease, atherosclerosis, arteriosclerosis, hypercholesterolemia, or hyperlipidemia chronic liver disease, gastrointestinal disease, fibrotic diseases such as primary biliary cirrhosis, primary sclerosing cholangitis, pulmonary fibrosis, renal fibrosis, liver fibrosis, renal disease, metabolic disease, inflammatory demyelinating disease, cancer (i.e., colorectal cancer), or neurological indications such as stroke.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, dyslipidemia, hypercholesterolemia, or hypertriglyceridemia.

In certain embodiments, the metabolic disease is insulin resistance, Type I and Type II diabetes, or obesity.

In one aspect, the compound is a selective FXR agonist over TGR5 activator.

Yet a further aspect of the present invention is a process of making any of the compounds delineated herein employing any of the synthetic means delineated herein.

It should be understood that the compounds encompassed by the present invention are those that are suitably stable for use as pharmaceutical agent.

Definitions

Listed below are definitions of various terms used to describe this invention. These definitions apply to the terms as they are used throughout this specification and claims, unless otherwise limited in specific instances, either individually or as part of a larger group.

The term "alkyl", as used herein, refers to a saturated, monovalent straight- or branched-chain hydrocarbon group. Preferred alkyl radicals include $C_1$-$C_6$ alkyl and $C_1$-$C_8$ alkyl radicals. Examples of $C_1$-$C_6$ alkyl groups include, but are not limited to, methyl, ethyl, propyl, isopropyl, n-butyl, tert-butyl, neopentyl, n-hexyl groups; and examples of $C_1$-$C_8$ alkyl groups include, but are not limited to, methyl, ethyl, propyl, isopropyl, n-butyl, tert-butyl, neopentyl, n-hexyl, heptyl, and octyl groups.

The term "alkenyl", as used herein, denote a monovalent group derived from a hydrocarbon moiety by the removal of a single hydrogen atom wherein the hydrocarbon moiety has at least one carbon-carbon double bond. Preferred alkenyl groups include $C_2$-$C_6$ alkenyl and $C_2$-$C_8$ alkenyl groups. Alkenyl groups include, but are not limited to, for example, ethenyl, propenyl, butenyl, 1-methyl-2-buten-1-yl, heptenyl, octenyl and the like.

The term "alkynyl", as used herein, denotes a monovalent group derived from a hydrocarbon moiety by the removal of a single hydrogen atom wherein the hydrocarbon moiety has at least one carbon-carbon triple bond. Preferred alkynyl groups include $C_2$-$C_6$ alkynyl and $C_2$-$C_8$ alkynyl groups. Representative alkynyl groups include, but are not limited to, for example, ethynyl, 1-propynyl, 1-butynyl, heptynyl, octynyl and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_8$ cycloalkyl and $C_3$-$C_{12}$ cycloalkyl groups. Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, cyclooctyl, bicyclo[2.2.1]heptyl, bicyclo[2.2.2]octyl, spiro[2.5]octyl, 3-methylenebicyclo[3.2.1]octyl, spiro[4.4]nonanyl, bicycle[3.1.0]hexanyl, spiro[2.3]hexanyl, bicycle[3.1.1] heptanyl, spiro[2.5]octanyl, bicycle[4.1.0]heptanyl, bicycle [3.1.0]hexan-6-yl, spiro[2.3]hexan-5-yl, bicycle[3.1.1]heptan-3-yl, spiro[2.5]octan-4-yl, and bicycle[4.1.0]heptan-3-yl and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_8$ cycloalkenyl and $C_3$-$C_{12}$ cycloalkenyl groups. Examples of $C_3$-$C_8$-cycloalkenyl include, but are not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4] non-1-enyl, bicyclo[4.2.1]non-3-en-9-yl, and the like.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

The term "aryl," as used herein, refers to a mono-, bi-, or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "arylalkyl," as used herein, refers to a functional group wherein an alkylene chain is attached to an aryl group, e.g., —CH$_2$CH$_2$-phenyl. The term "substituted arylalkyl" means an arylalkyl functional group in which the aryl group is substituted. Examples include, but are not limited to, benzyl, phenethyl and the like.

The term "heteroaryl," as used herein, refers to a mono-, bi-, or tri-cyclic aromatic radical or ring having from five to ten ring atoms of which at least one ring atom is selected from S, O and N; wherein any N or S contained within the ring may be optionally oxidized. Preferred heteroaryl groups are monocyclic or bicyclic. Heteroaryl groups include, but are not limited to, pyridinyl, pyrazolyl, pyrazinyl, pyrimidinyl, pyrrolyl, pyrazolyl, imidazolyl, thiazolyl, thienyl, triazolyl, isothiazolyl, oxazolyl, isooxazolyl, thiadiazolyl, oxadiazolyl, thiophenyl, furanyl, quinolinyl, isoquinolinyl, benzimidazolyl, benzooxazolyl, benzothienyl, quinoxalinyl, indolyl, indazolyl, benzisoxazolyl, benzofuranyl, benzotriazolyl, benzothiazolyl, and the like.

The term "heteroarylalkyl," as used herein, refers to an alkylene chain is attached to a heteroaryl group. The term "substituted heteroarylalkyl" means a heteroarylalkyl functional group in which the heteroaryl group is substituted. Examples include, but are not limited to, pyridinylmethyl, pyrimidinylethyl and the like.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, protected hydroxy, —NO$_2$, —N$_3$, —CN, —NH$_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)- heterocycloalkyl, —CONH$_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_8$-alkenyl, —OCO$_2$—$C_2$-$C_8$-alkynyl, —OCO$_2$—$C_3$-$C_{12}$-cycloalkyl, —OCO$_2$-aryl, —OCO$_2$-heteroaryl, —OCO$_2$-heterocycloalkyl, —CO$_2$—$C_1$-$C_{12}$ alkyl, —CO$_2$—$C_2$-$C_8$ alkenyl, —CO$_2$—$C_2$-$C_8$ alkynyl, CO$_2$—$C_3$-$C_{12}$-cycloalkyl, —CO$_2$— aryl, CO$_2$-heteroaryl, CO$_2$-heterocyloalkyl, —OCONH$_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_8$-alkenyl, —NHCO$_2$—$C_2$-$C_8$-alkynyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH— heterocycloalkyl, NHC(S)NH$_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH— heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —SO$_2$NH$_2$, —SO$_2$NH—$C_1$-$C_{12}$-alkyl, —SO$_2$NH—$C_2$-$C_8$-alkenyl, —SO$_2$NH—$C_2$-$C_8$-alkynyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_8$-alkenyl, —NHSO$_2$—$C_2$-$C_8$-alkynyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_3$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. In certain embodiments, the substituents are independently selected from halo, preferably Cl and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$- alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy, —CN; —OH; $NH_2$; $C_1$-$C_4$-alkylamino; di($C_1$-$C_4$-alkyl)amino; and $NO_2$. It is understood that the aryls, heteroaryls, alkyls, cycloalkyls and the like can be further substituted. In some cases, each substituent in a substituted moiety is additionally optionally substituted with one or more groups, each group being independently selected from $C_1$-$C_6$-alkyl, $CF_3$, —F, —Cl, —Br, —I, —OH, —$NO_2$, —CN, and —$NH_2$.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, heteroarylalkylene and heterocycloalkylene groups are to be included in the above definitions, and are applicable to provide the Formulas herein with proper valency.

The terms "halo" and "halogen," as used herein, refer to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part*-2, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "amino acid" refers to naturally occurring and synthetic α, β, γ, or δ amino acids, and includes but is not limited to, amino acids found in proteins or intermediates in metabolism of amino acids or proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, citrulline, arginine and histidine. In certain embodiments, the amino acid is in the L-configuration. In certain embodiments, the amino acid is in the D-configuration. In certain embodiments, the amino acid is provided as a substituent of a compound described herein, wherein the amino acid is a residue selected from the group consisting of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl and β-histidinyl.

The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —NR$^u$-G(S$_c$)—C(O)-Q$^1$, wherein Q$^1$ is —SR$^v$, —NR$^v$R$^v$ or alkoxyl, R$^v$ is hydrogen or alkyl, S$_c$ is a side-chain of a naturally occurring or non-naturally occurring amino acid, G is C$_1$-C$_2$ alkyl, and R$^u$ is hydrogen; or R$^u$ and S$_c$ are taken together with the atoms to which they are attached to form a five-membered heterocyclic ring. In an embodiment, an amino acid derivative is provided as a substituent of a compound described herein, wherein the substituent is —O—C(O)-G(S$_c$)—NH-Q$^2$, wherein Q$^2$ is hydrogen or alkoxyl, S$_c$ is a side-chain of a naturally occurring or non-naturally occurring amino acid and G is C$_1$-C$_2$ alkyl. In certain embodiments, Q$^2$ and S$_c$ are taken together with the atoms to which they are attached to form a five-membered heterocyclic ring. In certain embodiments, G is an optionally substituted methylene and S$_c$ is selected from the group consisting of hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl and hydroxylarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

When the compounds described herein contain one or more asymmetric centers they give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reaction of the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the Formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38 (1992); Bundgaard, J. of *Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired isoxazole products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert solid, semi-solid or liquid filler, diluent, encapsulating material or Formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable Formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
ACN for acetonitrile;
AcOH for acetic acid;
BINAP for 2,2'-bis(diphenylphosphino)-1,1'-binaphthyl;
BrettPhos for 2-(dicyclohexylphosphino)3,6-dimethoxy-2',4',6'-triisopropyl-1,1'-biphenyl;
BOM-Cl for Benzyl chloromethyl ether
BOP-Cl for bis(2-oxo-3-oxazolidinyl)phosphinic chloride;
CDI for carbonyldiimidazole;
DavePhos for 2-dicyclohexylphosphino-2'-(N,N-dimethylamino)biphenyl;
DBU for 1,8-diazabicycloundec-7-ene;
DCC for N,N'-dicyclohexylcarbodiimide;
DCM for dichloromethane;
DIAD for Diisopropyl azodicarboxylate;
DMA for Dimethylacetamide
DMAP for N,N-dimethylaminopyridine;
DMF for N,N-dimethyl formamide;
DMP for Dess-Martin periodinane;
DMSO for Dimethyl sulfoxide;
DPPA for diphenylphosphoryl azide;
DPPF for 1,1'-Ferrocenediyl-bis(diphenylphosphine);
EDC or EDCI for 1-(3-diethylaminopropyl)-3-ethylcarbodiimide hydrochloride;
Et$_3$N for triethylamine;
EtOAc for ethyl acetate;
HATU for 1-[bis(dimethylamino)methylene]-1H-1,2,3-triazolo[4,5-b]pyridinium 3-oxide hexafluorophosphate;
HCl for hydrochloric acid;
LAH for lithium aluminium hydride;
LHMDS for Lithium bis(trimethylsilyl)amide;
Mor-Dalphos for Di(1-adamantyl)-2-morpholinophenylphosphine;
MTBE for Methyl tert-butyl ether;
NCS for N-Chlorosuccinimide;
NaHMDS for Sodium bis(trimethylsilyl)amide;
PyAOP for 7-azabenzotriazol-1-yloxy)tripyrrolidinophosphonium hexafluorophosphate;

PyBOP for benzotriazol-1-yl-oxytripyrrolidinophosphonium hexafluorophosphate;
TFA for trifluoroacetic acid;
TFFH for tetramethylfluoroformamidinium hexafluorophosphate;
THF for tetrahydrofuran;
Xantphos for 4,5-Bis(diphenylphosphino)-9,9-dimethylxanthene;
XPhos for dicyclohexyl(2',4',6'-triisopropyl-[1,1'-biphenyl]-2-yl)phosphane or
2-Dicyclohexylphosphino-2',4',6'-triisopropylbiphenyl.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Scheme 1

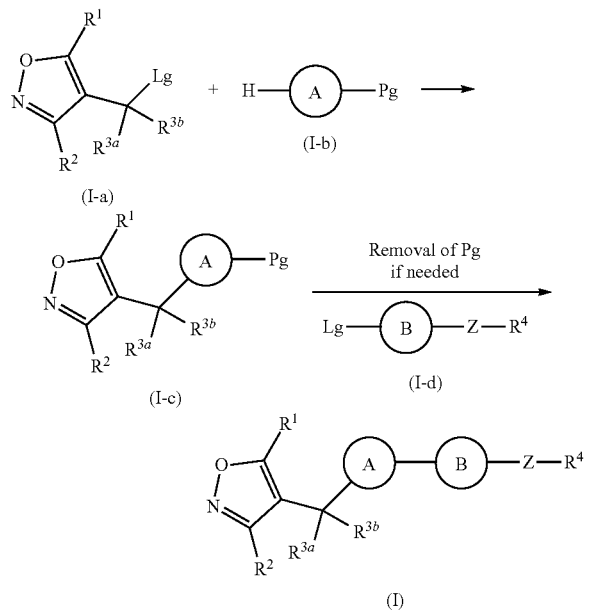

wherein, $R^1$, $R^2$, $R^{3a}$, $R^{3b}$, (A), (B), Z and $R^4$ are as previously defined. Lg is a leaving group such as halides, —OMs, —OTf, —OTs, —OAr. Pg is hydrogen or a protecting group for hydroxyl or amine whenever applicable such as, but not limited to, BOM, Boc, Cbz and benzyl. The protecting groups are common practices in organic synthesis (see T. W. Greene and P. G. M Wuts, "protective Groups in Organic Chemistry", 4$^{th}$ Ed., Wiley-Interscience, 2006).

As shown in Scheme 1, the compounds of formula (I-c) can be obtained through the coupling between the compounds of formula (I-a) and compounds of formula (I-b) employing suitable base such as but not limited to sodium tert-butoxide, potassium tert-butoxide, or cesium carbonate in the presence or absence of phase transfer reagent such as but not limited to 18-Crown-6, 15-Crown-5 or tetrabutylammonium iodide. The reaction temperature is from −20° C. to 140° C. The protecting group in compounds of formula (I-c) can be removed whenever applicable and coupled with the compounds of formula (I-d) to afford the compounds of formula (I). This coupling can be achieved employing suitable base such as but not limited to sodium tert-butoxide, potassium tert-butoxide, or cesium carbonate in the presence or absence of phase transfer reagent such as but not limited to 18-Crown-6, 15-Crown-5 or tetrabutylammonium iodide. Alternatively, the compounds of formula (I) could also be prepared from the deprotected form of compounds of formula (I-c) and the compounds of formula (I-d) via Buchwald-Hartwig amination. This process employing suitable palladium catalysts such as but not limited to $Pd(OAc)_2$, $Pd_2(dba)_3$, $PdCl_2(P(o-Tolyl)_3)_2$, $PdCl_2(DPPF)$ and $Pd(PPh_3)_4$ in presence or absence of a suitable ligand such as but not limited to XPhos, Xantphos, BINAP, BrettPhos, DavePhos, DPPF, PtBu$_3$, P(o-tolyl)$_3$ and Mor-Dalphos. This amination process may use a suitable base such as but not limited to $K_3PO_4$, $Cs_2CO_3$, NaOtBu, LiHMDS and NaHMDS. This amination process is carried out in an suitable solvent such as, but not limited to, toluene, dioxane or THF and the temperature can vary from −20° C. to 120° C. More detail about Buchwald-Hartwig amination could be found in literature. (Buchwald, S. L. et al., *Topics in Curr. Chem.*, 2002, 219, 131; Lundgren, R. J. et al., *Aldrichimica Acta*, 2012, 45, 59; Senra, J. D. et al., *Current Organic Synthesis*, 2011, 81, 53).

Scheme 2

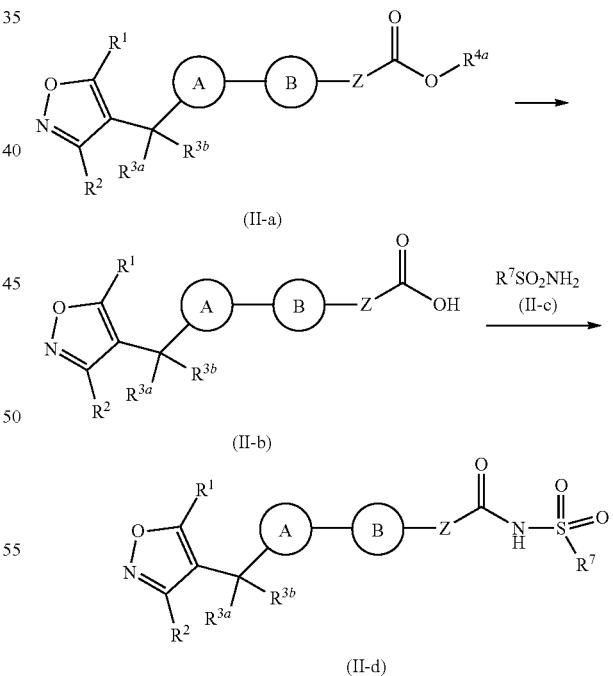

wherein, $R^1$, $R^2$, $R^{3a}$, $R^{3b}$, Z, $R^{4a}$, $R^7$, (A) and (B) are as previously defined.

As shown in Scheme 2, the hydrolysis of compounds of Formula (II-a) to the acids of Formula (II-b) can be achieved in the presence of suitable bases such as but not limited to sodium hydroxide, lithium hydroxide or potassium hydroxide. The novel isoxazole acylsulfonamide analogs of the compounds of Formula (II-d) can be prepared from the coupling between compounds of Formula (II-b) and sulfonamide (II-c) using suitable coupling reagents in presence of suitable bases. The coupling reagent can be selected from, but not limited to, DCC, EDCI, CDI, diisopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, DCM, DMF or THF. The reaction temperature can vary from −20° C. to 120° C.

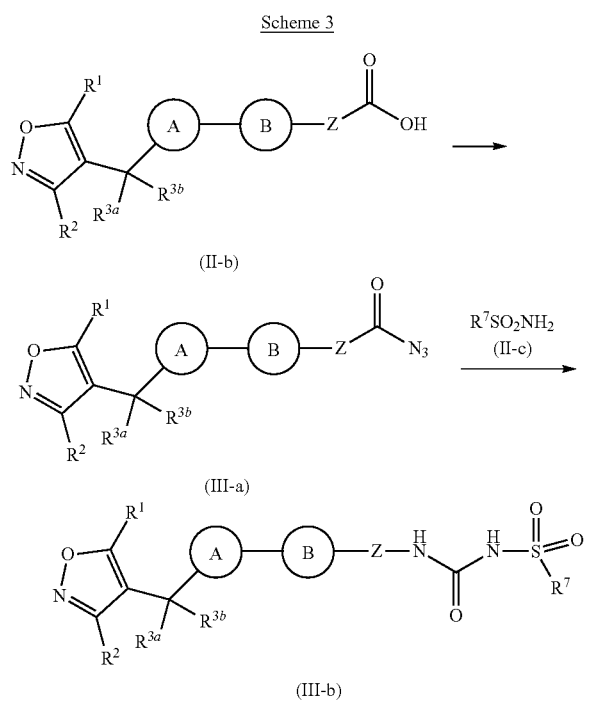

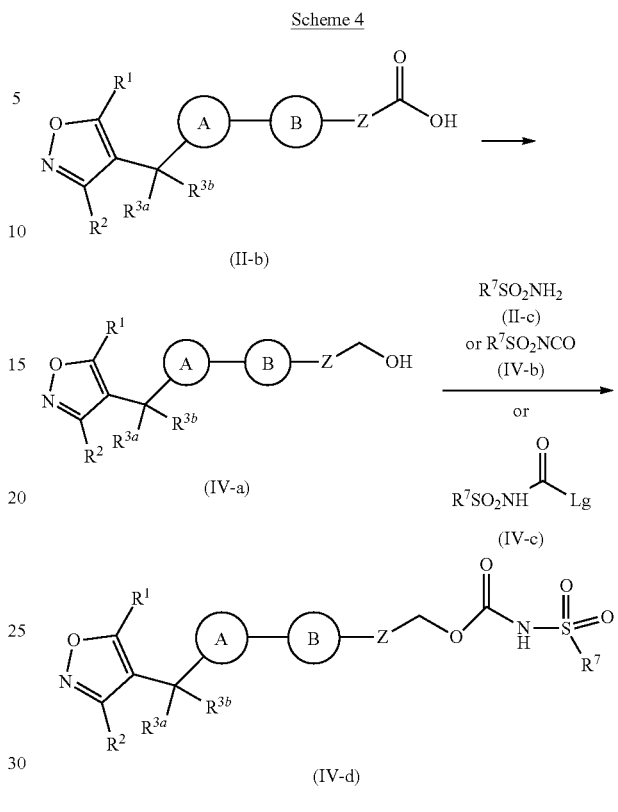

wherein, $R^1$, $R^2$, $R^{3a}$, $R^{3b}$, Z, $R^7$, (A) and (B) are as previously defined.

As shown in Scheme 3, novel isoxazole sulfonyl urea analogs of the compound of formula (III-b) are prepared from the compounds of formula (II-b), wherein $R^1$, $R^2$, $R^{3a}$, $R^{3b}$, $R^7$, Z, (A) and (B) are as previously defined. Thus, the compounds of formula (II-b) can be converted to the acyl azide compounds of formula (III-a) using suitable reagents such as, but not limited to, DPPA. The reaction solvents can be, but not limited to, THF, DCM and toluene. The reaction temperature is from −20° C. to 80° C. Alternatively, the acids of formula (II-b) could be transformed to the acyl azides of formula (III-a) via activated acid derivatives such as acyl chlorides or anhydrides in presence of azide source. The reagents for activation of acid includes, but not limited to, tetramethylfluoroformadinium hexafluorophosphate, phenyl dichlorophosphate, $SOCl_2$-DMF, triphosgene, cyanuric chloride, NCS-$Ph_3P$ and $Cl_3CCN$-$Ph_3P$. The azide source includes, but not limited to, sodium azide, tetrabutylammonium azide, trimethylsilyl azide and N,N,N',N'-tetramethylguanidinium azide. Curtius rearrangement of the compounds of formula (III-a) at elevated temperature preferably from 50° C. to 120° C. can lead to the isocyanate intermediates, which then can react with sulfonamides compound of formula (II-c) to afford the compounds of formula (III-b).

wherein, $R^1$, $R^2$, $R^{3a}$, $R^{3b}$, Z, $R^7$, (A) and (B) are as previously defined.

As shown in Scheme 4, the compounds of formula (IV-d) can be prepared from the compounds of formula (II-b), wherein $R^1$, $R^2$, $R^{3a}$, $R^{3b}$, $R^7$, Z, (A) and (B) are as previously defined and Lg is a leaving group such as halides, —OMs, —OTf, —OTs, —OAr. Thus, the compounds of formula (II-b) can be converted to alcohols of formula (IV-a) using suitable reducing reagents such as, but not limited to, LAH, $LiBH_4$, $BH_3$. Alternatively, the alcohols of formula (IV-a) can also be synthesized via the reduction of the derivatives of acid of formula (II-V). Such derivatives include, but not limited to, acyl chloride, mixed anhydride or ester derivatives of acids (II-b). The compounds of formula (IV-a) could be transformed to the carbamates of formula (IV-d) via coupling with sulfonamides of formula (II-C) employing CDI or phosgene as coupling reagent with or without addition of suitable bases such as, but not limited to, triethylamine, diisopropylethylamine, DBU, N-methylmorpholine and DMAP. Alternatively, this transformation could be achieved via direct coupling of alcohols of formula (IV-a) with isocyanates of formula (IV-b) in the presence or absence of suitable bases such as, but not limited to, triethylamine, diisopropylethylamine, DBU, N-methylmorpholine and DMAP. Moreover, the isocyanates of formula (IV-b) could be generated in situ from compounds of formula (IV-c).

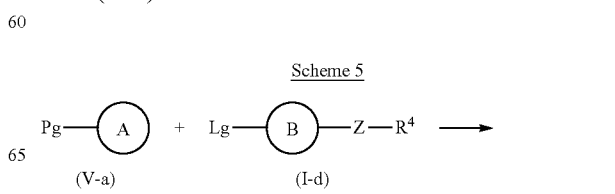

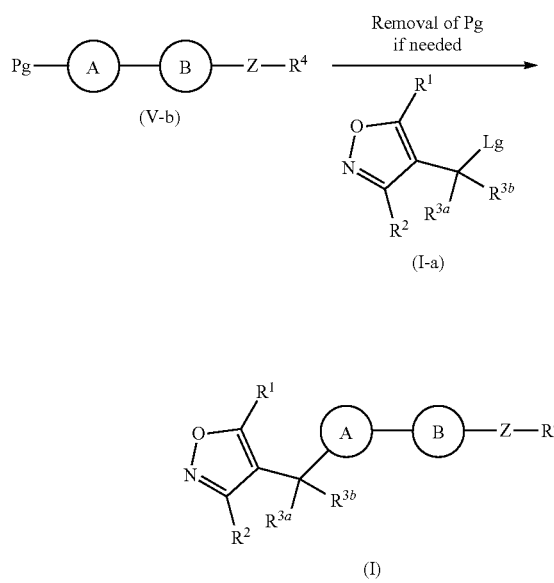

(V-b)

(I-a)

(I)

wherein, $R^1$, $R^2$, $R^{3a}$, $R^{3b}$, (A), (B), Z and $R^4$ are as previously defined. Lg is a leaving group such as halides, —OMs, —OTf, —OTs, —OAr. Pg is hydrogen or a protecting group for hydroxyl or amine whenever applicable such as, but not limited to, BOM, Boc, Cbz and benzyl. The protecting groups are common practices in organic synthesis (see T. W. Greene and P. G. M Wuts, "protective Groups in Organic Chemistry", $4^{th}$ Ed., Wiley-Interscience, 2006).

As shown in Scheme 5, the compounds of formula (V-b) can be synthesized through the coupling between the compounds of formula (V-a) and compounds of formula (I-d) employing suitable base such as but not limited to sodium tert-butoxide, potassium tert-butoxide, or cesium carbonate in the presence or absence of phase transfer reagent such as but not limited to 18-Crown-6, 15-Crown-5 or tetrabutylammonium iodide. The reaction temperature is from −20° C. to 140° C. The protecting group in compounds of formula (V-b) can be removed whenever applicable and coupled with the compounds of formula (I-a) to afford the compounds of formula (I). This coupling can be achieved employing suitable base such as but not limited to sodium tert-butoxide, potassium tert-butoxide, sodium hydride, LHMDS, NaHMDS or cesium carbonate in the presence or absence of phase transfer reagent such as but not limited to 18-Crown-6, 15-Crown-5 or tetrabutylammonium iodide.

In the reactions described, reactive functional groups such as hydroxyl, amino, imino, thio or carboxy groups, may be protected to avoid unwanted participation in the reactions. These protecting groups may be removed at suitable steps via solovolysis, reduction, photolysis. The protection and deprotection are common practices in organic synthesis (see T. W. Greene and P. G. M Wuts, "protective Groups in Organic Chemistry", $4^{th}$ Ed., Wiley-Interscience, 2006).

PREPARATIONS AND EXAMPLES

The following preparations and examples are intended to further illustrate the invention only and are not intended to limit the scope of the invention in any way.

Example 1

Step 1a

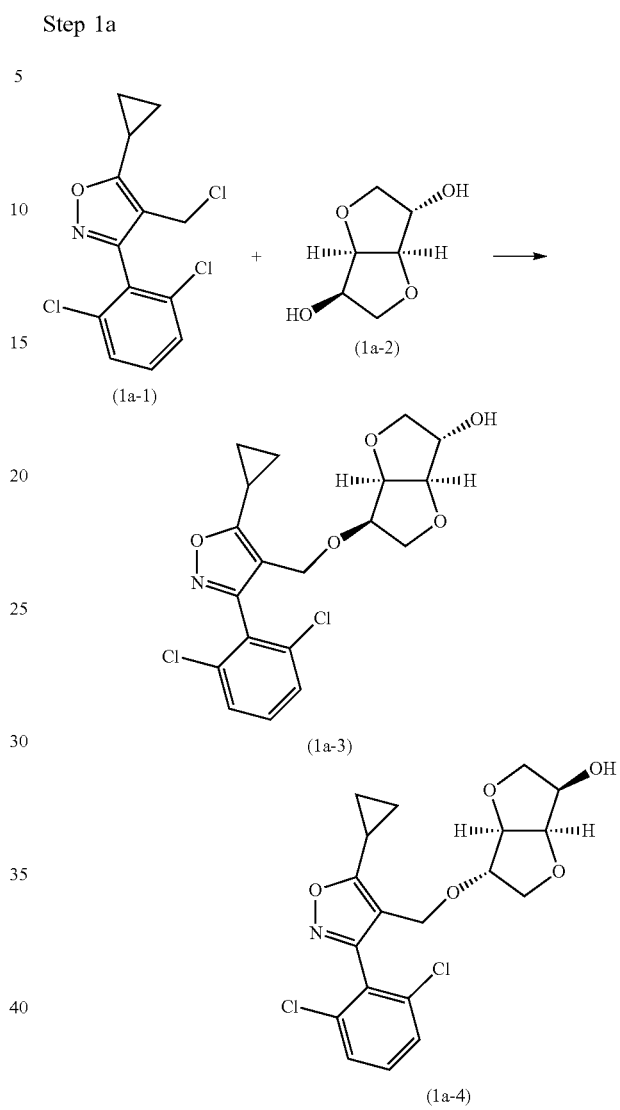

(1a-1)

(1a-2)

(1a-3)

(1a-4)

To (3R,3aR,6S,6aR)-hexahydrofuro[3,2-b]furan-3,6-diol (isosorbide, 1a-2) (2 g, 13.69 mmol) in THF (30 ml) was added 18-crown-6 (3.62 g, 13.69 mmol) and potassium tert-butoxide (27.4 ml, 27.4 mmol). The resulting mixture was stirred at RT for 1 h, and 4-(chloromethyl)-5-cyclopropyl-3-(2,6-dichlorophenyl)isoxazole (1a-2) (4.14 g, 13.69 mmol) was added in one portion. The mixture was stirred at RT for 16 h and diluted with EtOAc, washed with NaHCO$_3$ solution, water, brine. The organic layer was dried (Na$_2$SO$_4$), filtered and concentrated. The residue was purified by CombiFlash eluting with 0 to 90% Acetone/hexane to give (3S,3aR,6R,6aR)-6-((5-cyclopropyl-3-(2,6-dichlorophenyl)isoxazol-4-yl)methoxy)hexahydrofuro[3,2-b]furan-3-ol (1a-3) (802 mg). LC/MS observed [M+Na], 434.04; $^1$H NMR (400 MHz, Chloroform-d) δ 7.38-7.23 (m, 3H), 4.57-4.42 (m, 2H), 4.34-4.22 (m, 2H), 4.22-4.15 (m, 1H), 3.86 (td, J=6.8, 4.8 Hz, 1H), 3.82-3.71 (m, 2H), 3.66 (dd, J=9.0, 6.6 Hz, 1H), 3.37 (dd, J=9.0, 7.1 Hz, 1H), 2.21-2.06 (m, 1H), 1.73 (s, 1H), 1.29-1.14 (m, 2H), 1.12-0.98 (m, 2H).

(3R,3aR,6S,6aR)-6-((5-cyclopropyl-3-(2,6-dichlorophenyl)isoxazol-4-yl)methoxy)hexahydrofuro[3,2-b]furan-3-ol (1a-4) (182 mg) was also isolated. LC/MS observed

[M+Na], 434.04; ¹H NMR (500 MHz, Chloroform-d) δ 7.51-7.31 (m, 3H), 4.45 (t, J=4.9 Hz, 1H), 4.41-4.29 (m, 2H), 4.24 (dd, J=11.0, 5.1 Hz, 2H), 4.01-3.90 (m, 1H), 3.86-3.73 (m, 3H), 3.51 (dd, J=9.4, 5.8 Hz, 1H), 2.61 (s, 1H), 2.13 (tt, J=8.2, 5.0 Hz, 1H), 1.36-1.21 (m, 2H), 1.20-1.03 (m, 2H). Note: The stereochemistry of compounds (1a-3) and (1a-4) was assigned based on NOE observed as shown.

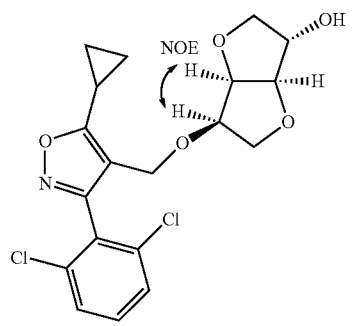

(1a-3)

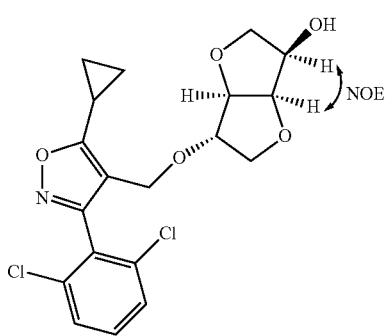

(1a-4)

Step 1b

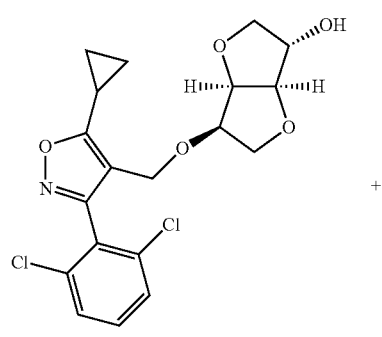

(1a-3)

+

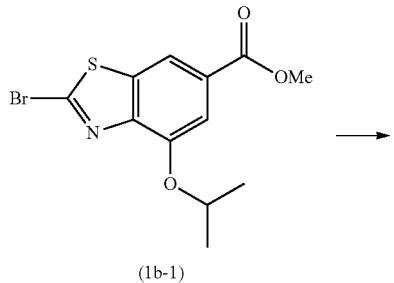

(1b-1)

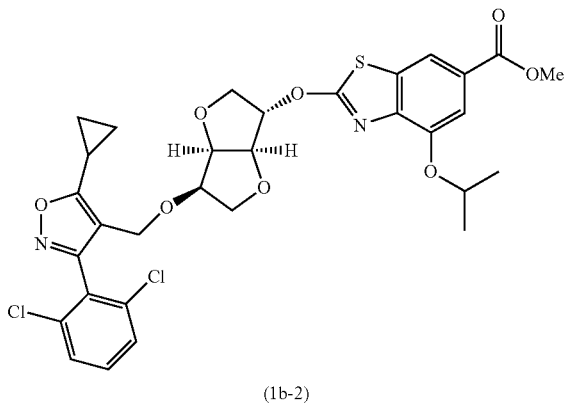

(1b-2)

To (3S,3aR,6R,6aR)-6-((5-cyclopropyl-3-(2,6-dichlorophenyl)isoxazol-4-yl)methoxy)hexa-hydrofuro[3,2-b]furan-3-ol (1a-3) (65 mg, 0.158 mmol) and methyl 2-bromo-4-isopropoxybenzo[d]thiazole-6-carboxylate (1b-1) (78 mg, 0.236 mmol) in DMF (2 ml) was added NaH (3.78 mg, 0.158 mmol, 60% dispersion in mineral oil) and the mixture was stirred at RT for 6 h. The mixture was diluted with EtOAc, washed with NaHCO₃ solution, water, brine, dried (Na₂SO₄), filtered and concentrated. The residue was purified by CombiFlash eluting with 0 to 45% acetone/hexane to give methyl 2-(((3S,3aR,6R,6aR)-6-((5-cyclopropyl-3-(2,6-dichlorophenyl)isoxazol-4-yl)methoxy)hexahydrofuro[3,2-b]furan-3-yl)oxy)-4-isopropoxybenzo[d]thiazole-6-carboxylate (1b-2) (46 mg, 0.070 mmol, 44.1% yield). LC/MS observed [M+H], 661.13; ¹H NMR (400 MHz, Chloroform-d) δ 7.91 (d, J=1.5 Hz, 1H), 7.50 (d, J=1.5 Hz, 1H), 7.35 (dq, J=8.4, 1.4 Hz, 2H), 7.32-7.23 (m, 1H), 5.58 (d, J=3.3 Hz, 1H), 4.78 (p, J=6.1 Hz, 1H), 4.59 (h, J=6.9, 5.7 Hz, 2H), 4.52 (d, J=12.4 Hz, 1H), 4.29 (d, J=12.4 Hz, 1H), 4.16-3.95 (m, 2H), 3.91 (td, J=6.6, 4.3 Hz, 1H), 3.85 (s, 5H), 3.72 (dd, J=9.1, 6.4 Hz, 1H), 3.47 (dd, J=9.1, 6.8 Hz, 1H), 2.27-2.06 (m, 1H), 1.93 (s, 3H), 1.76 (d, J=5.3 Hz, 1H), 1.35 dd, J=6.1, 1.4 Hz, 7H), 1.23-1.17 (m, 2H), 1.16-1.00 (m, 2H).

Step 1c

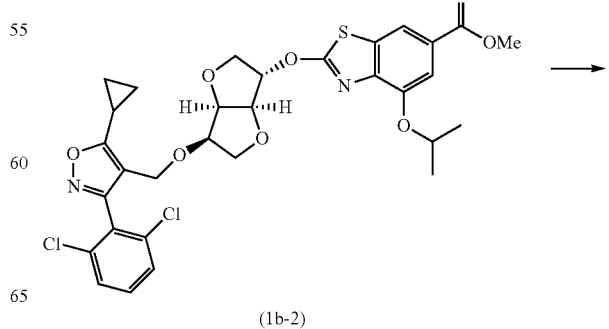

(1b-2)

Example 1

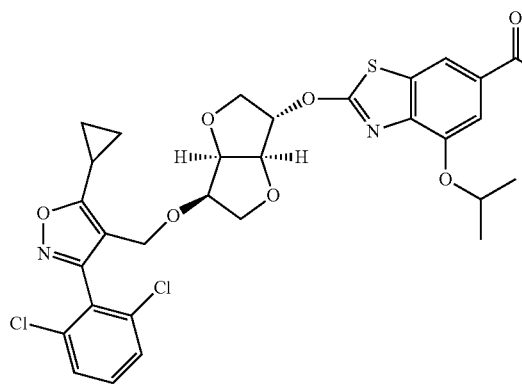

To methyl 2-(((3S,3aR,6R,6aR)-6-((5-cyclopropyl-3-(2,6-dichlorophenyl)isoxazol-4-yl)methoxy)hexahydrofuro[3,2-b]furan-3-yl)oxy)-4-isopropoxybenzo[d]thiazole-6-carboxylate (1b-2) (43 mg, 0.065 mmol) in Methanol (1 ml) and THF (1 ml) was added LiOH (0.097 ml, 0.097 mmol, 1M) and the mixture was stirred at 45° C. for 16 h. The mixture was concentrated, azeotroped with ACN. To the residue was added DCM/MeOH, and the mixture was filtered. The filtrate was collected and concentrated and the residue was lyophilized to give lithium 2-(((3S,3aR,6R,6aR)-6-((5-cyclopropyl-3-(2,6-dichlorophenyl)isoxazol-4-yl)methoxy)hexa-hydrofuro[3,2-b]furan-3-yl)oxy)-4-isopropoxybenzo[d]thiazole-6-carboxylate (Example 1) (44.8 mg, 0.069 mmol) as a white powder. LC/MS observed [M+H], 647.12.

Example 2

Step 2a

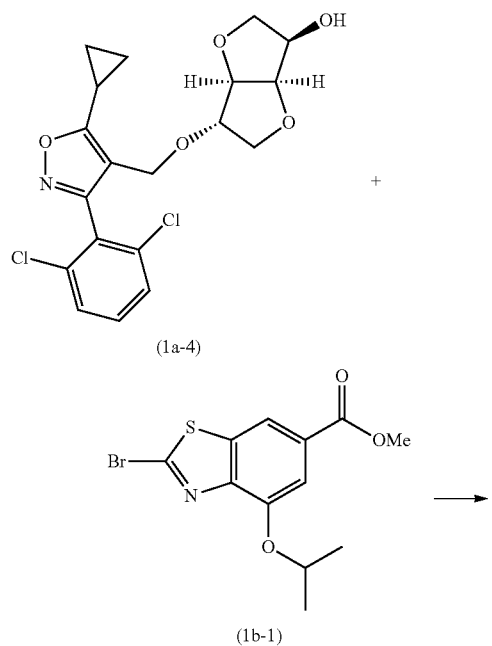

To (3R,3aR,6S,6aR)-6-((5-cyclopropyl-3-(2,6-dichlorophenyl)isoxazol-4-yl)methoxy)hexa-hydrofuro[3,2-b]furan-3-ol (1a-4) (50 mg, 0.121 mmol) and methyl 2-bromo-4-isopropoxybenzo-[d]thiazole-6-carboxylate (1b-1) (60.1 mg, 0.182 mmol) in DMF (2 ml) was added NaH (4.85 mg, 0.121 mmol) and the mixture was stirred at RT for 16 h. The mixture was diluted with EA, washed with NaHCO₃ solution, water, brine, dried (Na₂SO₄), filtered and concentrated. The residue was purified by CombiFlash eluting with hexane to 45% acetone/hexane to give methyl 2-(((3R,3aR,6S,6aR)-6-((5-cyclopropyl-3-(2,6-dichlorophenyl)-isoxazol-4-yl)methoxy)hexa-hydro-furo[3,2-b]furan-3-yl)oxy)-4-isopropoxybenzo[d]thiazole-6-carboxylate (2a) (58 mg, 0.088 mmol, 72.3% yield). LC/MS observed [M+H], 661.13; $^1$H NMR (400 MHz, Chloroform-d) δ 7.82 (d, J=1.5 Hz, 1H), 7.40 (d, J=1.6 Hz, 1H), 7.32-7.22 (m, 2H), 7.16 (t, J=8.1 Hz, 1H), 5.47 (td, J=6.3, 5.0 Hz, 1H), 4.77-4.58 (m, 2H), 4.31-4.09 (m, 3H), 3.94 (dd, J=9.6, 6.3 Hz, 1H), 3.84-3.55 (m, 5H), 3.76 (s, 3H), 2.01-1.85 (m, 1H), 1.27 (dd, J=6.1, 0.8 Hz, 6H), 1.18-1.04 (m, 2H), 1.04-0.79 (m, 2H).

Step 2b

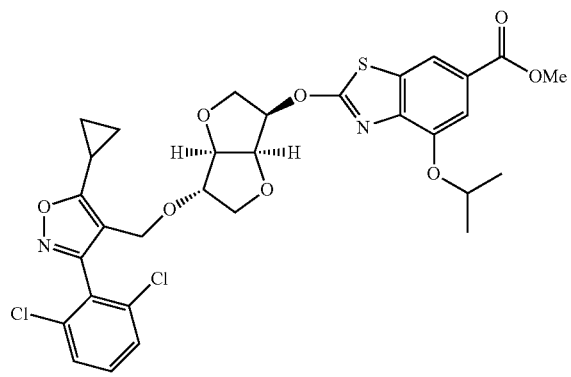

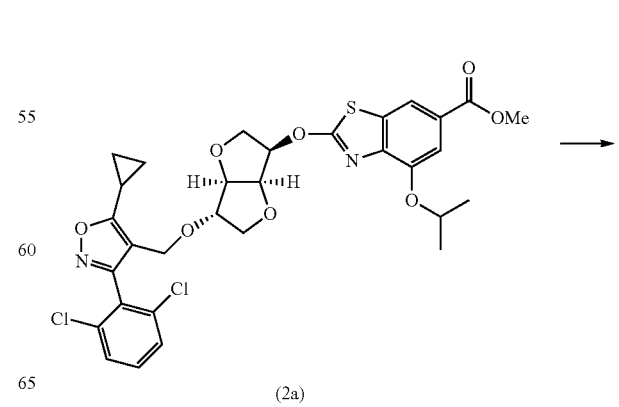

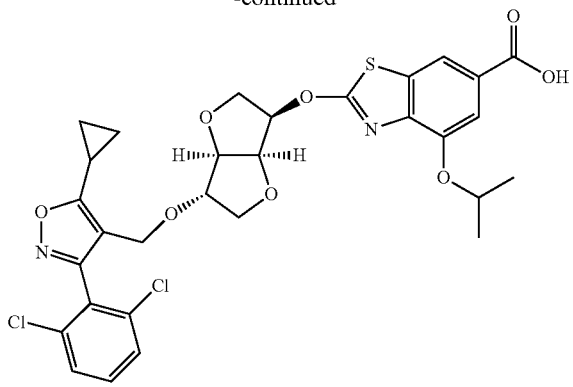

Example 2

Example 2 was synthesized by following the similar experimental procedure in step 1c for Example 1. LC/MS observed [M+H], 647.11.

Example 3

Step 3a

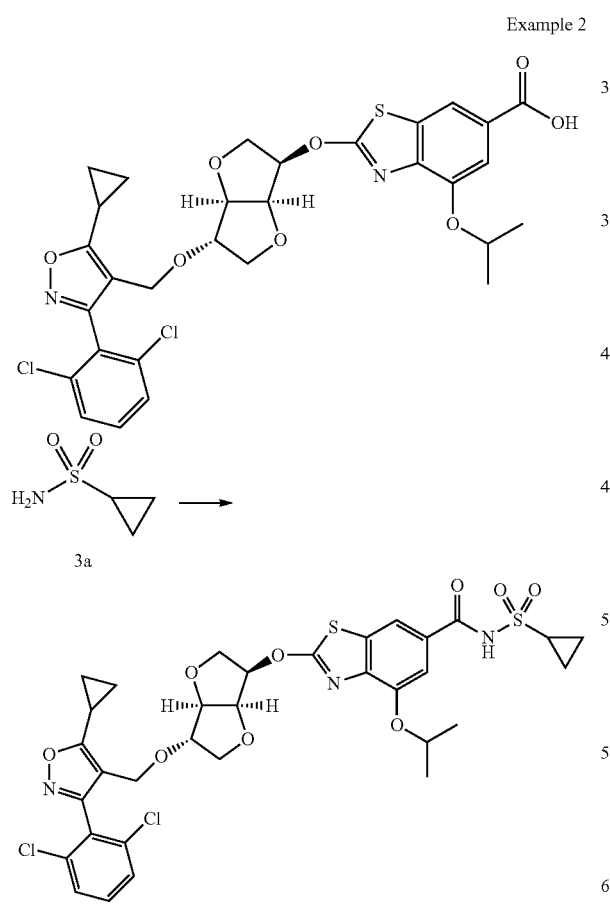

Example 3

To 2-(((3R,3aR,6S,6aR)-6-((5-cyclopropyl-3-(2,6-dichlorophenyl)isoxazol-4-yl)methoxy)hexa-hydrofuro[3,2-b]furan-3-yl)oxy)-4-isopropoxybenzo[d]thiazole-6-carboxylic acid (Example 2) (30 mg, 0.046 mmol), cyclopropanesulfonamide (3a) (8.42 mg, 0.069 mmol) and EDC (13.32 mg, 0.069 mmol) in DCM (0.8 ml) was added DMAP (8.49 mg, 0.069 mmol) and the mixture was stirred at RT for 16 h. The mixture was concentrated and the residue was purified by HPLC eluting with 0.1% formic acid in Water and ACN to give 2-(((3R,3aR,6S,6aR)-6-((5-cyclopropyl-3-(2,6-dichlorophenyl)isoxazol-4-yl)methoxy)hexahydrofuro[3,2-b]furan-3-yl)oxy)-N-(cyclopropylsulfonyl)-4-isopropoxybenzo[d]thiazole-6-carboxamide (example 3) (15 mg, 0.020 mmol, 43.1% yield). LC/MS observed [M+H], 750.14; $^1$H NMR (400 MHz, Chloroform-d) δ 7.78-7.56 (m, 1H), 7.48-7.21 (m, 4H), 5.54 (q, J=5.9 Hz, 1H), 4.76 (dq, J=12.1, 6.1, 5.3 Hz, 2H), 4.38-4.17 (m, 3H), 4.01 (dd, J=9.7, 6.3 Hz, 1H), 3.94-3.64 (m, 4H), 3.07 (tt, J=8.3, 4.7 Hz, 1H), 2.03 (tt, J=8.3, 5.0 Hz, 1H), 1.35 (ddd, J=8.5, 6.3, 2.8 Hz, 9H), 1.26-0.98 (m, 6H).

Example 4

Step 4a

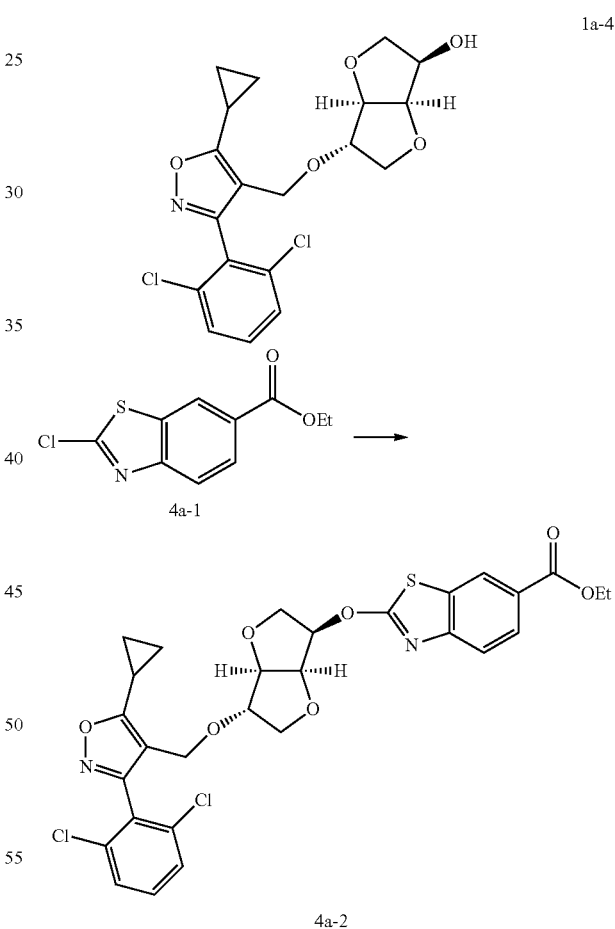

To (3R,3aR,6S,6aR)-6-((5-cyclopropyl-3-(2,6-dichlorophenyl)isoxazol-4-yl)methoxy)hexa-hydrofuro[3,2-b]furan-3-ol (1a-4) (58 mg, 0.141 mmol) in DMF (2 ml) was added NaH (8.44 mg, 0.211 mmol) and the mixture was stirred at RT for 30 min then added ethyl 2-chlorobenzo[d]thiazole-6-carboxylate (4a-1) (51.0 mg, 0.211 mmol). The mixture was stirred at RT for 16 h, then quenched with NaHCO₃ solution, extracted with EtOAc, organic layer separated and washed with water, brine, dried (Na₂SO₄), filtered and concentrated. The residue was purified by CombiFlash eluting with hexane to 60% acetone/hexane to give ethyl 2-(((3R,3aR,6S,6aR)-6-((5-cyclopropyl-3-(2,6-dichlorophenyl)isoxazol-4-yl)methoxy)hexahydrofuro[3,2-b]furan-3-yl)oxy)benzo[d]thiazole-6-carboxylate (4a-2) (65 mg). LC/MS observed [M+H], 617.10; ¹H NMR (400 MHz, Chloroform-d) δ 8.30 (d, J=1.6 Hz, 1H), 7.99 (dd, J=8.5, 1.7 Hz, 1H), 7.61 (d, J=8.5 Hz, 1H), 7.39-7.29 (m, 2H), 7.24 (t, J=8.0 Hz, 1H), 5.48 (q, J=5.7 Hz, 1H), 4.80 (t, J=4.8 Hz, 1H), 4.44-4.16 (m, 5H), 4.10-3.95 (m, 2H), 3.94-3.81 (m, 2H), 3.81-3.65 (m, 2H), 2.09-1.99 (m, 1H), 1.25-1.13 (m, 4H), 1.13-1.00 (m, 2H).

Step 4b

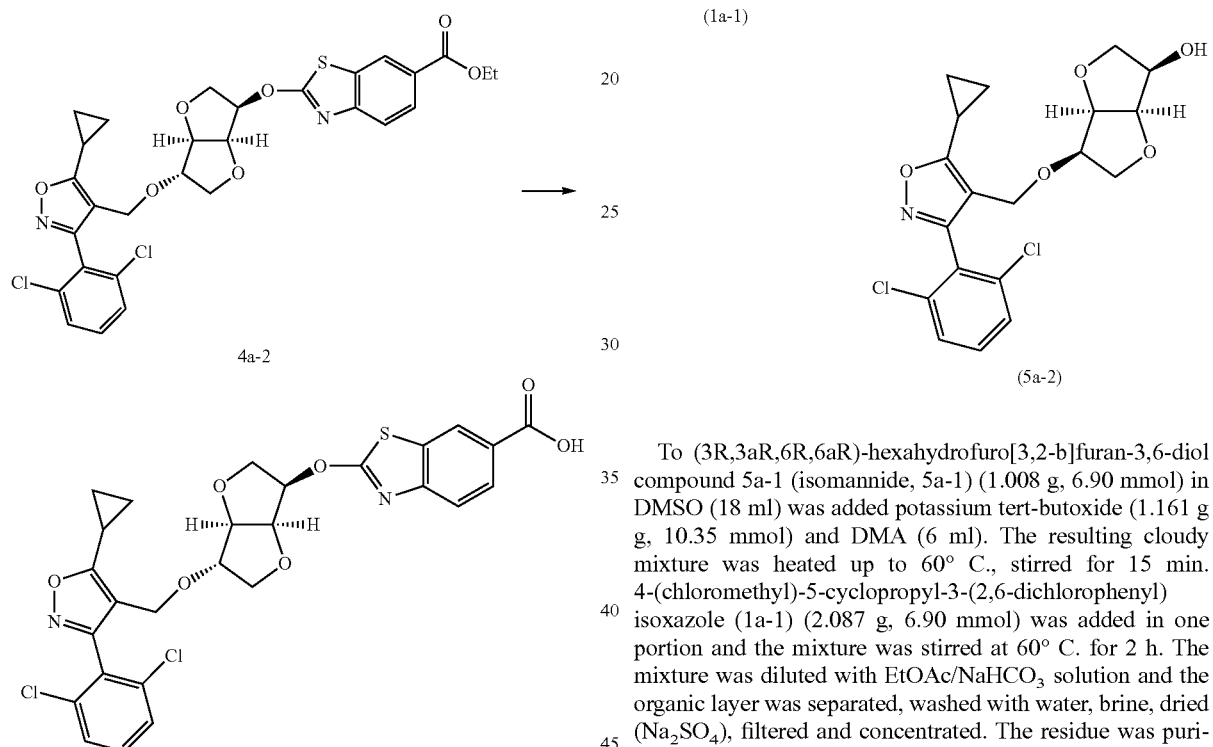

Example 4

To ethyl 2-(((3R,3aR,6S,6aR)-6-((5-cyclopropyl-3-(2,6-dichlorophenyl)isoxazol-4-yl)methoxy) hexahydrofuro[3,2-b]furan-3-yl)oxy)benzo[d]thiazole-6-carboxylate (4a-2) (65 mg, 0.105 mmol) in MeOH (1 ml) and Tetrahydrofuran (1 ml) was added LiOH (0.158 ml, 0.158 mmol, 1M), the mixture was stirred at RT for 16 h. The mixture was concentrated under reduced pressure and the residue was purified by HPLC eluting with 0.1% formic acid in Water and ACN to give 2-(((3R,3aR,6S,6aR)-6-((5-cyclopropyl-3-(2,6-dichlorophenyl)isoxazol-4-yl)methoxy)hexahydrofuro[3,2-b]furan-3-yl)oxy)benzo[d]thiazole-6-carboxylic acid (Example 4) (17 mg). LC/MS observed [M+H], 589.06; ¹H NMR (400 MHz, Chloroform-d) δ 8.33 (s, 1H), 8.02 (d, J=8.5 Hz, 1H), 7.63 (d, J=8.4 Hz, 1H), 7.40-7.20 (m, 3H), 5.49 (q, J=5.6 Hz, 1H), 4.82 (t, J=4.9 Hz, 1H), 4.44-4.18 (m, 3H), 4.01 (dd, J=9.8, 6.0 Hz, 1H), 3.95-3.67 (m, 4H), 2.03 (tt, J=8.4, 5.1 Hz, 1H), 1.32-1.12 (m, 2H), 1.10-0.81 (m, 2H).

Example 5

Step 5a

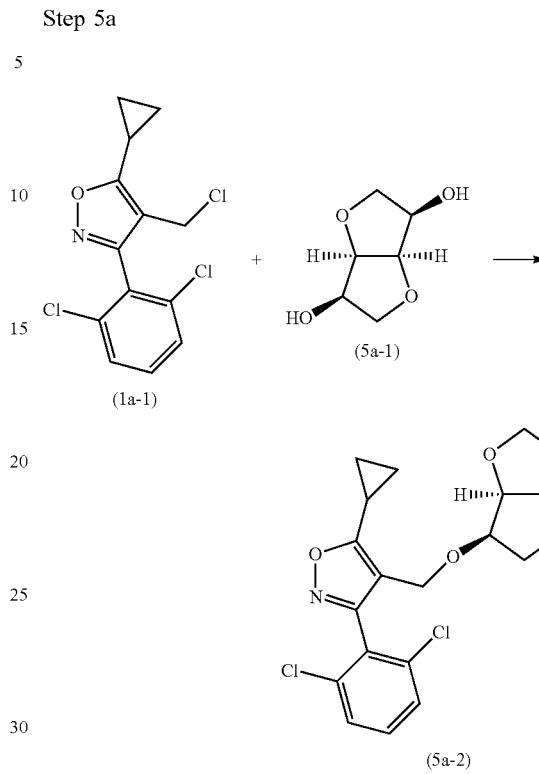

To (3R,3aR,6R,6aR)-hexahydrofuro[3,2-b]furan-3,6-diol compound 5a-1 (isomannide, 5a-1) (1.008 g, 6.90 mmol) in DMSO (18 ml) was added potassium tert-butoxide (1.161 g g, 10.35 mmol) and DMA (6 ml). The resulting cloudy mixture was heated up to 60° C., stirred for 15 min. 4-(chloromethyl)-5-cyclopropyl-3-(2,6-dichlorophenyl) isoxazole (1a-1) (2.087 g, 6.90 mmol) was added in one portion and the mixture was stirred at 60° C. for 2 h. The mixture was diluted with EtOAc/NaHCO₃ solution and the organic layer was separated, washed with water, brine, dried (Na₂SO₄), filtered and concentrated. The residue was purified by CombiFlash purification eluting with 0% to 90% acetone/hexane to give (3R,3aR,6R,6aR)-6-((5-cyclopropyl-3-(2,6-dichlorophenyl)isoxazol-4-yl)methoxy)hexahydrofuro[3,2-b]furan-3-ol (5a-2) (1.89 g, 66.5%). LC/MS observed [M+H], 412.06; 1H NMR (400 MHz, Chloroform-d) δ 7.42-7.23 (m, 3H), 4.51 (d, J=12.4 Hz, 1H), 4.42-4.31 (m, 2H), 4.26 (d, J=12.5 Hz, 1H), 4.14 (s, 1H), 3.96-3.73 (m, 3H), 3.47 (dt, J=9.3, 7.0 Hz, 2H), 2.64 (s, 1H), 2.17-2.08 (m, 1H), 1.29-1.15 (m, 2H), 1.15-0.99 (m, 2H).

Step 5b

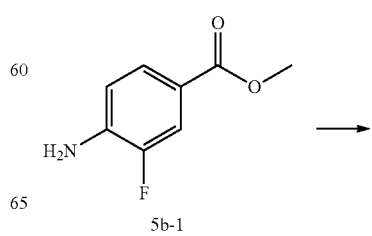

-continued

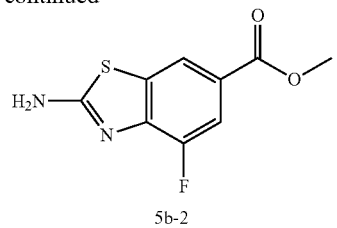

5b-2

To methyl 4-amino-3-fluorobenzoate (5b-1) (45 g, 266 mmol) and sodium thiocyanate (86 g, 1064 mmol) in acetic acid (350 ml) at 0° C. was added bromine (13.57 ml, 263 mmol) in AcOH (100 ml) via additional funnel over 1 h, and the mixture was warmed up to RT and stirred for 2 days. The mixture was filtered to collect the first crop of solid, washed with water and dried in the open air to give methyl 2-amino-4-fluorobenzo[d]thiazole-6-carboxylate (5b-2) (65 g) as yellow solid. $^1$H NMR (400 MHz, DMSO-d6) δ 8.28-8.02 (m, 1H), 7.58 (dd, J=11.5, 1.6 Hz, 1H), 3.84 (s, 3H).

Step 5c

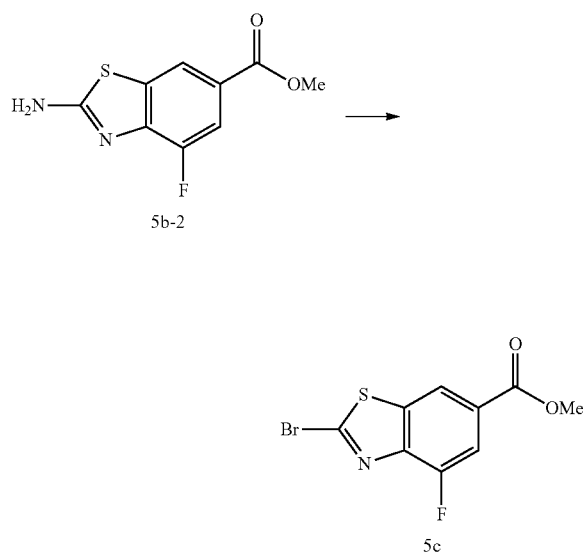

To copper(II) bromide (29.6 g, 133 mmol) and methyl 2-amino-4-fluorobenzo[d]thiazole-6-carboxylate (5b-2) (20 g, 88 mmol) in acetonitrile (300 ml) with water bath was slowly added tert-butyl nitrite (12.85 ml, 97 mmol) over 10 min. The resulting mixture was stirred for 2 days and diluted with MTBE and water, stirred for 10 min, a lot of precipitate formed. The mixture was filtered through celite and organic layer was separated, washed with water (3×), brine (2×), dried, filtered, concentrated. The residue was purified by CombiFlash eluting with 0 to 25% acetone/Hexane. The fractions containing product was combined and concentrated then triturated with hexane. The white solid was collected via filtration to give methyl 2-bromo-4-fluorobenzo[d]thiazole-6-carboxylate (5c) (5.43 g). $^1$H NMR (400 MHz, Chloroform-d) δ 8.34 (dd, J=1.4, 0.6 Hz, 1H), 7.85 (dd, J=10.5, 1.4 Hz, 1H), 3.97 (s, 3H), 1.56 (s, 9H).

Step 5d

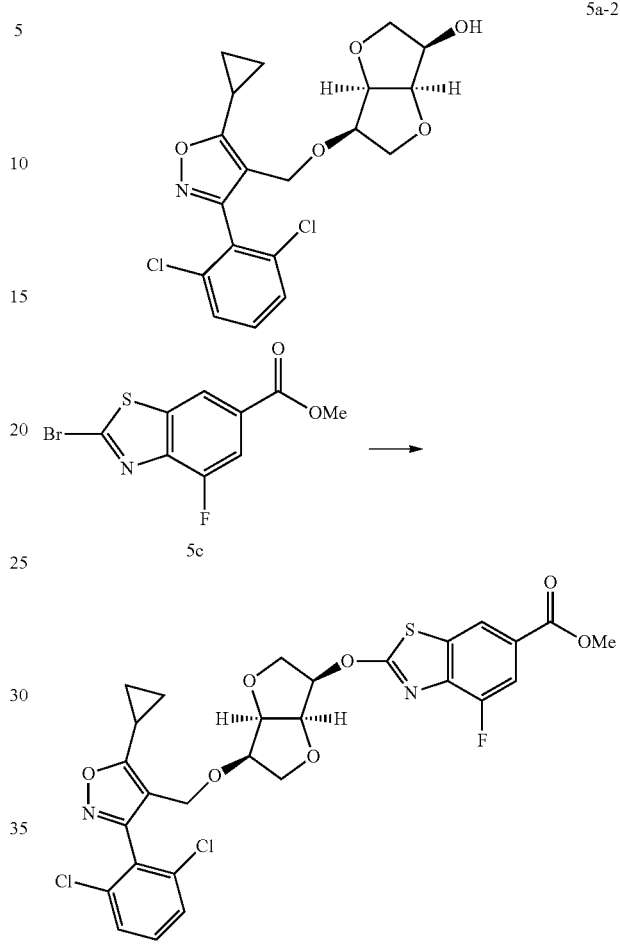

To (3R,3aR,6R,6aR)-6-((5-cyclopropyl-3-(2,6-dichlorophenyl)isoxazol-4-yl)methoxy)hexa-hydrofuro[3,2-b]furan-3-ol (5a-2) (33 mg, 0.080 mmol) and methyl 2-bromo-4-fluorobenzo[d]thiazole-6-carboxylate (5c) (27.9 mg, 0.096 mmol) in DMA (0.8 ml) and acetonitrile (0.800 ml) was added cesium carbonate (78 mg, 0.240 mmol). The mixture was heated up at 90° C. for 16 h and then diluted with EtOAc, washed with water, brine, dried, filtered and concentrated. The mixture was purified by CombiFlash eluting with 0 to 50% EtOAc/hexane to give methyl 2-(((3R,3aR,6R,6aR)-6-((5-cyclopropyl-3-(2,6-dichlorophenyl)isoxazol-4-yl)methoxy)hexahydrofuro[3,2-b]furan-3-yl)oxy)-4-fluorobenzo[d]thiazole-6-carboxylate (5d) (20 mg, 40%). LC/MS observed [M+H], 621.08; $^1$H NMR (400 MHz, Chloroform-d) δ 8.16 (d, J=1.5 Hz, 1H), 7.76 (dd, J=10.9, 1.5 Hz, 1H), 7.51-7.32 (m, 3H), 5.62 (td, J=6.4, 5.5 Hz, 1H), 4.94 (t, J=5.2 Hz, 1H), 4.58 (d, J=12.5 Hz, 1H), 4.48 (t, J=5.0 Hz, 1H), 4.34 (d, J=12.4 Hz, 1H), 4.13 (dd, J=9.7, 6.3 Hz, 1H), 4.07-3.90 (m, 2H), 3.94 (s, 3H), 3.84 (dd, J=8.7, 6.7 Hz, 1H), 3.57 (t, J=8.5 Hz, 1H), 2.32-2.20 (m, 1H), 1.35-1.24 (m, 2H), 1.22-1.09 (m, 2H).

Step 5e

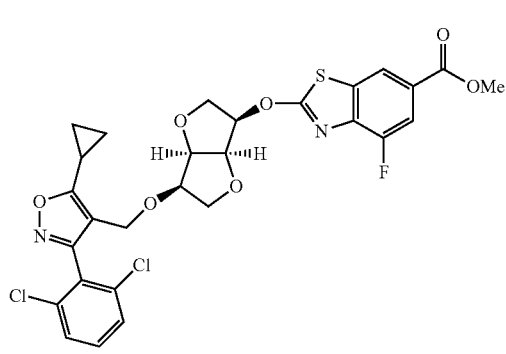

5d

Example 6

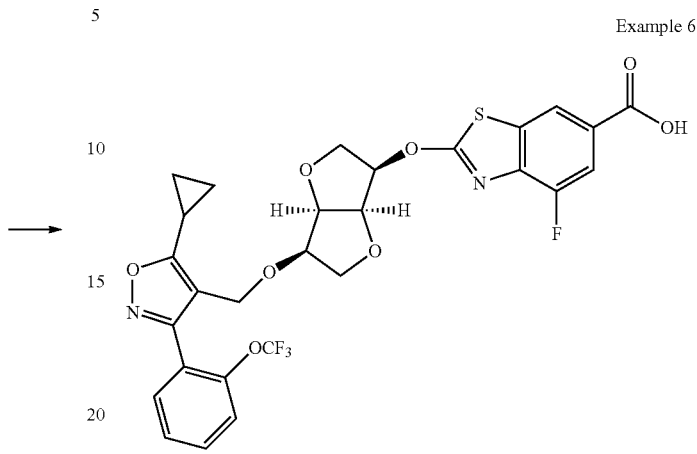

Example 6

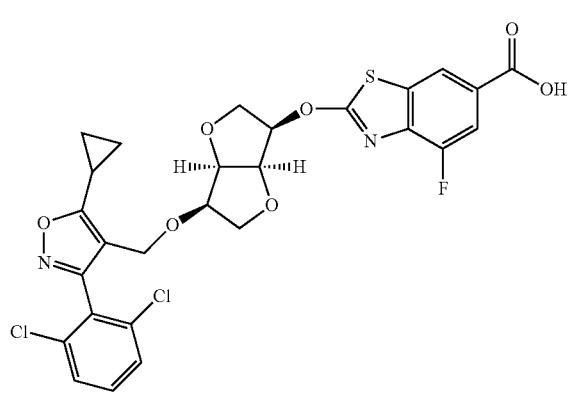

Example 5

To methyl 2-(((3R,3aR,6R,6aR)-6-((5-cyclopropyl-3-(2,6-dichlorophenyl)isoxazol-4-yl)methoxy)hexahydrofuro[3,2-b]furan-3-yl)oxy)-4-fluorobenzo[d]thiazole-6-carboxylate (5d) (20 mg, 0.032 mmol) in tetrahydrofuran (1 ml) was added LiOH (1 M) (0.064 ml, 0.064 mmol) and the mixture was stirred at RT for 16 h. The mixture was diluted with EtOAc, adjust pH to ~5 with 1N HCl, the organic layer was separated, washed with water, brine, dried, filtered and concentrated. The residue was purified by CombiFlash eluting with 0% to 60% acetone/hexane to give 2-(((3R,3aR,6R,6aR)-6-((5-cyclopropyl-3-(2,6-dichlorophenyl)isoxazol-4-yl)methoxy)hexahydrofuro[3,2-b]furan-3-yl)oxy)-4-fluorobenzo[d]thiazole-6-carboxylic acid (Example 5) (11.3 mg, 0.019 mmol, 57.8% yield). LC/MS observed [M+H], 607.06; $^1$H NMR (400 MHz, Chloroform-d) δ 8.19 (d, J=1.4 Hz, 1H), 7.79 (dd, J=10.7, 1.5 Hz, 1H), 7.49-7.39 (m, 2H), 7.39-7.31 (m, 1H), 5.63 (q, J=6.2 Hz, 1H), 4.97 (t, J=5.2 Hz, 1H), 4.58 (d, J=12.5 Hz, 1H), 4.49 (t, J=5.0 Hz, 1H), 4.35 (d, J=12.5 Hz, 1H), 4.24-4.09 (m, 1H), 4.06-3.94 (m, 2H), 3.85 (dd, J=8.7, 6.8 Hz, 1H), 3.58 (t, J=8.5 Hz, 1H), 2.29-2.19 (m, 1H), 1.36-1.27 (m, 2H), 1.20-1.09 (m, 2H).

Example 6 was synthesized by following the similar experimental procedure as for Example 5. LC/MS observed [M+H], 623.12; $^1$H NMR (400 MHz, Chloroform-d) δ 8.21 (d, J=1.5 Hz, 1H), 7.80 (dd, J=10.7, 1.5 Hz, 1H), 7.63-7.47 (m, 2H), 7.47-7.36 (m, 2H), 5.65 (q, J=6.1 Hz, 1H), 4.97 (t, J=5.2 Hz, 1H), 4.66 (d, J=11.9 Hz, 1H), 4.51 (t, J=5.0 Hz, 1H), 4.38 (d, J=11.8 Hz, 1H), 4.26-4.07 (m, 1H), 4.07-3.92 (m, 2H), 3.84 (dd, J=8.7, 6.7 Hz, 1H), 3.60 (t, J=8.6 Hz, 1H), 2.22 (tt, J=8.5, 5.1 Hz, 1H), 1.33-1.22 (m, 2H), 1.13 (dd, J=8.2, 3.2 Hz, 2H).

Example 7

Step 7a

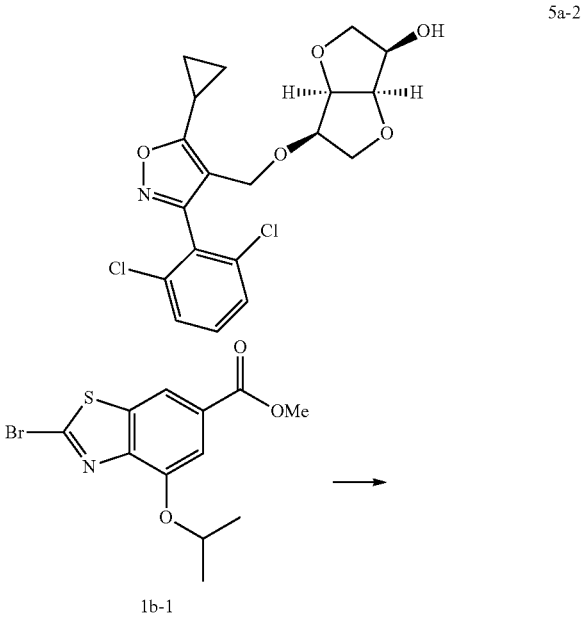

5a-2

1b-1

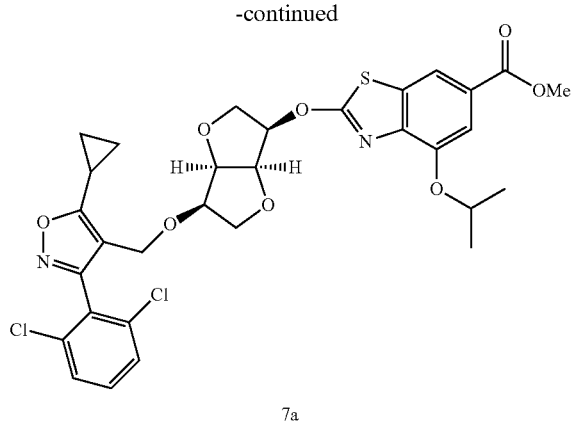

7a

Method A:

To (3R,3aR,6R,6aR)-6-((5-cyclopropyl-3-(2,6-dichlorophenyl)isoxazol-4-yl)methoxy)hexa-hydrofuro[3,2-b]furan-3-ol (5a-2) (41 mg, 0.099 mmol) and methyl 2-bromo-4-isopropoxybenzo[d] thiazole-6-carboxylate (1b-1) (49.3 mg, 0.149 mmol) in DMF (2 ml) was added sodium hydride (5.97 mg, 0.149 mmol) and the mixture was stirred at RT for 16 h. The mixture was diluted with EtOAc, washed with NaHCO$_3$ solution, water, brine, dried (Na$_2$SO$_4$), filtered and concentrated. The residue was purified by CombiFlash eluting with hexane to 50% EA/hexane to give methyl 2-(((3R,3aR,6R,6aR)-6-((5-cyclopropyl-3-(2,6-dichlorophenyl)-isoxazol-4-yl)methoxy)hexahydrofuro[3,2-b]furan-3-yl)oxy)-4-isopropoxybenzo[d]thiazole-6-carboxylate (7a) (22 mg, 33% yield). LC/MS observed [M+H], 661.13.

Method B:

To (3R,3aR,6R,6aR)-6-((5-cyclopropyl-3-(2,6-dichlorophenyl)isoxazol-4-yl)methoxy)hexa-hydrofuro[3,2-b]furan-3-ol (5a-2) (313 mg, 0.759 mmol) and methyl 2-bromo-4-isopropoxybenzo [d]thiazole-6-carboxylate (1b-1) (376 mg, 1.139 mmol) in DMA (3 ml) and acetonitrile (3.00 ml) was added cesium carbonate (742 mg, 2.278 mmol). The resulting mixture was stirred at 90° C. for 20 h. The mixture was diluted with EA, washed with 1N HCl, water, brine, dried, filtered and concentrated. The residue was purified by CombiFlash eluting with a gradient of 0% to 80% ethyl acetate/hexane to give methyl 2-(((3R,3aR,6R,6aR)-6-((5-cyclopropyl-3-(2,6-dichlorophenyl)isoxazol-4-yl)methoxy)hexahydrofuro[3,2-b]furan-3-yl)oxy)-4-isopropoxybenzo[d]thiazole-6-carboxylate (7a) (402 mg, 0.608 mmol, 80% yield). LC/MS observed [M+H], 661.13; $^1$H NMR (500 MHz, Chloroform-d) δ 8.00 (d, J=1.5 Hz, 1H), 7.58 (d, J=1.5 Hz, 1H), 7.50-7.41 (m, 2H), 7.41-7.32 (m, 1H), 5.65 (td, J=6.7, 5.4 Hz, 1H), 4.91 (t, J=5.1 Hz, 1H), 4.84 (hept, J=6.1 Hz, 1H), 4.60 (d, J=12.5 Hz, 1H), 4.51 (t, J=4.9 Hz, 1H), 4.37 (d, J=12.5 Hz, 1H), 4.19 (dd, J=9.6, 6.5 Hz, 1H), 3.99 (ddd, J=8.2, 6.8, 5.0 Hz, 1H), 3.94 (s, 3H), 3.87 (dd, J=8.7, 6.8 Hz, 2H), 3.60 (t, J=8.5 Hz, 1H), 2.32-2.15 (m, 1H), 1.44 (dd, J=6.1, 3.0 Hz, 6H), 1.39-1.24 (m, 2H), 1.24-1.09 (m, 2H).

Step 7b

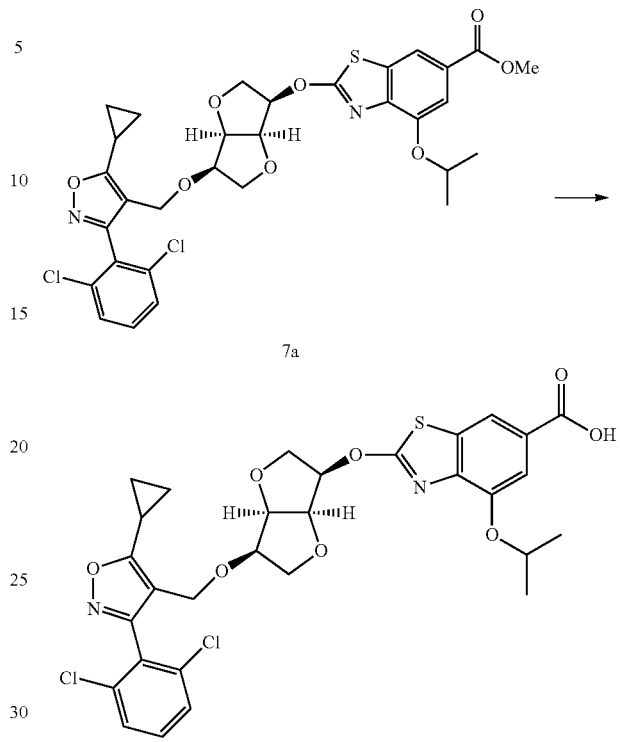

Example 7

Method A:

To methyl 2-(((3R,3aR,6R,6aR)-6-((5-cyclopropyl-3-(2,6-dichlorophenyl)isoxazol-4-yl)methoxy)hexahydrofuro[3,2-b]furan-3-yl)oxy)-4-isopropoxybenzo[d]thiazole-6-carboxylate (7a) (400 mg, 0.605 mmol) in Tetrahydrofuran (8 ml) was added potassium trimethylsilanolate (172 mg, 1.209 mmol) and the mixture was heated up to 40° C. for 2 h. The mixture was diluted with EtOAc/water, the organic layer was washed with water. The aq. layer was combined, acidified with 1N HCl and then extracted with EtOAc (3×). The organic layer was washed with brine, dried, filtered and concentrated. The residue was purified by CombiFlash eluting with a gradient of 0% to 60% (10% MeOH in ethyl acetate)/hexane to give 2-(((3R,3aR,6R,6aR)-6-((5-cyclopropyl-3-(2,6-dichlorophenyl)isoxazol-4-yl)methoxy)hexahydrofuro[3,2-b]furan-3-yl)oxy)-4-isopropoxybenzo[d]thiazole-6-carboxylic acid (Example 7) (193 mg, 0.298 mmol, 49.3% yield). LC/MS observed [M+H], 647.11; $^1$H NMR (400 MHz, Chloroform-d) δ 7.96 (d, J=1.5 Hz, 1H), 7.51 (d, J=1.5 Hz, 1H), 7.39-7.21 (m, 3H), 5.56 (td, J=6.7, 5.4 Hz, 1H), 4.82 (t, J=5.1 Hz, 1H), 4.74 (hept, J=6.1 Hz, 1H), 4.49 (d, J=12.5 Hz, 1H), 4.41 (t, J=4.9 Hz, 1H), 4.26 (d, J=12.5 Hz, 1H), 4.09 (dd, J=9.6, 6.5 Hz, 1H), 3.94-3.70 (m, 3H), 3.50 (t, J=8.5 Hz, 1H), 2.17-2.08 (m, 1H), 1.35 (dd, J=6.1, 2.0 Hz, 6H), 1.24-1.16 (m, 2H), 1.14-0.97 (m, 2H).

Method B:

To methyl 2-(((3R,3aR,6R,6aR)-6-((5-cyclopropyl-3-(2,6-dichlorophenyl)isoxazol-4-yl)methoxy)hexahydrofuro[3,2-b]furan-3-yl)oxy)-4-isopropoxybenzo[d]thiazole-6-carboxylic (7a) (278 g, 0.420 mmol) in tetrahydrofuran (2 ml) was added LiOH (0.504 ml, 0.504 mmol) and the mixture was stirred at RT for 28 h. The mixture was washed with MTBE, and the aq. layer was separated, acidified and extracted with EtOAc, the organic layer was separated and washed with water, brine, dried, filtered and concentrated.

The residue was purified by CombiFlash eluting with a gradient of 0% to 35% acetone-hexane to give 2-(((3R,3aR,6R,6aR)-6-((5-cyclopropyl-3-(2,6-dichlorophenyl)isoxazol-4-yl)methoxy)hexahydrofuro[3,2-b]furan-3-yl)oxy)-4-isopropoxybenzo[d]thiazole-6-carboxylic acid (Example 7) (203 mg, 74.6% yield).

Example 8

Step 8a

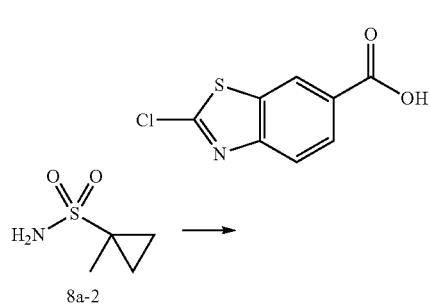

methylene)amino)-N,N-dimethylpropan-1-amine hydrochloride (1.974 g, 10.30 mmol) and DMAP (2.52 g, 20.60 mmol). The resulting mixture was stirred at RT for 16 h and then concentrated under reduced pressure. The residue was diluted with EtOAc, washed with 1N HCl, water, brine, dried, filtered and concentrated to give 2-chloro-N-((1-methylcyclopropyl)sulfonyl)benzo[d]thiazole-6-carboxamide (8a-3) (1.085 g, 35%).

Step 8b

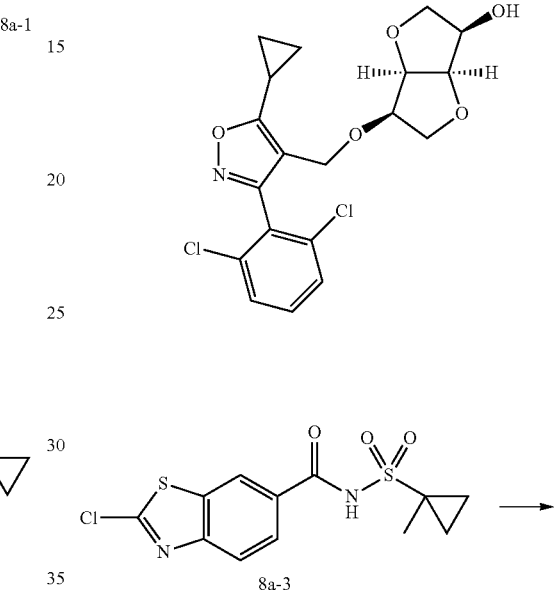

Method A:

To a suspension of 2-chlorobenzo[d]thiazole-6-carboxylic acid (8a-1) (10.7 g, 50.1 mmol) in DCM (180 ml) was added DMF (0.194 ml, 2.504 mmol). To the resulting suspension was added oxalyl dichloride (4.72 ml, 55.1 mmol) dropwise at 0° C., and the resulting mixture was stirred at RT for 20 h. Another portion of oxalyl chloride (0.94 ml) was added and the suspension became a slightly cloudy solution after 6 h. The mixture was concentrated and chased with DCM to give a light yellow solid.

To this solid was added DCM (180 ml), DMAP (0.306 g, 2.504 mmol) and 1-methylcyclopropane-1-sulfonamide (8a-2) (7.11 g, 52.6 mmol) at 0° C. Triethylamine (10.47 ml, 75 mmol) was added dropwise at 0° C. and the suspension turn into a light yellow clear solution. The resulting mixture was stirred at RT for 14 h and then concentrated. The residue was diluted with EtOAc, washed with 1N HCl, water, brine, dried and concentrated to give crude product as light yellow solid. The crude product was purified by crystallization from MTBE to give 2-chloro-N-((1-methylcyclopropyl)sulfonyl)benzo[d]thiazole-6-carboxamide (8a-3) (11.34 g, 68.4%).
$^1$H NMR (400 MHz, Chloroform-d) δ 8.46 (s, 1H), 8.38 (d, J=1.8 Hz, 1H), 8.06 (d, J=8.5 Hz, 1H), 7.92 (dd, J=8.6, 1.9 Hz, 1H), 1.96-1.77 (m, 2H), 1.62 (s, 3H), 1.07-0.96 (m, 2H).
Method B:

To 3-(((ethylimino)methylene)amino)-N,N-dimethylpropan-1-amine hydrochloride (8a-1) (1.974 g, 10.30 mmol) and 1-methylcyclopropane-1-sulfonamide (8a-2) (1.266 g, 9.36 mmol) in DCM (20 ml) was added 3-(((ethylimino)

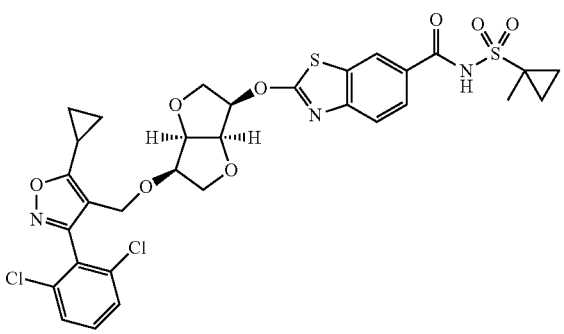

Example 8

To (3R,3aR,6R,6aR)-6-((5-cyclopropyl-3-(2,6-dichlorophenyl)isoxazol-4-yl)methoxy)hexa-hydrofuro[3,2-b]furan-3-ol (5a-2) (29 mg, 0.070 mmol), 2-chloro-N-((1-methylcyclopropyl)-sulfonyl) benzo[d]thiazole-6-carboxamide (8a-3) (34.9 mg, 0.106 mmol) in DMA (1 ml) was added cesium carbonate (68.8 mg, 0.211 mmol) and the mixture was run in microwave reactor at 120° C. for 30 min, and then 140° C. for 1 h. The mixture was filtered through celite and purified by HPLC to give 2-(((3R,3aR,6R,6aR)-6-((5-cyclopropyl-3-(2,6-dichlorophenyl)isoxazol-4-yl)methoxy)hexa hydrofuro[3,2-b]furan-3-yl)oxy)-N-((1-methylcyclopropyl) sulfonyl)benzo-[d]thiazole-6-carboxamide (Example 8) (38 mg, 76%). LC/MS observed [M+H], 706.10.

Example 9

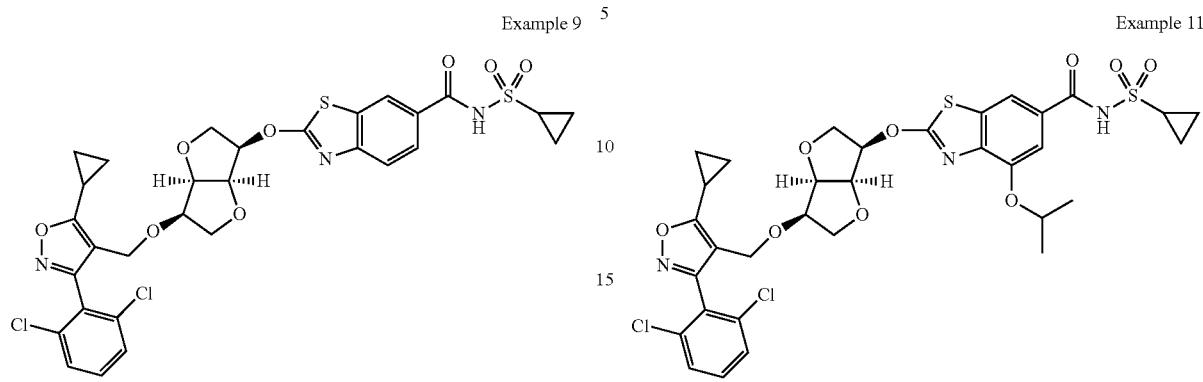

Example 9

Example 9 was synthesized by following the similar experimental procedure as for Example 8. LC/MS observed [M+H], 692.09; $^1$H NMR (400 MHz, Chloroform-d) δ 9.20 (s, 1H), 8.08 (d, J=1.8 Hz, 1H), 7.71 (dd, J=8.5, 1.9 Hz, 1H), 7.53 (d, J=8.5 Hz, 1H), 7.39-7.20 (m, 3H), 5.46 (q, J=6.1 Hz, 1H), 4.87 (t, J=5.2 Hz, 1H), 4.50 (d, J=12.5 Hz, 1H), 4.42 (t, J=5.0 Hz, 1H), 4.27 (d, J=12.5 Hz, 1H), 4.04 (dd, J=9.8, 6.2 Hz, 1H), 3.98-3.85 (m, 2H), 3.78 (dd, J=8.7, 6.8 Hz, 1H), 3.51 (t, J=8.6 Hz, 1H), 3.08 (tt, J=8.1, 4.8 Hz, 1H), 2.13 (tt, J=8.5, 5.1 Hz, 1H), 1.34 (dt, J=7.5, 3.5 Hz, 2H), 1.20 (ddd, J=6.9, 5.2, 3.8 Hz, 2H), 1.12-0.90 (m, 4H).

Example 10

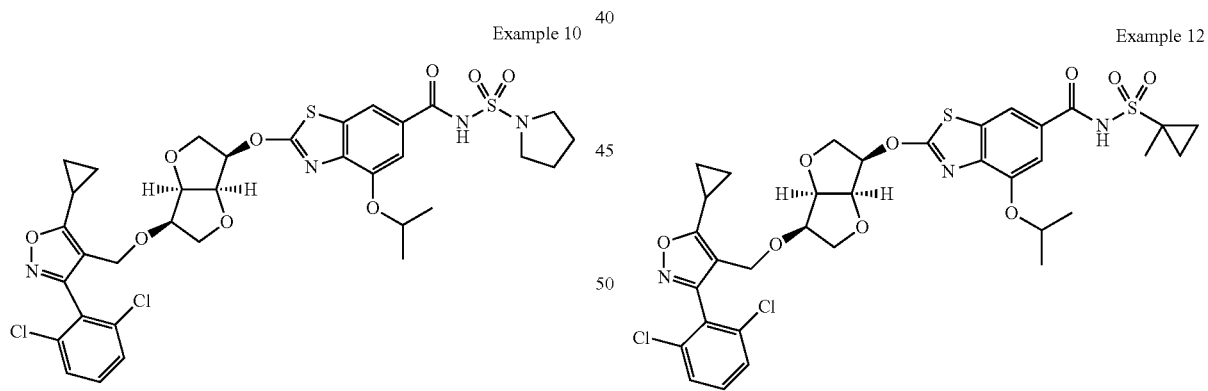

Example 10

Example 10 was synthesized by following the similar experimental procedure in step 3a as for Example 3.

LC/MS observed [M+H], 779.17; $^1$H NMR (400 MHz, Chloroform-d) δ 8.97 (s, 1H), 7.90-7.66 (m, 1H), 7.52-7.33 (m, 4H), 5.60 (q, J=5.9 Hz, 1H), 4.94 (t, J=5.2 Hz, 1H), 4.86 (p, J=6.0 Hz, 1H), 4.59 (d, J=12.5 Hz, 1H), 4.51 (t, J=5.0 Hz, 1H), 4.37 (d, J=12.4 Hz, 1H), 4.15 (dd, J=9.9, 6.1 Hz, 1H), 4.07-3.94 (m, 2H), 3.87 (dd, J=8.7, 6.8 Hz, 1H), 3.71-3.48 (m, 4H), 2.32-2.18 (m, 2H), 2.00-1.89 (m, 3H), 1.43 (d, J=6.0 Hz, 6H), 1.36-1.23 (m, 2H), 1.24-1.13 (m, 2H), 0.95-0.81 (m, 1H).

Example 11

Example 11

Example 11 was synthesized by following the similar experimental procedure in step 3a as for Example 3. LC/MS observed [M+H], 750.14; $^1$H NMR (400 MHz, Chloroform-d) δ 7.78 (d, J=1.6 Hz, 1H), 7.49-7.30 (m, 4H), 5.61 (q, J=6.0 Hz, 1H), 4.94 (t, J=5.2 Hz, 1H), 4.84 (p, J=6.1 Hz, 1H), 4.59 (d, J=12.5 Hz, 1H), 4.51 (t, J=5.0 Hz, 1H), 4.36 (d, J=12.5 Hz, 1H), 4.14 (dd, J=9.8, 6.2 Hz, 1H), 4.06-3.93 (m, 2H), 3.87 (dd, J=8.7, 6.8 Hz, 1H), 3.59 (t, J=8.6 Hz, 1H), 3.15 (tt, J=8.1, 4.8 Hz, 1H), 2.36-2.12 (m, 2H), 1.51-1.44 (m, 2H), 1.42 (d, J=6.1 Hz, 6H), 1.36-1.26 (m, 2H), 1.26-1.04 (m, 4H).

Example 12

Example 12

Example 12 was synthesized by following the similar experimental procedure in step 3a as for Example 3. LC/MS observed [M+H], 764.15; $^1$H NMR (400 MHz, Chloroform-d) δ 8.89 (s, 1H), 7.80 (d, J=1.6 Hz, 1H), 7.51-7.33 (m, 4H), 5.61 (q, J=6.1 Hz, 1H), 4.94 (t, J=5.2 Hz, 1H), 4.85 (h, J=6.1 Hz, 1H), 4.60 (d, J=12.5 Hz, 1H), 4.52 (t, J=5.0 Hz, 1H), 4.37 (d, J=12.5 Hz, 1H), 4.15 (dd, J=9.8, 6.2 Hz, 1H), 4.08-3.95 (m, 2H), 3.88 (dd, J=8.7, 6.8 Hz, 1H), 3.60 (t, J=8.6 Hz, 1H), 2.31-2.12 (m, 4H), 1.92-1.77 (m, 2H), 1.43 (d, J=6.1 Hz, 6H), 1.38-1.26 (m, 2H), 1.26-1.12 (m, 2H), 1.12-0.94 (m, 2H).

Example 13

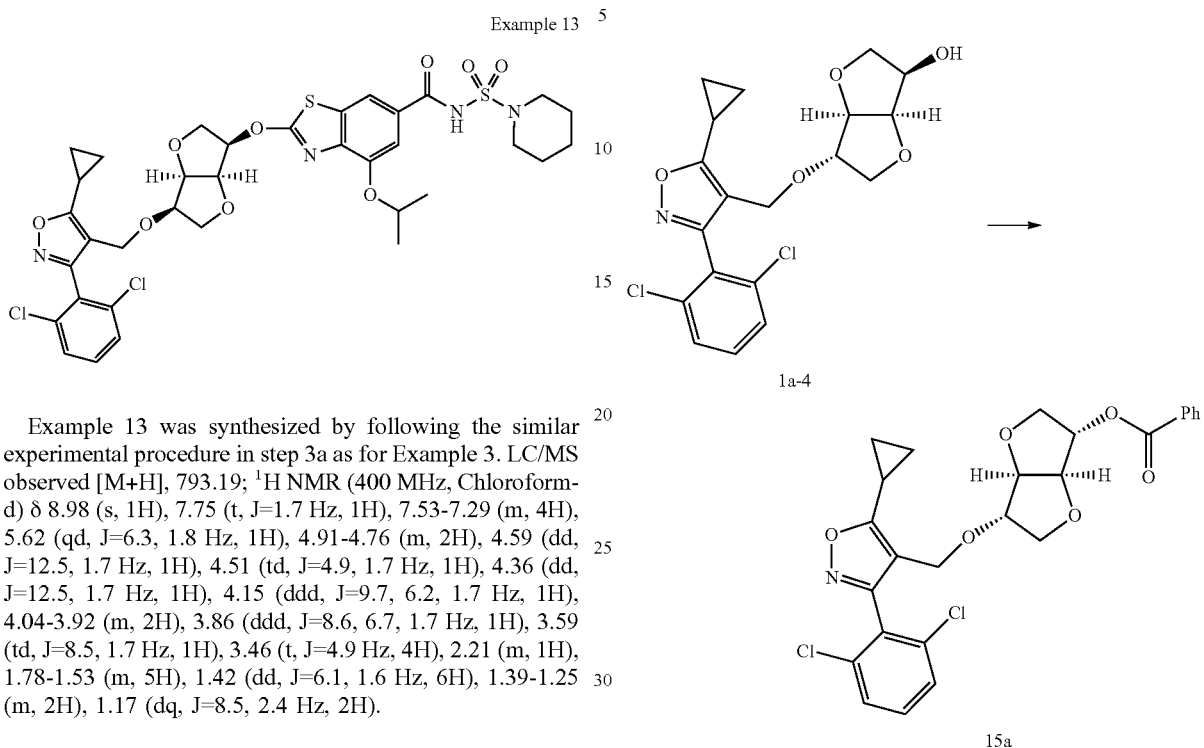

Example 13

Example 13 was synthesized by following the similar experimental procedure in step 3a as for Example 3. LC/MS observed [M+H], 793.19; $^1$H NMR (400 MHz, Chloroform-d) δ 8.98 (s, 1H), 7.75 (t, J=1.7 Hz, 1H), 7.53-7.29 (m, 4H), 5.62 (qd, J=6.3, 1.8 Hz, 1H), 4.91-4.76 (m, 2H), 4.59 (dd, J=12.5, 1.7 Hz, 1H), 4.51 (td, J=4.9, 1.7 Hz, 1H), 4.36 (dd, J=12.5, 1.7 Hz, 1H), 4.15 (ddd, J=9.7, 6.2, 1.7 Hz, 1H), 4.04-3.92 (m, 2H), 3.86 (ddd, J=8.6, 6.7, 1.7 Hz, 1H), 3.59 (td, J=8.5, 1.7 Hz, 1H), 3.46 (t, J=4.9 Hz, 4H), 2.21 (m, 1H), 1.78-1.53 (m, 5H), 1.42 (dd, J=6.1, 1.6 Hz, 6H), 1.39-1.25 (m, 2H), 1.17 (dq, J=8.5, 2.4 Hz, 2H).

Example 14

Example 14

Example 14 was synthesized by following the similar experimental procedures as for Example 7. LC/MS observed [M+H], 589.06; $^1$H NMR (400 MHz, Chloroform-d) δ 8.40 (d, J=1.6 Hz, 1H), 8.08 (dd, J=8.5, 1.7 Hz, 1H), 7.69 (d, J=8.5 Hz, 1H), 7.47-7.31 (m, 3H), 5.56 (q, J=6.3 Hz, 1H), 4.94 (t, J=5.2 Hz, 1H), 4.58 (d, J=12.5 Hz, 1H), 4.50 (t, J=5.0 Hz, 1H), 4.35 (d, J=12.4 Hz, 1H), 4.14 (dd, J=9.7, 6.3 Hz, 1H), 4.06-3.93 (m, 2H), 3.86 (dd, J=8.7, 6.8 Hz, 1H), 3.58 (t, J=8.5 Hz, 1H), 2.31-2.09 (m, 1H), 1.33-1.24 (m, 3H), 1.18-1.06 (m, 2H).

Example 15

Step 15a

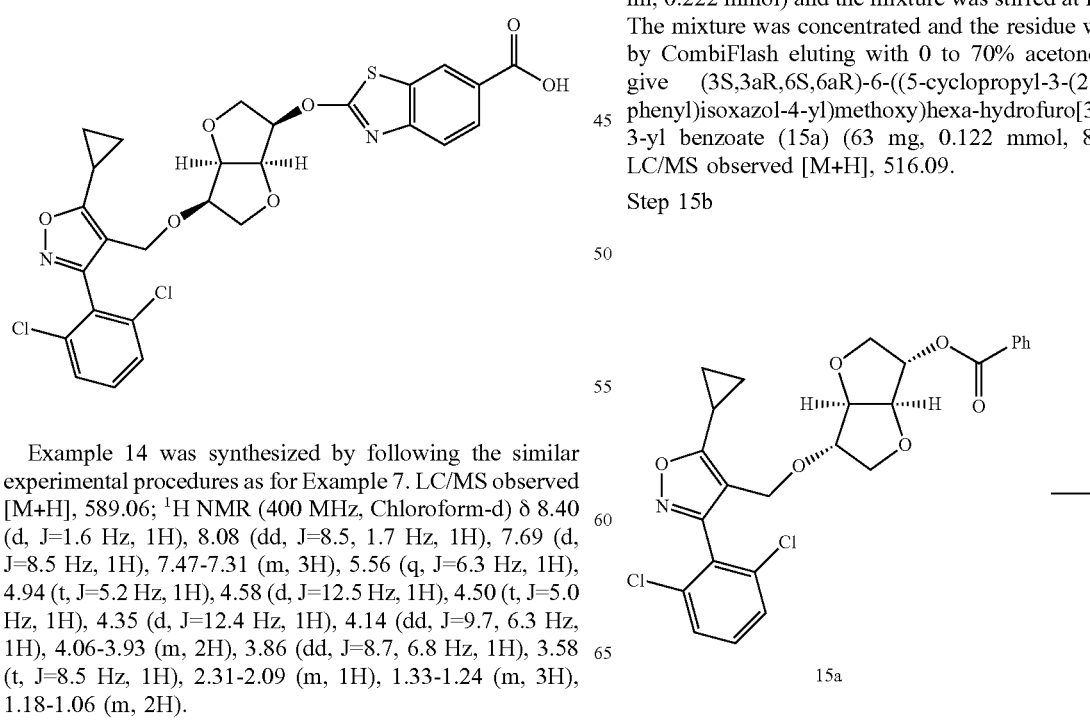

To (3R,3aR,6R,6aR)-6-((5-cyclopropyl-3-(2,6-dichlorophenyl)isoxazol-4-yl)methoxy)hexa-hydrofuro[3,2-b]furan-3-ol (1a-4) (61 mg, 0.148 mmol), benzoic acid (27.1 mg, 0.222 mmol) and triphenylphosphine (58.2 mg, 0.222 mmol) in tetrahydrofuran (1.5 ml) was added DIAD (0.043 ml, 0.222 mmol) and the mixture was stirred at RT for 20 h. The mixture was concentrated and the residue was purified by CombiFlash eluting with 0 to 70% acetone/hexane to give (3S,3aR,6S,6aR)-6-((5-cyclopropyl-3-(2,6-dichlorophenyl)isoxazol-4-yl)methoxy)hexa-hydrofuro[3,2-b]furan-3-yl benzoate (15a) (63 mg, 0.122 mmol, 82% yield). LC/MS observed [M+H], 516.09.

Step 15b

-continued

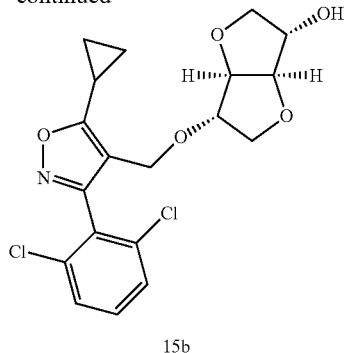

15b

To (3S,3aR,6S,6aR)-6-((5-cyclopropyl-3-(2,6-dichlorophenyl)isoxazol-4-yl)methoxy)hexa-hydrofuro[3,2-b]furan-3-yl benzoate (15a) (63 mg, 0.122 mmol) in tetrahydrofuran (1 ml) and MeOH (1 ml) was added LiOH (0.183 ml, 0.183 mmol, 1M) and the mixture was stirred at RT for 3 h. The mixture was diluted with EtOAc, washed with water, brine, dried (Na$_2$SO$_4$), filtered and concentrated. The residue was purified by CombiFlash eluting with 0 to 70% acetone-hexane to give (3S,3aR,6S,6aR)-6-((5-cyclopropyl-3-(2,6-dichlorophenyl)isoxazol-4-yl)methoxy)hexa-hydrofuro[3,2-b]furan-3-ol (15b) (29 mg, 0.070 mmol, 57.7% yield). $^1$H NMR (400 MHz, Chloroform-d) δ 7.50-7.30 (m, 3H), 4.48-4.41 (m, 1H), 4.37 (d, J=5.5 Hz, 3H), 4.31-4.21 (m, 1H), 3.94-3.85 (m, 1H), 3.84-3.74 (m, 2H), 3.68 (qd, J=10.1, 3.0 Hz, 2H), 2.17-2.09 (m, 1H), 1.28 (ddt, J=7.1, 5.3, 3.0 Hz, 2H), 1.22-1.03 (m, 2H).

Step 15c

To (3S,3aR,6S,6aR)-6-((5-cyclopropyl-3-(2,6-dichlorophenyl)isoxazol-4-yl)methoxy)hexa-hydrofuro[3,2-b]furan-3-ol (15b) (29 mg, 0.070 mmol) and methyl 2-bromo-4-isopropoxybenzo[d]thiazole-6-carboxylate (1b-1) (34.8 mg, 0.106 mmol) in DMA (0.8 ml) and acetonitrile (0.800 ml) was added cesium carbonate (34.4 mg, 0.106 mmol). The resulting mixture was stirred at in microwave reactor at 120° C. for 2.5 h. The mixture was diluted with EtOAc, washed with water, brine, dried (Na$_2$SO$_4$), filtered and concentrated. The residue was purified by CombiFlash eluting with a gradient of 0% to 45% acetone-hexane to give methyl 2-(((3S,3aR,6S,6aR)-6-((5-cyclopropyl-3-(2,6-dichlorophenyl)isoxazol-4-yl)methoxy)-hexahydrofuro[3,2-b]furan-3-yl)oxy)-4-isopropoxybenzo[d]thiazole-6-carboxylate (15c) (25 mg, 0.038 mmol, 53.7% yield). LC/MS observed [M+H], 661.13.

Step 15d

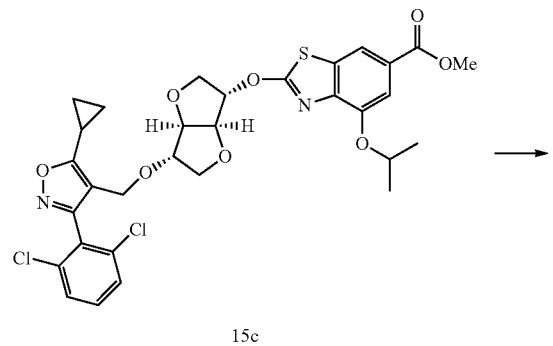

15c

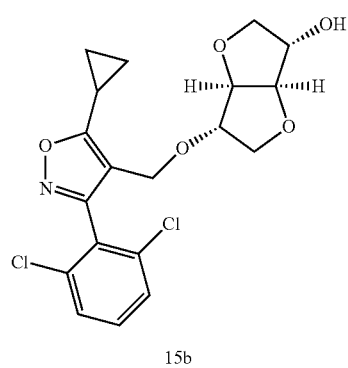

15b

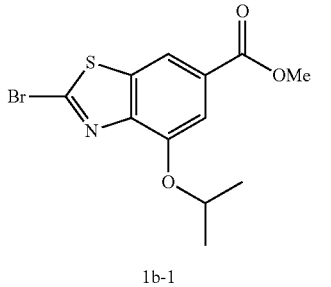

1b-1

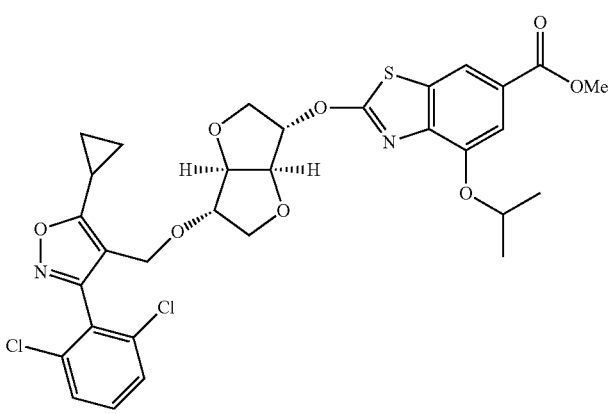

15c

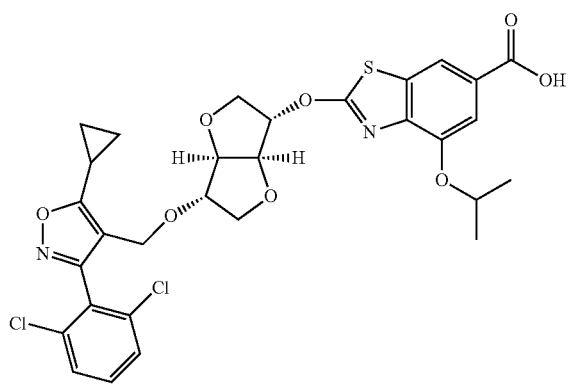

Example 15

To methyl 2-(((3S,3aR,6S,6aR)-6-((5-cyclopropyl-3-(2,6-dichlorophenyl)isoxazol-4-yl)methoxy)hexahydrofuro[3,2-b]furan-3-yl)oxy)-4-isopropoxybenzo[d]thiazole-6-carboxylate (15c) (25 mg, 0.038 mmol) in tetrahydrofuran (1 ml) was added LiOH (0.057 ml, 0.057 mmol, 1M) and the mixture was stirred at RT for 24 h. The mixture was diluted with EA/1N HCl, the organic layer was separated and washed with water, brine, dried, filtered and concentrated. The residue was purified by CombiFlash eluting with 0 to 70% acetone/hexane to give 2-(((3S,3aR,6S,6aR)-6-((5-cyclopropyl-3-(2,6-dichlorophenyl)isoxazol-4-yl)methoxy)-hexahydrofuro[3,2-b]furan-3-yl)oxy)-4-isopropoxybenzo[d]thiazole-6-carboxylic acid (Example 15) (11.5 mg, 0.018 mmol, 47.0% yield). LC/MS observed [M+H], 647.11; $^1$H NMR (500 MHz, Chloroform-d) δ 8.00 (d, J=1.5 Hz, 1H), 7.56 (d, J=1.5 Hz, 1H), 7.41-7.30 (m, 2H), 7.26 (dd, J=17.1, 7.6 Hz, 1H), 5.61 (d, J=3.3 Hz, 1H), 4.80 (p, J=6.1 Hz, 1H), 4.58 (d, J=3.8 Hz, 1H), 4.38 (dd, J=9.0, 3.8 Hz, 1H), 4.36-4.25 (m, 3H), 4.06 (d, J=11.1 Hz, 1H), 3.95 (dd, J=11.1, 3.6 Hz, 1H), 3.91-3.84 (m, 1H), 3.75-3.64 (m, 2H), 2.05 (tt, J=8.3, 5.0 Hz, 1H), 1.37 (dd, J=6.1, 2.8 Hz, 6H), 1.28-1.15 (m, 2H), 1.07 (ddd, J=8.4, 3.3, 1.8 Hz, 2H).

Example 16

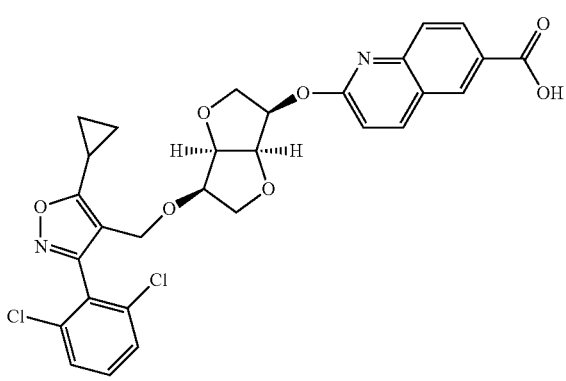 [SMILES: O=C(O)c1ccc2nc(O[C@@H]3CO[C@H]4[C@@H]3OC[C@H]4OCc3c(-c4c(Cl)cccc4Cl)noc3C3CC3)ccc2c1]

Example 16 was synthesized by following the similar experimental procedure in step 7b as for Example 7. LC/MS observed [M+H], 583.10; $^1$H NMR (400 MHz, Chloroform-d) δ 8.40 (d, J=1.9 Hz, 1H), 8.14 (dd, J=8.8, 2.0 Hz, 1H), 8.02 (d, J=8.8 Hz, 1H), 7.75 (d, J=8.8 Hz, 1H), 7.41-7.21 (m, 3H), 6.97 (d, J=8.9 Hz, 1H), 5.64-5.44 (m, 1H), 4.91 (t, J=5.0 Hz, 1H), 4.60-4.44 (m, 2H), 4.29 (d, J=12.5 Hz, 1H), 4.18 (dd, J=9.1, 6.8 Hz, 1H), 3.92 (ddd, J=8.1, 6.8, 5.0 Hz, 1H), 3.87-3.74 (m, 2H), 3.55 (t, J=8.5 Hz, 1H), 2.17 (dt, J=8.4, 5.1 Hz, 1H), 1.32-1.17 (m, 2H), 1.11-1.04 (m, 2H).

Example 17

Step 17a

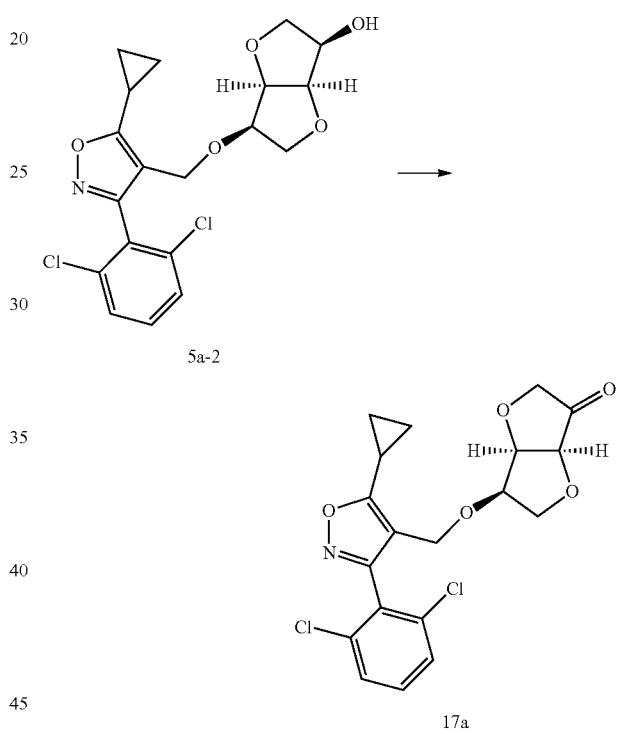

To (3R,3aR,6R,6aR)-6-((5-cyclopropyl-3-(2,6-dichlorophenyl)isoxazol-4-yl)methoxy) hexahydrofuro[3,2-b]furan-3-ol (5a-2) (1.6 g, 3.88 mmol) in DCM (30 ml) was added DMP (2.469 g, 5.82 mmol) in portions, and the mixture was stirred at RT for 16 h. To the mixture was added MTBE/water, and the mixture was filtered through celite. The organic layer was separated and washed with water, brine, dried (Na$_2$SO$_4$ for 16 h), filtered, concentrated to give (3aS,6R,6aR)-6-((5-cyclopropyl-3-(2,6-dichlorophenyl)isoxazol-4-yl)methoxy)tetrahydrofuro[3,2-b]furan-3(2H)-one (17a) (1.63 g) as crude Product. $^1$H NMR (400 MHz, Chloroform-d) δ 7.51-7.31 (m, 4H), 4.81 (dd, J=6.1, 5.0 Hz, 1H), 4.53 (d, J=12.4 Hz, 1H), 4.39 (d, J=12.4 Hz, 1H), 4.24 (d, J=6.2 Hz, 1H), 4.09 (d, J=17.5 Hz, 1H), 3.96 (d, J=17.5 Hz, 1H), 3.88 (dd, J=9.4, 5.9 Hz, 1H), 3.61 (dd, J=9.4, 6.3 Hz, 1H), 2.17 (tt, J=8.4, 5.1 Hz, 1H), 1.35-1.24 (m, 2H), 1.15 (ddd, J=8.2, 7.0, 4.2 Hz, 2H).

Step 17b

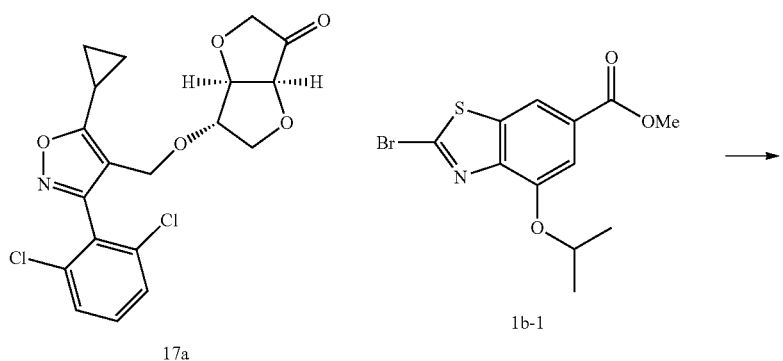

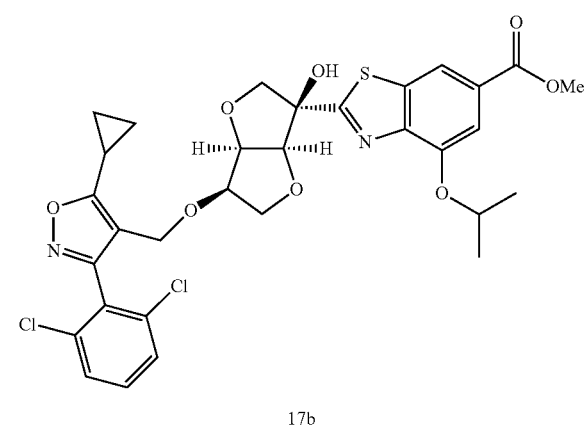

To methyl 2-bromo-4-isopropoxybenzo[d]thiazole-6-carboxylate (1b-1) (127 mg, 0.384 mmol) in tetrahydrofuran (2 ml) at −78° C. was added isopropylmagnesium chloride (0.192 ml, 0.384 mmol) dropwise, color getting darker but still a clear solution. After 30 min, to this mixture was added (3aS,6R,6aR)-6-((5-cyclopropyl-3-(2,6-dichlorophenyl)isoxazol-4-yl)methoxy)tetrahydrofuro[3,2-b]furan-3(2H)-one (17a) (105 mg, 0.256 mmol) in THF (2 ml) and the mixture was stirred at −78° C. for 1 h, then warmed up to 0° C. and quenched with NaHCO₃ solution. The mixture was diluted with EtOAc/water, and the organic layer was separated and washed with water, brine, dried, filtered, concentrated. The residue was purified by CombiFlash eluting with 0 to 45% EtOAc/hexane to give methyl 2-((3R,3aS,6R,6aR)-6-((5-cyclopropyl-3-(2,6-dichlorophenyl)isoxazol-4-yl)methoxy)-3-hydroxyhexahydrofuro[3,2-b]furan-3-yl)-4-isopropoxybenzo[d]thiazole-6-carboxylate (17b) (41 mg, 24.2%). LC/MS observed [M+H], 661.13; $^1$H NMR (500 MHz, Chloroform-d) δ 8.19 (d, J=1.4 Hz, 1H), 7.59 (d, J=1.5 Hz, 1H), 7.47-7.40 (m, 2H), 7.40-7.33 (m, 1H), 4.94-4.87 (m, 2H), 4.82-4.74 (m, 1H), 4.68-4.61 (m, 1H), 4.49-4.40 (m, 1H), 4.33 (d, J=9.8 Hz, 1H), 4.17-4.10 (m, 1H), 3.97-3.88 (m, 5H), 3.81 (dd, J=8.6, 6.7 Hz, 1H), 2.23 (tt, J=8.4, 5.0 Hz, 1H), 1.47 (dd, J=6.1, 1.7 Hz, 6H), 1.37-1.24 (m, 2H), 1.24-1.07 (m, 2H).

Step 17c

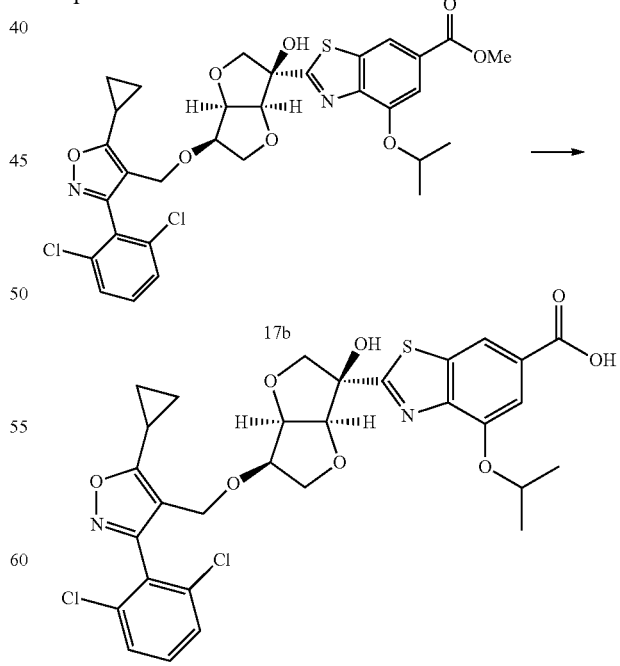

Example 17 was synthesized by following the similar experimental procedure in step 1c for Example 1. LC/MS observed [M+H], 647.11; $^1$H NMR (400 MHz, Chloroform-d) δ 8.27 (d, J=1.4 Hz, 1H), 7.63 (d, J=1.4 Hz, 1H), 7.46-7.31 (m, 3H), 4.96-4.86 (m, 2H), 4.80 (t, J=5.0 Hz, 1H), 4.65 (d, J=12.6 Hz, 1H), 4.42 (d, J=12.5 Hz, 1H), 4.34 (d, J=9.8 Hz, 1H), 4.17-4.12 (m, 1H), 3.96 (ddd, J=16.4, 7.7, 5.2 Hz, 2H), 3.82 (dd, J=8.4, 6.4 Hz, 1H), 2.23 (tt, J=8.3, 5.1 Hz, 1H), 1.50-1.45 (d, J=6.0 Hz, 6H), 1.34-1.24 (m, 2H), 1.20-1.11 (m, 2H).

Example 18

Step 18a

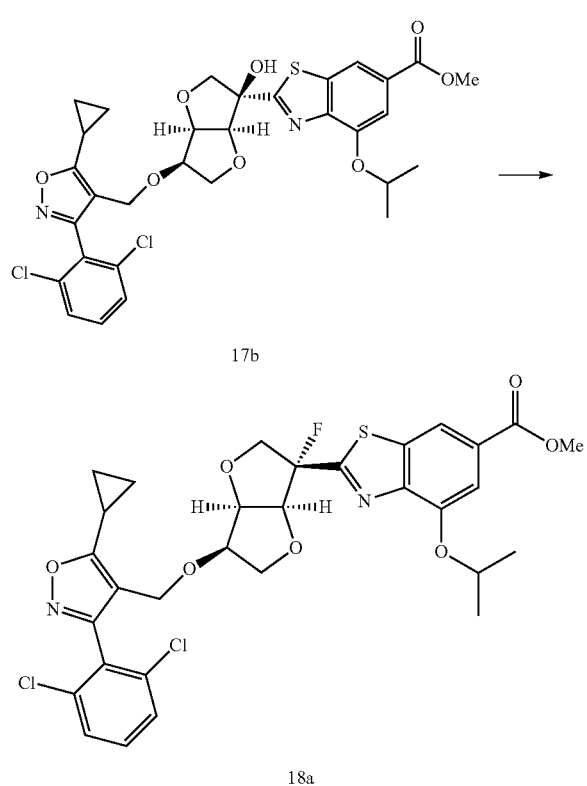

17b

18a

To methyl 2-((3R,3aS,6R,6aR)-6-((5-cyclopropyl-3-(2,6-dichlorophenyl)isoxazol-4-yl)methoxy)-3-hydroxyhexahydrofuro[3,2-b]furan-3-yl)-4-isopropoxybenzo[d]thiazole-6-carboxylate (17b) (32 mg, 0.048 mmol) in DCM (1 ml) at −78° C. was added deoxofluor (0.089 ml, 0.484 mmol) and the mixture was stirred at −78° C. for 2 h, then slowly warmed up to at 0° C. and quenched with NaHCO₃ solution. The mixture was diluted with EtOAc/water, and the organic layer was separated and washed with water, brine, and dried, concentrated. The residue was purified by CombiFlash eluting with 0 to 40% EtOAc-hexane to give methyl 2-((3S,3aS,6R,6aR)-6-((5-cyclopropyl-3-(2,6-dichlorophenyl)isoxazol-4-yl)methoxy)-3-fluorohexahydrofuro[3,2-b]furan-3-yl)-4-isopropoxybenzo[d]thiazole-6-carboxylate (18a) (24 mg, 0.036 mmol, 74.8% yield) as yellow foam. LC/MS observed [M+H], 663.13; $^1$H NMR (500 MHz, Chloroform-d) δ 8.21 (d, J=1.4 Hz, 1H), 7.60 (d, J=1.5 Hz, 1H), 7.43 (ddd, J=8.4, 4.1, 1.3 Hz, 2H), 7.35 (t, J=8.1 Hz, 1H), 4.95 (hept, J=6.1 Hz, 1H), 4.89-4.81 (m, 1H), 4.74 (ddd, J=11.7, 4.7, 1.3 Hz, 1H), 4.64 (d, J=12.2 Hz, 1H), 4.58 (dd, J=30.8, 11.6 Hz, 1H), 4.42 (ddd, J=20.3, 11.6, 1.4 Hz, 1H), 4.36 (d, J=12.3 Hz, 1H), 4.01 (ddd, J=8.1, 7.0, 5.2 Hz, 1H), 3.95 (s, 3H), 3.81 (ddd, J=9.4, 6.9, 2.7 Hz, 1H), 3.60 (t, J=8.6 Hz, 1H), 2.22 (tt, J=8.4, 5.1 Hz, 1H), 1.46 (dd, J=6.1, 1.8 Hz, 6H), 1.35-1.25 (m, 2H), 1.22-1.08 (m, 2H).

Step 18b

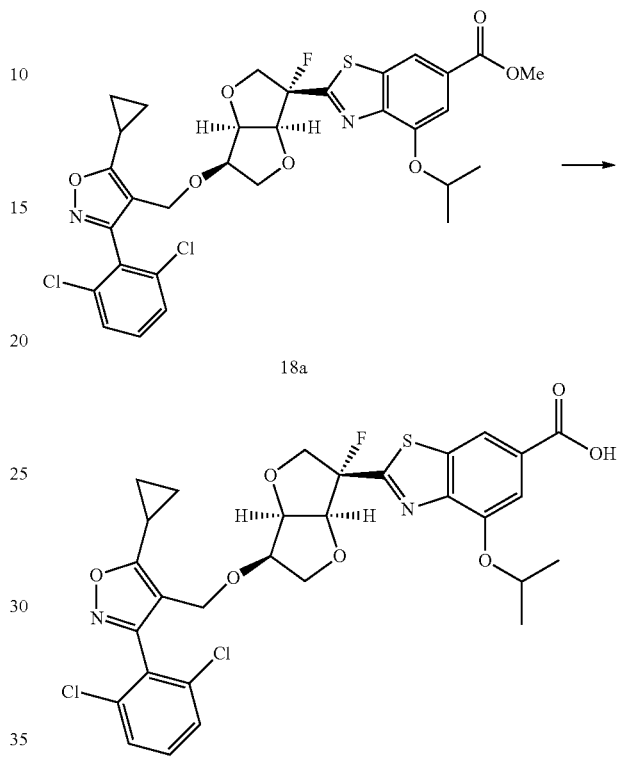

18a

Example 18

Example 18 was synthesized by following the similar experimental procedure in step 1c for Example 1. LC/MS observed [M+H], 649.11; $^1$H NMR (400 MHz, Chloroform-d) δ 8.28 (s, 1H), 7.65 (s, 1H), 7.51-7.29 (m, 3H), 4.96 (hept, J=6.2 Hz, 1H), 4.85 (t, J=4.9 Hz, 1H), 4.75 (dd, J=11.7, 4.7 Hz, 1H), 4.68-4.30 (m, 4H), 4.02 (td, J=7.4, 5.1 Hz, 1H), 3.83 (ddd, J=9.5, 6.9, 2.6 Hz, 1H), 3.61 (t, J=8.6 Hz, 1H), 2.29-2.18 (m, 1H), 1.48 (d, J=6.0 Hz, 6H), 1.34-1.24 (m, 2H), 1.23-1.11 (m, 2H).

Example 19

Step 19a

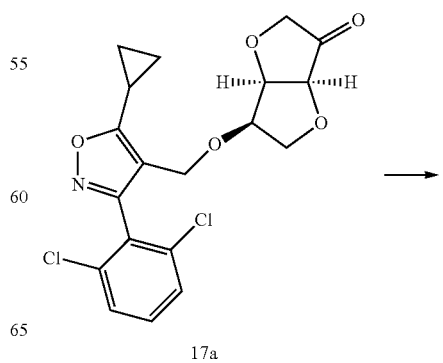

17a

-continued

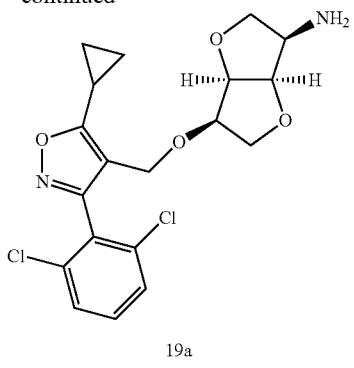

19a

To a solution of (3aS,6R,6aR)-6-((5-cyclopropyl-3-(2,6-dichlorophenyl)isoxazol-4-yl)methoxy)-tetrahydrofuro[3,2-b]furan-3(2H)-one (17a) (90 mg, 0.219 mmol) in MeOH (1 ml) under $N_2$ at RT was added ammonium acetate (169 mg, 2.194 mmol). The mixture was stirred under $N_2$ for 7 hours. sodium cyanoborohydride (13.79 mg, 0.219 mmol) was added into the mixture. The mixture was stirred under $N_2$ for 36 hours and the reaction mixture was concentrated and quenched by addition of water (2 ml) and 1M aqueous HCl (1 ml) dropwise. The reaction mixture was diluted by DCM (5 ml). The pH of reaction mixture was adjusted to 8.5 by addition of 1M aqueous KOH. The mixture was extracted by DCM (10 ml×3). The combined organic layers was dried over $Na_2SO_4$, filtered and concentrated to give a crude product. The crude product was purified by CombiFlash eluting with 0 to 10% MeOH/DCM to give (3R,3aR,6R,6aS)-6-((5-cyclopropyl-3-(2,6-dichlorophenyl)isoxazol-4-yl)methoxy)hexa-hydrofuro[3,2-b]furan-3-amine (19a) (13 mg) as an oil. LC/MS observed [M+H], 411.07; $^1$H NMR (400 MHz, Chloroform-d) δ 7.45-7.28 (m, 3H), 4.53 (d, J=12.4 Hz, 1H), 4.46 (t, J=4.7 Hz, 1H), 4.28 (d, J=12.4 Hz, 1H), 4.22 (t, J=4.7 Hz, 1H), 3.96-3.86 (m, 2H), 3.78 (dd, J=9.0, 6.5 Hz, 1H), 3.52-3.38 (m, 2H), 3.33-3.20 (m, 1H), 2.22-2.11 (m, 1H), 2.05-1.95 (m, 2H), 1.32-1.20 (m, 2H), 1.17-1.04 (m, 2H).

Step 19b

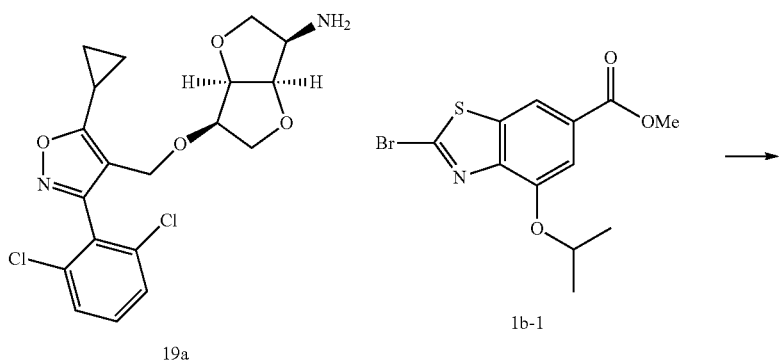

19a      1b-1

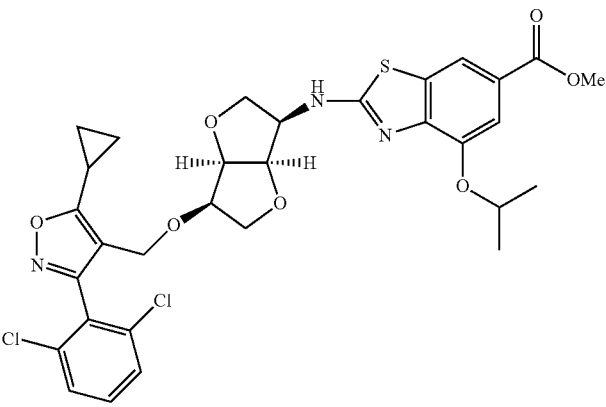

19b

To (3R,3aR,6R,6aS)-6-((5-cyclopropyl-3-(2,6-dichlorophenyl)isoxazol-4-yl)methoxy)hexa-hydrofuro[3,2-b]furan-3-amine (19a) (12 mg, 0.030 mmol), methyl 2-bromo-4-isopropoxybenzo[d]thiazole-6-carboxylate (1b-1) (12 mg, 0.036 mmol) and cesium carbonate (30 mg, 0.090 mmol) was added DMA (0.6 ml). The mixture was stirred at 70° C. for 24 hours. The solvent was removed. The mixture was treated with DCM, filtered, the filtrate was purified by Combiflash eluting with 0 to 100% EtOAc/hexane to give methyl 2-(((3R,3aR,6R,6aS)-6-((5-cyclopropyl-3-(2,6-dichlorophenyl)isoxazol-4-yl)methoxy)hexa-hydrofuro[3,2-b]furan-3-yl)amino)-4-isopropoxybenzo[d]thiazole-6-carboxylate (19b) (3 mg) as a colorless oil. LC/MS observed [M+H], 660.15; $^1$H NMR (400 MHz, Chloroform-d) δ 7.91 (d, J=1.5 Hz, 1H), 7.51 (d, J=1.5 Hz, 1H), 7.43-7.29 (m, 3H), 4.79 (hept, J=6.0 Hz, 1H), 4.62-4.52 (m, 3H), 4.31 (d, J=12.3 Hz, 1H), 4.26-4.19 (m, 1H), 4.01-3.93 (m, 1H), 3.89 (s, 3H), 3.87-3.80 (m, 1H), 3.58-3.44 (m, 2H), 2.21-2.12 (m, 1H), 1.42 (d, J=6.0 Hz, 6H), 1.29-1.20 (m, 2H), 1.16-1.08 (m, 2H).

Step 19c

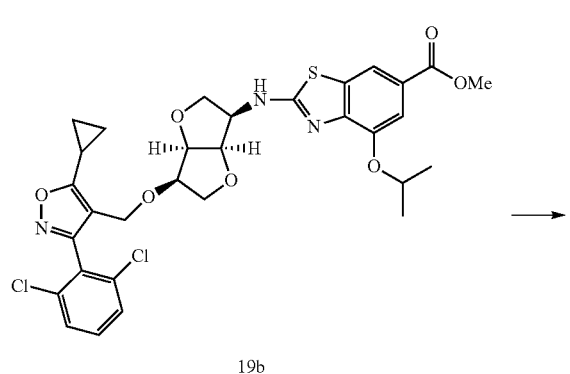

19b

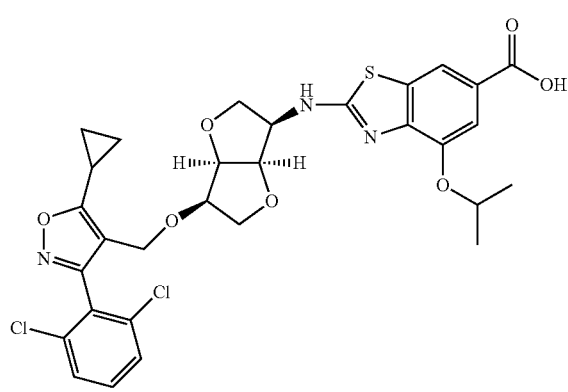

Example 19

Example 19 was synthesized by following the similar experimental procedure in step 1c for Example 1. LC/MS observed [M+H], 646.13; $^1$H NMR (500 MHz, Methanol-d$_4$) δ 7.91 (d, J=1.5 Hz, 1H), 7.58-7.43 (m, 4H), 4.85-4.80 (m, 1H), 4.67-4.61 (m, 3H), 4.59 (d, J=12.0 Hz, 1H), 4.34 (d, J=12.0 Hz, 1H), 4.15-4.09 (m, 1H), 4.05-3.99 (m, 1H), 3.82 (dd, J=9.0, 6.5 Hz, 1H), 3.52 (dd, J=9.0, 6.5 Hz, 1H), 3.48-3.39 (m, 1H), 2.39-2.30 (m, 1H), 1.40 (d, J=6.0 Hz, 6H), 1.21-1.16 (m, 2H), 0.94-0.87 (m, 2H).

Example 20

Step 20a

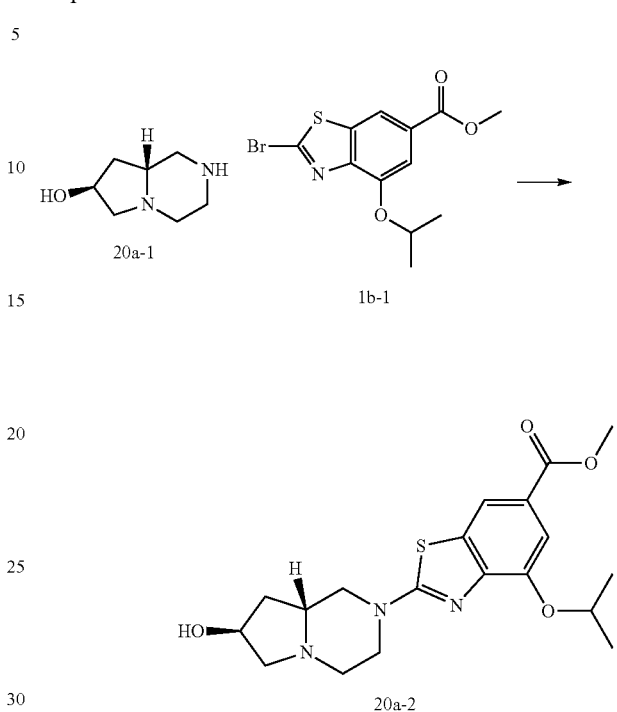

A mixture of (7S,8aR)-octahydropyrrolo[1,2-a]pyrazin-7-ol (20a-1) (213 mg, 1.5 mmol), methyl 2-bromo-4-isopropoxybenzo[d]thiazole-6-carboxylate (1b-1) (495 mg, 1.500 mmol), and cesium carbonate (977 mg, 3.00 mmol) in DMA (4 ml) was stirred overnight at RT. To the mixture was added water, and extracted with EtOAc. The combined organic layers were washed with brine and concentrated. The residue was purified by CombiFlash eluting with 0 to 65% acetone/hexane to give methyl 2-((7S,8aR)-7-hydroxyhexahydropyrrolo[1,2-a]pyrazin-2(1H)-yl)-4-isopropoxybenzo[d]thiazole-6-carboxylate (20a-2) (329 mg, 56%) as an off-white solid. $^1$H NMR (400 MHz, DMSO-d$_6$) δ 8.05 (t, J=1.2 Hz, 1H), 7.38 (d, J=1.6 Hz, 1H), 4.91-4.79 (m, 2H), 4.30-4.23 (m, 1H), 4.12 (d, J=12.1 Hz, 1H), 4.00 (d, J=12.7 Hz, 1H), 3.84 (s, 3H), 3.28-3.17 (m, 1H), 3.03 (d, J=10.7 Hz, 1H), 2.88 (t, J=11.3 Hz, 1H), 2.39-2.23 (m, 2H), 2.06-1.97 (m, 1H), 1.72-1.62 (m, 2H), 1.31 (d, J=6.0 Hz, 6H).

Step 20b

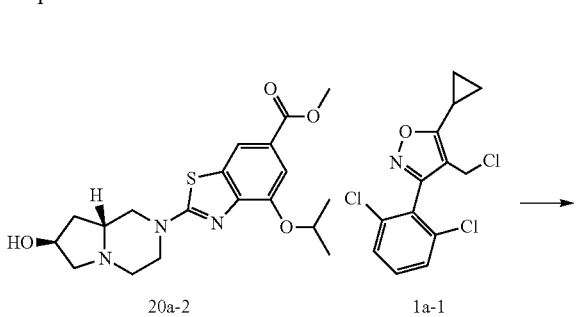

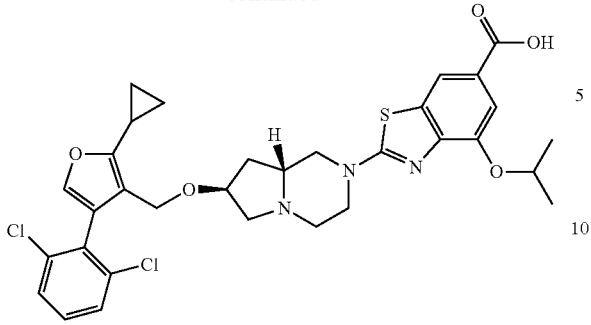

Example 20

To a solution of methyl 2-((7S,8aR)-7-hydroxyhexahydropyrrolo[1,2-a]pyrazin-2(1H)-yl)-4-isopropoxybenzo[d]thiazole-6-carboxylate (20a-2) (200 mg, 0.511 mmol) in THF (4 ml) at rt was added 18-crown-6 (162 mg, 0.613 mmol), followed by potassium tert-butoxide in THF 1M (1.533 ml, 1.533 mmol). After 15 min stirring, 4-(chloromethyl)-5-cyclopropyl-3-(2,6-dichlorophenyl)isoxazole (1a-1) (201 mg, 0.664 mmol) was added. The reaction mixture was stirred at RT for 2 h, quenched with water/brine, and extracted with ethyl acetate. The combined organic layers were washed with brine and concentrated. The residue was purified by CombiFlash eluting with 0 to 60% acetone/hexane to give the 2-((7S,8aR)-7-((5-cyclopropyl-3-(2,6-dichlorophenyl)isoxazol-4-yl)methoxy)hexahydropyrrolo[1,2-a]pyrazin-2(1H)-yl)-4-isopropoxybenzo[d]thiazole-6-carboxylic acid (Example 20) as a pale yellow foam. LC/MS observed [M+H], 643.17; $^1$H NMR (500 MHz, DMSO-d6) δ 12.75 (s, 1H), 8.01 (d, J=1.4 Hz, 1H), 7.63 (d, J=8.0 Hz, 2H), 7.55 (dd, J=8.8, 7.4 Hz, 1H), 7.39 (d, J=1.5 Hz, 1H), 4.84 (hept, J=6.1 Hz, 1H), 4.25-4.15 (m, 2H), 4.07 (d, J=12.1 Hz, 1H), 3.98-3.89 (m, 2H), 3.29 (dd, J=9.5, 6.6 Hz, 1H), 3.24-3.15 (m, 1H), 2.95 (dd, J=10.7, 2.7 Hz, 1H), 2.85-2.77 (m, 1H), 2.37-2.28 (m, 1H), 2.15-2.06 (m, 1H), 2.01-1.91 (m, 1H), 1.77 (dd, J=9.4, 5.0 Hz, 1H), 1.49-1.42 (m, 2H), 1.32 (t, J=6.1 Hz, 6H), 1.20-1.06 (m, 4H).

Example 21

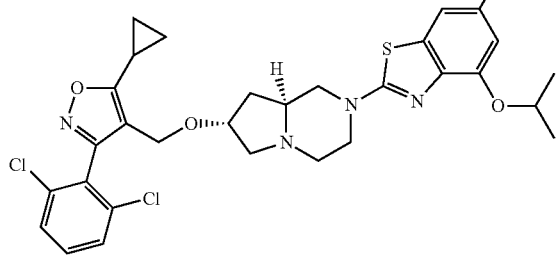

Example 21

Example 21 was synthesized by following the similar experimental procedure as for Example 20. LC/MS observed [M+H], 643.17; $^1$H NMR (400 MHz, DMSO-d$_6$) δ 12.73 (s, 1H), 8.01 (d, J=1.5 Hz, 1H), 7.67-7.60 (m, 2H), 7.60-7.50 (m, 1H), 7.39 (d, J=1.6 Hz, 1H), 4.84 (p, J=6.1 Hz, 1H), 4.26-4.14 (m, 2H), 4.07 (d, J=12.1 Hz, 1H), 3.98-3.89 (m, 2H), 3.28 (d, J=6.6 Hz, 1H), 3.18 (dd, J=12.1, 3.3 Hz, 1H), 2.95 (d, J=10.5 Hz, 1H), 2.81 (dd, J=12.2, 10.5 Hz, 1H), 2.39-2.27 (m, 1H), 2.18-2.03 (m, 1H), 1.96-1.89 (m, 1H), 1.77 (dd, J=9.4, 5.0 Hz, 1H), 1.44 (dd, J=9.1, 5.4 Hz, 2H), 1.32 (d, J=6.0 Hz, 6H), 1.23-1.05 (m, 4H).

Example 22

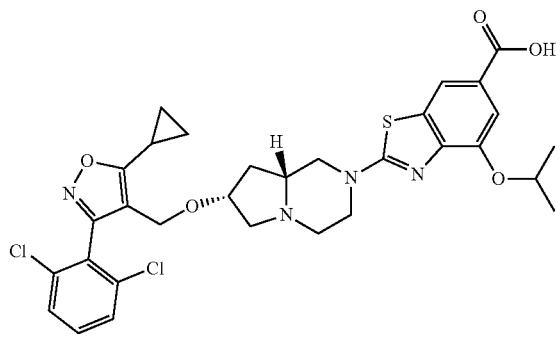

Example 22

Step 22a

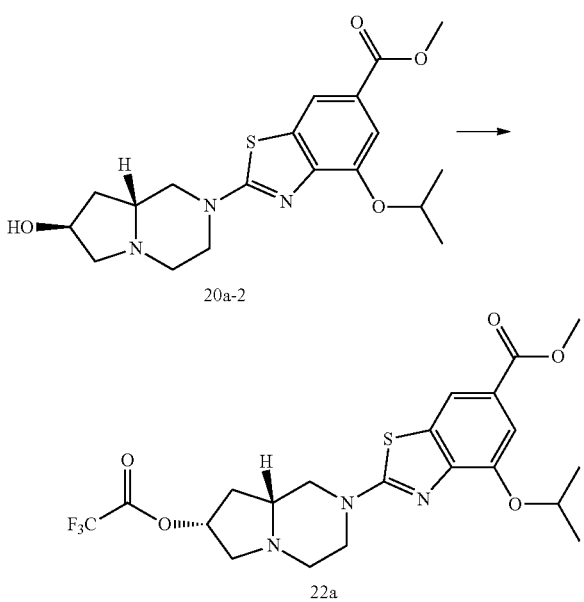

To a solution of methyl 2-((7S,8aR)-7-hydroxyhexahydropyrrolo[1,2-a]pyrazin-2(1H)-yl)-4-isopropoxybenzo[d]thiazole-6-carboxylate (20a-2) (100 mg, 0.255 mmol) and triphenylphosphine (167 mg, 0.639 mmol) in THF (3 ml) at 0° C. was added TFA (0.049 ml, 0.639 mmol) and DIAD (0.124 ml, 0.639 mmol). The mixture was stirred at 0° C. for 10 min and then warmed up to rt. Sodium benzoate (92 mg, 0.639 mmol) was added, and the reaction mixture was stirred at rt for 3 h, quenched with water/brine, and extracted with ethyl acetate. The organic layer was washed with brine and concentrated. The residue was purified by chromatography on silica gel eluting with 0 to 50% acetone/hexane to give compound 22a as a colorless oil (60 mg).

Step 22b

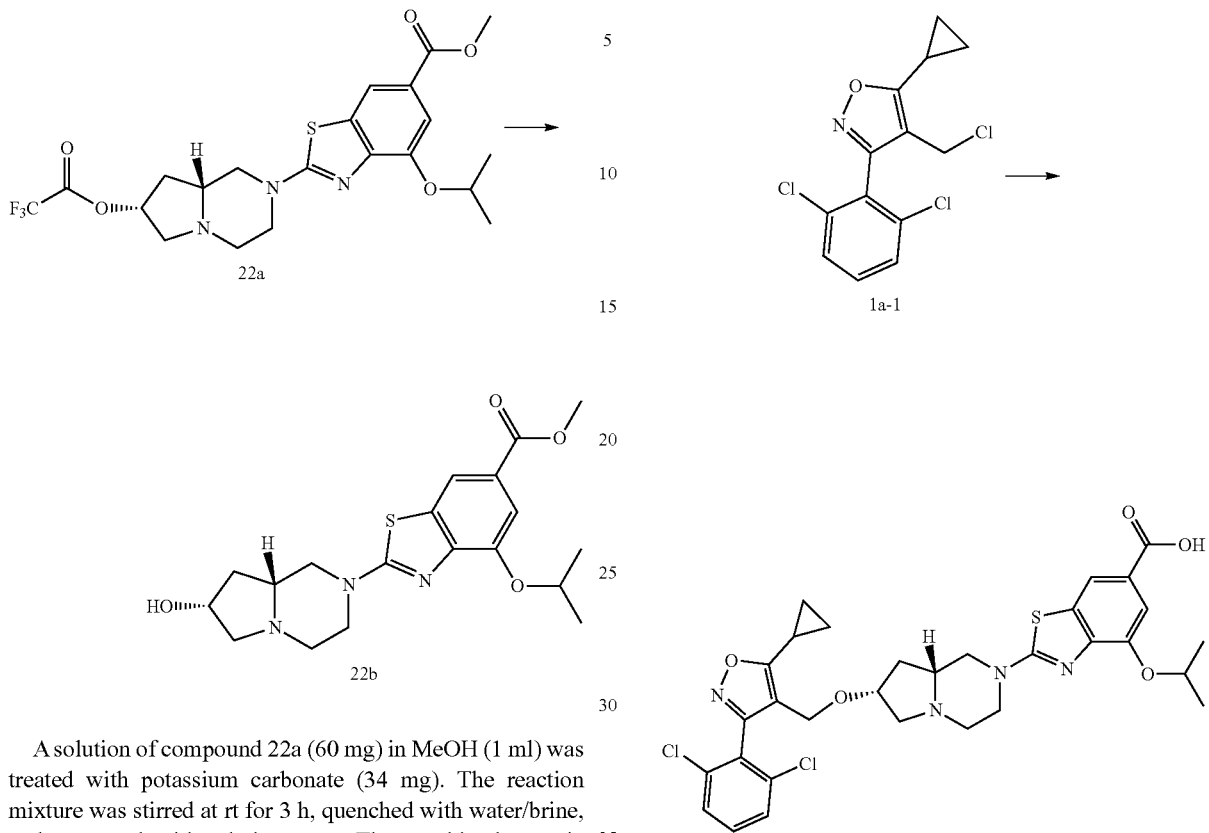

A solution of compound 22a (60 mg) in MeOH (1 ml) was treated with potassium carbonate (34 mg). The reaction mixture was stirred at rt for 3 h, quenched with water/brine, and extracted with ethyl acetate. The combined organic layers were washed with brine and concentrated. The residue was purified by chromatography on silica gel eluting with 0 to 60% acetone/hexane to give a methyl 2-((7R,8aR)-7-hydroxyhexahydropyrrolo[1,2-a]pyrazin-2(1H)-yl)-4-isopropoxybenzo[d]thiazole-6-carboxylate (22b) as a white solid (31 mg). LC/MS observed, [M+H], 392.15. $^1$H NMR (400 MHz, DMSO-$d_6$) δ 8.04 (d, J=1.4 Hz, 1H), 7.38 (d, J=1.5 Hz, 1H), 4.90-4.79 (m, 2H), 4.22 (s, 1H), 4.12 (d, J=12.3 Hz, 1H), 4.00 (d, J=12.6 Hz, 1H), 3.84 (s, 3H), 3.59 (s, 1H), 3.03 (t, J=11.4 Hz, 1H), 2.89 (d, J=9.7 Hz, 1H), 2.27 (td, J=10.7, 9.2, 6.5 Hz, 2H), 2.20-2.07 (m, 2H), 2.01 (d, J=9.1 Hz, 1H), 1.31 (d, J=6.0 Hz, 6H).

Step 22c

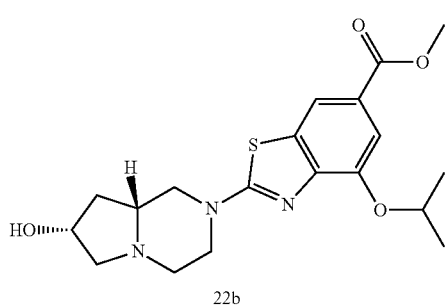

To a solution of methyl 2-((7R,8aR)-7-hydroxyhexahydropyrrolo[1,2-a]pyrazin-2(1H)-yl)-4-isopropoxybenzo[d]thiazole-6-carboxylate (compound 22b) (30 mg, 0.077 mmol) in THF (1 ml) at rt was added 18-crown-6 (30.4 mg, 0.115 mmol), followed by potassium tert-butoxide in THF 1M (0.230 ml, 0.230 mmol). After 15 min stirring, 4-(chloromethyl)-5-cyclopropyl-3-(2,6-dichlorophenyl)isoxazole (1a-1) (34.8 mg, 0.115 mmol) was added. The reaction mixture was stirred at rt for 3 h, quenched with water/brine, and extracted with ethyl acetate. The combined organic layers were washed with brine and concentrated. The residue was purified by chromatography on silica gel eluting with 0 to 60% acetone/hexane to give 2-((7R,8aR)-7-((5-cyclopropyl-3-(2,6-dichlorophenyl)isoxazol-4-yl)methoxy)hexahydropyrrolo[1,2-a]pyrazin-2(1H)-yl)-4-isopropoxybenzo[d]thiazole-6-carboxylic acid (Example 22) as a pale yellow foam (17 mg). LC-MS M+H LC/MS observed [M+H], 643.17; $^1$H NMR (400 MHz, DMSO-$d_6$) δ 12.80 (s, 1H), 7.99 (s, 1H), 7.70-7.62 (m, 2H), 7.58 (ddd, J=9.3, 6.8, 1.1 Hz, 1H), 7.37 (t, J=1.4 Hz, 1H), 4.83 (p, J=6.1 Hz, 1H), 4.21 (s, 2H), 4.06 (d, J=12.1 Hz, 1H), 3.95 (d, J=11.9 Hz, 1H), 3.88 (s, 1H), 3.23 (d, J=10.8 Hz, 1H), 2.97 (d, J=11.0 Hz, 1H), 2.94-2.81 (m, 2H), 2.34 (t, J=6.8 Hz, 2H), 2.11 (q, J=9.9, 7.5 Hz, 4H), 1.97 (d, J=7.4 Hz, 1H), 1.31 (dd, J=6.1, 1.1 Hz, 6H), 1.26-1.11 (m, 2H), 1.15-1.06 (m, 2H).

Example 23

Step 23a

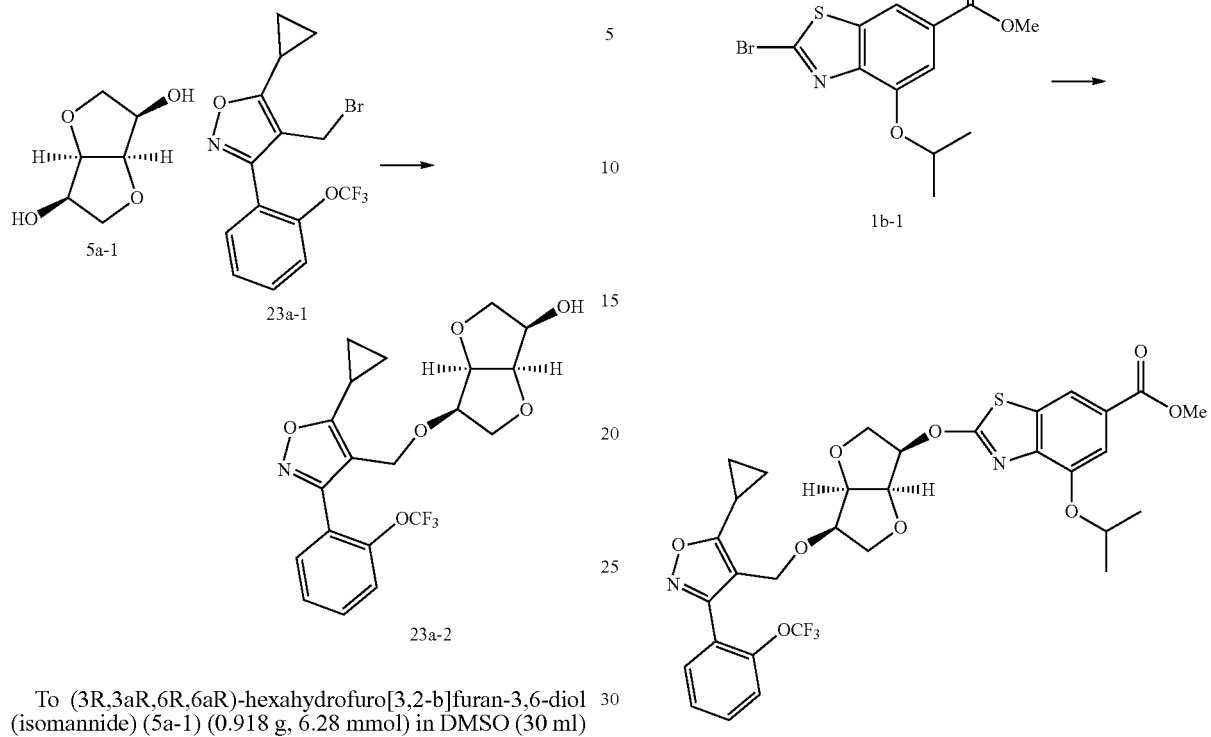

To (3R,3aR,6R,6aR)-hexahydrofuro[3,2-b]furan-3,6-diol (isomannide) (5a-1) (0.918 g, 6.28 mmol) in DMSO (30 ml) was added potassium tert-butoxide (0.846 g, 7.54 mmol) and the suspension was heated at 60° C. for 30 min. To this milky mixture was added 4-(bromomethyl)-5-cyclopropyl-3-(2-(trifluoromethoxy)phenyl)isoxazole (23a-1) (1.82 g, 5.03 mmol) in DMSO (5 ml) and the mixture was stirred at 60° C., after 30 min, most of the suspension went into solution. The mixture was stirred for another 1.5 h. The mixture was diluted with MTBE, washed with water, brine, dried, filtered and concentrated. The residue was purified by CombiFlash eluting with a 0-60% gradient of acetone/hexane to give (3R,3aR,6R,6aR)-6-((5-cyclopropyl-3-(2-(trifluoromethoxy)phenyl)isoxazol-4-yl)methoxy)hexahydrofuro[3,2-b]furan-3-ol (23a-2) (1.28 g, 3.00 mmol, 59.6% yield) as light yellow oil. LC/MS observed [M+H], 428.12; $^1$H NMR (400 MHz, Chloroform-d) δ 7.67-7.45 (m, 2H), 7.39 (dd, J=8.6, 5.8 Hz, 2H), 4.64 (d, J=11.8 Hz, 1H), 4.43 (dt, J=13.0, 5.0 Hz, 2H), 4.35 (d, J=11.8 Hz, 1H), 4.19 (dt, J=12.1, 5.9 Hz, 1H), 3.95 (td, J=6.9, 4.7 Hz, 1H), 3.87 (dt, J=10.9, 5.7 Hz, 2H), 3.65-3.44 (m, 2H), 2.92 (d, J=8.4 Hz, 1H), 2.21 (tt, J=8.8, 5.1 Hz, 1H), 1.21 (td, J=9.3, 8.8, 5.1 Hz, 2H), 1.11 (dt, J=8.4, 4.0 Hz, 2H).

Step 23b

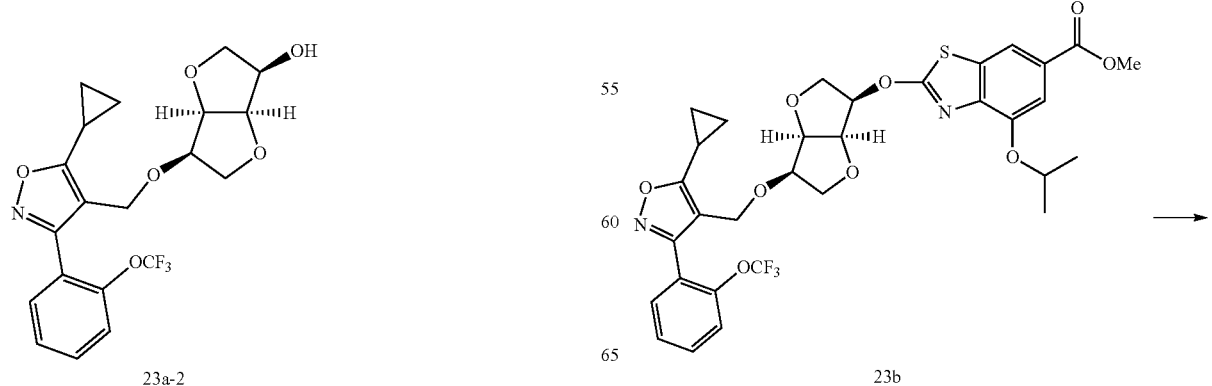

Compound 23b was synthesized following a similar experimental procedure as in Step 5d. LC/MS observed [M+H], 677.20; $^1$H NMR (400 MHz, Chloroform-d) δ 7.98 (d, J=1.5 Hz, 1H), 7.62-7.46 (m, 3H), 7.39 (tt, J=7.6, 1.0 Hz, 2H), 5.65 (td, J=6.6, 5.4 Hz, 1H), 4.90 (t, J=5.1 Hz, 1H), 4.82 (p, J=6.1 Hz, 1H), 4.65 (d, J=11.8 Hz, 1H), 4.51 (t, J=4.9 Hz, 1H), 4.38 (d, J=11.8 Hz, 1H), 4.17 (dd, J=9.6, 6.5 Hz, 1H), 4.02-3.88 (m, 2H), 3.92 (s, 3H), 3.84 (dd, J=8.8, 6.8 Hz, 1H), 3.60 (t, J=8.5 Hz, 1H), 2.22 (tt, J=8.4, 5.1 Hz, 1H), 1.42 (dd, J=6.1, 2.5 Hz, 6H), 1.33-1.19 (m, 2H), 1.19-1.03 (m, 2H).

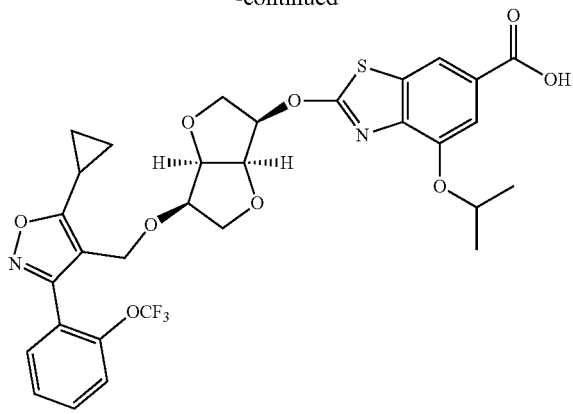

Example 23

Example 23 was synthesized following a similar experimental procedure as in Step 5e. LC/MS observed [M+H], 663.18; 1H NMR (400 MHz, Chloroform-d) δ 8.17-7.92 (m, 1H), 7.59 (dd, J=7.8, 1.7 Hz, 2H), 7.51 (td, J=7.8, 1.8 Hz, 1H), 7.45-7.33 (m, 2H), 5.66 (q, J=6.3 Hz, 1H), 4.92 (t, J=5.1 Hz, 1H), 4.82 (hept, J=6.2 Hz, 1H), 4.65 (d, J=11.9 Hz, 1H), 4.52 (t, J=4.9 Hz, 1H), 4.38 (d, J=11.8 Hz, 1H), 4.22-4.12 (m, 1H), 4.04-3.90 (m, 2H), 3.84 (t, J=8.0 Hz, 1H), 3.61 (t, J=8.5 Hz, 1H), 2.22 (tt, J=8.4, 5.1 Hz, 1H), 1.43 (dd, J=6.1, 2.1 Hz, 6H), 1.30-1.19 (m, 2H), 1.19-1.05 (m, 2H).

Example 24

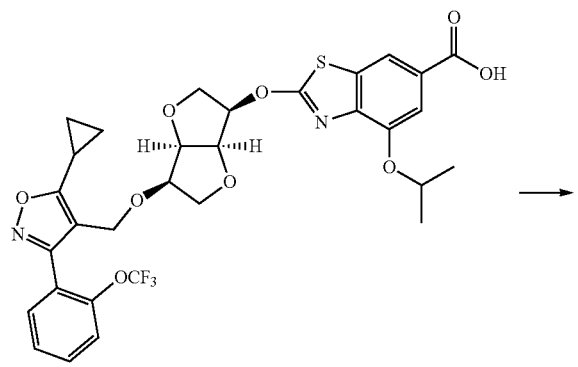

Example 23

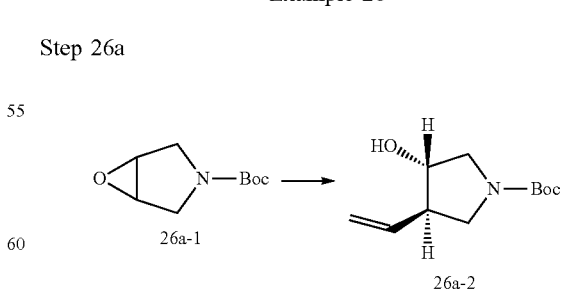

Example 24

Example 24 was synthesized following a similar experimental procedure as in Step 3a. LC/MS observed [M+H], 780.22; $^1$H NMR (400 MHz, Chloroform-d) δ 8.79 (s, 1H), 7.76 (d, J=1.7 Hz, 1H), 7.58 (dd, J=7.9, 1.8 Hz, 1H), 7.52 (td, J=7.8, 1.8 Hz, 1H), 7.46-7.33 (m, 3H), 5.65 (q, J=6.1 Hz, 1H), 4.92 (t, J=5.2 Hz, 1H), 4.65 (d, J=11.9 Hz, 1H), 4.51 (t, J=4.9 Hz, 1H), 4.38 (d, J=11.8 Hz, 1H), 4.15 (dd, J=9.7, 6.3 Hz, 1H), 3.96 (dd, J=9.9, 6.5 Hz, 2H), 3.84 (dd, J=8.7, 6.8 Hz, 1H), 3.60 (t, J=8.6 Hz, 1H), 2.41-2.15 (m, 1H), 1.82 (q, J=5.3 Hz, 2H), 1.59 (s, 3H), 1.42 (d, J=6.1 Hz, 6H), 1.25 (q, J=4.5 Hz, 3H), 1.12 (dd, J=8.3, 3.2 Hz, 2H), 1.08-0.93 (m, 2H).

Example 25

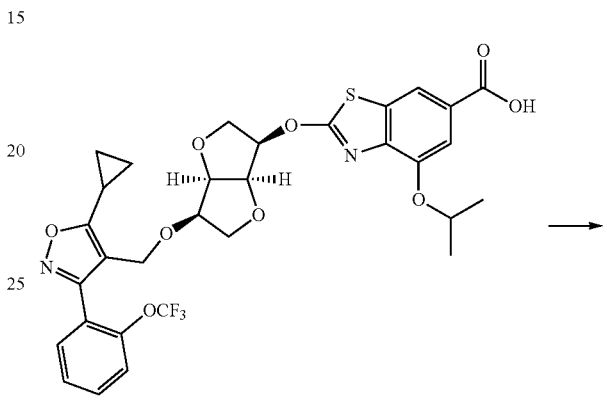

Example 23

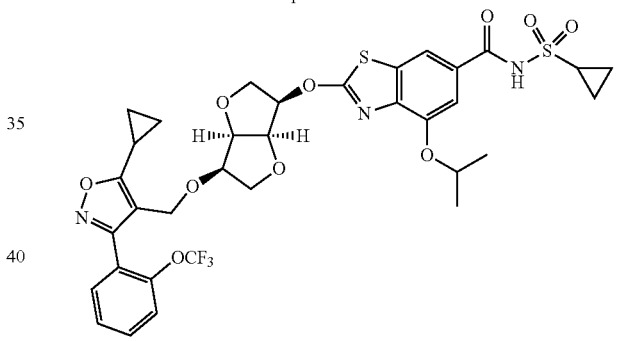

Example 25

Example 25 was synthesized following a similar experimental procedure as in Step 3a. LC/MS observed [M+H], LC/MS observed [M+H], 766.20.

Example 26

Step 26a

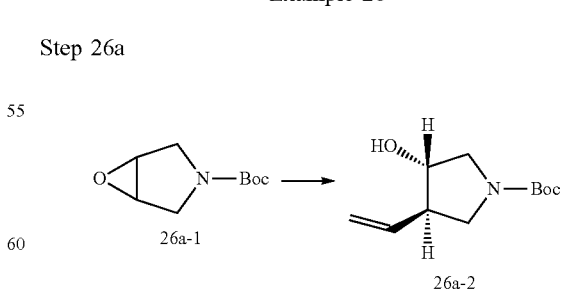

To copper (I) bromide dimethyl sulfide complex (650 mg) and tert-butyl 6-oxa-3-azabicyclo-[3.1.0]hexane-3-carboxylate (26a-1) (2.9 g, 15.66 mmol) in tetrahydrofuran (90 ml) at −30° C. was added vinylmagnesium chloride (39.1 ml, 62.6 mmol) and the mixture was stirred at −30° C. to −10° C. for 2.5 h, slowly warmed up to 0° C. and stirred for 1 h, then quenched with NaHCO₃ solution, filtered through celite. The organic layer was separated, washed with water, brine, dried, filtered and concentrated to give racemic tert-butyl (3S,4R)-3-hydroxy-4-vinylpyrrolidine-1-carboxylate (26a-2) (3.12 g, 14.63 mmol, 93% yield) as crude product and used without further purification. ¹H NMR (400 MHz, Chloroform-d) δ 5.78-5.64 (m, 1H), 5.26-5.10 (m, 2H), 4.10 (q, J=6.0 Hz, 1H), 3.80-3.57 (m, 2H), 3.35-3.10 (m, 1H), 2.69 (dd, J=12.3, 6.3 Hz, 1H), 1.46 (s, 9H).

Step 26b

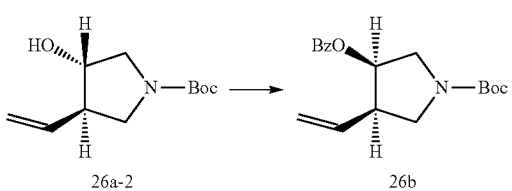

To the solution of tert-butyl (3S,4R)-3-hydroxy-4-vinylpyrrolidine-1-carboxylate (26a-2) (3.12 g, 14.63 mmol), benzoic acid (2.322 g, 19.02 mmol) and triphenylphosphine (4.99 g, 19.02 mmol) in tetrahydrofuran (100 ml) was added DIAD (3.70 ml, 19.02 mmol) and the mixture was stirred at RT for 1 h. The mixture was concentrated and purified by CombiFlash eluting with 0 to 30% EtOAc/hexane to give tert-butyl (3R,4R)-3-(benzoyloxy)-4-vinylpyrrolidine-1-carboxylate (26b) (1.557 g, 4.91 mmol, 33.5% yield). ¹H NMR (400 MHz, Chloroform-d) δ 8.02 (d, J=7.4 Hz, 2H), 7.58 (t, J=7.4 Hz, 1H), 7.45 (t, J=7.4 Hz, 2H), 6.01-5.74 (m, 1H), 5.63-5.46 (m, 1H), 5.19 (dd, J=19.6, 14.2 Hz, 2H), 3.87-3.63 (m, 2H), 3.63-3.30 (m, 2H), 3.05 (b, 1H), 1.45 and 1.49 (s, 9H).

Step 26c

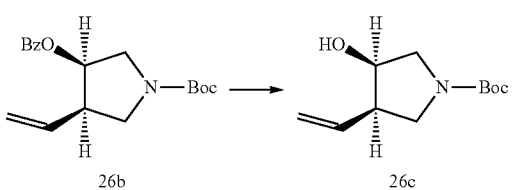

To tert-butyl (3R,4R)-3-(benzoyloxy)-4-vinylpyrrolidine-1-carboxylate (26b) (1.45 g, 4.57 mmol) in tetrahydrofuran (1 ml) and MeOH (0.5 ml) was added NaOH (6.85 ml, 6.85 mmol) and the mixture was stirred at RT for 3 h. The mixture was diluted with EtOAc, washed with 1N NaOH, water, brine, dried, filtered and concentrated to give tert-butyl (3R,4R)-3-hydroxy-4-vinylpyrrolidine-1-carboxylate (26c) (940 mg, 4.41 mmol, 96% yield) as crude Product. ¹H NMR (400 MHz, Chloroform-d) δ 6.07-5.65 (m, 1H), 5.38-5.07 (m, 3H), 4.28 (d, J=3.8 Hz, 1H), 3.64-3.24 (m, 5H), 2.99-2.60 (m, 1H), 1.46 (s, 9H).

Step 26d

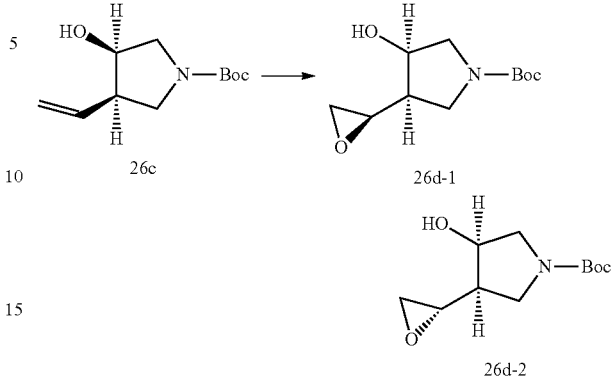

Method A:

To tert-butyl (3R,4R)-3-hydroxy-4-vinylpyrrolidine-1-carboxylate (compound 26c) (640 mg, 3.00 mmol) and sodium bicarbonate (756 mg, 9.00 mmol) in DCM (20 ml) was added m-CPBA (1036 mg, 6.00 mmol) and the mixture was stirred at RT for 16 h. The volatiles were removed under vacuo and the residue was partitioned between EtOAc and water, organic layer was separated and washed with 1N LiOH, water, brine, dried, filtered and concentrated. The residue was purified by CombiFlash eluting with 0 to 80% EtOAc/hexane to afford tert-butyl (3R,4R)-3-hydroxy-4-((R)-oxiran-2-yl)pyrrolidine-1-carboxylate (compound 26d-1) (255 mg). ¹H NMR (400 MHz, Chloroform-d) δ 4.44 (q, J=3.3 Hz, 1H), 3.70-3.30 (m, 4H), 3.22 (ddd, J=6.7, 4.1, 2.8 Hz, 1H), 3.08 (d, J=3.3 Hz, 1H), 2.98-2.85 (m, 1H), 2.68 (td, J=5.1, 2.6 Hz, 1H), 2.03-1.90 (m, 1H), 1.46 (s, 9H).

tert-butyl (3R,4R)-3-hydroxy-4-((S)-oxiran-2-yl)pyrrolidine-1-carboxylate (compound 26d-2) (37 mg) was also isolated. ¹H NMR (400 MHz, Chloroform-d) δ 4.56-4.25 (m, 1H), 3.57 (dd, J=10.6, 8.3 Hz, 1H), 3.53-3.43 (m, 2H), 3.20 (dt, J=6.7, 3.3 Hz, 1H), 2.82 (tt, J=10.0, 5.0 Hz, 2H), 2.62-2.53 (m, 1H), 1.46 (s, 9H).

Method B:

To tert-butyl (3R,4R)-3-hydroxy-4-vinylpyrrolidine-1-carboxylate (compound 26c) (190 mg, 0.891 mmol) and sodium bicarbonate (599 mg, 7.13 mmol) in acetone (5.00 ml) and water (5 ml) at 0° C. was added oxone (2738 mg, 4.45 mmol) in water (5 ml) (a suspension) portionwise over 1 h. The mixture was stirred at 0° C. for another 1 h and then diluted with EtOAc/water. The organic layer was separated, washed with water and brine, then dried, filtered and concentrated. The residue was purified by CombiFlash eluting with 0 to 70% EtOAc/hexane to afford tert-butyl (3R,4R)-3-hydroxy-4-((R)-oxiran-2-yl)pyrrolidine-1-carboxylate (compound 26d-1) (60 mg). ¹H NMR (400 MHz, Chloroform-d) δ δ 4.37 (t, J=3.7 Hz, 1H), 3.66-3.27 (m, 4H), 3.15 (ddd, J=6.8, 4.0, 2.9 Hz, 1H), 2.89-2.78 (m, 1H), 2.61 (td, J=4.6, 2.3 Hz, 1H), 1.91 (pd, J=8.9, 8.1, 3.5 Hz, 1H), 1.39 (s, 9H).

To tert-butyl (3R,4R)-3-hydroxy-4-((S)-oxiran-2-yl)pyrrolidine-1-carboxylate (compound 26d-2) (70 mg) was also isolated. ¹H NMR (400 MHz, Chloroform-d) δ 4.45 (q, J=4.1, 3.2 Hz, 1H), 3.65-3.55 (m, 1H), 3.54-3.31 (m, 3H), 3.21 (b, 1H), 2.83 (m, 1H), 2.57 (b, 1H), 2.01 (b, 1H), 1.47 (s, 9H).

Step 26e

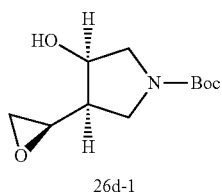

26d-1

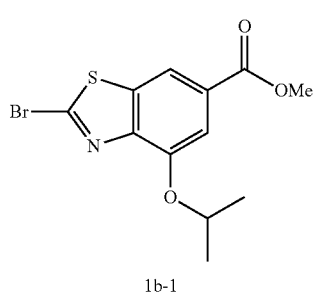

1b-1

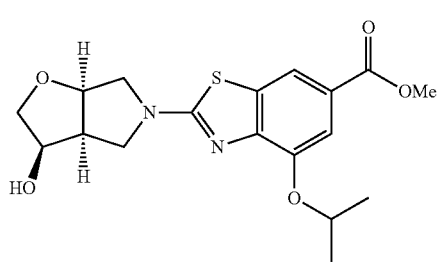

26e

Step 26f

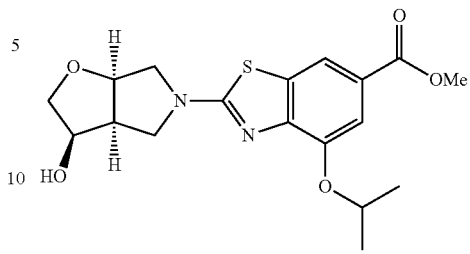

26e

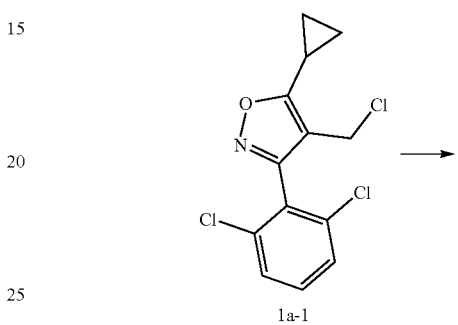

1a-1

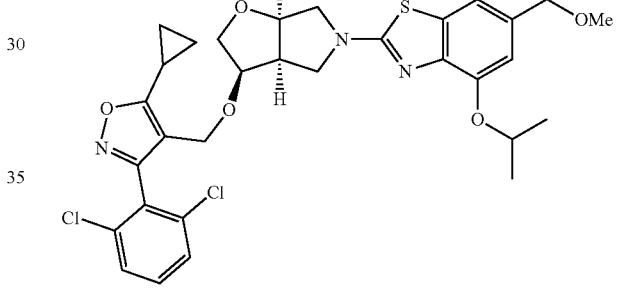

26f

To tert-butyl (3R,4R)-3-hydroxy-4-(oxiran-2-yl)pyrrolidine-1-carboxylate (26d-1) (12 mg, 0.052 mmol) in DCM (1 ml) at −78° C. was added $BF_3$ diethyl etherate (0.013 ml, 0.105 mmol) and the mixture was stirred for 1 h then warmed up to 0° C. and quenched with MeOH. The mixture was concentrated under vacuo. To the residue was added methyl 2-bromo-4-isopropoxybenzo-[d]thiazole-6-carboxylate (1b-1) (34.6 mg, 0.105 mmol) and cesium carbonate (51.2 mg, 0.157 mmol) and DMA (1.000 ml). The mixture was stirred at RT for 2 days. The mixture was diluted with EtOAc, washed with water, brine, dried, filtered and concentrated. The residue was purified by CombiFlash eluting with 0 to 60% EtOAc/hexane to give methyl 2-((3aS,6aR)-3-hydroxyhexahydro-5H-furo[2,3-c]pyrrol-5-yl)-4-isopropoxybenzo [d]thiazole-6-carboxylate (26e) (3.5 mg). LC/MS observed [M+H], 379.11; $^1$H NMR (400 MHz, Chloroform-d) δ 7.97 (d, J=1.6 Hz, 1H), 7.53 (d, J=1.6 Hz, 1H), 4.85 (p, J=6.1 Hz, 1H), 4.74 (ddd, J=7.1, 5.4, 1.5 Hz, 1H), 4.52 (d, J=7.9 Hz, 1H), 4.18 (dd, J=11.3, 3.5 Hz, 1H), 3.95 (dd, J=12.0, 1.5 Hz, 1H), 3.93-3.78 (m, 2H), 3.90 (s, 3H), 3.66 (dd, J=12.0, 5.4 Hz, 1H), 3.56 (dd, J=11.2, 8.6 Hz, 1H), 3.09 (dtd, J=8.5, 6.9, 3.5 Hz, 1H), 1.52-1.34 (m, 6H).

To methyl 2-((3R,3aS,6aR)-3-hydroxyhexahydro-5H-furo[2,3-c]pyrrol-5-yl)-4-isopropoxybenzo [d]thiazole-6-carboxylate (26e) (5.3 mg, 0.014 mmol) and 4-(chloromethyl)-5-cyclopropyl-3-(2,6-dichlorophenyl)isoxazole (1a-1) (8.48 mg, 0.028 mmol) in DMSO (1 ml) was added potassium tert-butoxide (2.357 mg, 0.021 mmol) and the mixture was stirred at RT for 1.5 h. The mixture was quenched with 1N HCl at 0° C. and then partitioned between EtOAc and water. The organic layer was separated, washed with water, brine, dried, filtered and concentrated. The residue was purified by HPLC eluting with 0.1% formic acid in acetonitrile/water to give methyl 2-((3R,3aR,6aR)-3-((5-cyclopropyl-3-(2,6-dichlorophenyl)-isoxazol-4-yl)methoxy)hexahydro-5H-furo[2,3-c]pyrrol-5-yl)-4-isopropoxybenzo[d]thiazole-6-carboxylate (26f) (2.3 mg, 25.5% yield). LC/MS observed [M+H], 644.15; $^1$H NMR (500 MHz, Chloroform-d) δ 7.90 (d, J=1.5 Hz, 1H), 7.50-7.40 (m, 3H), 7.30 (t, J=8.2 Hz, 1H), 4.78 (h, J=6.1 Hz, 1H), 4.65-4.49 (m, 1H), 4.24 (s, 2H), 4.15 (q, J=6.6 Hz, 1H), 3.84 (s, 3H), 3.79 (dd, J=9.2, 6.4 Hz, 2H), 3.62 (dd, J=10.9, 6.1 Hz, 2H), 3.56 (dd, J=9.2, 6.4 Hz, 1H), 3.40 (t, J=10.3 Hz, 1H), 2.96 (dq, J=9.2, 6.4 Hz, 1H), 2.04 (tt, J=8.3, 5.1 Hz, 1H), 1.38 (dd, J=6.1, 4.8 Hz, 6H), 1.28-1.14 (m, 2H), 1.16-1.00 (m, 2H)

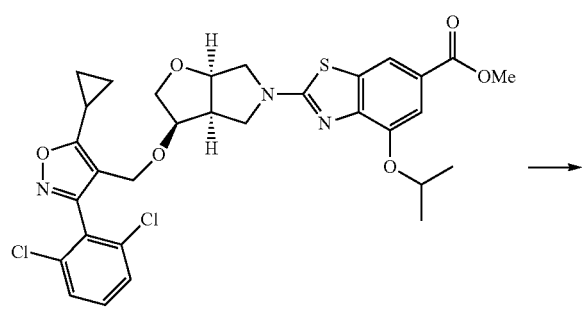

26f

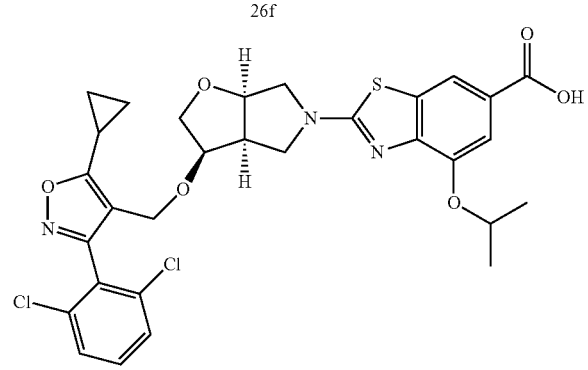

Example 26

Example 26 was synthesized following a similar experimental procedure as in Step 5e. LC/MS observed [M+H], 630.13.

Example 27

Step 27a

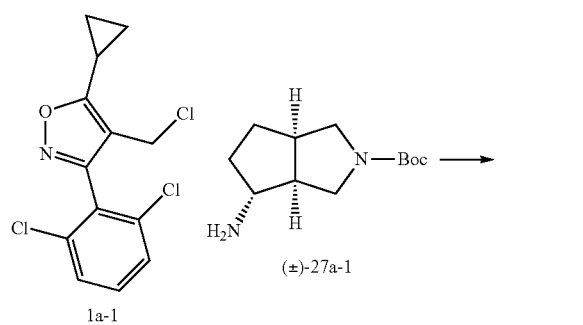

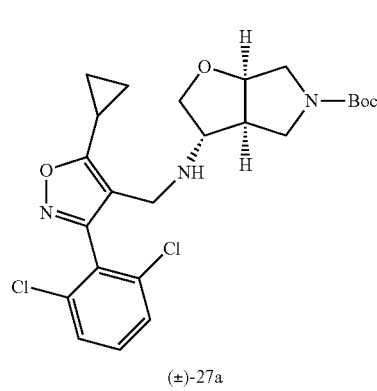

(±)-27a

To 4-(chloromethyl)-5-cyclopropyl-3-(2,6-dichlorophenyl)isoxazole (1a-1) (147 mg, 0.486 mmol) and racemic tert-butyl 4-aminohexahydrocyclopenta[c]pyrrole-2(1H)-carboxylate ((±)-27a-1) (100 mg, 0.442 mmol) in acetonitrile (3 ml) was added cesium carbonate (288 mg, 0.884 mmol) and the mixture was stirred at RT for 16 h and at 50° C. for 6 h. To the mixture was added sodium iodide (33.1 mg, 0.221 mmol) and the resulted mixture was stirred at 50° C. for 16 h. The mixture was diluted with EtOAc, washed with water, brine, dried, filtered and concentrated. The residue was purified by 1 CombiFlash eluting with 0 to 70% EtOAc/hexane to give racemic tert-butyl (3aS,4R,6aR)-4-(((5-cyclopropyl-3-(2,6-dichlorophenyl)isoxazol-4-yl)methyl)amino)hexahydrocyclopenta[c]pyrrole-2(1H)-carboxylate ((±)-27a) (150 mg, 0.305 mmol, 68.9% yield). LC/MS observed [M+H], 492.17; $^1$H NMR (400 MHz, Chloroform-d) δ 7.57-7.30 (m, 3H), 3.59-3.33 (m, 4H), 3.07 (b, 2H), 2.80 (b, 1H), 2.59 (b, 1H), 2.33-2.06 (m, 2H), 1.97-1.78 (m, 2H), 1.45 (s, 9H), 1.41-1.21 (m, 3H), 1.21-1.05 (m, 2H).

Step 27b

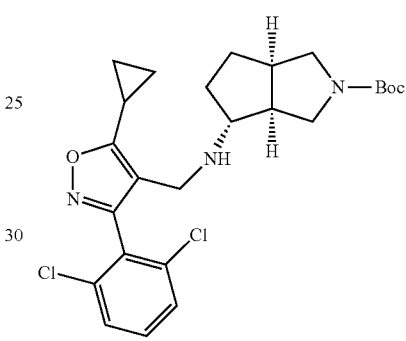

(±)-27a

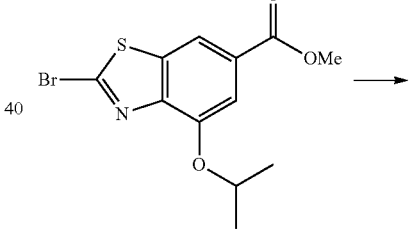

1b-1

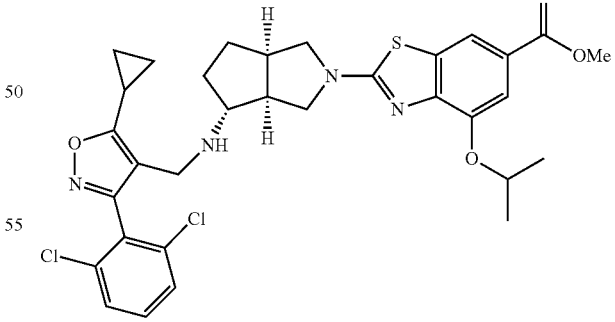

(±)-27b

To tert-butyl (3aS,4R,6aR)-4-(((5-cyclopropyl-3-(2,6-dichlorophenyl)isoxazol-4-yl)methyl)amino)hexahydrocyclopenta[c]pyrrole-2(1H)-carboxylate ((+)-27a) (75 mg, 0.152 mmol) in CH$_2$Cl$_2$ (1.5 ml) was added TFA (1.5 ml), and the mixture was stirred at RT for 2 h. The mixture was concentrated, and chased with DCM. To the residue was added methyl 2-bromo-4-isopropoxybenzo[d]thiazole-6-carboxylate (75 mg, 0.228 mmol), cesium carbonate (298 mg, 0.914 mmol) and DMA (3 ml). The mixture was stirred at RT for 16 h and then diluted with EtOAc/Water. The organic layer was separated, washed with water, brine, dried, filtered and concentrated. The residue was purified by CombiFlash eluting with 0 to 70% EtOAc/Hexane to give methyl 2-((3aS,4R,6aR)-4-(((5-cyclopropyl-3-(2,6-dichlorophenyl)isoxazol-4-yl)methyl)amino)hexahydrocyclopenta[c]pyrrol-2(1H)-yl)-4-isopropoxybenzo[d]thiazole-6-carboxylate ((±)-27b) (65 mg, 0.101 mmol, 66.5% yield). LC/MS observed [M+H], 641.19; $^1$H NMR (500 MHz, Chloroform-d) δ 7.88 (d, J=1.4 Hz, 1H), 7.44 (d, J=1.5 Hz, 1H), 7.41-7.33 (m, 2H), 7.29 (t, J=8.1 Hz, 1H), 4.77 (hept, J=6.2 Hz, 1H), 3.83 (s, 3H), 3.62 (dt, J=11.0, 8.3 Hz, 2H), 3.50 (d, J=13.7 Hz, 1H), 3.42 (d, J=13.6 Hz, 1H), 3.34-3.21 (m, 2H), 2.81 (q, J=5.5 Hz, 1H), 2.74 (qt, J=8.5, 4.8 Hz, 1H), 2.33 (tt, J=8.8, 4.6 Hz, 1H), 2.15-2.03 (m, 1H), 1.94-1.78 (m, 2H), 1.37 (dd, J=6.1, 1.5 Hz, 6H), 1.32-1.23 (m, 1H), 1.23-1.16 (m, 3H), 1.06 (tt, J=10.5, 6.6 Hz, 2H).

Step 27c

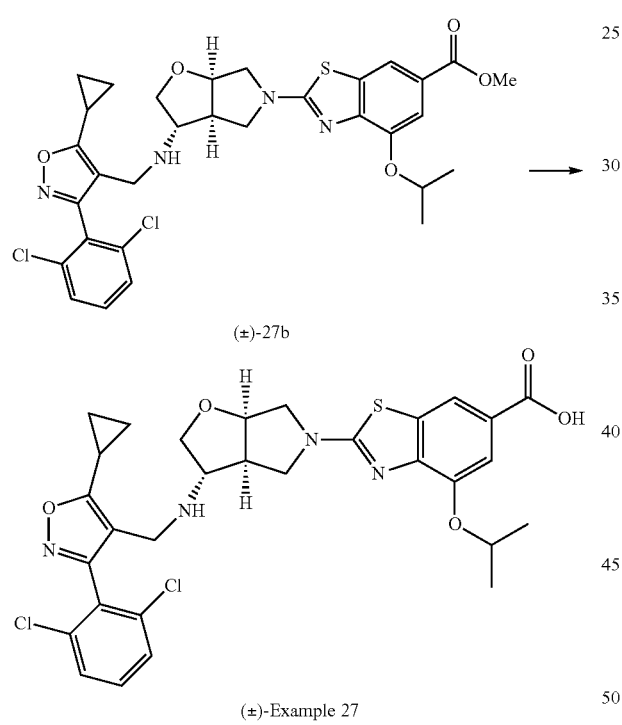

To methyl 2-((3aS,4R,6aR)-4-(((5-cyclopropyl-3-(2,6-dichlorophenyl)isoxazol-4-yl)methyl)amino)hexahydrocyclopenta[c]pyrrol-2(1H)-yl)-4-isopropoxybenzo[d]thiazole-6-carboxylate ((±)-27b) (65 mg, 0.101 mmol) in tetrahydrofuran (1.000 ml) and MeOH (1 ml) was added NaOH (0.152 ml, 0.152 mmol, 1N in water) and the mixture was stirred at RT for 16 h. Another portion of NaOH (0.152 ml, 0.152 mmol, 1N) was added and the mixture was stirred at 50° C. for 6 h. The mixture was acidified with 1N HCl, and diluted with EtOAc/water, the organic layer was separated and washed with water, brine, dried, filtered and concentrated to give (±)-Example 27 (53 mg, 0.084 mmol, 83% yield). LC/MS observed [M+H], 627.17; $^1$H NMR (500 MHz, Chloroform-d) δ 9.87 (s, 1H), 7.84 (s, 1H), 7.52-7.24 (m, 4H), 5.00 (s, 1H), 4.68 (p, J=6.2 Hz, 1H), 3.81-3.50 (m, 3H), 3.50-3.18 (m, 3H), 3.18-3.00 (m, 1H), 3.00-2.66 (m, 2H), 1.31 (dd, J=24.7, 6.0 Hz, 6H), 1.23-1.01 (m, 4H).

Example 28

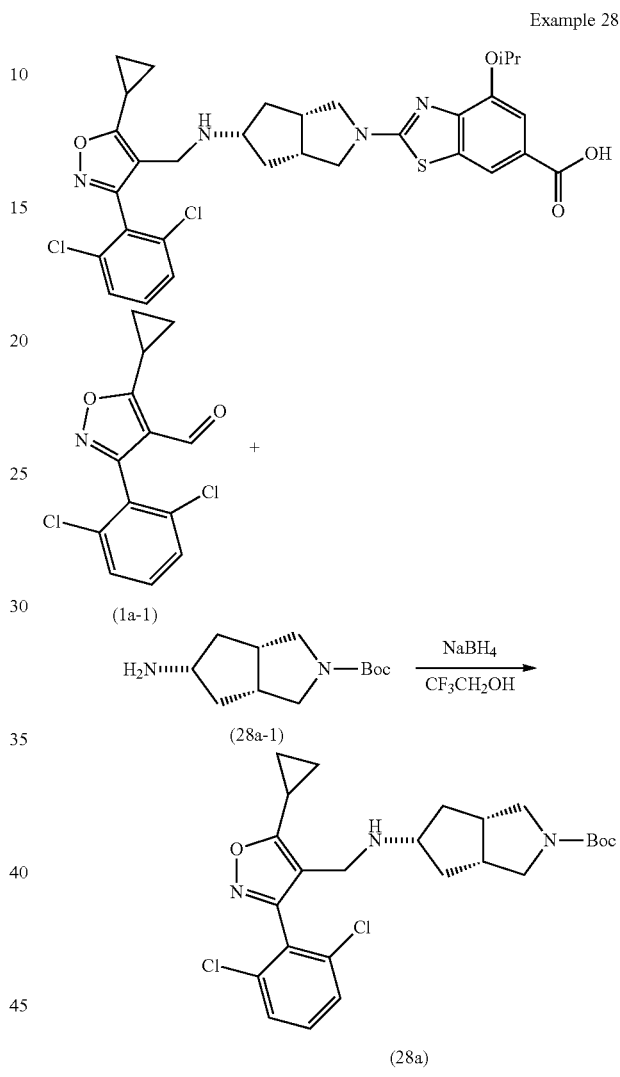

To a flask containing 5-cyclopropyl-3-(2,6-dichlorophenyl)isoxazole-4-carbaldehyde (317 mg, 1.124 mmol) and tert-butyl (3aR,5r,6aS)-5-aminohexahydrocyclopenta[c]pyrrole-2(1H)-carboxylate (242 mg, 1.067 mmol), was added 2,2,2-trifluoroethan-1-ol (1.3 ml, 18.61 mmol). The suspension was heated up to 50° C. for 30 min to form a light yellow solution. Then it was cooled to 45° C. Sodium tetrahydroborate (powder) (51 mg, 1.348 mmol) was added. Followed by adding 2,2,2-trifluoroethan-1-ol (1 ml) to wash NaBH$_4$ on the flask wall into the solution. The mixture was stirred at 45° C. for 16 h. The mixture was cooled down and concentrated under vacuum. The residue was precipitated in EtOAc (50 ml) and water (15 ml), organic layer was separated. The aqueous layer was extracted by EtOAc. The combined organic layers were washed with 10% aqueous potassium sodium tartrate solution and brine. The organic layer was dried and concentrated to give crude product. The crude product was purified by combiflash (12 g silica gel, 0-100% EtOAc in hexane) to give product 28a (248 mg) as a colorless oil. LCMS: 492.19 (M+1); $^1$H NMR (400 MHz, Chloroform-d) δ 7.41-7.36 (m, 2H), 7.34-7.29 (m, 1H), 3.46 (s, 2H), 3.43-3.33 (m, 2H), 3.18-3.06 (m, 2H), 3.06-2.95 (m, 1H), 2.52-2.39 (m, 2H), 2.17-2.07 (m, 1H), 2.03-1.93 (m, 2H), 1.42 (s, 9H), 1.24-1.17 (m, 2H), 1.10-1.04 (m, 2H), 1.04-0.95 (m, 2H).

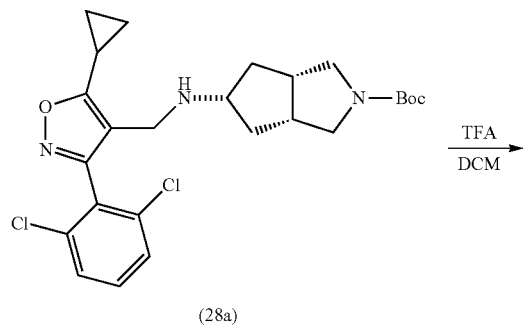

(28a)

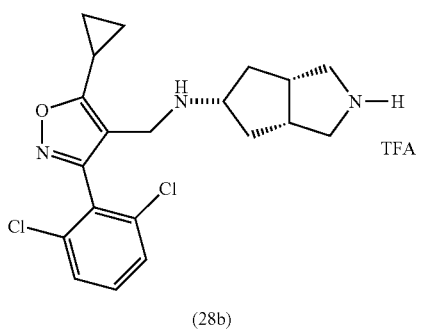

(28b)

To a solution of compound 28a (152 mg, 0.309 mmol) in DCM (1.5 ml) at 0° C., was added TFA (0.76 ml, 9.88 mmol) dropwise. The mixture was stirred at 0° C. for 2 h. The solvent was removed by rotovap. The trace amount of TFA was removed by adding DCM (3 times) to the crude mixture and then removing by rotovap three times. The crude product (175 mg, 0.309 mmol) is a pale yellow oil. The crude product (28b) was used directly in next steps without purification. LCMS: 392.14 (M+1).

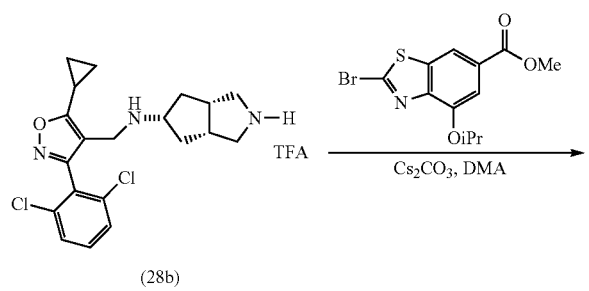

(28b)

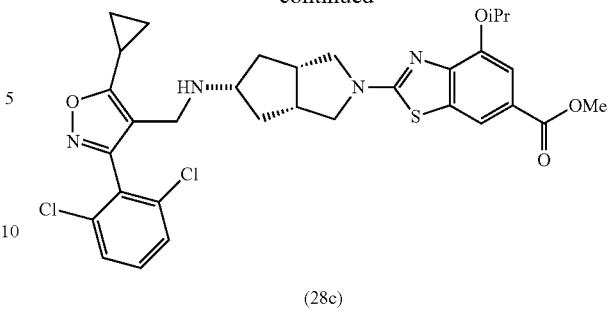

(28c)

To a vial containing the above crude oil (28b, 0.154 mmol), methyl 2-bromo-4-isopropoxybenzo[d]thiazole-6-carboxylate (55.9 mg, 0.169 mmol) and cesium carbonate (201 mg, 0.616 mmol), was added N,N-dimethylacetamide (1.5 ml). The mixture was stirred at 70° C. for 20 h. The solvent was removed by N$_2$ blowing. The mixture was treated with DCM. The resulting slurry was filtered. The filtrate was loaded into a silica cartridge and purified by combiflash (8 silica gel, 0-100% EtOAc in hex) to give the product (28c) (103 mg) as a white solid. LCMS: 641.17 (M+1); $^1$H NMR (400 MHz, Chloroform-d) δ 7.94 (d, J=1.2 Hz, 1H), 7.49 (d, J=1.2 Hz, 1H), 7.39-7.34 (m, 2H), 7.31-7.25 (m, 1H), 4.82 (hept, J=6.0 Hz, 1H), 3.88 (s, 3H), 3.73-3.65 (m, 2H), 3.50-3.39 (m, 4H), 3.16-3.05 (m, 1H), 2.75-2.64 (m, 2H), 2.14-2.03 (m, 3H), 1.42 (d, J=6.0 Hz, 6H), 1.21-1.17 (m, 2H), 1.17-1.10 (m, 2H), 1.08-1.00 m, 2H).

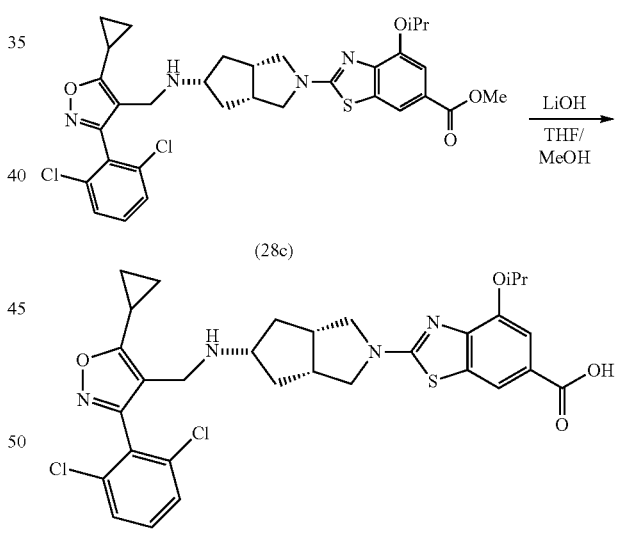

(example 28)

To a solution of the methyl ester above (28c; 103 mg, 0.161 mmol) in MeOH (1.6 ml) and THF (3.3 ml), was added aqueous lithium hydroxide (1M) (1.6 ml, 1.6 mmol). The resulting solution was stirred at rt for 16 h. Most of solvent was removed. Water (3 ml) and EtOAc (10 ml) were added, Added 1M HCl was added to pH=5. Two clear layers were formed, the organic layer was separated, and the aqueous layer was extracted with EtOAc (2×10 ml). The combined organic layers were washed with brine, dried, filtered, and concentrated to give the crude product (103 mg) as a syrup. The crude product was treated with MeOH (3 ml). The mixture was stirred at rt for 10 min to form a white slurry, The slurry was filtered to give the pure example 28 as a white solid (26 mg). LCMS: 627.16 (M+1); $^1$H NMR (400 MHz, DMSO-d$_6$) δ 7.99 (d, J=1.5 Hz, 1H), 7.68-7.43 (m, 3H), 7.37 (d, J=1.6 Hz, 1H), 4.86 (hept, J=6.0 Hz, 1H), 3.68-3.57 (m, 2H), 3.42-3.29 (m, 4H), 3.10-2.92 (m, 1H), 2.74-2.62 (m, 2H), 2.39-2.26 (m, 1H), 2.03-1.92 (m, 2H), 1.31 (d, J=6.0 Hz, 6H), 1.20-0.95 (m, 6H).

Example 29

J=1.4 Hz, 1H), 4.84 (p, J=6.0 Hz, 1H), 4.57-4.50 (m, 2H), 4.16 (d, J=12.4 Hz, 1H), 4.08 (d, J=12.8 Hz, 1H), 3.95-3.84 (m, 2H), 3.63-3.57 (m, 1H), 3.14-3.03 (m, 1H), 2.97-2.86 (m, 2H), 2.38 (dd, J=8.9, 4.3 Hz, 1H), 1.99-1.84 (m, 1H), 1.80 (ddd, J=14.0, 7.3, 3.3 Hz, 1H), 1.32 (d, J=6.0 Hz, 6H), 1.17 (s, 2H), 1.20-1.07 (m, 2H).

Example 30

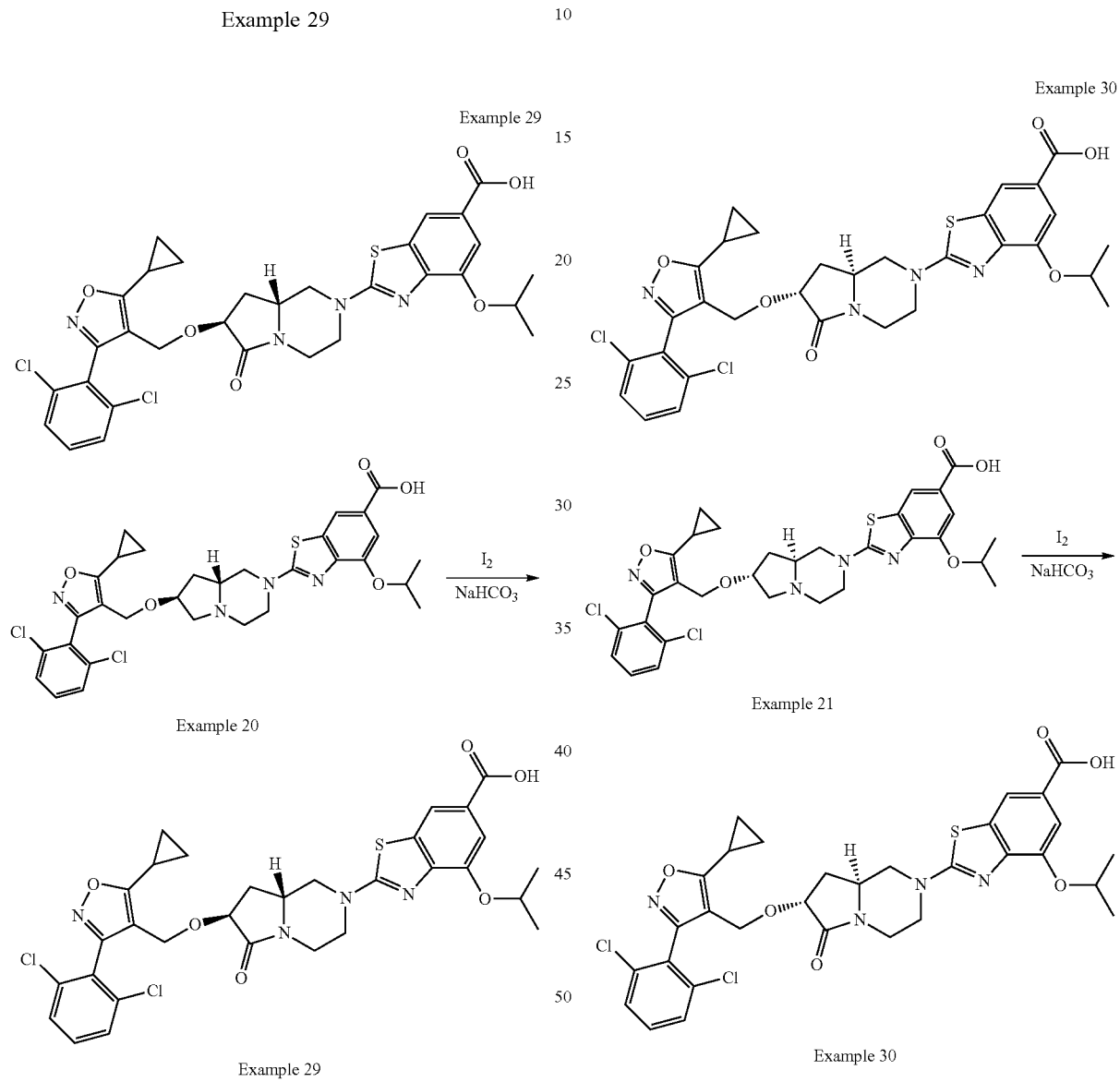

To a mixture of Example 20 (65 mg, 0.101 mmol) and sodium bicarbonate (85 mg, 1.01 mmol) in THF (3 ml)/Water (1.2 ml) was added iodine (192 mg, 0.757 mmol) at rt. The reaction mixture was stirred at rt for 4 h, quenched with brine/1N HCl (pH 4), and extracted with ethyl acetate. The combined organic layers were washed with brine, dried over Na$_2$SO$_4$, and concentrated. The residue was purified by chromatography on silica gel using hexane/acetone (100/0 to 30/70, 15 min) to give Example 29 as a brown solid. LC-MS: M+H=657.12, calcd. 657.13; $^1$H NMR (400 MHz, DMSO-d$_6$) δ 12.77 (s, 1H), 8.03 (t, J=1.3 Hz, 1H), 7.63 (ddt, J=8.0, 6.8, 1.2 Hz, 2H), 7.55 (td, J=8.1, 1.0 Hz, 1H), 7.40 (d, Example 30 was synthesized by following the similar experimental procedure as for Example 29. Example 30: LC-MS M+H=257.12, calcd. 257.13; $^1$H NMR (400 MHz, DMSO-d$_6$) δ 12.79 (s, 1H), 8.02 (d, J=1.5 Hz, 1H), 7.63 (ddd, J=8.2, 6.7, 1.3 Hz, 2H), 7.62-7.47 (m, 1H), 7.40 (d, J=1.6 Hz, 1H), 4.84 (p, J=6.0 Hz, 1H), 4.56 (d, J=12.2 Hz, 1H), 4.50 (d, J=12.2 Hz, 1H), 4.16 (d, J=12.5 Hz, 1H), 4.08 (d, J=12.9 Hz, 1H), 3.89 (ddd, J=18.9, 9.9, 3.2 Hz, 2H), 3.60 (h, J=6.0 Hz, 1H), 3.08 (td, J=12.6, 3.6 Hz, 1H), 2.91 (td, J=12.5, 12.1, 4.1 Hz, 2H), 2.38 (tt, J=8.2, 5.2 Hz, 1H), 1.95-1.74 (m, 2H), 1.32 (d, J=6.0 Hz, 6H), 1.22-1.04 (m, 4H).

Example 31

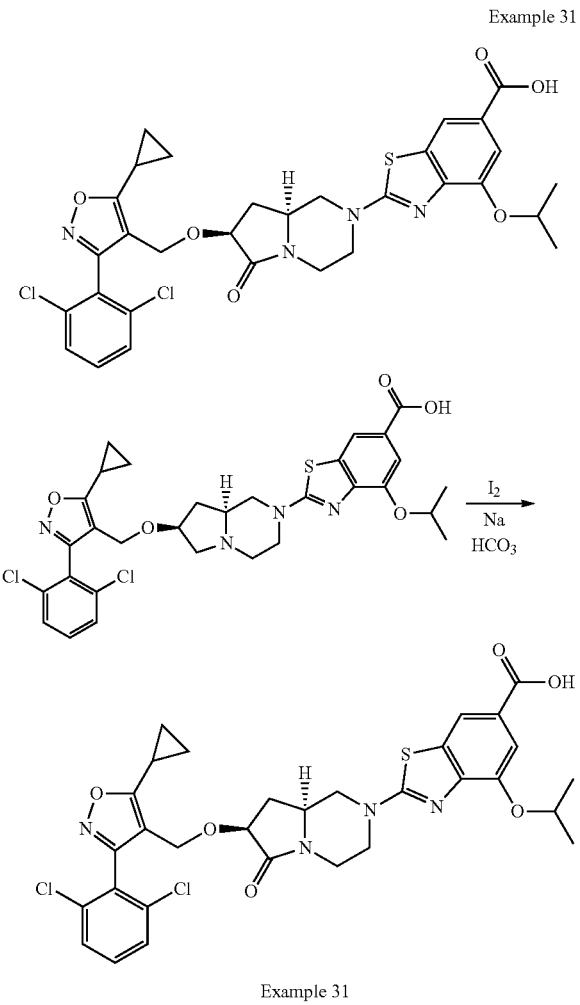

Example 31

Example 31 was synthesized by following the similar experimental procedure as for Example 29. Example 31: LC-MS M+H=257.12, calcd. 257.13; $^1$H NMR (400 MHz, DMSO-$d_6$) δ 12.79 (s, 1H), 7.99 (d, J=11.6 Hz, 1H), 7.69-7.62 (m, 2H), 7.62-7.53 (m, 1H), 7.42-7.35 (m, 1H), 4.83 (t, J=6.2 Hz, 1H), 4.68 (d, J=12.2 Hz, 1H), 4.53 (d, J=12.1 Hz, 1H), 4.20 (d, J=15.1 Hz, 1H), 4.14 (s, 1H), 4.11-3.98 (m, 2H), 3.87 (d, J=12.0 Hz, 1H), 3.57-3.50 (m, 2H), 3.06-3.02 (m, 1H), 2.93-2.79 (m, 2H), 2.43-2.35 (m, 1H), 1.32 (d, J=5.9 Hz, 6H), 1.19-1.10 (m, 4H).

Assays

Human FXR (NR1H4) Assay

Determination of a ligand mediated Gal4 promoter driven transactivation to quantify ligand binding mediated activation of FXR. FXR Reporter Assay kit purchased from Indigo Bioscience (Catalogue number: IB00601) to determine the potency and efficacy of compound developed by Enanta that can induce FXR activation. The principle application of this reporter assay system is to quantify functional activity of human FXR. The assay utilizes non-human mammalian cells, CHO (Chinese hamster ovary) cells engineered to express human NR1H4 protein (referred to as FXR). Reporter cells also incorporate the cDNA encoding beetle luciferase which catalyzes the substrates and yields photon emission. Luminescence intensity of the reaction is quantified using a plate-reading luminometer, Envision. Reporter Cells include the luciferase reporter gene functionally linked to an FXR responsive promoter. Thus, quantifying changes in luciferase expression in the treated reporter cells provides a sensitive surrogate measure of the changes in FXR activity. $EC_{50}$ and efficacy (normalize to CDCA set as 100%) is determined by XLFit. The assay is according to the manufacturer's instructions. In brief, the assay was performed in white, 96 well plates using final volume of 100 ul containing cells with different doses of compounds. Retrieve Reporter Cells from −80° C. storage. Perform a rapid thaw of the frozen cells by transferring a 10 ml volume of 37° C. cell recovery medium into the tube of frozen cells. Recap the tube of Reporter Cells and immediately place it in a 37° C. water bath for 5-10 minutes. Retrieve the tube of Reporter Cell Suspension from the water bath. Sanitize the outside surface of the tube with a 70% alcohol swab, and then transfer it into the cell culture hood. Dispense 90 μl of cell suspension into each well of the 96-well Assay Plate. Transfer the plate into 37° C. incubator, allowing the cells adherent to the bottom of the well. Dilute compounds in Dilution Plate (DP), and administrate to cells at Assay Plate (AP). DMSO content of the samples was kept at 0.2%. Cells were incubated for additional 22 hours before luciferase activities were measured. Thirty minutes before intending to quantify FXR activity, remove Detection Substrate and Detection Buffer from the refrigerator and place them in a low-light area so that they may equilibrate to room temperature. Remove the plate's lid and discard all media contents by ejecting it into an appropriate waste container. Gently tap the inverted plate onto a clean absorbent paper towel to remove residual droplets. Cells will remain tightly adhered to well bottoms. Add 100 μl of luciferase detection reagent to each well of the assay plate. Allow the assay plate to rest at room temperature for at least 5 minutes following the addition of LDR. Set the instrument (Envision) to perform a single 5 second "plate shake" prior to reading the first assay well. Read time may be 0.5 second (500 mSec) per well. $EC_{50}$ and Efficacy (normalize to CDCA set as 100%) is determined by XLFit.

To assess the FXR agonistic potency of the example compounds as well as for reference compound, potency ranges were determined in the Human FXR (NR1H4) Assay as listed below in Table 9. The efficacy was normalized to CDCA set as 100%. (A=EC50<0.030 μM; B=0.030 μM<EC50<0.2 μM; C=0.2 μM<EC50<1.0 μM; D=EC50>1.0 μM)

TABLE 9

| Example # | EC50 | Efficacy (%) |
|---|---|---|
| CDCA | D | 100 |
| 6-ECDCA | C | 130 |
| 1 | C | 51 |
| 2 | B | 82 |
| 3 | C | 33.5 |
| 4 | C | 40 |
| 5 | B | 55 |
| 6 | B | 56 |
| 7 | A | 93.1 |
| 8 | C | 20 |
| 9 | C | 5.5 |
| 10 | A | 103 |
| 11 | B | 57 |
| 12 | B | 70 |

TABLE 9-continued

| Example # | EC50 | Efficacy (%) |
|---|---|---|
| 13 | A | 96.5 |
| 14 | B | 67.5 |
| 15 | C | 66.5 |
| 16 | B | 85 |
| 17 | D | 9 |
| 18 | C | 45 |
| 19 | C | 82.3 |
| 20 | C | 44 |
| 21 | B | 72 |
| 22 | B | 82 |
| 23 | A | 103 |
| 24 | B | 78 |
| 25 | B | 66 |
| 26 | C | 7 |
| 27 | C | 49 |
| 28 | C | 57 |
| 29 | D | 21 |
| 30 | B | 70 |
| 31 | B | 110 |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (I),

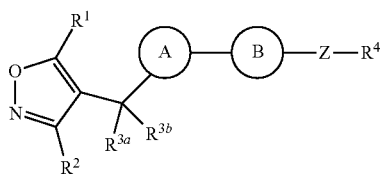

or a pharmaceutically acceptable salt thereof, wherein:
$R^1$ is hydrogen, halogen, cyano, optionally substituted —$C_1$-$C_6$ alkyl, optionally substituted —$C_2$-$C_6$ alkenyl, optionally substituted —$C_2$-$C_6$ alkynyl, optionally substituted —$C_3$-$C_6$ cycloalkyl or optionally substituted 3- to 6-membered heterocycloalkyl;
$R^2$ is optionally substituted aryl, optionally substituted heteroaryl, optionally substituted —$C_3$-$C_{12}$ cycloalkyl or optionally substituted 3- to 12-membered heterocycloalkyl;
$R^{3a}$ and $R^{3b}$ are each independently selected from the group consisting of hydrogen, halogen, optionally substituted —$C_1$-$C_6$ alkyl, optionally substituted —$C_1$-$C_6$ alkoxy and optionally substituted —$C_3$-$C_6$ cycloalkyl; alternatively, $R^{3a}$ and $R^{3b}$ are taken together with the carbon atom to which they are attached to form optionally substituted —$C_3$-$C_6$ cycloalkyl, optionally substituted 3- to 6-membered heterocycloalkyl, or optionally substituted —$C_3$-$C_6$ cycloalkenyl;
Ⓐ is

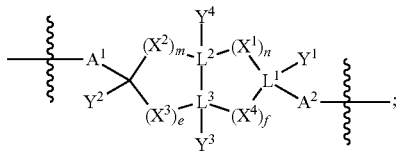

$L^1$, $L^2$, $L^3$ are each independently C or N;
e, f, m, and n are each independently 0, 1, 2, 3, or 4;
$A^1$ is O, $NR^{3c}$, S, S(O) or S(O)$_2$;
$A^2$ is absent, O, $NR^{3c}$, S, S(O) or S(O)$_2$;
$A^1$ is attached to —$CR^{3a}R^{3b}$—, and $A^2$ is attached to Ⓑ;
Each $X^1$, $X^2$, $X^3$ and $X^4$ is independently selected from the group consisting of: O, C(O), S, S(O), S(O)$_2$, $NR^{3c}$, and $CR^{3d}R^{3e}$; wherein $R^{3d}$ and $R^{3e}$ are each independently selected from hydrogen, halogen, optionally substituted —$C_1$-$C_6$ alkyl, optionally substituted —$C_3$-$C_6$ cycloalkyl, and optionally substituted —O—$C_1$-$C_6$ alkyl; alternatively, $R^{3d}$ and $R^{3e}$ are taken together with the carbon atom to which they are attached to form a optionally substituted —$C_3$-$C_6$ cycloalkyl or optionally substituted 3- to 6-membered heterocycloalkyl; $R^{3c}$ is hydrogen, optionally substituted —$C_1$-$C_6$ alkyl, optionally substituted —$C_3$-$C_6$ cycloalkyl, formyl, or acetyl;
$Y^1$ is absent when $L^1$ is N, and hydrogen, hydroxyl, halogen, optionally substituted —$C_1$-$C_6$ alkyl, optionally substituted —$C_3$-$C_6$ cycloalkyl, or optionally substituted —O—$C_1$-$C_6$ alkyl when $L^1$ is C;
$Y^3$ is absent when $L^3$ is N, and hydrogen, hydroxyl, halogen, optionally substituted —$C_1$-$C_6$ alkyl, optionally substituted —$C_3$-$C_6$ cycloalkyl, or optionally substituted —O—$C_1$-$C_6$ alkyl when $L^3$ is C;
$Y^4$ is absent when $L^4$ is N, and hydrogen, hydroxyl, halogen, optionally substituted —$C_1$-$C_6$ alkyl, optionally substituted —$C_3$-$C_6$ cycloalkyl, or optionally substituted —O—$C_1$-$C_6$ alkyl when $L^4$ is C;
$Y^2$ is hydrogen, hydroxyl, halogen, optionally substituted —$C_1$-$C_6$ alkyl, optionally substituted —$C_3$-$C_6$ cycloalkyl, or optionally substituted —O—$C_1$-$C_6$ alkyl;
provided that Ⓐ is not

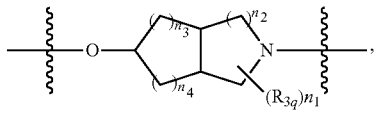

wherein $n_1$, $n_2$, $n_3$, and $n_4$ are 0, 1, 2 or 3; $R_{3q}$ is selected from hydrogen, halogen, optionally substituted —$C_1$-$C_3$ alkyl, optionally substituted —$C_3$-$C_6$ cycloalkyl, optionally substituted —O—$C_1$-$C_3$ alkyl, alternatively two $R_{3q}$ groups are linked together to form a —$C_3$-$C_6$ cycloalkyl, aryl, heteroaryl or 3- to 6-membered heterocycloalkyl;
Ⓑ is optionally substituted aryl, optionally substituted heteroaryl, or optionally substituted 3-12 membered heterocycloalkyl;
Z is selected from the group consisting of:
1) Absent;
2) Optionally substituted —$C_1$-$C_6$ alkyl;
3) Optionally substituted —$C_2$-$C_6$ alkenyl;
4) Optionally substituted —$C_2$-$C_6$ alkynyl;
5) Optionally substituted —$C_3$-$C_8$ cycloalkyl;
6) Optionally substituted 3- to 8-membered heterocycloalkyl;
7) Optionally substituted —$C_3$-$C_8$ cycloalkenyl;
8) Optionally substituted aryl; and
9) Optionally substituted heteroaryl;
$R^4$ is hydroxy, protected hydroxy, —O-(hydroxy prodrug group), tetrazolyl, cyano, —$CO_2R^5$, —O—Y—$CO_2R^5$, —$NR^{4b}$—Y—$CO_2R^5$, —$CONR^{4a}R^{4b}$,

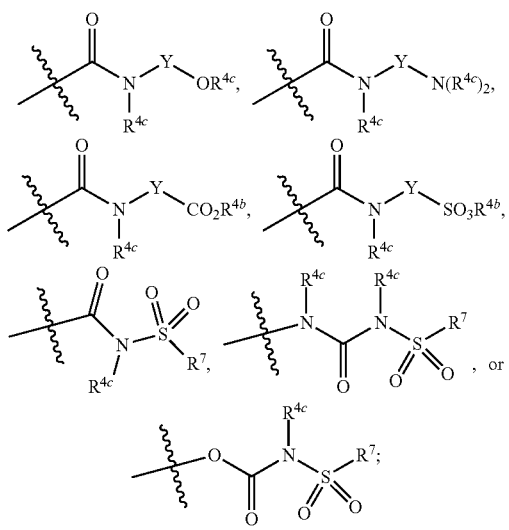

wherein,
Y is absent or optionally substituted —$C_1$-$C_6$ alkyl;
$R^{4a}$ and $R^{4b}$ are independently selected from the group consisting of:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl; and
5) Optionally substituted —$C_3$-$C_8$ cycloalkyl;
$R^{4c}$ is hydrogen or optionally substituted —$C_1$-$C_6$ alkyl;
$R^5$ is selected from the group consisting of:
1) Hydrogen;
2)

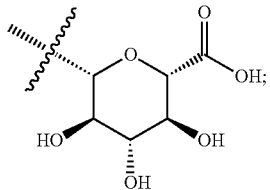

3) Optionally substituted —$C_1$-$C_8$ alkyl;
4) Optionally substituted —$C_2$-$C_8$ alkenyl;
5) Optionally substituted —$C_2$-$C_8$ alkynyl; and
6) Optionally substituted —$C_3$-$C_8$ cycloalkyl;
$R^7$ is selected from the group consisting of:
1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_8$ cycloalkyl;
5) Optionally substituted —$C_3$-$C_8$ cycloalkenyl;
6) Optionally substituted 3- to 8-membered heterocycloalkyl;
7) Optionally substituted 3- to 8-membered heterocycloalkenyl;
8) Optionally substituted aryl;
9) Optionally substituted —$C_1$-$C_8$ arylalkyl;
10) Optionally substituted heteroaryl;
11) Optionally substituted —$C_1$-$C_8$ heteroarylalkyl; and 12) $NR^9R^{10}$; wherein $R^9$ and $R^{10}$ are each independently selected from hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted aryl, optionally substituted alkylaryl, optionally substituted 3- to 8-membered heterocycloalkyl, optionally substituted heteroaryl, optionally substituted alkylheteroaryl; alternatively, $R^9$ and $R^{10}$ are taken together with the nitrogen atom to which they are attached to form a heterocyclic ring.

2. The compound of claim 1, wherein (A) is selected from the groups set forth below:

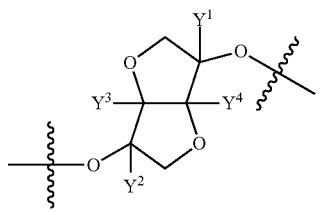

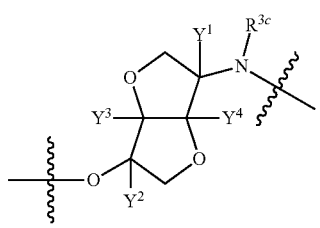

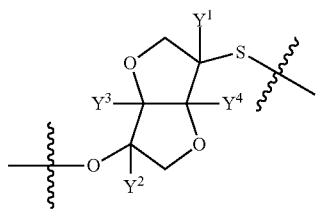

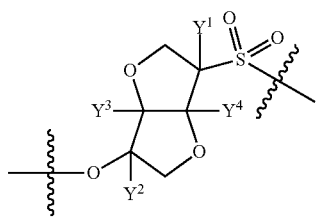

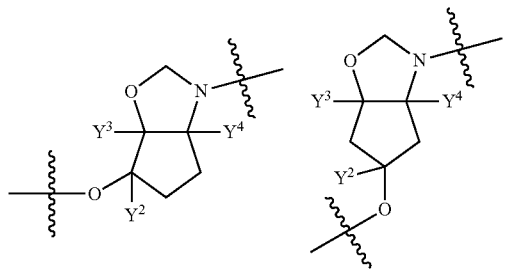

313
-continued
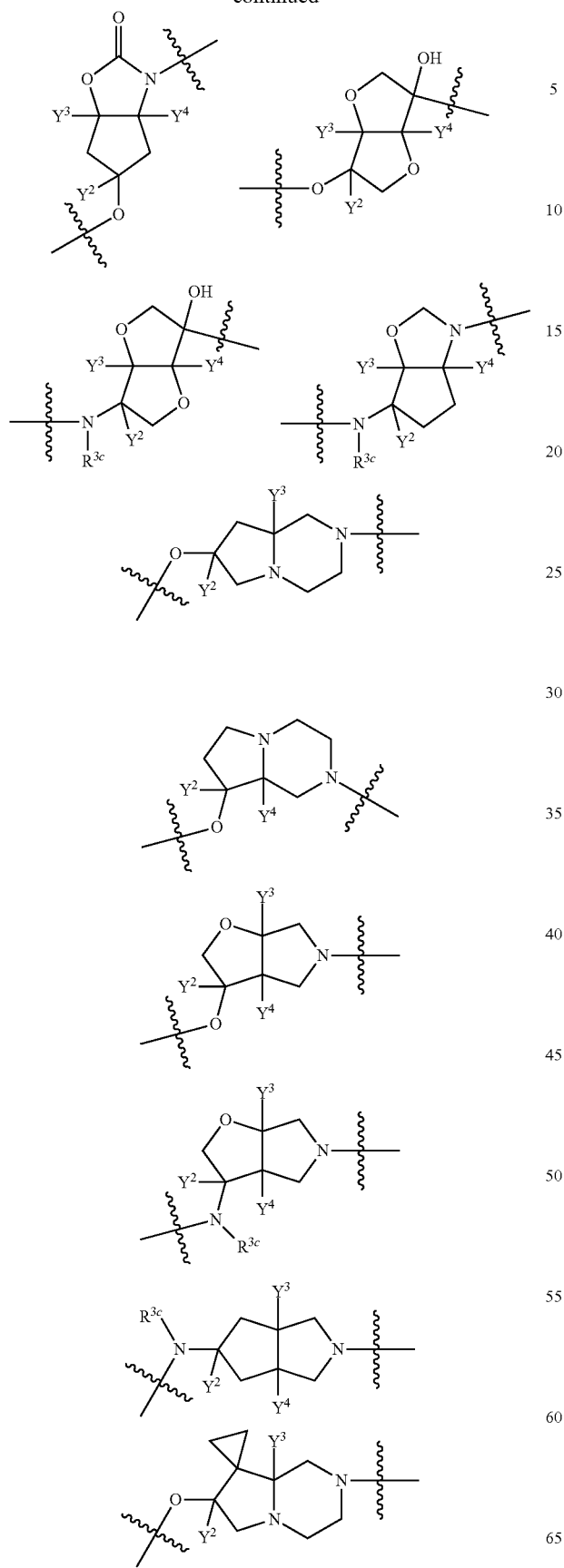
314
-continued
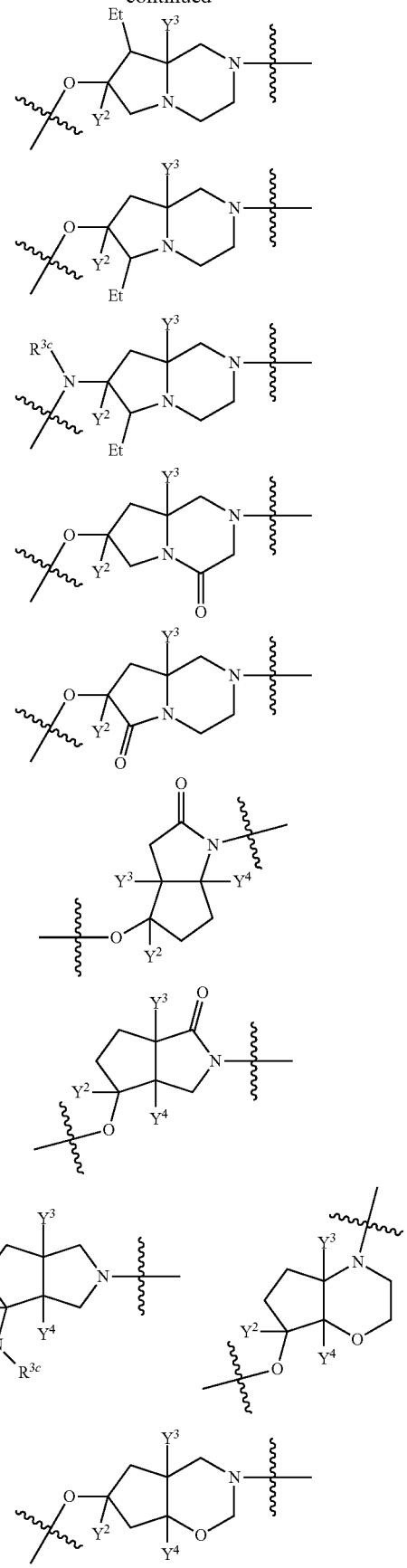

-continued
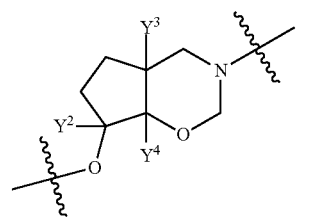
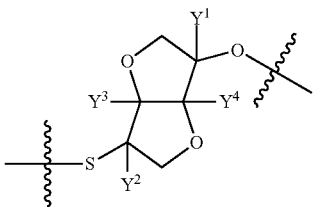
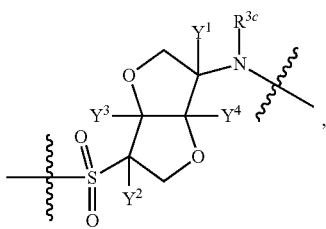
wherein each of said groups is optionally further substituted.
3. The compound of claim 1, wherein Ⓑ is selected from the groups set forth below:
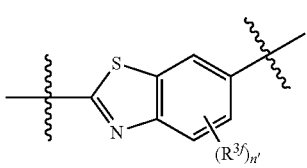
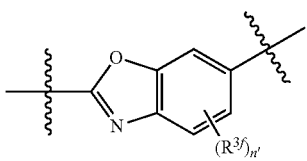
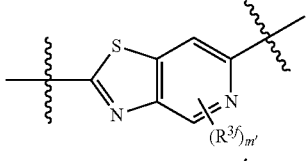
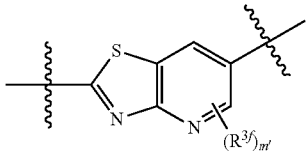
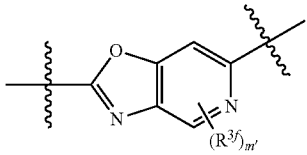
-continued
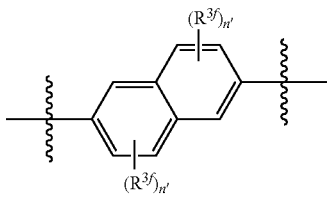
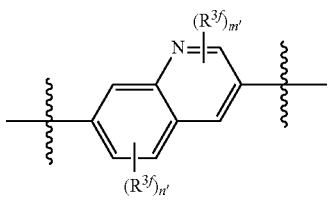
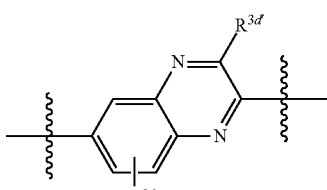
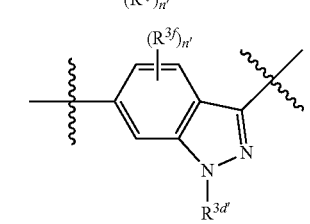
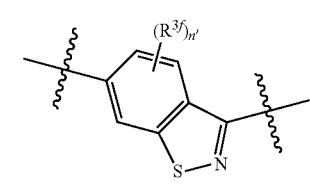
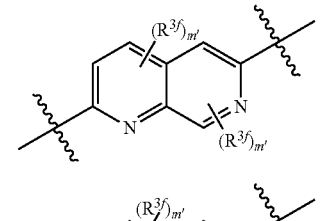
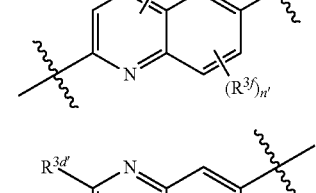
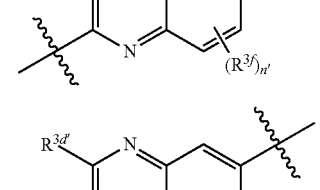
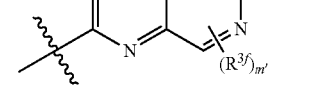

317
-continued

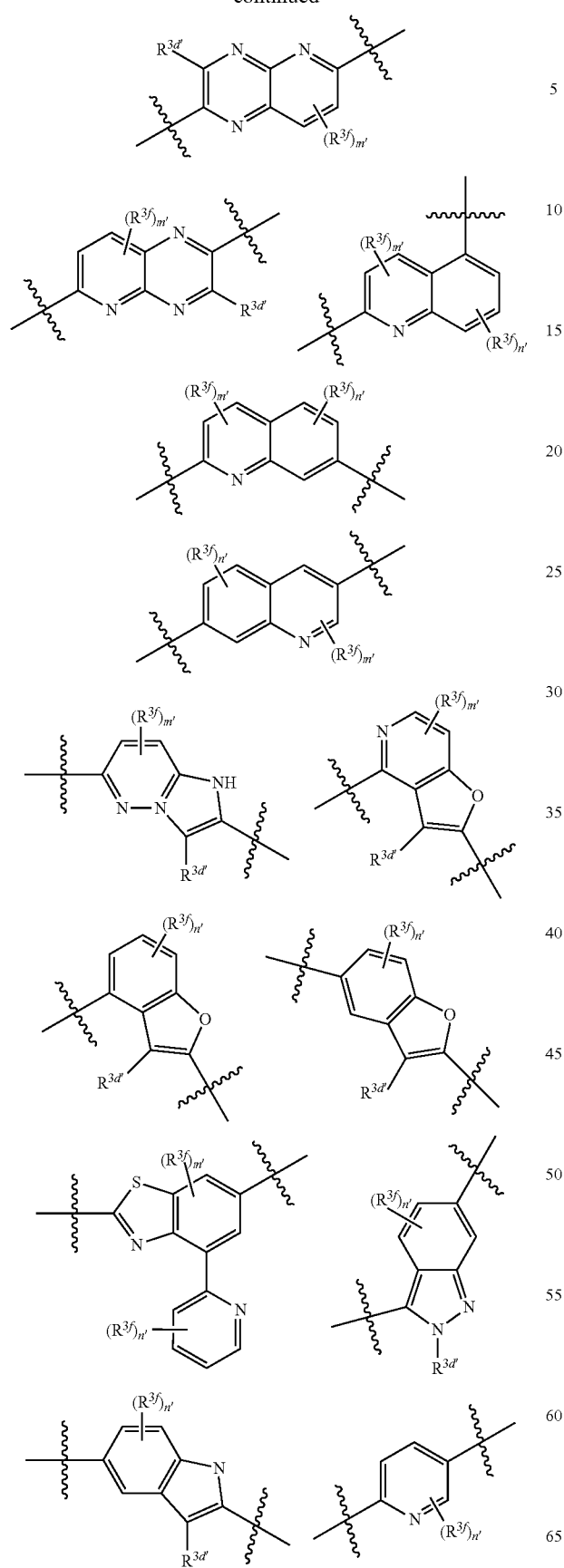

318
-continued

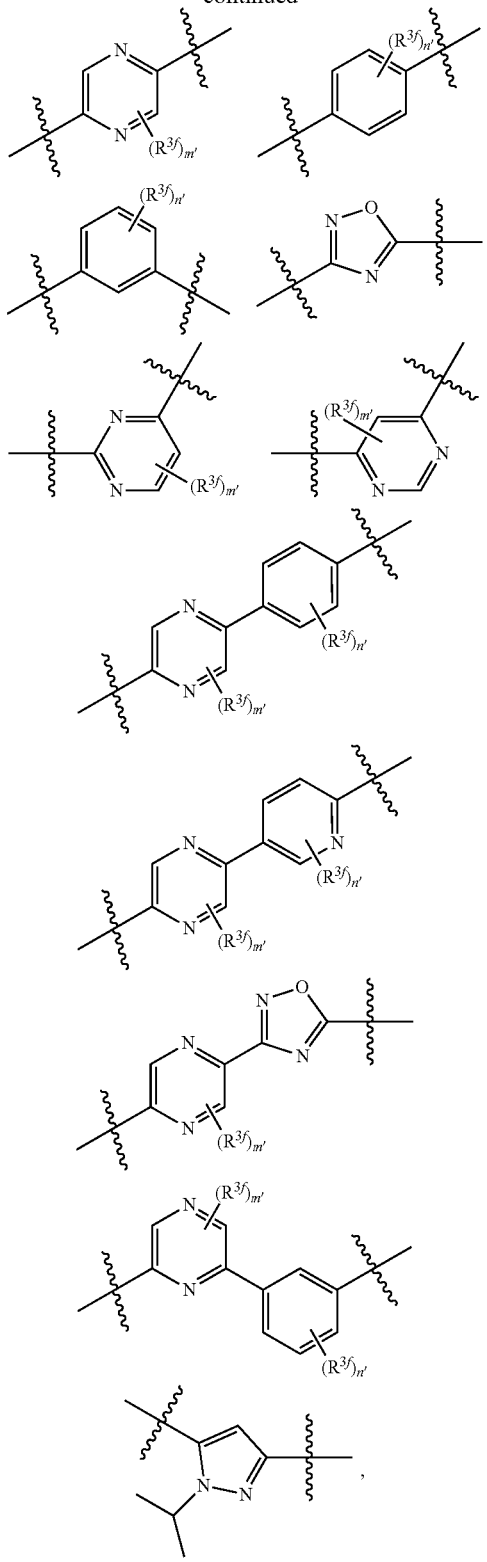

wherein, one of the indicated valences is the point of attachment to A and the other is the point of attachment to Z; $R^{3f}$ is selected from a group consisting of halogen, —CN, —NO$_2$, —NH$_2$, optionally substituted $C_1$-$C_6$ alkyl, optionally substituted $C_1$-$C_6$ alkoxy, optionally substituted $C_3$-$C_6$ cycloalkyl, optionally substituted $C_3$-$C_6$ cycloalkenyl, optionally substituted aryl, and optionally substituted heteroaryl; $R^{3d'}$ is selected from a group consisting of hydrogen, halogen, —CN, —NO$_2$, —NH$_2$, optionally substituted C$_1$-C$_6$ alkyl, optionally substituted C$_1$-C$_6$ alkoxy, optionally substituted C$_3$-C$_6$ cycloalkyl, optionally substituted C$_3$-C$_6$ cycloalkenyl, optionally substituted aryl, and optionally substituted heteroaryl; m' 0, 1 or 2; and n' is 0, 1, 2 or 3.

4. The compound of claim 1, represented by Formula (IIa) or (IIb), or a pharmaceutically acceptable salt thereof,

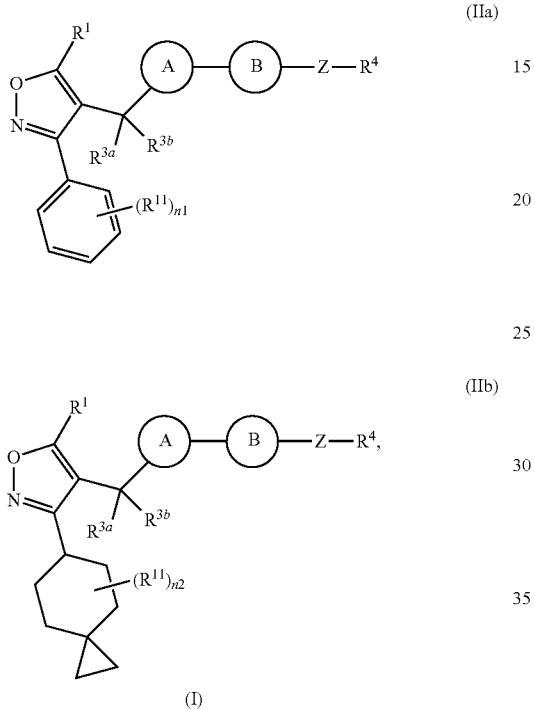

wherein $R^{11}$ at each occurrence is independently selected from the group consisting of halogen, optionally substituted —C$_1$-C$_6$ alkyl, optionally substituted —C$_1$-C$_6$ alkoxy, optionally substituted —C$_3$-C$_6$ cycloalkyl, optionally substituted —C$_3$-C$_6$ cycloalkenyl, optionally substituted aryl, and optionally substituted heteroaryl; n1 is 0, 1, 2, 3, 4, or 5; n2 is 0, 1, 2 or 3; and $R^1$, $R^{3a}$, $R^{3b}$, (A), (B), and $R^4$ are as defined in claim 1.

5. The compound of claim 1, represented by Formula (VIIa), (VIIb), (VIIc), or (VIId), or a pharmaceutically acceptable salt thereof,

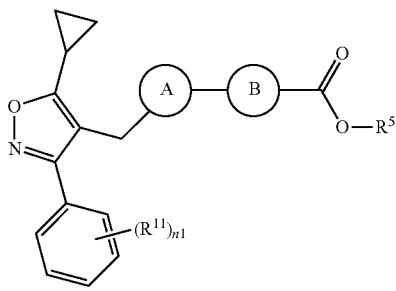

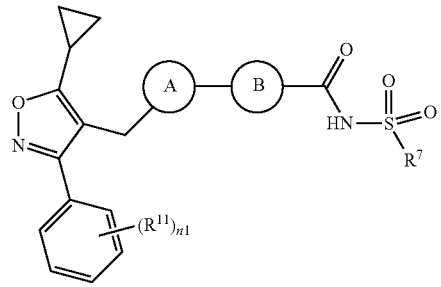

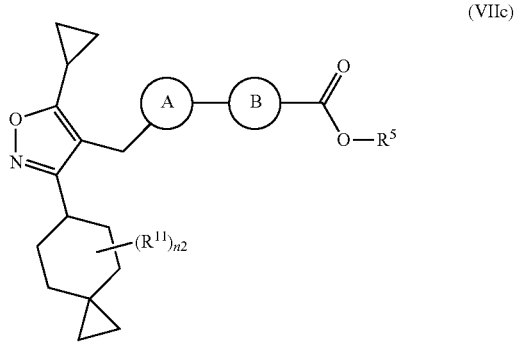

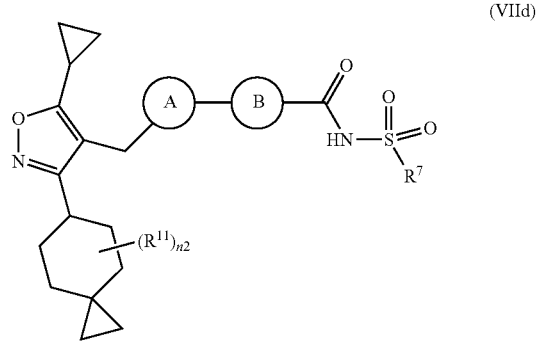

wherein $R^{11}$ at each occurrence is independently selected from the group consisting of halogen, optionally substituted —C$_1$-C$_6$ alkyl, optionally substituted —C$_1$-C$_6$ alkoxy, optionally substituted —C$_3$-C$_6$ cycloalkyl, optionally substituted —C$_3$-C$_6$ cycloalkenyl, optionally substituted aryl, and optionally substituted heteroaryl; n1 is 0, 1, 2, 3, 4, or 5; n2 is 0, 1, 2 or 3; $R^5$, $R^7$, (A), and (B) are as defined in claim 1.

6. The compound of claim 1, represented by Formula (VIIa-1), (VIIa-2), (VIIa-3), (VIIa-4), (VIIa-5), (VIIa-6), (VIIb-1), (VIIb-2), (VIIb-3), (VIIb-4), (VIIb-5), or (VIIb-6), or a pharmaceutically acceptable salt thereof,

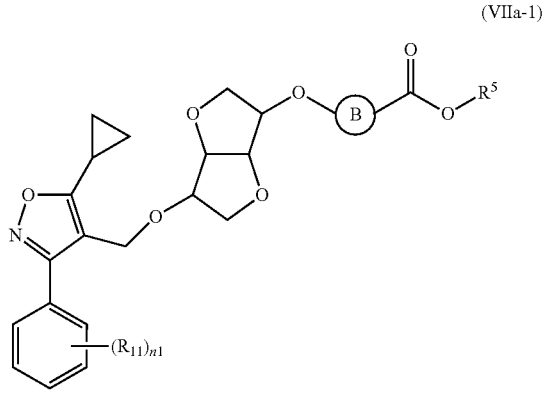
(VIIa-1)
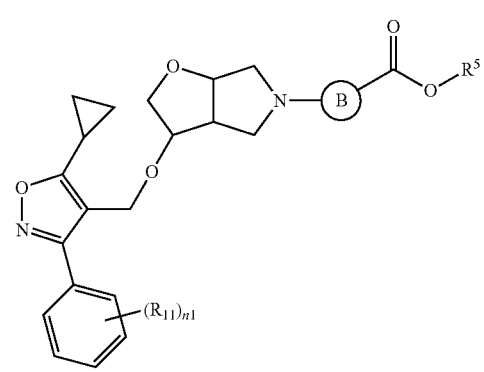
(VIIa-5)
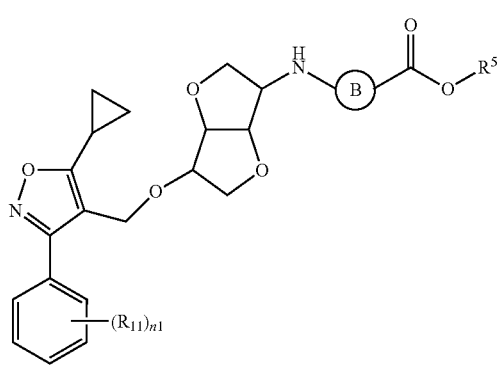
(VIIa-2)
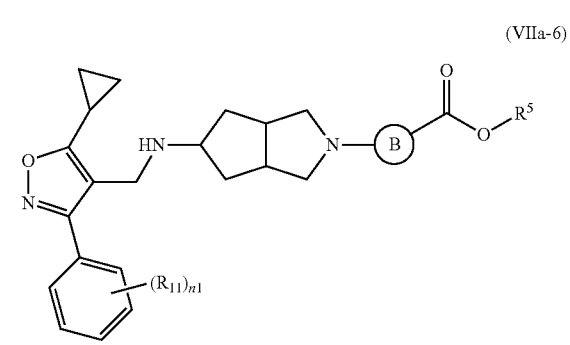
(VIIa-6)
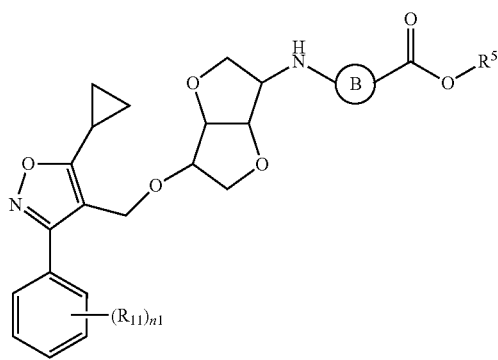
(VIIa-3)
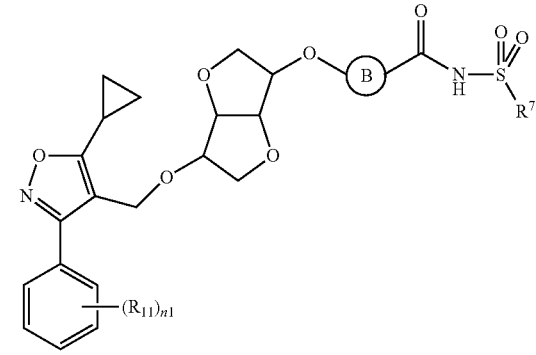
(VIIb-1)
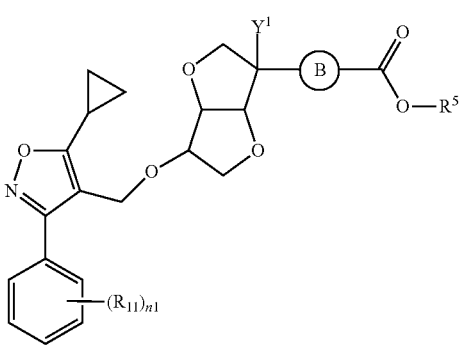
(VIIa-4)
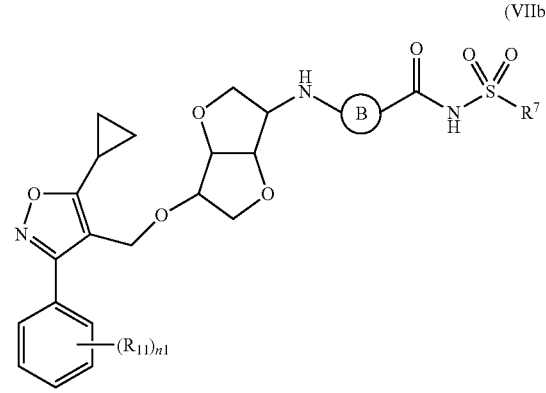
(VIIb-2)

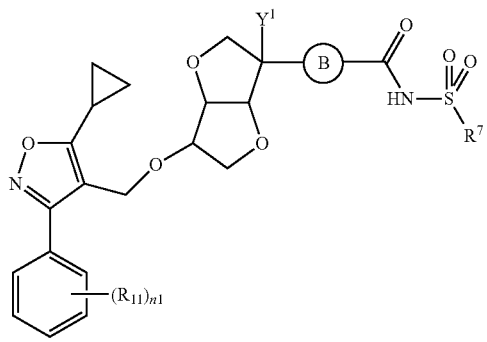

(VIIb-3)

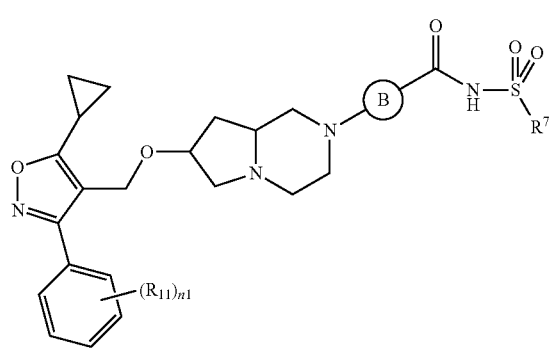

(VIIb-4)

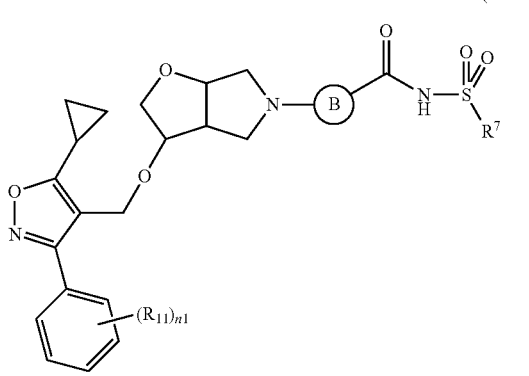

(VIIb-5)

(VIIb-6)

wherein $R^{11}$ at each occurrence is independently selected from the group consisting of halogen, optionally substituted —$C_1$-$C_6$ alkyl, optionally substituted —$C_1$-$C_6$ alkoxy, optionally substituted —$C_3$-$C_6$ cycloalkyl, optionally substituted —$C_3$-$C_6$ cycloalkenyl, optionally substituted aryl, and optionally substituted heteroaryl; n1 is 0, 1, 2, 3, 4, or 5; n2 is 0, 1, 2 or 3; and $R^5$, $R^7$, Ⓐ, and Ⓑ are as defined in claim 1.

7. The compound of claim 1, represented by Formula (VIII), or a pharmaceutically acceptable salt thereof,

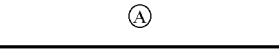

(VIII)

wherein Ⓐ, Ⓑ, Z and $R^4$ are as defined in claim 1.

8. The compound of claim 7, selected from compounds of Formula (VIII) wherein Ⓐ, Ⓑ, and Z—$R^4$ are delineated for each compound in Table 1, or a pharmaceutically acceptable salt thereof:

TABLE 1

| Compound | Ⓐ | Ⓑ | —Z—$R^4$ |
|---|---|---|---|
| 1 | 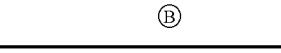 | 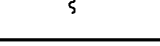 |  |

TABLE 1-continued

| Compound | Ⓐ | Ⓑ | ⸺Z—R⁴ |
|---|---|---|---|
| 2 | isosorbide-type bicyclic diether (stereo a) | benzothiazole with OiPr at 4-position | 2-methylpropanoic acid (C(CH₃)₂COOH) |
| 3 | isosorbide-type bicyclic diether (stereo b) | benzothiazole with OiPr at 4-position | 2-methylpropanoic acid |
| 4 | isosorbide-type bicyclic diether (stereo c) | benzothiazole with OiPr at 4-position | 2-methylpropanoic acid |
| 5 | isosorbide-type bicyclic diether (stereo a) | benzothiazole with F at 4-position | 2-methylpropanoic acid |
| 6 | isosorbide-type bicyclic diether (stereo b) | benzothiazole with F at 4-position | 2-methylpropanoic acid |
| 7 | isosorbide-type bicyclic diether (stereo c) | benzothiazole with F at 4-position | 2-methylpropanoic acid |

TABLE 1-continued

| Compound | Ⓐ | Ⓑ | —Z—R⁴ |
|---|---|---|---|
| 8 | isosorbide-like bicyclic diether | 2-yl-7-fluoro-benzothiazol-6-yl | 2-methyl-2-carboxypropyl (C(CH₃)₂COOH) |
| 9 | isosorbide-like bicyclic diether | 2-yl-4-methoxy-benzothiazol-6-yl (OMe) | C(CH₃)₂COOH |
| 10 | isosorbide-like bicyclic diether (alt stereo) | 2-yl-4-methoxy-benzothiazol-6-yl (OMe) | C(CH₃)₂COOH |
| 11 | isosorbide-like bicyclic diether | 2-yl-4-methoxy-benzothiazol-6-yl (OMe) | C(CH₃)₂COOH |
| 12 | isosorbide-like bicyclic diether | 2-yl-4-methoxy-benzothiazol-6-yl (OMe) | C(CH₃)₂COOH |
| 13 | isosorbide-like bicyclic diether | 2-yl-benzothiazol-6-yl | C(CH₃)₂COOH |

TABLE 1-continued

| Compound | Ⓐ | Ⓑ | —Z—R⁴ |
|---|---|---|---|
| 14 | isosorbide-like bicyclic diether | benzothiazole-2,6-diyl | C(CH₃)₂COOH |
| 15 | isosorbide-like bicyclic diether | benzothiazole-2,6-diyl | C(CH₃)₂COOH |
| 16 | isosorbide-like bicyclic diether | benzothiazole-2,6-diyl | C(CH₃)₂COOH |
| 17 | isosorbide-like bicyclic diether | benzothiazole-2,6-diyl, 7-OCHF₂ | C(CH₃)₂COOH |
| 18 | isosorbide-like bicyclic diether | benzothiazole-2,6-diyl, 7-OCF₃ | C(CH₃)₂COOH |
| 19 | isosorbide-like bicyclic diether | benzothiazole-2,6-diyl, 7-OCH₂F | C(CH₃)₂COOH |

TABLE 1-continued

| Compound | Ⓐ | Ⓑ | —Z—R⁴ |
|---|---|---|---|
| 20 | isosorbide-like bicyclic diether | 2-yl-7-CF₃-benzothiazol-6-yl | C(CH₃)₂COOH |
| 21 | isosorbide-like bicyclic diether | 2-yl-7-Me-benzothiazol-5-yl | C(CH₃)₂COOH |
| 22 | isosorbide-like bicyclic diether | 2-yl-7-Br-benzothiazol-6-yl | C(CH₃)₂COOH |
| 23 | isosorbide-like bicyclic diether | 2-yl-7-Cl-benzothiazol-6-yl | C(CH₃)₂COOH |
| 24 | isosorbide-like bicyclic diether | 2-yl-7-cyclopropyl-benzothiazol-6-yl | C(CH₃)₂COOH |
| 25 | isosorbide-like bicyclic diether | 2-yl-5-Me-benzothiazol-6-yl | C(CH₃)₂COOH |

TABLE 1-continued

| Compound | Ⓐ | Ⓑ | —ξ—Z—R⁴ |
|---|---|---|---|
| 26 | isosorbide-like bicyclic diether | 4-Me-benzothiazol-2,6-diyl | C(CH₃)₂COOH |
| 27 | isosorbide-like bicyclic diether | benzoxazol-2,6-diyl | C(CH₃)₂COOH |
| 28 | isosorbide-like bicyclic diether | 7-F-benzoxazol-2,6-diyl | C(CH₃)₂COOH |
| 29 | isosorbide-like bicyclic diether | 7-OMe-benzoxazol-2,6-diyl | C(CH₃)₂COOH |
| 30 | isosorbide-like bicyclic diether | 7-OiPr-benzoxazol-2,6-diyl | C(CH₃)₂COOH |
| 31 | isosorbide-like bicyclic diether | 5-F-quinolin-2,6-diyl | C(CH₃)₂COOH |

TABLE 1-continued

| Compound | Ⓐ | Ⓑ | —ξ—Z—R⁴ |
|---|---|---|---|
| 32 | isosorbide-like bicyclic diether | 7-fluoroquinoline-2,6-diyl | 2-methylpropanoic acid (C(CH₃)₂COOH) |
| 33 | isosorbide-like bicyclic diether | quinoline-2,6-diyl | 2-methylpropanoic acid |
| 34 | isosorbide-like bicyclic diether | quinoline-3,7-diyl | 2-methylpropanoic acid |
| 35 | isosorbide-like bicyclic diether | 3-fluoroquinoline-2,6-diyl | 2-methylpropanoic acid |
| 36 | isosorbide-like bicyclic diether | 3-methoxyquinoline-2,6-diyl | 2-methylpropanoic acid |
| 37 | isosorbide-like bicyclic diether | quinoxaline-2,6-diyl | 2-methylpropanoic acid |

TABLE 1-continued

| Compound | Ⓐ | Ⓑ | —ξ—Z—R⁴ |
|---|---|---|---|
| 38 | isosorbide diyl | 3-MeO-quinoxaline-2,6-diyl | C(CH₃)₂COOH |
| 39 | isosorbide diyl | 3-Cl-quinoxaline-2,6-diyl | C(CH₃)₂COOH |
| 40 | isosorbide diyl | 5-OiPr-quinoxaline-2,6-diyl | C(CH₃)₂COOH |
| 41 | isosorbide diyl | naphthalene-2,6-diyl | C(CH₃)₂COOH |
| 42 | isosorbide diyl | 8-F-naphthalene-2,6-diyl | C(CH₃)₂COOH |
| 43 | isosorbide diyl | 3-F-naphthalene-2,6-diyl | C(CH₃)₂COOH |

TABLE 1-continued

| Compound | Ⓐ | Ⓑ | ⸺Z—R⁴ |
|---|---|---|---|
| 44 | isosorbide diyl | 1-methoxy-naphthalene-3,7-diyl (MeO) | 2-methylpropanoic acid |
| 45 | isosorbide diyl | naphthalene-2,6-diyl | 2-methylpropanoic acid |
| 46 | isosorbide diyl | 5-methoxy-naphthalene-2,6-diyl (OMe) | 2-methylpropanoic acid |
| 47 | isosorbide diyl | isoquinoline-3,7-diyl | 2-methylpropanoic acid |
| 48 | isosorbide diyl | quinoline-2,5-diyl | 2-methylpropanoic acid |
| 49 | isosorbide diyl | quinoline-2,5-diyl | 2-methylpropanoic acid |

TABLE 1-continued

| Compound | Ⓐ | Ⓑ | —Z—R⁴ |
|---|---|---|---|
| 50 | isosorbide diyl | 8-fluoroquinoline-2,6-diyl | 2-methylpropanoic acid |
| 51 | isosorbide diyl | quinoxaline-2,6-diyl | 2-methylpropanoic acid |
| 52 | isosorbide diyl | quinazoline-2,6-diyl | 2-methylpropanoic acid |
| 53 | isosorbide diyl | quinazoline-4,7-diyl | 2-methylpropanoic acid |
| 54 | isosorbide diyl | 4-methylbenzofuran-2,5-diyl | 2-methylpropanoic acid |
| 55 | isosorbide diyl | pyrazolo[1,5-a]pyrimidine-2,6-diyl | 2-methylpropanoic acid |

TABLE 1-continued

| Compound | Ⓐ | Ⓑ | —ξ—Z—R⁴ |
|---|---|---|---|
| 56 | isosorbide diyl | imidazo[1,2-a]pyridine-6,3-diyl | 2-methylpropanoic acid |
| 57 | isosorbide diyl | 5-fluoro-1,2-benzisothiazole-3,6-diyl | 2-methylpropanoic acid |
| 58 | isosorbide diyl | 1,2-benzisothiazole-3,6-diyl | 2-methylpropanoic acid |
| 59 | isosorbide diyl | pyrazine-2,5-diyl | 2-methylpropanoic acid |
| 60 | isosorbide diyl | 3-fluoropyrazine-2,5-diyl | 2-methylpropanoic acid |
| 61 | isosorbide diyl | 2-fluoro-1,4-phenylene | 2-methylpropanoic acid |

TABLE 1-continued

| Compound | Ⓐ | Ⓑ | —⁓Z—R⁴ |
|---|---|---|---|
| 62 | isosorbide-diyl | 2-fluoro-1,4-phenylene | 2-methyl-2-carboxypropyl (C(CH₃)₂COOH) |
| 63 | isosorbide-diyl | pyrazine-2,5-diyl | C(CH₃)₂COOH |
| 64 | isosorbide-diyl | pyridine-2,6-diyl | C(CH₃)₂COOH |
| 65 | isosorbide-diyl | 4-methylpyrimidine-2,6-diyl | C(CH₃)₂COOH |
| 66 | isosorbide-diyl | 4-fluoropyridine-2,5-diyl | C(CH₃)₂COOH |
| 67 | isosorbide-diyl | pyridine-2,5-diyl | C(CH₃)₂COOH |

TABLE 1-continued

| Compound | Ⓐ | Ⓑ | ⸺Z—R⁴ |
|---|---|---|---|
| 68 | isosorbide-diyl | 2,5-thiazolediyl | C(CH₃)₂COOH |
| 69 | isosorbide-diyl | 2,4-thiazolediyl | C(CH₃)₂COOH |
| 70 | isosorbide-diyl | 2,6-pyridinediyl | C(CH₃)₂COOH |
| 71 | isosorbide-diyl | 4-methyl-2,5-pyridinediyl | C(CH₃)₂COOH |
| 72 | isosorbide-diyl | 3-fluoro-2,5-pyridinediyl | C(CH₃)₂COOH |
| 73 | isosorbide-diyl | 3-methyl-2,5-pyridinediyl | C(CH₃)₂COOH |

TABLE 1-continued

| Compound | Ⓐ | Ⓑ | ⸺Z—R⁴ |
|---|---|---|---|
| 74 | isosorbide-diyl | 3-(CF₃)-pyridine-2,5-diyl | 2-methylpropanoic acid |
| 75 | isosorbide-diyl | 3-cyclopropyl-pyridine-2,5-diyl | 2-methylpropanoic acid |
| 76 | isosorbide-diyl | 2,6-difluoro-phenylene | 2-methylpropanoic acid |
| 77 | isosorbide-diyl | 1,2,4-oxadiazole-3,5-diyl | 2-methylpropanoic acid |
| 78 | isosorbide-diyl | 1,2,4-oxadiazole-3,5-diyl | 3-benzoic acid |
| 79 | isosorbide-diyl | 1,2,4-oxadiazole-3,5-diyl | pyridine-2,6-dicarboxylic acid |

TABLE 1-continued

| Compound | Ⓐ | Ⓑ | $-\xi-Z-R^4$ |
|---|---|---|---|
| 80 | isosorbide-diyl-dioxy | 1,2,4-oxadiazole-3,5-diyl | 4-fluoro-3-carboxyphenyl |
| 81 | isosorbide-diyl-dioxy | 1,2,4-oxadiazole-3,5-diyl | 4-carboxyphenyl |
| 82 | isosorbide-diyl-dioxy | 1,2,4-oxadiazole-3,5-diyl | 3-carboxycyclohexyl |
| 83 | isosorbide-diyl-dioxy | 4-OiPr-benzothiazole-2,6-diyl | CN |
| 84 | isosorbide-diyl-dioxy | 4-OiPr-benzothiazole-2,6-diyl | tetrazol-5-yl |
| 85 | isosorbide-diyl-dioxy | pyrazine-2,5-diyl | CN |

TABLE 1-continued

| Compound | Ⓐ | Ⓑ | —Z—R⁴ |
|---|---|---|---|
| 86 | isosorbide-diyl | pyrazine-2,5-diyl | tetrazol-5-yl |
| 87 | isosorbide-diyl | 2-fluoro-1,4-phenylene | CN |
| 88 | isosorbide-diyl | 3-fluoro-1,4-phenylene | tetrazol-5-yl |
| 89 | isosorbide-diyl | 3-methoxy-1,4-phenylene | CN |
| 90 | isosorbide-diyl | 2-methoxy-1,4-phenylene | tetrazol-5-yl |
| 91 | isosorbide-diyl | benzothiazole-2,6-diyl | —O—C(O)—NH—S(O)₂—C₆H₄—O—iPr |

TABLE 1-continued

| Compound | Ⓐ | Ⓑ | ⟿−Z−R⁴ |
|---|---|---|---|
| 92 | | | |
| 93 | | | |
| 94 | | | |
| 95 | | | |
| 96 | | | |
| 97 | | | |

TABLE 1-continued

| Compound | Ⓐ | Ⓑ | $-\!\!\!\!\xi\!\!\!-\!Z\!-\!R^4$ |
|---|---|---|---|
| 98 | isosorbide-like bicyclic diether | 2-linked-7-OiPr-benzothiazole-6-yl | -OC(O)NHSO₂-(4-OtBu-phenyl) |
| 99 | isosorbide-like bicyclic diether | 2-linked-benzothiazole-6-yl | -OC(O)NHSO₂-(6-piperidin-1-yl-pyridin-3-yl) |
| 100 | isosorbide-like bicyclic diether | 2-linked-7-F-benzothiazole-6-yl | -OC(O)NHSO₂-(6-piperidin-1-yl-pyridin-3-yl) |
| 101 | isosorbide-like bicyclic diether | 2-linked-7-OiPr-benzothiazole-6-yl | -OC(O)NHSO₂-(6-piperidin-1-yl-pyridin-3-yl) |
| 102 | isosorbide-like bicyclic diether | 2-linked-7-cyclopropyl-benzothiazole-6-yl | -OC(O)NHSO₂-(6-piperidin-1-yl-pyridin-3-yl) |
| 103 | isosorbide-like bicyclic diether | 2-linked-benzothiazole-6-yl | -OC(O)NHSO₂-(4-OtBu-phenyl) |

TABLE 1-continued

| Compound | Ⓐ | Ⓑ | ⸺Z—R⁴ |
|---|---|---|---|
| 104 | isosorbide-diyl | 4-F-benzothiazol-2,6-diyl | neopentyl-O-C(O)-NH-SO₂-(4-tBuO-phenyl) |
| 105 | isosorbide-diyl | 4-OiPr-benzothiazol-2,6-diyl | neopentyl-O-C(O)-NH-SO₂-(4-tBuO-phenyl) |
| 106 | isosorbide-diyl | 4-cyclopropyl-benzothiazol-2,6-diyl | neopentyl-O-C(O)-NH-SO₂-(4-tBuO-phenyl) |
| 107 | isosorbide-diyl | benzothiazol-2,6-diyl | -NH-C(O)-NH-SO₂-(4-tBu-phenyl) |
| 108 | isosorbide-diyl | 4-F-benzothiazol-2,6-diyl | -NH-C(O)-NH-SO₂-(4-tBu-phenyl) |
| 109 | isosorbide-diyl | 4-OiPr-benzothiazol-2,6-diyl | -NH-C(O)-NH-SO₂-(4-tBu-phenyl) |

TABLE 1-continued

| Compound | Ⓐ | Ⓑ | ⸺Z—R⁴ |
|---|---|---|---|
| 110 | bicyclic diether (isosorbide-type), both O-linked | 2-linked-6-yl benzothiazole, 4-cyclopropyl | —NHC(O)NHS(O)₂-(4-tBu-C₆H₄) |
| 111 | bicyclic diether (isosorbide-type), both O-linked | 2-linked-6-yl benzothiazole | —CH₂NHC(O)NHS(O)₂-(4-tBu-C₆H₄) |
| 112 | bicyclic diether (isosorbide-type), both O-linked | 2-linked-6-yl benzothiazole, 4-F | —CH₂NHC(O)NHS(O)₂-(4-tBu-C₆H₄) |
| 113 | bicyclic diether (isosorbide-type), both O-linked | 2-linked-6-yl benzothiazole, 4-OiPr | —CH₂NHC(O)NHS(O)₂-(4-tBu-C₆H₄) |
| 114 | bicyclic diether (isosorbide-type), both O-linked | 2-linked-6-yl benzothiazole, 4-cyclopropyl | —CH₂NHC(O)NHS(O)₂-(4-tBu-C₆H₄) |
| 115 | bicyclic diether (isosorbide-type), both O-linked | 2-linked-6-yl benzothiazole, 4-OiPr | —CO₂Me |

TABLE 1-continued

| Compound | Ⓐ | Ⓑ | ⸺Z—R⁴ |
|---|---|---|---|
| 116 | isosorbide-diO | 4-OiPr-benzothiazole-2,6-diyl | —CO₂t-Bu |
| 117 | isosorbide-diO | 4-OiPr-benzothiazole-2,6-diyl | —C(Me)₂CO₂Me |
| 118 | isosorbide-diO | 4-OiPr-benzothiazole-2,6-diyl | —C(Me)₂CO₂H |
| 119 | isosorbide-diO | 4-OiPr-benzothiazole-2,6-diyl | —C(Me)₂CH₂CO₂Me |
| 120 | isosorbide-diO | 4-OiPr-benzothiazole-2,6-diyl | —C(Me)₂CH₂CO₂H |
| 121 | isosorbide-diO | 4-OiPr-benzothiazole-2,6-diyl | —C(Me)₂CH₂OCH₂CO₂Me |

TABLE 1-continued

| Compound | Ⓐ | Ⓑ | —Z—R⁴ |
|---|---|---|---|
| 122 | isosorbide-diyl | 4-OiPr-benzothiazole-2,6-diyl | —CH₂—O—CH₂COOH |
| 123 | isosorbide-diyl | 4-OiPr-benzothiazole-2,6-diyl | —CH₂—NH—CH₂C(O)OMe |
| 124 | isosorbide-diyl | 4-OiPr-benzothiazole-2,6-diyl | —CH₂—NH—CH₂COOH |
| 125 | isosorbide-diyl | 4-OiPr-benzothiazole-2,6-diyl | —CH₂—N(Me)—CH₂C(O)OMe |
| 126 | isosorbide-diyl | 4-OiPr-benzothiazole-2,6-diyl | —CH₂—N(Me)—CH₂COOH |
| 127 | isosorbide-diyl | 4-OiPr-benzothiazole-2,6-diyl | —CH₂OH |

TABLE 1-continued

| Compound | Ⓐ | Ⓑ | —Z—R⁴ |
|---|---|---|---|
| 128 | isosorbide-diyl-dioxy | 4-OiPr-benzothiazole-2,6-diyl | —C(Me)₂CH₂OH |
| 129 | isosorbide-diyl-dioxy | 4-OiPr-benzothiazole-2,6-diyl | 1-(CO₂Me)cyclopropyl |
| 130 | isosorbide-diyl-dioxy | 4-OiPr-benzothiazole-2,6-diyl | 1-(CO₂H)cyclopropyl |
| 131 | isosorbide-diyl-dioxy | 4-OiPr-benzothiazole-2,6-diyl | 1-(CH₂CO₂Me)cyclopropyl |
| 132 | isosorbide-diyl-dioxy | 4-OiPr-benzothiazole-2,6-diyl | 1-(CH₂CO₂H)cyclopropyl |
| 133 | isosorbide-diyl-dioxy | 4-OiPr-benzothiazole-2,6-diyl | —C(Me)₂CF₂CO₂Me |

TABLE 1-continued

| Compound | (A) | (B) | —Z—R⁴ |
|---|---|---|---|
| 134 | isosorbide-diyl | 2-linked-6-linked-4-OiPr-benzothiazole | —C(CF₂)(CH₃)—COOH (gem-difluoro acid) |
| 135 | isosorbide-diyl | 2-linked-6-linked-4-OiPr-benzothiazole | —C(CH₃)₂—CN |
| 136 | isosorbide-diyl | 2-linked-6-linked-4-OiPr-benzothiazole | —C(CH₃)₂—(1H-tetrazol-5-yl) |
| 137 | isosorbide-diyl | 2-linked-6-linked-4-OiPr-benzothiazole | —C(CH₃)₂—C(O)NH—CH₂—C(O)O-tBu |
| 138 | isosorbide-diyl | 2-linked-6-linked-4-OiPr-benzothiazole | —C(CH₃)₂—C(O)NH—CH₂—COOH |
| 139 | isosorbide-diyl | 2-linked-6-linked-4-OiPr-benzothiazole | —C(CH₃)₂—C(O)NH—C(CH₃)₂—COOH |

TABLE 1-continued

| Compound | Ⓐ | Ⓑ | ⸨-Z—R⁴ |
|---|---|---|---|
| 140 | isosorbide-diyl | 4-OiPr-benzothiazole-2,6-diyl | -C(=O)NH-CH(CH₃)-COOH |
| 141 | isosorbide-diyl | 4-OiPr-benzothiazole-2,6-diyl | -C(=O)NH-CH₂CH₂-SO₃Me |
| 142 | isosorbide-diyl | 4-OiPr-benzothiazole-2,6-diyl | -C(=O)NH-CH₂CH₂-SO₃H |
| 143 | isosorbide-diyl | 4-OiPr-benzothiazole-2,6-diyl | -C(=O)NH-C(cyclopropyl)-CH₂-SO₃H |
| 144 | isosorbide-diyl | 4-OiPr-benzothiazole-2,6-diyl | -C(=O)NH-C(CH₃)₂-CH₂-SO₃H |
| 145 | isosorbide-diyl | 4-OiPr-benzothiazole-2,6-diyl | -C(=O)NH-CH₂-O-CH₂-OSO₃H |

TABLE 1-continued

| Compound | Ⓐ | Ⓑ | —⸺Z—R⁴ |
|---|---|---|---|
| 146 | isosorbide-type bis-ether | 4-OiPr-benzothiazole-2,6-diyl | -C(O)NHCH₂NHCH₂OSO₃H |
| 147 | isosorbide-type bis-ether | benzothiazole-2,6-diyl | quinic acid ester |
| 148 | isosorbide-type bis-ether | 4-OMe-benzothiazole-2,6-diyl | quinic acid ester |
| 149 | isosorbide-type bis-ether | 4-F-benzothiazole-2,6-diyl | quinic acid ester |
| 150 | isosorbide-type bis-ether | 4-OiPr-benzothiazole-2,6-diyl | quinic acid ester |
| 151 | isosorbide-type bis-ether | 4-OiPr-benzothiazole-2,6-diyl | -C(CH₃)₂COOH |

TABLE 1-continued

| Compound | Ⓐ | Ⓑ | —⁎—Z—R⁴ |
|---|---|---|---|
| 152 | bicyclic furanofuran with NH and O linkers | benzothiazole with OiPr | C(CH₃)₂COOH |
| 153 | bicyclic furanofuran with O and NH linkers | benzothiazole with OiPr | C(CH₃)₂COOH |
| 154 | bicyclic furanofuran with NH and NH linkers | benzothiazole with OiPr | C(CH₃)₂COOH |
| 155 | bicyclic furanofuran with OH, C and NH linkers | benzothiazole with OiPr | C(CH₃)₂COOH |
| 156 | bicyclic furanofuran with F, C and NH linkers | benzothiazole with OiPr | C(CH₃)₂COOH |
| 157 | bicyclic furanofuran with OH, C and O linkers | benzothiazole with OiPr | C(CH₃)₂COOH |
| 158 | bicyclic furanofuran with F, C and O linkers | benzothiazole with OiPr | C(CH₃)₂COOH |

TABLE 1-continued

| Compound | Ⓐ | Ⓑ | —Z—R⁴ |
|---|---|---|---|
| 159 | | | |
| 160 | | | |
| 161 | | | |
| 162 | | | |
| 163 | | | |
| 164 | | | |
| 165 | | | |

TABLE 1-continued

| Compound | Ⓐ | Ⓑ | —Z—R⁴ |
|---|---|---|---|
| 166 | bicyclic oxazolidine with NH, cyclopentane-fused | 2-substituted-7-OiPr-benzothiazole (6-yl) | C(CH₃)₂COOH |
| 167 | bicyclic oxazolidine, cyclopentane-fused, with O-linker | 2-substituted-7-OiPr-benzothiazole (6-yl) | C(CH₃)₂COOH |
| 168 | bicyclic oxazolidinone (C=O), cyclopentane-fused, with O-linker | 2-substituted-7-OiPr-benzothiazole (6-yl) | C(CH₃)₂COOH |
| 169 | bicyclic bis-NH substituted bicyclo[3.3.0] | 2-substituted-7-OiPr-benzothiazole (6-yl) | C(CH₃)₂COOH |
| 170 | bicyclic O/NH substituted bicyclo[3.3.0] | 2-substituted-7-OiPr-benzothiazole (6-yl) | C(CH₃)₂COOH |
| 171 | bicyclic NH/N-substituted octahydrocyclopenta[c]pyrrole | 2-substituted-7-OiPr-benzothiazole (6-yl) | C(CH₃)₂COOH |

TABLE 1-continued

| Compound | Ⓐ | Ⓑ | —Z—R⁴ |
|---|---|---|---|
| 172 | HN-[bicyclic pyrrolidine with F] | benzothiazole with OiPr | C(CH₃)₂COOH |
| 173 | O-[bicyclic pentalene with OH] | benzothiazole with OiPr | C(CH₃)₂COOH |
| 174 | O-[bicyclic pentalene with F] | benzothiazole with OiPr | C(CH₃)₂COOH |
| 175 | [furo-pyrrolidine with O] | benzothiazole with OiPr | C(CH₃)₂COOH |
| 176 | [thieno-pyrrolidine with O] | benzothiazole with OiPr | C(CH₃)₂COOH |
| 177 | [furo-pyrrolidine with NH] | benzothiazole with OiPr | C(CH₃)₂COOH |
| 178 | [thieno-pyrrolidine with NH] | benzothiazole with OiPr | C(CH₃)₂COOH |

TABLE 1-continued

| Compound | Ⓐ | Ⓑ | —ξ—Z—R⁴ |
|---|---|---|---|
| 179 | (pyrrolopiperazine with O-linker) | benzothiazole with OiPr | 2-methylpropanoic acid |
| 180 | (pyrrolopiperazine with NH-linker) | benzothiazole with OiPr | 2-methylpropanoic acid |
| 181 | (stereochemistry-defined pyrrolopiperazine with O-linker) | benzothiazole with OiPr | 2-methylpropanoic acid |
| 182 | (stereochemistry-defined pyrrolopiperazine with O-linker) | benzothiazole with OiPr | 2-methylpropanoic acid |
| 183 | (stereochemistry-defined pyrrolopiperazine with O-linker) | benzothiazole with OiPr | 2-methylpropanoic acid |
| 184 | (stereochemistry-defined pyrrolopiperazine with O-linker) | benzothiazole with OiPr | 2-methylpropanoic acid |
| 185 | (pyrrolopiperazine with HN-linker) | benzothiazole with OiPr | 2-methylpropanoic acid |

TABLE 1-continued

| Compound | Ⓐ | Ⓑ | ⋰⋰⋰—Z—R⁴ |
|---|---|---|---|
| 186 | spirocyclopropane-pyrrolizidine with O-linker and piperazine N-linker | 2-linked-6-linked benzothiazole, 4-OiPr | 2-methylpropanoic acid (C(CH₃)₂COOH) |
| 187 | pyrrolizidinone with O-linker and piperazine-like N-linker | 2-linked-6-linked benzothiazole, 4-OiPr | 2-methylpropanoic acid |
| 188 | hexahydrocyclopenta[b][1,4]oxazine with N- and O-linkers | 2-linked-6-linked benzothiazole, 4-OiPr | 2-methylpropanoic acid |
| 189 | hexahydrocyclopenta[b][1,4]oxazine with N- and O-linkers (isomer) | 2-linked-6-linked benzothiazole, 4-OiPr | 2-methylpropanoic acid |
| 190 | hexahydrocyclopenta[b][1,4]oxazine with N- and NH-linkers | 2-linked-6-linked benzothiazole, 4-OiPr | 2-methylpropanoic acid |
| 191 | hexahydrocyclopenta[e][1,3]oxazine with N- and O-linkers | 2-linked-6-linked benzothiazole, 4-OiPr | 2-methylpropanoic acid |
| 192 | hexahydrocyclopenta[e][1,3]oxazine with N- and O-linkers (isomer) | 2-linked-6-linked benzothiazole, 4-OiPr | 2-methylpropanoic acid. |

9. The compound of claim 1, represented by Formula (IX), or a pharmaceutically acceptable salt thereof,
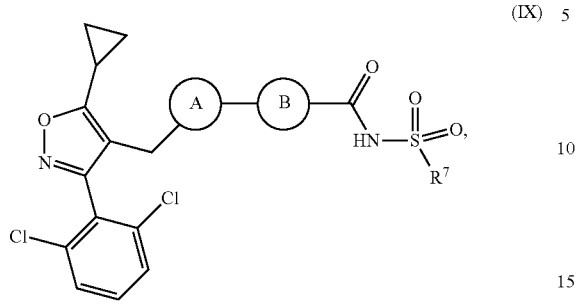
wherein Ⓐ, Ⓑ, and IC are as defined in claim 1.
10. The compound of claim 9, selected from compounds of Formula (IX) wherein Ⓐ, Ⓑ, and IC are delineated for each compound in Table 2, or a pharmaceutically acceptable salt thereof:
TABLE 2
| compound | Ⓐ | Ⓑ | $R^7$ |
| --- | --- | --- | --- |
| 201 | | | |
| 202 | | | |
| 203 | | | |
| 204 | | | |

TABLE 2-continued

| compound | Ⓐ | Ⓑ | R⁷ |
|---|---|---|---|
| 205 | isosorbide-like bicyclic diether | benzothiazole with OiPr | cyclopropyl-CH₂OH |
| 206 | isosorbide-like bicyclic diether | benzothiazole with OiPr | cyclopropyl-CHF₂ |
| 207 | isosorbide-like bicyclic diether | benzothiazole with OiPr | cyclopropyl-CF₃ |
| 208 | isosorbide-like bicyclic diether | benzothiazole with OiPr | cyclopropyl-F |
| 209 | isosorbide-like bicyclic diether | benzothiazole with OiPr | cyclopropyl-Cl |
| 210 | isosorbide-like bicyclic diether | benzothiazole with OiPr | cyclopropyl-CH₂F |
| 211 | isosorbide-like bicyclic diether | benzothiazole with OiPr | cyclopropyl-CH₂OMe |

TABLE 2-continued

| compound | Ⓐ | Ⓑ | R⁷ |
|---|---|---|---|
| 212 | isosorbide-type bicyclic diether (exo-O, endo-O) | 2-yl-4-OiPr-benzothiazol-6-yl | 1-cyanocyclopropyl (CN) |
| 213 | isosorbide-type bicyclic diether | 2-yl-4-OiPr-benzothiazol-6-yl | 1-carboxycyclopropyl (CO₂H) |
| 214 | isosorbide-type bicyclic diether (alternate stereochem) | 2-yl-4-OiPr-benzothiazol-6-yl | 1-carboxycyclopropyl (CO₂H) |
| 215 | isosorbide-type bicyclic diether | 2-yl-4-OiPr-benzothiazol-6-yl | 1-(pyrrolidin-1-ylsulfonylaminocarbonyl)cyclopropyl |
| 216 | isosorbide-type bicyclic diether | 2-yl-4-OiPr-benzothiazol-6-yl | 1-carbamoylcyclopropyl (C(O)NH₂) |
| 217 | isosorbide-type bicyclic diether | 2-yl-4-OiPr-benzothiazol-6-yl | 2,2-difluoro-1-methylcyclopropyl |

TABLE 2-continued

| compound | Ⓐ | Ⓑ | R⁷ |
| --- | --- | --- | --- |
| 218 | isosorbide-like bicyclic diether | 7-OiPr-benzothiazole-2,6-diyl | 2,2-difluorocyclopropyl |
| 219 | isosorbide-like bicyclic diether | 7-OiPr-benzothiazole-2,6-diyl | azetidin-1-yl |
| 220 | isosorbide-like bicyclic diether | 7-OiPr-benzothiazole-2,6-diyl | pyrrolidin-1-yl |
| 221 | isosorbide-like bicyclic diether | 7-OiPr-benzothiazole-2,6-diyl | piperidin-1-yl |
| 222 | isosorbide-like bicyclic diether | 7-OiPr-benzothiazole-2,6-diyl | 4,4-difluoropiperidin-1-yl |
| 223 | isosorbide-like bicyclic diether | 7-OiPr-benzothiazole-2,6-diyl | cyclopentyl |
| 224 | isosorbide-like bicyclic diether | 7-OiPr-benzothiazole-2,6-diyl | morpholin-4-yl |

TABLE 2-continued

| compound | Ⓐ | Ⓑ | R⁷ |
|---|---|---|---|
| 225 | isosorbide-like bicyclic diether | 7-OiPr-benzothiazole-2,6-diyl | 1-methylcyclopentyl |
| 226 | isosorbide-like bicyclic diether | 7-OiPr-benzothiazole-2,6-diyl | cyclohexyl |
| 227 | isosorbide-like bicyclic diether | 7-OiPr-benzothiazole-2,6-diyl | NH₂ |
| 228 | isosorbide-like bicyclic diether | 7-OiPr-benzothiazole-2,6-diyl | NHCH₃ |
| 229 | isosorbide-like bicyclic diether | 7-OiPr-benzothiazole-2,6-diyl | N(CH₃)₂ |
| 230 | isosorbide-like bicyclic diether | 7-OiPr-benzothiazole-2,6-diyl | NHiPr |

TABLE 2-continued

| compound | Ⓐ | Ⓑ | R⁷ |
|---|---|---|---|
| 231 | isosorbide-like bicyclic diether | 4-OiPr-benzothiazole-2,6-diyl | -NH-cyclopropyl |
| 232 | isosorbide-like bicyclic diether | 4-OiPr-benzothiazole-2,6-diyl | -NH-cyclobutyl |
| 233 | isosorbide-like bicyclic diether | 4-OiPr-benzothiazole-2,6-diyl | -NH-cyclopentyl |
| 234 | isosorbide-like bicyclic diether | 4-OiPr-benzothiazole-2,6-diyl | -NH-cyclohexyl |
| 235 | isosorbide-like bicyclic diether | 4-OiPr-benzothiazole-2,6-diyl | -NH-phenyl |
| 236 | isosorbide-like bicyclic diether | 4-OiPr-benzothiazole-2,6-diyl | -NH-(4-F-phenyl) |
| 237 | isosorbide-like bicyclic diether | 4-OiPr-benzothiazole-2,6-diyl | -NH-(2-OCF₃-phenyl) |

TABLE 2-continued

| compound | Ⓐ | Ⓑ | R⁷ |
|---|---|---|---|
| 238 | isosorbide-type bis-ether linker | 2-yl-4-OiPr-benzothiazol-6-yl | —NH-(pyridin-4-yl) |
| 239 | isosorbide-type bis-ether linker | 2-yl-4-OiPr-benzothiazol-6-yl | —Me |
| 240 | isosorbide-type bis-ether linker | 2-yl-4-OiPr-benzothiazol-6-yl | —CF₃ |
| 241 | isosorbide-type bis-ether linker | 2-yl-4-OiPr-benzothiazol-6-yl | —CH(Me)₂ |
| 242 | isosorbide-type bis-ether linker | 2-yl-4-OiPr-benzothiazol-6-yl | —CH₂Me |
| 243 | isosorbide-type bis-ether linker | 2-yl-4-OiPr-benzothiazol-6-yl | —CH₂C(Me)₃ |

TABLE 2-continued

| compound | Ⓐ | Ⓑ | R⁷ |
|---|---|---|---|
| 244 | isosorbide-type bicyclic diether | 2-linked-4-OiPr-6-linked-benzothiazole | tert-butyl (neopentyl-type) |
| 245 | isosorbide-type bicyclic diether | 2-linked-4-OiPr-6-linked-benzothiazole | cyclopropylmethyl |
| 246 | isosorbide-type bicyclic diether | 2-linked-4-OiPr-6-linked-benzothiazole | −CH₂C(CH₃)₂CH₂OBn |
| 247 | isosorbide-type bicyclic diether | 2-linked-4-OiPr-6-linked-benzothiazole | benzyl |
| 248 | isosorbide-type bicyclic diether | 2-linked-4-OiPr-6-linked-benzothiazole | allyl |
| 249 | isosorbide-type bicyclic diether | 2-linked-4-OiPr-6-linked-benzothiazole | −Bu |
| 250 | isosorbide-type bicyclic diether | 2-linked-4-OiPr-6-linked-benzothiazole | n-propyl |

TABLE 2-continued

| compound | Ⓐ | Ⓑ | R⁷ |
|---|---|---|---|
| 251 | isosorbide-type bicyclic diether (both exo) | benzothiazole with OiPr | phenyl |
| 252 | isosorbide-type bicyclic diether (both exo) | benzothiazole with OiPr | 4-fluorophenyl |
| 253 | isosorbide-type bicyclic diether | benzothiazole with OiPr | 2-pyridyl |
| 254 | isosorbide-type bicyclic diether | benzothiazole with OiPr | 4-tert-butylphenyl |
| 255 | isosorbide-type bicyclic diether | benzothiazole with OiPr | 4-pyridyl |
| 256 | isosorbide-type bicyclic diether | benzothiazole with OiPr | 3-pyridyl |

TABLE 2-continued

| compound | Ⓐ | Ⓑ | R⁷ |
|---|---|---|---|
| 257 | isosorbide-diyl | 4-OiPr-benzothiazole-2,6-diyl | thiazol-5-yl |
| 258 | isosorbide-diyl | 4-OiPr-benzothiazole-2,6-diyl | 5-fluoropyridin-2-yl |
| 259 | isosorbide-diyl | 4-OiPr-benzothiazole-2,6-diyl | 1H-imidazol-2-yl |
| 260 | isosorbide-diyl | 4-OiPr-benzothiazole-2,6-diyl | thiazol-2-yl |
| 261 | isosorbide-diyl | 4-OiPr-benzothiazole-2,6-diyl | 2-(trifluoromethoxy)phenyl |
| 262 | isosorbide-diyl | 4-OiPr-benzothiazole-2,6-diyl | 1-methyl-1H-imidazol-2-yl |
| 263 | isosorbide-diyl | 4-OiPr-benzothiazole-2,6-diyl | naphthalen-2-yl |

TABLE 2-continued

| compound | Ⓐ | Ⓑ | R⁷ |
|---|---|---|---|
| 264 | isosorbide linker | 2-/6- benzothiazole, 4-OiPr | 2-methoxyphenyl |
| 265 | isosorbide linker | 2-/6- benzothiazole, 4-OiPr | 4-biphenyl |
| 266 | isosorbide linker | 2-/6- benzothiazole, 4-OiPr | 5-(pyridin-4-yl)pyridin-2-yl |
| 267 | isosorbide linker | 2-/6- benzothiazole, 4-OiPr | 4-(pyridin-4-yl)phenyl |
| 268 | isosorbide linker | 2-/6- benzothiazole, 4-OiPr | 2,3-dihydrobenzo[b][1,4]dioxin-6-yl |
| 269 | isosorbide linker | 2-/6- benzothiazole, 4-OiPr | benzo[d][1,3]dioxol-5-yl |

TABLE 2-continued

| compound | Ⓐ | Ⓑ | R⁷ |
|---|---|---|---|
| 270 | isosorbide-type bis-O linker | 2-linked-6-linked-4-OiPr-benzothiazole | 2,3-dihydro-1H-indene |
| 271 | isosorbide-type bis-O linker | 2-linked-6-linked-4-F-benzothiazole | cyclopropyl |
| 272 | isosorbide-type bis-O linker | 2-linked-6-linked-4-F-benzothiazole | 1-methylcyclopropyl |
| 273 | isosorbide-type bis-O linker | 2-linked-6-linked-benzothiazole | cyclopropyl |
| 274 | isosorbide-type bis-O linker | 2-linked-6-linked-benzothiazole | 1-methylcyclopropyl |
| 275 | isosorbide-type bis-O linker | 2-linked-6-linked-4-OiPr-benzoxazole | cyclopropyl |
| 276 | isosorbide-type bis-O linker | 2-linked-6-linked-4-OiPr-benzoxazole | 1-methylcyclopropyl |

TABLE 2-continued
| compound | A | B | R⁷ |
|---|---|---|---|
| 277 | 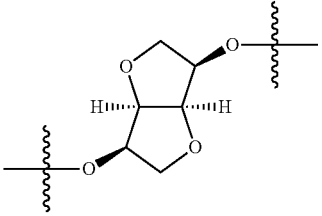 [SMILES: *O[C@@H]1CO[C@H]2[C@@H]1OC[C@H]2O*] | 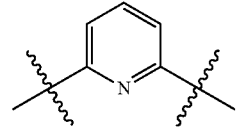 [SMILES: *c1cccc(*)n1] | 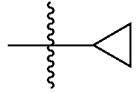 [SMILES: *C1CC1] |
| 278 | 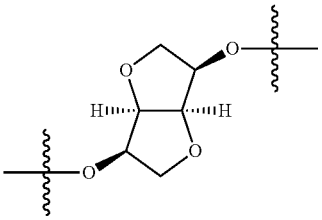 [SMILES: *O[C@@H]1CO[C@H]2[C@@H]1OC[C@H]2O*] | 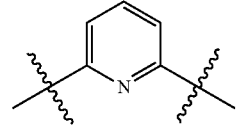 | 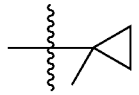 [SMILES: *C1(C)CC1] |
| 279 | 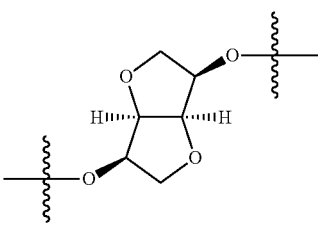 [SMILES: *O[C@@H]1CO[C@H]2[C@@H]1OC[C@H]2O*] | 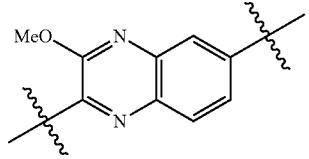 | 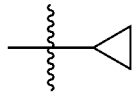 |
| 280 | 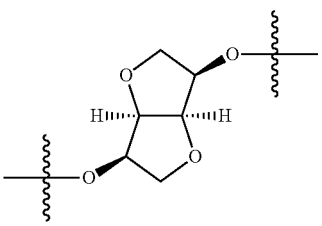 [SMILES: *O[C@@H]1CO[C@H]2[C@@H]1OC[C@H]2O*] | 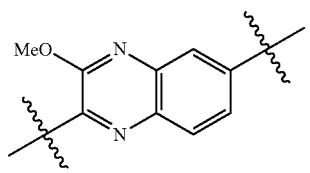 | 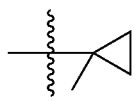 [SMILES: *C1(C)CC1] |
| 281 | 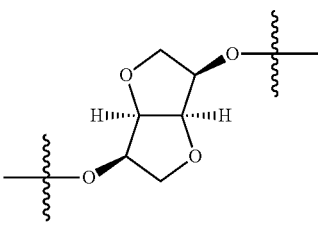 [SMILES: *O[C@@H]1CO[C@H]2[C@@H]1OC[C@H]2O*] | 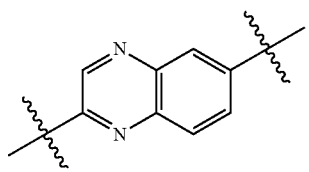 | 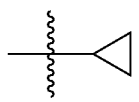 [SMILES: *C1CC1] |
| 282 | 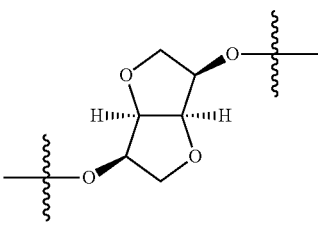 [SMILES: *O[C@@H]1CO[C@H]2[C@@H]1OC[C@H]2O*] | 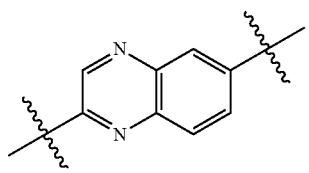 | 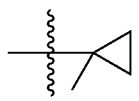 [SMILES: *C1(C)CC1] |

TABLE 2-continued
| compound | Ⓐ | Ⓑ | R⁷ |
|---|---|---|---|
| 283 | 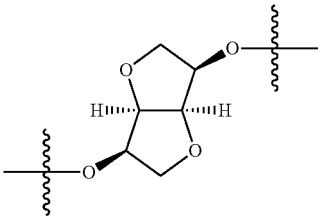 [SMILES: *O[C@@H]1CO[C@H]2[C@@H]1OC[C@H]2O*] | 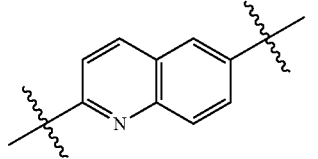 | 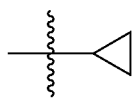 [SMILES: *C1CC1] |
| 284 | 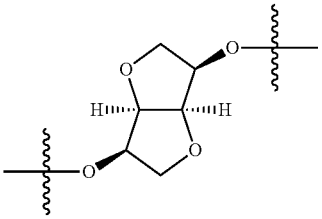 [SMILES: *O[C@@H]1CO[C@H]2[C@@H]1OC[C@H]2O*] | 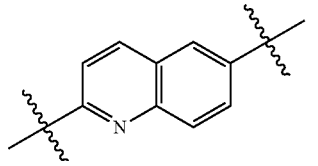 | 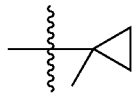 |
| 285 | 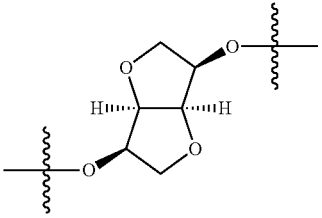 [SMILES: *O[C@@H]1CO[C@H]2[C@@H]1OC[C@H]2O*] | 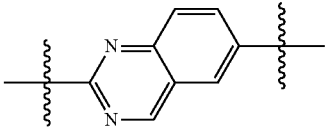 [SMILES: *c1ccc2nc(*)ncc2c1] | 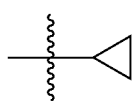 |
| 286 | 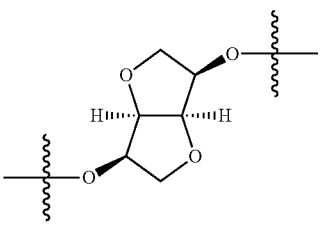 [SMILES: *O[C@@H]1CO[C@H]2[C@@H]1OC[C@H]2O*] | 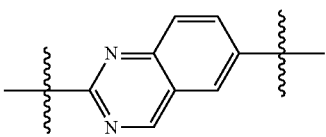 | 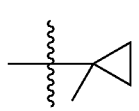 |
| 287 | 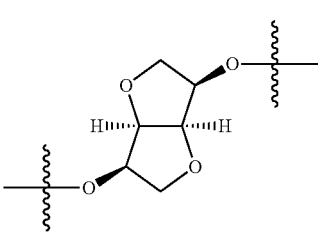 [SMILES: *O[C@@H]1CO[C@H]2[C@@H]1OC[C@H]2O*] | 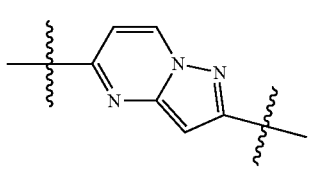 [SMILES: *c1ccn2nc(*)cc2n1] | 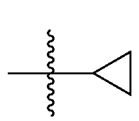 |
| 288 | 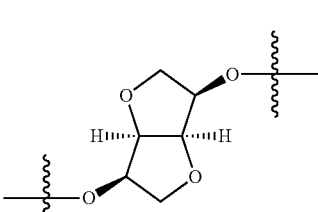 | 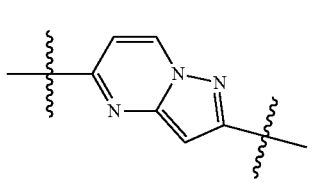 [SMILES: *c1ccn2nc(*)cc2n1] | 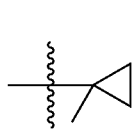 [SMILES: *C1(C)CC1] |
| 289 | 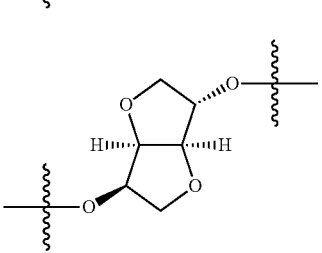 | 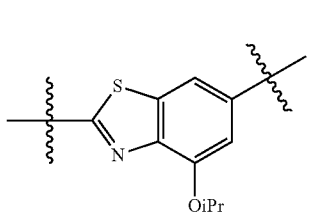 [SMILES: *c1cc(OC(C)C)c2nc(*)sc2c1] | 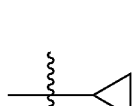 |

TABLE 2-continued

| compound | Ⓐ | Ⓑ | R⁷ |
| --- | --- | --- | --- |
| 290 | (bicyclic dioxa ring with H stereochem, O-linked both ends) | benzothiazole with OiPr | 1-methylcyclopropyl |
| 291 | (bicyclic dioxa ring, NH-linked and O-linked) | benzothiazole with OiPr | cyclopropyl |
| 292 | (bicyclic dioxa ring, NH-linked and O-linked) | benzothiazole with OiPr | 1-methylcyclopropyl |
| 293 | (bicyclic dioxa ring, NH-linked and O-linked) | benzothiazole with OiPr | cyclopropyl |
| 294 | (bicyclic dioxa ring, NH-linked and O-linked) | benzothiazole with OiPr | 1-methylcyclopropyl |
| 295 | (bicyclic dioxa ring, NH-linked both ends, H stereochem) | benzothiazole with OiPr | cyclopropyl |

TABLE 2-continued

| compound | Ⓐ | Ⓑ | R⁷ |
|---|---|---|---|
| 296 | (bicyclic furofuran diamine) | benzothiazole with OiPr | 1-methylcyclopropyl |
| 297 | (bicyclic furofuran with F, NH) | benzothiazole with OiPr | cyclopropyl |
| 298 | (bicyclic furofuran with F, NH) | benzothiazole with OiPr | 1-methylcyclopropyl |
| 299 | (bicyclic furofuran with F, O) | benzothiazole with OiPr | cyclopropyl |
| 300 | (bicyclic furofuran with F, O) | benzothiazole with OiPr | 1-methylcyclopropyl |
| 301 | (bicyclic furofuran with OH, O) | benzothiazole with OiPr | cyclopropyl |
| 302 | (bicyclic furofuran with OH, O) | benzothiazole with OiPr | 1-methylcyclopropyl |

TABLE 2-continued

| compound | Ⓐ | Ⓑ | R⁷ |
|---|---|---|---|
| 303 | | | |
| 304 | | | |
| 305 | | | |
| 306 | | | |
| 307 | | | |
| 308 | | | |
| 309 | | | |

TABLE 2-continued

| compound | Ⓐ | Ⓑ | R⁷ |
|---|---|---|---|
| 310 | | | |
| 311 | | | |
| 312 | | | |
| 313 | | | |
| 314 | | | |
| 315 | | | |
| 316 | | | |

TABLE 2-continued

| compound | Ⓐ | Ⓑ | R⁷ |
|---|---|---|---|
| 317 | (bicyclic pentalene with O-linker and OH, other position linker) | benzothiazole with OiPr | cyclopropyl |
| 318 | (bicyclic pentalene with O-linker and F) | benzothiazole with OiPr | 1-methylcyclopropyl |
| 319 | (furo-pyrrolidine, O-linker via C3) | benzothiazole with OiPr | cyclopropyl |
| 320 | (thieno-pyrrolidine, O-linker) | benzothiazole with OiPr | 1-methylcyclopropyl |
| 321 | (furo-pyrrolidine, NH-linker) | benzothiazole with OiPr | cyclopropyl |
| 322 | (thieno-pyrrolidine, NH-linker) | benzothiazole with OiPr | 1-methylcyclopropyl |
| 323 | (octahydropyrrolo[1,2-a]pyrazine, O-linker) | benzothiazole with OiPr | cyclopropyl |
| 324 | (octahydropyrrolo[1,2-a]pyrazine, NH-linker) | benzothiazole with OiPr | 1-methylcyclopropyl |

TABLE 2-continued

| compound | Ⓐ | Ⓑ | R[7] |
|---|---|---|---|
| 325 | (pyrrolopiperazine with H, O-attached, wedge bond) | benzothiazole with OiPr | cyclopropyl |
| 326 | (pyrrolopiperazine with H, O-attached, dashed wedge) | benzothiazole with OiPr | methylcyclopropyl |
| 327 | (pyrrolopiperazine with H, O-attached, wedge) | benzothiazole with OiPr | cyclopropyl |
| 328 | (pyrrolopiperazine with H, O-attached, dashed wedge) | benzothiazole with OiPr | methylcyclopropyl |
| 329 | (pyrrolopiperazine with HN-attached) | benzothiazole with OiPr | cyclopropyl |
| 330 | (spirocyclopropyl pyrrolopiperazine with O) | benzothiazole with OiPr | methylcyclopropyl |
| 331 | (pyrrolopiperazinone with O) | benzothiazole with OiPr | cyclopropyl |

TABLE 2-continued

| compound | Ⓐ | Ⓑ | R⁷ |
|---|---|---|---|
| 332 | (hexahydrocyclopenta[b][1,4]oxazine with N-attachment and O-attachment) | benzothiazole with OiPr | 1-methylcyclopropyl |
| 333 | (hexahydrocyclopenta[b][1,4]oxazine with N-attachment and O-attachment) | benzothiazole with OiPr | cyclopropylmethyl |
| 334 | (hexahydrocyclopenta[b][1,4]oxazine with N-attachment and NH-attachment) | benzothiazole with OiPr | 1-methylcyclopropyl |
| 335 | (hexahydrocyclopenta[e][1,3]oxazine with N-attachment and O-attachment) | benzothiazole with OiPr | cyclopropyl |
| 336 | (hexahydrocyclopenta[e][1,3]oxazine with N-attachment and O-attachment) | benzothiazole with OiPr | 1-methylcyclopropyl |

11. The compound of claim 1, represented by Formula (X), or a pharmaceutically acceptable salt thereof,
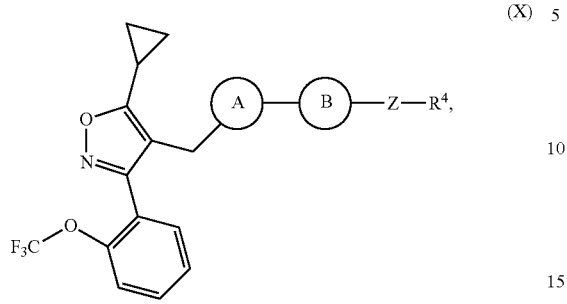
(X)
wherein Ⓐ, Ⓑ, Z and $R^4$ are as defined in claim 1.
12. The compound of claim 11, selected from compounds according to Formula (X), wherein Ⓐ, Ⓑ, and Z—$R^4$ are delineated for each compound in Table 3, or a pharmaceutically acceptable salt thereof:
TABLE 3
| compound | Ⓐ | Ⓑ | —Z—$R^4$ |
|---|---|---|---|
| 401 | | | |
| 402 | | | |
| 403 | | | |
| 404 | | | |

TABLE 3-continued

| compound | Ⓐ | Ⓑ | ⸺Z—R⁴ |
|---|---|---|---|
| 405 | isosorbide-type bicyclic diether | 6-linked-4-F-benzothiazol-2-yl | 2-methylpropanoic acid (α,α-dimethyl-CH₂COOH) |
| 406 | isosorbide-type bicyclic diether (stereoisomer) | 6-linked-4-F-benzothiazol-2-yl | 2-methylpropanoic acid |
| 407 | isosorbide-type bicyclic diether (stereoisomer) | 6-linked-4-F-benzothiazol-2-yl | 2-methylpropanoic acid |
| 408 | isosorbide-type bicyclic diether (stereoisomer) | 6-linked-4-F-benzothiazol-2-yl | 2-methylpropanoic acid |
| 409 | isosorbide-type bicyclic diether | 6-linked-4-OMe-benzothiazol-2-yl | 2-methylpropanoic acid |
| 410 | isosorbide-type bicyclic diether | 6-linked-4-OMe-benzothiazol-2-yl | 2-methylpropanoic acid |

TABLE 3-continued

| compound | Ⓐ | Ⓑ | ⸙–Z—R⁴ |
|---|---|---|---|
| 411 | [isosorbide-type bicyclic diether] | [benzothiazole with OMe] | [carboxylic acid, CH(CH₃)COOH] |
| 412 | [isosorbide-type bicyclic diether] | [benzothiazole with OMe] | [carboxylic acid, CH(CH₃)COOH] |
| 413 | [isosorbide-type bicyclic diether] | [benzothiazole] | [carboxylic acid, CH(CH₃)COOH] |
| 414 | [isosorbide-type bicyclic diether] | [benzothiazole] | [carboxylic acid, CH(CH₃)COOH] |
| 415 | [isosorbide-type bicyclic diether] | [benzothiazole] | [carboxylic acid, CH(CH₃)COOH] |
| 416 | [isosorbide-type bicyclic diether] | [benzothiazole] | [carboxylic acid, CH(CH₃)COOH] |

TABLE 3-continued

| compound | Ⓐ | Ⓑ | ⋮—Z—R⁴ |
|---|---|---|---|
| 417 | isosorbide diether | benzothiazole, OCHF₂ | 2-methylpropanoic acid |
| 418 | isosorbide diether | benzothiazole, OCF₃ | 2-methylpropanoic acid |
| 419 | isosorbide diether | benzothiazole, OCH₂F | 2-methylpropanoic acid |
| 420 | isosorbide diether | benzothiazole, CF₃ | 2-methylpropanoic acid |
| 421 | isosorbide diether | benzothiazole, CH₃ | 2-methylpropanoic acid |
| 422 | isosorbide diether | benzothiazole, Br | 2-methylpropanoic acid |

TABLE 3-continued

| compound | Ⓐ | Ⓑ | ⸺Z—R⁴ |
|---|---|---|---|
| 423 | isosorbide-diyl | 4-Cl-benzothiazole-2,6-diyl | 2-methylpropanoic acid |
| 424 | isosorbide-diyl | 4-cyclopropyl-benzothiazole-2,6-diyl | 2-methylpropanoic acid |
| 425 | isosorbide-diyl | 5-Me-benzothiazole-2,6-diyl | 2-methylpropanoic acid |
| 426 | isosorbide-diyl | 4-Me-benzothiazole-2,6-diyl | 2-methylpropanoic acid |
| 427 | isosorbide-diyl | benzoxazole-2,6-diyl | 2-methylpropanoic acid |
| 428 | isosorbide-diyl | 4-F-benzoxazole-2,6-diyl | 2-methylpropanoic acid |

TABLE 3-continued

| compound | Ⓐ | Ⓑ | ⸺Z—R⁴ |
|---|---|---|---|
| 429 | isosorbide-like bicyclic diether | benzoxazole with OMe | –C(CH₃)₂COOH |
| 430 | isosorbide-like bicyclic diether | benzoxazole with OiPr | –C(CH₃)₂COOH |
| 431 | isosorbide-like bicyclic diether | quinoline with F (5-position) | –C(CH₃)₂COOH |
| 432 | isosorbide-like bicyclic diether | quinoline with F (7-position) | –C(CH₃)₂COOH |
| 433 | isosorbide-like bicyclic diether | quinoline (2,6-disubstituted) | –C(CH₃)₂COOH |
| 434 | isosorbide-like bicyclic diether | quinoline (3,7-disubstituted) | –C(CH₃)₂COOH |

TABLE 3-continued

| compound | Ⓐ | Ⓑ | ⸺Z—R⁴ |
|---|---|---|---|
| 435 | isosorbide-O linker | 3-F quinoline (2,6-linked) | 2-methylpropanoic acid |
| 436 | isosorbide-O linker | 3-MeO quinoline (2,6-linked) | 2-methylpropanoic acid |
| 437 | isosorbide-O linker | quinoxaline (2,6-linked) | 2-methylpropanoic acid |
| 438 | isosorbide-O linker | 3-MeO quinoxaline (2,6-linked) | 2-methylpropanoic acid |
| 439 | isosorbide-O linker | 3-Cl quinoxaline (2,6-linked) | 2-methylpropanoic acid |
| 440 | isosorbide-O linker | 5-OiPr quinoxaline (2,6-linked) | 2-methylpropanoic acid |

TABLE 3-continued

| compound | Ⓐ | Ⓑ | ⸾⸾⸾Z—R⁴ |
|---|---|---|---|
| 441 | isosorbide | naphthalene-2,6-diyl | –C(CH₃)(COOH)– |
| 442 | isosorbide | 1-fluoronaphthalene-3,6-diyl | –C(CH₃)(COOH)– |
| 443 | isosorbide | 3-fluoronaphthalene-2,6-diyl | –C(CH₃)(COOH)– |
| 444 | isosorbide | 1-methoxynaphthalene-3,6-diyl | –C(CH₃)(COOH)– |
| 445 | isosorbide | naphthalene-2,6-diyl | –C(CH₃)(COOH)– |
| 446 | isosorbide | 4-methoxynaphthalene-2,6-diyl | –C(CH₃)(COOH)– |

TABLE 3-continued

| compound | Ⓐ | Ⓑ | ⸺Z—R⁴ |
|---|---|---|---|
| 447 | isosorbide diether | isoquinoline-3,7-diyl | 2-methylpropanoic acid |
| 448 | isosorbide diether | quinoline-2,5-diyl | 2-methylpropanoic acid |
| 449 | isosorbide diether | quinoline-2,5-diyl | 2-methylpropanoic acid |
| 450 | isosorbide diether | 8-fluoroquinoline-2,6-diyl | 2-methylpropanoic acid |
| 451 | isosorbide diether | quinoxaline-2,6-diyl | 2-methylpropanoic acid |
| 452 | isosorbide diether | quinazoline-2,6-diyl | 2-methylpropanoic acid |

TABLE 3-continued
| compound | Ⓐ | Ⓑ | ⸺Z—R⁴ |
|---|---|---|---|
| 453 | 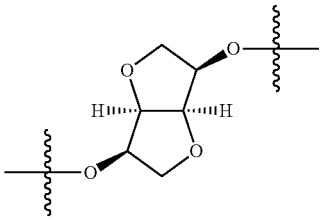 [SMILES: *O[C@@H]1CO[C@H]2[C@@H]1OC[C@H]2O*] | 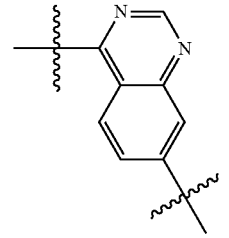 [SMILES: *c1ccc2c(*)ncnc2c1] | 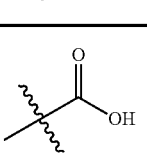 |
| 454 | 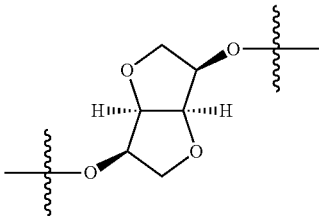 [SMILES: *O[C@@H]1CO[C@H]2[C@@H]1OC[C@H]2O*] | 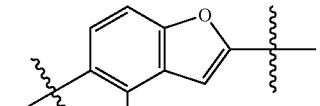 | 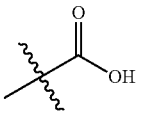 [SMILES: *C(=O)O] |
| 455 | 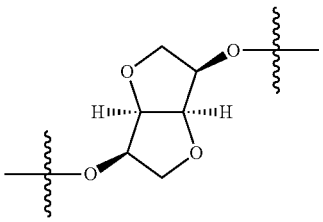 [SMILES: *O[C@@H]1CO[C@H]2[C@@H]1OC[C@H]2O*] | 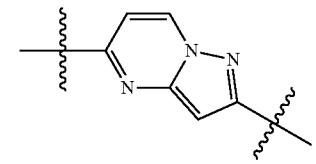 [SMILES: *c1ccn2nc(*)cc2n1] | 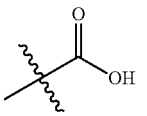 [SMILES: *C(=O)O] |
| 456 | 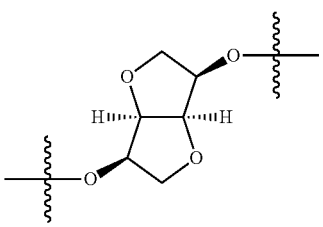 [SMILES: *O[C@@H]1CO[C@H]2[C@@H]1OC[C@H]2O*] | 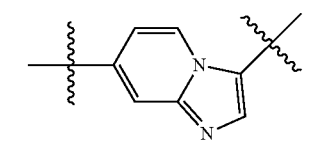 [SMILES: *c1ccn2c(*)cnc2c1] | 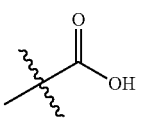 [SMILES: *C(=O)O] |
| 457 | 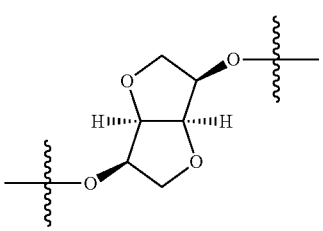 [SMILES: *O[C@@H]1CO[C@H]2[C@@H]1OC[C@H]2O*] | 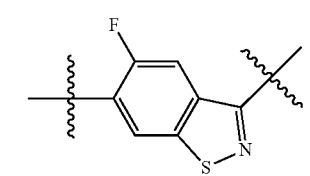 [SMILES: *c1cc2snc(*)c2cc1F] | 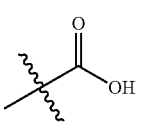 [SMILES: *C(=O)O] |
| 458 | 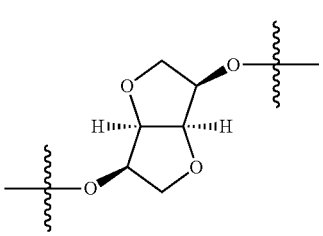 [SMILES: *O[C@@H]1CO[C@H]2[C@@H]1OC[C@H]2O*] | 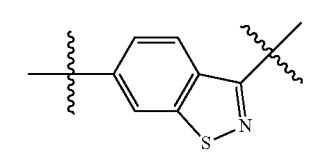 [SMILES: *c1ccc2c(*)nsc2c1] | 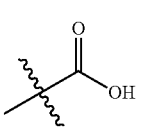 [SMILES: *C(=O)O] |

TABLE 3-continued

| compound | Ⓐ | Ⓑ | ⸺Z—R⁴ |
|---|---|---|---|
| 459 | isosorbide-type bicyclic diether | pyrazine-2,5-diyl | —C(CH₃)(COOH)— |
| 460 | isosorbide-type bicyclic diether | 3-fluoropyrazine-2,5-diyl | —C(CH₃)(COOH)— |
| 461 | isosorbide-type bicyclic diether | 2-fluoro-1,4-phenylene | —C(CH₃)(COOH)— |
| 462 | isosorbide-type bicyclic diether | 2-fluoro-1,4-phenylene | —C(CH₃)(COOH)— |
| 463 | isosorbide-type bicyclic diether | pyrazine-2,5-diyl | —C(CH₃)(COOH)— |
| 464 | isosorbide-type bicyclic diether | pyridine-2,6-diyl | —C(CH₃)(COOH)— |

TABLE 3-continued

| compound | Ⓐ | Ⓑ | ⸺Z—R⁴ |
|---|---|---|---|
| 465 | isosorbide-like bicyclic diether | 4-methylpyrimidine-2,6-diyl | 2-methylpropanoic acid (–C(CH₃)₂COOH) |
| 466 | isosorbide-like bicyclic diether | 4-fluoropyridine-2,5-diyl | 2-methylpropanoic acid |
| 467 | isosorbide-like bicyclic diether | pyridine-2,5-diyl | 2-methylpropanoic acid |
| 468 | isosorbide-like bicyclic diether | thiazole-2,5-diyl | 2-methylpropanoic acid |
| 469 | isosorbide-like bicyclic diether | thiazole-2,4-diyl | 2-methylpropanoic acid |
| 470 | isosorbide-like bicyclic diether | pyridine-2,6-diyl | 2-methylpropanoic acid |

TABLE 3-continued

| compound | Ⓐ | Ⓑ | ⸺Z—R⁴ |
|---|---|---|---|
| 471 | [isosorbide diether] | 2,6-disubstituted-4-methylpyridine | CH(CH₃)C(O)OH |
| 472 | [isosorbide diether] | 3-fluoro-2,5-disubstituted pyridine | CH(CH₃)C(O)OH |
| 473 | [isosorbide diether] | 3-methyl-2,5-disubstituted pyridine | CH(CH₃)C(O)OH |
| 474 | [isosorbide diether] | 3-trifluoromethyl-2,5-disubstituted pyridine | CH(CH₃)C(O)OH |
| 475 | [isosorbide diether] | 3-cyclopropyl-2,5-disubstituted pyridine | CH(CH₃)C(O)OH |
| 476 | [isosorbide diether] | 2,3-difluoro-1,4-disubstituted benzene | CH(CH₃)C(O)OH |

TABLE 3-continued

| compound | Ⓐ | Ⓑ | ⸺Z—R⁴ |
|---|---|---|---|
| 477 | isosorbide-like bicyclic diether | 1,2,4-oxadiazole | 2-methylpropanoic acid |
| 478 | isosorbide-like bicyclic diether | 1,2,4-oxadiazole | 3-carboxyphenyl |
| 479 | isosorbide-like bicyclic diether | 1,2,4-oxadiazole | 6-carboxypyridin-2-yl |
| 480 | isosorbide-like bicyclic diether | 1,2,4-oxadiazole | 3-carboxy-4-fluorophenyl |
| 481 | isosorbide-like bicyclic diether | 1,2,4-oxadiazole | 4-carboxyphenyl |
| 482 | isosorbide-like bicyclic diether | 1,2,4-oxadiazole | 3-carboxycyclohexyl |

TABLE 3-continued

| compound | Ⓐ | Ⓑ | ⸨Z—R⁴ |
|---|---|---|---|
| 483 | isosorbide-like bicyclic diether | benzothiazole with OiPr | —CN |
| 484 | isosorbide-like bicyclic diether | benzothiazole with OiPr | tetrazole (NH) |
| 485 | isosorbide-like bicyclic diether | pyrazine | —CN |
| 486 | isosorbide-like bicyclic diether | pyrazine | tetrazole (NH) |
| 487 | isosorbide-like bicyclic diether | fluorophenyl | —CN |
| 488 | isosorbide-like bicyclic diether | fluorophenyl | tetrazole (NH) |

TABLE 3-continued

| compound | Ⓐ | Ⓑ | ⌇—Z—R⁴ |
|---|---|---|---|
| 489 | isosorbide-diyl | 2-methoxy-1,4-phenylene | —CN |
| 490 | isosorbide-diyl | 2-methoxy-1,4-phenylene | 2H-tetrazol-5-yl |
| 491 | isosorbide-diyl | benzothiazole-2,6-diyl | —O-C(O)-NH-SO₂-C₆H₄-OiPr |
| 492 | isosorbide-diyl | benzothiazole-2,6-diyl | —O-C(O)-NH-SO₂-C₆H₄-OiPr |
| 493 | isosorbide-diyl | 4-OiPr-benzothiazole-2,6-diyl | —O-C(O)-NH-SO₂-C₆H₄-OiPr |
| 494 | isosorbide-diyl | 4-OiPr-benzothiazole-2,6-diyl | —O-C(O)-NH-SO₂-C₆H₄-OiPr |

TABLE 3-continued

| compound | Ⓐ | Ⓑ | ⸙—Z—R⁴ |
|---|---|---|---|
| 495 | isosorbide-type bicyclic diether | benzothiazole-6-yl | carbamoyl-sulfonyl-(4-tert-butoxyphenyl) |
| 496 | isosorbide-type bicyclic diether (isomer) | benzothiazole-6-yl | carbamoyl-sulfonyl-(4-tert-butoxyphenyl) |
| 497 | isosorbide-type bicyclic diether | 7-OiPr-benzothiazole-6-yl | carbamoyl-sulfonyl-(4-tert-butoxyphenyl) |
| 498 | isosorbide-type bicyclic diether (isomer) | 7-OiPr-benzothiazole-6-yl | carbamoyl-sulfonyl-(4-tert-butoxyphenyl) |
| 499 | isosorbide-type bicyclic diether | benzothiazole-6-yl | carbamoyl-sulfonyl-(6-piperidin-1-yl-pyridin-3-yl) |
| 500 | isosorbide-type bicyclic diether | 7-F-benzothiazole-6-yl | carbamoyl-sulfonyl-(6-piperidin-1-yl-pyridin-3-yl) |

TABLE 3-continued

| compound | Ⓐ | Ⓑ | ⸨Z—R⁴ |
|---|---|---|---|
| 501 | isosorbide-like bicyclic diether | benzothiazole with OiPr | carbamate-SO₂-pyridyl-piperidine |
| 502 | isosorbide-like bicyclic diether | benzothiazole with cyclopropyl | carbamate-SO₂-pyridyl-piperidine |
| 503 | isosorbide-like bicyclic diether | benzothiazole | carbamate-SO₂-C₆H₄-OtBu |
| 504 | isosorbide-like bicyclic diether | benzothiazole with F | carbamate-SO₂-C₆H₄-OtBu |
| 505 | isosorbide-like bicyclic diether | benzothiazole with OiPr | carbamate-SO₂-C₆H₄-OtBu |
| 506 | isosorbide-like bicyclic diether | benzothiazole with cyclopropyl | carbamate-SO₂-C₆H₄-OtBu |

TABLE 3-continued

| compound | Ⓐ | Ⓑ | ⸺Z—R⁴ |
|---|---|---|---|
| 507 | isosorbide-like bicyclic diether | 2-yl-benzothiazol-6-yl | —NHC(O)NHSO₂-C₆H₄-tBu |
| 508 | isosorbide-like bicyclic diether | 7-F-2-yl-benzothiazol-6-yl | —NHC(O)NHSO₂-C₆H₄-tBu |
| 509 | isosorbide-like bicyclic diether | 7-OiPr-2-yl-benzothiazol-6-yl | —NHC(O)NHSO₂-C₆H₄-tBu |
| 510 | isosorbide-like bicyclic diether | 7-cyclopropyl-2-yl-benzothiazol-6-yl | —NHC(O)NHSO₂-C₆H₄-tBu |
| 511 | isosorbide-like bicyclic diether | 2-yl-benzothiazol-6-yl | —CH₂NHC(O)NHSO₂-C₆H₄-tBu |
| 512 | isosorbide-like bicyclic diether | 7-F-2-yl-benzothiazol-6-yl | —CH₂NHC(O)NHSO₂-C₆H₄-tBu |

TABLE 3-continued

| compound | Ⓐ | Ⓑ | ⸺Z—R⁴ |
|---|---|---|---|
| 513 | isosorbide-type bicyclic diether | benzothiazole with OiPr | ⸺CH₂NHC(O)NHSO₂-C₆H₄-t-Bu |
| 514 | isosorbide-type bicyclic diether | benzothiazole with cyclopropyl | ⸺CH₂NHC(O)NHSO₂-C₆H₄-t-Bu |
| 515 | isosorbide-type bicyclic diether | benzothiazole with OiPr | ⸺CO₂Me |
| 516 | isosorbide-type bicyclic diether | benzothiazole with OiPr | ⸺CO₂t-Bu |
| 517 | isosorbide-type bicyclic diether | benzothiazole with OiPr | ⸺CH(Me)CO₂Me |
| 518 | isosorbide-type bicyclic diether | benzothiazole with OiPr | ⸺CH(Me)CO₂H |

TABLE 3-continued

| compound | Ⓐ | Ⓑ | ⟿—Z—R⁴ |
|---|---|---|---|
| 519 | isosorbide linker | 7-OiPr-benzothiazole-2,6-diyl | -CH₂CH₂C(O)OMe |
| 520 | isosorbide linker | 7-OiPr-benzothiazole-2,6-diyl | -CH₂CH₂C(O)OH |
| 521 | isosorbide linker | 7-OiPr-benzothiazole-2,6-diyl | -CH₂OCH₂C(O)OMe |
| 522 | isosorbide linker | 7-OiPr-benzothiazole-2,6-diyl | -CH₂OCH₂C(O)OH |
| 523 | isosorbide linker | 7-OiPr-benzothiazole-2,6-diyl | -CH₂NHCH₂C(O)OMe |
| 524 | isosorbide linker | 7-OiPr-benzothiazole-2,6-diyl | -CH₂NHCH₂C(O)OH |

TABLE 3-continued

| compound | Ⓐ | Ⓑ | ⸺Z—R⁴ |
|---|---|---|---|
| 525 | isosorbide-like bicyclic diether | benzothiazole with OiPr | CH₂-N(Me)-CH₂-C(O)OMe |
| 526 | isosorbide-like bicyclic diether | benzothiazole with OiPr | CH₂-N(Me)-CH₂-C(O)OH |
| 527 | isosorbide-like bicyclic diether | benzothiazole with OiPr | C(Me)₂-CH₂OH |
| 528 | isosorbide-like bicyclic diether | benzothiazole with OiPr | C(Me)₂-CH₂CH₂OH |
| 529 | isosorbide-like bicyclic diether | benzothiazole with OiPr | cyclopropyl-CO₂Me |
| 530 | isosorbide-like bicyclic diether | benzothiazole with OiPr | cyclopropyl-CO₂H |

TABLE 3-continued

| compound | Ⓐ | Ⓑ | ⸙—Z—R⁴ |
|---|---|---|---|
| 531 | isosorbide-like bicyclic diether | 2-linked-6-linked-7-OiPr-benzothiazole | cyclopropyl-CH₂-C(=O)OMe |
| 532 | isosorbide-like bicyclic diether | 2-linked-6-linked-7-OiPr-benzothiazole | cyclopropyl-CH₂-C(=O)OH |
| 533 | isosorbide-like bicyclic diether | 2-linked-6-linked-7-OiPr-benzothiazole | C(CF₂)(CH₃)-CO₂Me |
| 534 | isosorbide-like bicyclic diether | 2-linked-6-linked-7-OiPr-benzothiazole | C(CF₂)(CH₃)-C(=O)OH |
| 535 | isosorbide-like bicyclic diether | 2-linked-6-linked-7-OiPr-benzothiazole | CH(CH₃)-CN |
| 536 | isosorbide-like bicyclic diether | 2-linked-6-linked-7-OiPr-benzothiazole | 1H-tetrazol-5-yl |

TABLE 3-continued

| compound | Ⓐ | Ⓑ | ⟶Z—R⁴ |
|---|---|---|---|
| 537 | isosorbide-like bicyclic diether linker | 2-yl-7-OiPr-benzothiazol-6-yl | —C(O)NH-CH₂-C(O)O-tBu |
| 538 | isosorbide-like bicyclic diether linker | 2-yl-7-OiPr-benzothiazol-6-yl | —C(O)NH-CH₂-COOH |
| 539 | isosorbide-like bicyclic diether linker | 2-yl-7-OiPr-benzothiazol-6-yl | —C(O)NH-C(CH₃)₂-COOH |
| 540 | isosorbide-like bicyclic diether linker | 2-yl-7-OiPr-benzothiazol-6-yl | —C(O)NH-CH(CH₃)-COOH |
| 541 | isosorbide-like bicyclic diether linker | 2-yl-7-OiPr-benzothiazol-6-yl | —C(O)NH-CH₂CH₂-SO₃Me |
| 542 | isosorbide-like bicyclic diether linker | 2-yl-7-OiPr-benzothiazol-6-yl | —C(O)NH-CH₂CH₂-SO₃H |

TABLE 3-continued

| compound | Ⓐ | Ⓑ | ⸜⸝-Z—R⁴ |
|---|---|---|---|
| 543 | isosorbide-like bicyclic diether | benzothiazole, 7-OiPr | -C(O)NH-C(cyclopropyl)(CH₂SO₃H) |
| 544 | isosorbide-like bicyclic diether | benzothiazole, 7-OiPr | -C(O)NH-C(CH₃)₂CH₂SO₃H |
| 545 | isosorbide-like bicyclic diether | benzothiazole, 7-OiPr | -C(O)NH-CH₂-O-CH₂-OSO₃H |
| 546 | isosorbide-like bicyclic diether | benzothiazole, 7-OiPr | -C(O)NH-CH₂-NH-CH₂-OSO₃H |
| 547 | isosorbide-like bicyclic diether | benzothiazole | quinic acid ester |
| 548 | isosorbide-like bicyclic diether | benzothiazole, 7-OMe | quinic acid ester |

TABLE 3-continued

| compound | Ⓐ | Ⓑ | ⸜Z—R⁴ |
|---|---|---|---|
| 549 | [structure] | [benzothiazole with F] | [quinic acid ester] |
| 550 | [structure] | [benzothiazole with OiPr] | [quinic acid ester] |
| 551 | [structure] | [benzothiazole with OiPr] | [2-methylpropanoic acid] |
| 552 | [structure] | [benzothiazole with OiPr] | [2-methylpropanoic acid] |
| 553 | [structure] | [benzothiazole with OiPr] | [2-methylpropanoic acid] |
| 554 | [structure] | [benzothiazole with OiPr] | [2-methylpropanoic acid] |
| 555 | [structure] | [benzothiazole with OiPr] | [2-methylpropanoic acid] |

TABLE 3-continued

| compound | Ⓐ | Ⓑ | ⸺Z—R⁴ |
|---|---|---|---|
| 556 | | | |
| 557 | | | |
| 558 | | | |
| 559 | | | |
| 560 | | | |
| 561 | | | |
| 562 | | | |

TABLE 3-continued

| compound | Ⓐ | Ⓑ | ⟋⟍Z—R⁴ |
|---|---|---|---|
| 563 | | | |
| 564 | | | |
| 565 | | | |
| 566 | | | |
| 567 | | | |
| 568 | | | |

TABLE 3-continued

| compound | Ⓐ | Ⓑ | ⸨Z—R⁴ |
|---|---|---|---|
| 569 | | | |
| 570 | | | |
| 571 | | | |
| 572 | | | |
| 573 | | | |
| 574 | | | |
| 575 | | | |

TABLE 3-continued

| compound | Ⓐ | Ⓑ | ⸾⸾Z—R⁴ |
|---|---|---|---|
| 576 | thiophene-fused pyrrolidine with O-linker | benzothiazole with OiPr | CH(CH₃)COOH |
| 577 | furan-fused pyrrolidine with NH-linker | benzothiazole with OiPr | CH(CH₃)COOH |
| 578 | thiophene-fused pyrrolidine with NH-linker | benzothiazole with OiPr | CH(CH₃)COOH |
| 579 | pyrrolo-piperazine with O-linker | benzothiazole with OiPr | CH(CH₃)COOH |
| 580 | pyrrolo-piperazine with NH-linker | benzothiazole with OiPr | CH(CH₃)COOH |
| 581 | pyrrolizidine with O-linker (H stereochem) | benzothiazole with OiPr | CH(CH₃)COOH |
| 582 | pyrrolizidine with O-linker (H stereochem, opposite) | benzothiazole with OiPr | CH(CH₃)COOH |

TABLE 3-continued

| compound | Ⓐ | Ⓑ | ⸻Z—R⁴ |
|---|---|---|---|
| 583 | | | |
| 584 | | | |
| 585 | | | |
| 586 | | | |
| 587 | | | |
| 588 | | | |
| 589 | | | |

TABLE 3-continued

| compound | (A) | (B) | —Z—R⁴ |
|---|---|---|---|
| 590 | | | |
| 591 | | | |
| 592 | | | |

13. The compound of claim 1, represented by Formula (XI), or a pharmaceutically acceptable salt thereof, (XI)

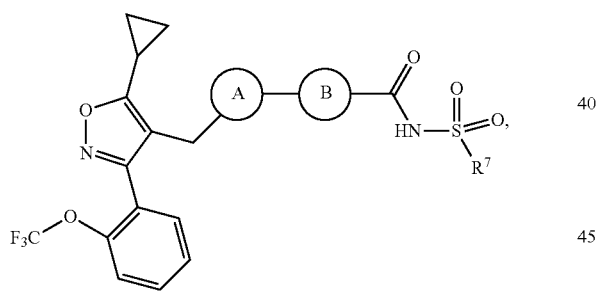

wherein (A), (B), and R⁷ are as defined in claim 1.

14. The compound of claim 13, selected from compounds according to Formula (XI), wherein (A), (B), and R⁷ are delineated for each compound in Table 4, or a pharmaceutically acceptable salt thereof:

TABLE 4

| compound | (A) | (B) | R⁷ |
|---|---|---|---|
| 701 | | | |

TABLE 4-continued

| compound | Ⓐ | Ⓑ | R⁷ |
|---|---|---|---|
| 702 | isosorbide linker | 2-benzothiazolyl, 7-OiPr | 1-methylcyclopropyl |
| 703 | isosorbide linker | 2-benzothiazolyl, 7-OiPr | 1-(CHO)cyclopropyl |
| 704 | isosorbide linker | 2-benzothiazolyl, 7-OiPr | 1-(CD₃)cyclopropyl |
| 705 | isosorbide linker | 2-benzothiazolyl, 7-OiPr | 1-(CH₂OH)cyclopropyl |
| 706 | isosorbide linker | 2-benzothiazolyl, 7-OiPr | 1-(CHF₂)cyclopropyl |
| 707 | isosorbide linker | 2-benzothiazolyl, 7-OiPr | 1-(CF₃)cyclopropyl |
| 708 | isosorbide linker | 2-benzothiazolyl, 7-OiPr | 1-(F)cyclopropyl |

TABLE 4-continued

| compound | Ⓐ | Ⓑ | R⁷ |
|---|---|---|---|
| 709 | isosorbide-like bicyclic diether | 4-OiPr-benzothiazole (2,6-linked) | 1-Cl-cyclopropyl |
| 710 | isosorbide-like bicyclic diether | 4-OiPr-benzothiazole (2,6-linked) | 1-(CH₂F)-cyclopropyl |
| 711 | isosorbide-like bicyclic diether | 4-OiPr-benzothiazole (2,6-linked) | 1-(CH₂OMe)-cyclopropyl |
| 712 | isosorbide-like bicyclic diether | 4-OiPr-benzothiazole (2,6-linked) | 1-CN-cyclopropyl |
| 713 | isosorbide-like bicyclic diether | 4-OiPr-benzothiazole (2,6-linked) | 1-(COOH)-cyclopropyl |
| 714 | isosorbide-like bicyclic diether | 4-OiPr-benzothiazole (2,6-linked) | 1-(COOMe)-cyclopropyl |

TABLE 4-continued

| compound | Ⓐ | Ⓑ | R⁷ |
|---|---|---|---|
| 715 | isosorbide linker | 2-linked-7-OiPr-benzothiazol-6-yl | cyclopropane-1-carboxamide N-sulfonyl pyrrolidine |
| 216 | isosorbide linker | 2-linked-7-OiPr-benzothiazol-6-yl | 1-carbamoylcyclopropyl |
| 717 | isosorbide linker | 2-linked-7-OiPr-benzothiazol-6-yl | 2,2-difluoro-1-methylcyclopropyl |
| 718 | isosorbide linker | 2-linked-7-OiPr-benzothiazol-6-yl | 2,2-difluorocyclopropyl |
| 719 | isosorbide linker | 2-linked-7-OiPr-benzothiazol-6-yl | azetidin-1-yl |
| 720 | isosorbide linker | 2-linked-7-OiPr-benzothiazol-6-yl | pyrrolidin-1-yl |
| 721 | isosorbide linker | 2-linked-7-OiPr-benzothiazol-6-yl | piperidin-1-yl |

TABLE 4-continued

| compound | Ⓐ | Ⓑ | R⁷ |
|---|---|---|---|
| 722 | (isosorbide-like bicyclic diether) | 2-yl-7-OiPr-benzothiazol-6-yl | 4,4-difluoropiperidin-1-yl |
| 723 | (isosorbide-like bicyclic diether) | 2-yl-7-OiPr-benzothiazol-6-yl | cyclopentyl |
| 724 | (isosorbide-like bicyclic diether) | 2-yl-7-OiPr-benzothiazol-6-yl | morpholin-4-yl |
| 725 | (isosorbide-like bicyclic diether) | 2-yl-7-OiPr-benzothiazol-6-yl | 1-methylcyclopentyl |
| 726 | (isosorbide-like bicyclic diether) | 2-yl-7-OiPr-benzothiazol-6-yl | cyclohexyl |
| 727 | (isosorbide-like bicyclic diether) | 2-yl-7-OiPr-benzothiazol-6-yl | NH₂ |

TABLE 4-continued

| compound | Ⓐ | Ⓑ | R⁷ |
| --- | --- | --- | --- |
| 728 | isosorbide linker | 2-benzothiazolyl, 7-OiPr | -NHMe |
| 729 | isosorbide linker | 2-benzothiazolyl, 7-OiPr | -NMe₂ |
| 730 | isosorbide linker | 2-benzothiazolyl, 7-OiPr | -NH-iPr |
| 731 | isosorbide linker | 2-benzothiazolyl, 7-OiPr | -NH-cyclopropyl |
| 732 | isosorbide linker | 2-benzothiazolyl, 7-OiPr | -NH-cyclobutyl |
| 733 | isosorbide linker | 2-benzothiazolyl, 7-OiPr | -NH-cyclopentyl |
| 734 | isosorbide linker | 2-benzothiazolyl, 7-OiPr | -NH-cyclohexyl |

TABLE 4-continued

| compound | Ⓐ | Ⓑ | R⁷ |
|---|---|---|---|
| 735 | isosorbide-type bicyclic diether (H down, H down) | 2-yl-7-OiPr-benzothiazol-6-yl | —NH—Ph |
| 736 | isosorbide-type bicyclic diether (H down, H down) | 2-yl-7-OiPr-benzothiazol-6-yl | —NH—(4-F-C₆H₄) |
| 737 | isosorbide-type bicyclic diether (H down, H down) | 2-yl-7-OiPr-benzothiazol-6-yl | —NH—(2-OCF₃-C₆H₄) |
| 738 | isosorbide-type bicyclic diether (H up, H up) | 2-yl-7-OiPr-benzothiazol-6-yl | —NH-(pyridin-4-yl) |
| 739 | isosorbide-type bicyclic diether (H up, H up) | 2-yl-7-OiPr-benzothiazol-6-yl | —Me |
| 740 | isosorbide-type bicyclic diether (H up, H up) | 2-yl-7-OiPr-benzothiazol-6-yl | —CF₃ |

TABLE 4-continued

| compound | Ⓐ | Ⓑ | R⁷ |
|---|---|---|---|
| 741 | isosorbide-diyl | 7-OiPr-benzothiazole-2,6-diyl | isopropyl |
| 742 | isosorbide-diyl | 7-OiPr-benzothiazole-2,6-diyl | ethyl (Me-CH<) |
| 743 | isosorbide-diyl | 7-OiPr-benzothiazole-2,6-diyl | neopentyl |
| 744 | isosorbide-diyl | 7-OiPr-benzothiazole-2,6-diyl | tert-butyl |
| 745 | isosorbide-diyl | 7-OiPr-benzothiazole-2,6-diyl | cyclopropylmethyl |
| 746 | isosorbide-diyl | 7-OiPr-benzothiazole-2,6-diyl | -C(Me)₂CH₂OBn |
| 747 | isosorbide-diyl | 7-OiPr-benzothiazole-2,6-diyl | benzyl |

TABLE 4-continued

| compound | Ⓐ | Ⓑ | R⁷ |
|---|---|---|---|
| 748 | isosorbide (exo-endo) | 4-OiPr-benzothiazole (2,6) | vinyl |
| 749 | isosorbide (exo-endo) | 4-OiPr-benzothiazole (2,6) | Bu |
| 750 | isosorbide (endo-exo) | 4-OiPr-benzothiazole (2,6) | propyl |
| 751 | isosorbide (endo-exo) | 4-OiPr-benzothiazole (2,6) | phenyl |
| 752 | isosorbide (endo-exo) | 4-OiPr-benzothiazole (2,6) | 4-F-phenyl |
| 753 | isosorbide (endo-exo) | 4-OiPr-benzothiazole (2,6) | 2-pyridyl |

TABLE 4-continued

| compound | Ⓐ | Ⓑ | R⁷ |
| --- | --- | --- | --- |
| 754 | isosorbide | 4-OiPr-benzothiazole-2,6-diyl | 4-tert-butylphenyl |
| 755 | isosorbide | 4-OiPr-benzothiazole-2,6-diyl | pyridin-4-yl |
| 756 | isosorbide | 4-OiPr-benzothiazole-2,6-diyl | pyridin-3-yl |
| 757 | isosorbide | 4-OiPr-benzothiazole-2,6-diyl | thiazol-5-yl |
| 758 | isosorbide | 4-OiPr-benzothiazole-2,6-diyl | 5-fluoropyridin-2-yl |
| 759 | isosorbide | 4-OiPr-benzothiazole-2,6-diyl | 1H-imidazol-2-yl |
| 760 | isosorbide | 4-OiPr-benzothiazole-2,6-diyl | thiazol-2-yl |

TABLE 4-continued

| compound | Ⓐ | Ⓑ | R[7] |
|---|---|---|---|
| 761 | isosorbide-type bicyclic diether | 4-OiPr-benzothiazole-2,6-diyl | 2-(trifluoromethoxy)phenyl |
| 762 | isosorbide-type bicyclic diether | 4-OiPr-benzothiazole-2,6-diyl | 1-methyl-1H-imidazol-2-yl |
| 763 | isosorbide-type bicyclic diether | 4-OiPr-benzothiazole-2,6-diyl | naphthalen-2-yl |
| 764 | isosorbide-type bicyclic diether | 4-OiPr-benzothiazole-2,6-diyl | 2-methoxyphenyl |
| 765 | isosorbide-type bicyclic diether | 4-OiPr-benzothiazole-2,6-diyl | biphenyl-4-yl |
| 766 | isosorbide-type bicyclic diether | 4-OiPr-benzothiazole-2,6-diyl | [2,4'-bipyridin]-5-yl |

TABLE 4-continued

| compound | Ⓐ | Ⓑ | R[7] |
|---|---|---|---|
| 767 | isosorbide linker | 2-yl-6-yl benzothiazole, 4-OiPr | 4-(pyridin-4-yl)phenyl |
| 768 | isosorbide linker | 2-yl-6-yl benzothiazole, 4-OiPr | 2,3-dihydro-1,4-benzodioxin-6-yl |
| 769 | isosorbide linker | 2-yl-6-yl benzothiazole, 4-OiPr | 1,3-benzodioxol-5-yl |
| 770 | isosorbide linker | 2-yl-6-yl benzothiazole, 4-OiPr | 2,3-dihydro-1H-inden-5-yl |
| 771 | isosorbide linker | 2-yl-6-yl benzothiazole, 4-F | cyclopropyl |
| 772 | isosorbide linker | 2-yl-6-yl benzothiazole, 4-F | 1-methylcyclopropyl |
| 773 | isosorbide linker | 2-yl-6-yl benzothiazole | cyclopropyl |

TABLE 4-continued

| compound | Ⓐ | Ⓑ | R⁷ |
|---|---|---|---|
| 774 | isosorbide-type bicyclic diether | benzothiazol-2,6-diyl | 1-methylcyclopropyl |
| 775 | isosorbide-type bicyclic diether | 7-OiPr-benzothiazol-2,6-diyl | cyclopropyl |
| 776 | isosorbide-type bicyclic diether | 7-OiPr-benzothiazol-2,6-diyl | 1-methylcyclopropyl |
| 777 | isosorbide-type bicyclic diether | pyridine-2,6-diyl | cyclopropyl |
| 778 | isosorbide-type bicyclic diether | pyridine-2,6-diyl | 1-methylcyclopropyl |
| 779 | isosorbide-type bicyclic diether | 3-MeO-quinoxaline-2,6-diyl | cyclopropyl |

TABLE 4-continued

| compound | Ⓐ | Ⓑ | R⁷ |
|---|---|---|---|
| 780 | isosorbide-like bicyclic diether | MeO-quinoxaline | 1-methylcyclopropyl |
| 781 | isosorbide-like bicyclic diether | quinoxaline | cyclopropyl |
| 782 | isosorbide-like bicyclic diether | quinoxaline | 1-methylcyclopropyl |
| 783 | isosorbide-like bicyclic diether | quinoline | cyclopropyl |
| 784 | isosorbide-like bicyclic diether | quinoline | 1-methylcyclopropyl |
| 785 | isosorbide-like bicyclic diether | quinazoline | cyclopropyl |
| 786 | isosorbide-like bicyclic diether | quinazoline | 1-methylcyclopropyl |

TABLE 4-continued

| compound | Ⓐ | Ⓑ | R⁷ |
|---|---|---|---|
| 787 | isosorbide-diyl (diether) | pyrazolo[1,5-a]pyrimidine-2,5-diyl | cyclopropyl |
| 788 | isosorbide-diyl (diether) | pyrazolo[1,5-a]pyrimidine-2,5-diyl | 1-methylcyclopropyl |
| 789 | isosorbide-diyl (diether) | 4-OiPr-benzothiazole-2,6-diyl | cyclopropyl |
| 790 | isosorbide-diyl (diether) | 4-OiPr-benzothiazole-2,6-diyl | 1-methylcyclopropyl |
| 791 | isosorbide amino-ether | 4-OiPr-benzothiazole-2,6-diyl | cyclopropyl |
| 792 | isosorbide amino-ether | 4-OiPr-benzothiazole-2,6-diyl | 1-methylcyclopropyl |
| 793 | isosorbide amino-ether (alt stereo) | 4-OiPr-benzothiazole-2,6-diyl | cyclopropyl |

TABLE 4-continued

| compound | Ⓐ | Ⓑ | R⁷ |
|---|---|---|---|
| 794 | | | |
| 795 | | | |
| 796 | | | |
| 797 | | | |
| 798 | | | |
| 799 | | | |
| 800 | | | |

TABLE 4-continued

| compound | Ⓐ | Ⓑ | R⁷ |
|---|---|---|---|
| 801 | (bicyclic furan diol with OH, O-linker) | benzothiazole with OiPr | cyclopropyl |
| 802 | (bicyclic furan diol with OH, O-linker) | benzothiazole with OiPr | 1-methylcyclopropyl |
| 803 | (bicyclic furan with SO₂ linker, O-linker) | benzothiazole with OiPr | cyclopropyl |
| 804 | (bicyclic furan with S linker, O-linker) | benzothiazole with OiPr | 1-methylcyclopropyl |
| 805 | (bicyclic furan with S(O) linker, O-linker) | benzothiazole with OiPr | cyclopropyl |
| 806 | (bicyclic furan with F and SO₂ linker, O-linker) | benzothiazole with OiPr | 1-methylcyclopropyl |
| 807 | (bicyclic furan with O linker, S-linker) | benzothiazole with OiPr | cyclopropyl |

TABLE 4-continued

| compound | Ⓐ | Ⓑ | R⁷ |
|---|---|---|---|
| 808 | (tetrahydrofuro-furan with NH and sulfonyl substituents) | 2-yl-6-yl-7-OiPr-benzothiazole | 1-methylcyclopropyl |
| 809 | (oxazolidine fused cyclopentane with O linker) | 2-yl-6-yl-7-OiPr-benzothiazole | cyclopropyl |
| 810 | (oxazolidine fused cyclopentane with NH linker) | 2-yl-6-yl-7-OiPr-benzothiazole | 1-methylcyclopropyl |
| 811 | (oxazolidine fused cyclopentane with O linker) | 2-yl-6-yl-7-OiPr-benzothiazole | cyclopropyl |
| 812 | (oxazolidinone fused cyclopentane with O linker) | 2-yl-6-yl-7-OiPr-benzothiazole | 1-methylcyclopropyl |
| 813 | (bicyclic diaminooctahydropentalene) | 2-yl-6-yl-7-OiPr-benzothiazole | cyclopropyl |
| 814 | (bicyclic aminooxy-octahydropentalene) | 2-yl-6-yl-7-OiPr-benzothiazole | 1-methylcyclopropyl |

TABLE 4-continued

| compound | Ⓐ | Ⓑ | R⁷ |
|---|---|---|---|
| 815 | cis-hexahydrocyclopenta[c]pyrrole with HN- substituent | benzothiazole with OiPr | cyclopropyl |
| 816 | hexahydrocyclopenta[c]pyrrole with HN- and F substituents | benzothiazole with OiPr | 1-methylcyclopropyl |
| 817 | hexahydropentalene with O- and OH substituents | benzothiazole with OiPr | cyclopropyl |
| 818 | hexahydropentalene with O- and F substituents | benzothiazole with OiPr | 1-methylcyclopropyl |
| 819 | hexahydrofuro[3,2-c]pyrrole with O-substituent | benzothiazole with OiPr | cyclopropyl |
| 820 | hexahydrothieno[3,2-c]pyrrole with O-substituent | benzothiazole with OiPr | 1-methylcyclopropyl |
| 821 | hexahydrofuro[3,2-c]pyrrole with NH-substituent | benzothiazole with OiPr | cyclopropyl |
| 822 | hexahydrothieno[3,2-c]pyrrole with NH-substituent | benzothiazole with OiPr | 1-methylcyclopropyl |

TABLE 4-continued

| compound | Ⓐ | Ⓑ | R⁷ |
|---|---|---|---|
| 823 | (pyrrolopiperazine with O-linker) | benzothiazole with OiPr | cyclopropyl |
| 824 | (pyrrolopiperazine with NH-linker) | benzothiazole with OiPr | cyclopropyl |
| 825 | (pyrrolopiperazine with O-linker, H stereochem) | benzothiazole with OiPr | cyclopropyl |
| 826 | (pyrrolopiperazine with O-linker, H stereochem) | benzothiazole with OiPr | cyclopropyl |
| 827 | (pyrrolopiperazine with O-linker, H stereochem) | benzothiazole with OiPr | cyclopropyl |
| 828 | (pyrrolopiperazine with O-linker, H stereochem) | benzothiazole with OiPr | cyclopropyl |
| 829 | (pyrrolopiperazine with HN-linker) | benzothiazole with OiPr | cyclopropyl |
| 830 | (spiro-cyclopropyl pyrrolopiperazine with O-linker) | benzothiazole with OiPr | cyclopropyl |

TABLE 4-continued

| compound | Ⓐ | Ⓑ | R⁷ |
|---|---|---|---|
| 831 | | | |
| 832 | | | |
| 833 | | | |
| 834 | | | |
| 835 | | | |
| 836 | | | |

15. The compound of claim 1, selected from the compounds set forth below or a pharmaceutically acceptable salt thereof:
| Compound | Structure |
| --- | --- |
| 1 | 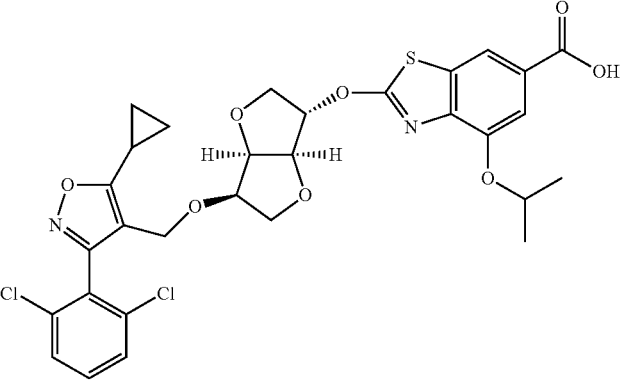 [SMILES: CC(C)Oc1cc(C(=O)O)cc2sc(O[C@H]3CO[C@H]4[C@@H]3OC[C@H]4OCc3c(-c4c(Cl)cccc4Cl)noc3C3CC3)nc12] |
| 2 | 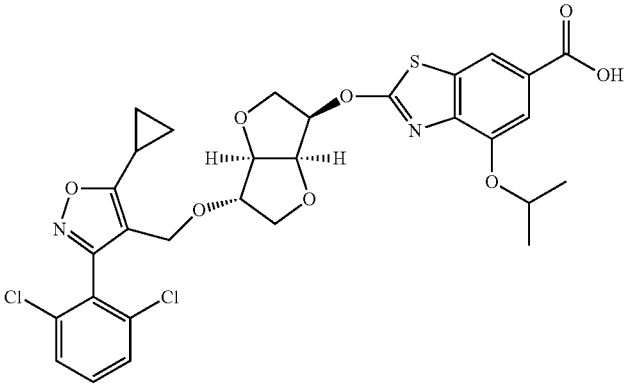 [SMILES: CC(C)Oc1cc(C(=O)O)cc2sc(O[C@@H]3CO[C@H]4[C@@H]3OC[C@@H]4OCc3c(-c4c(Cl)cccc4Cl)noc3C3CC3)nc12] |
| 3 | 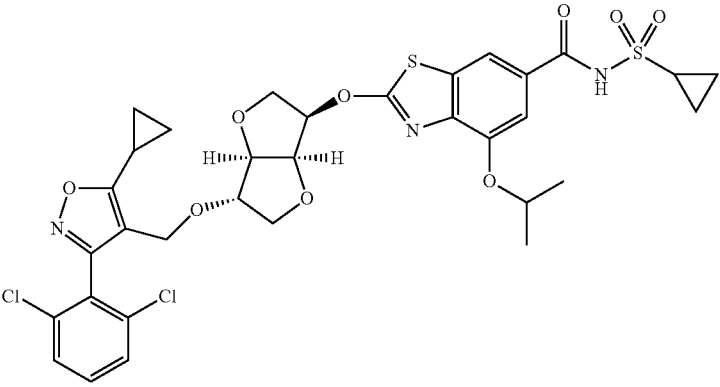 [SMILES: CC(C)Oc1cc(C(=O)NS(=O)(=O)C2CC2)cc2sc(O[C@@H]3CO[C@H]4[C@@H]3OC[C@@H]4OCc3c(-c4c(Cl)cccc4Cl)noc3C3CC3)nc12] |

-continued
| Compound | Structure |
|---|---|
| 4 | 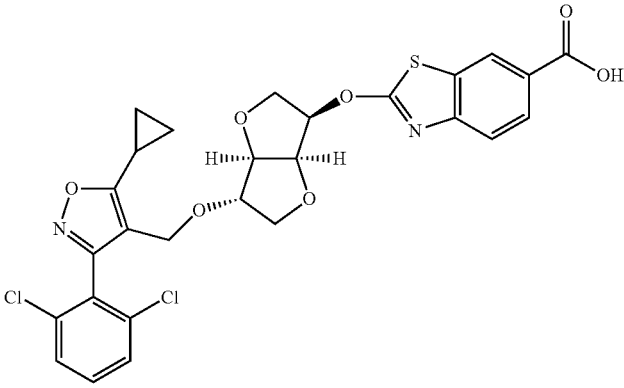 [SMILES: O=C(O)c1ccc2nc(O[C@@H]3CO[C@H]4[C@@H]3OC[C@@H]4OCc3c(-c4c(Cl)cccc4Cl)noc3C3CC3)sc2c1] |
| 5 | 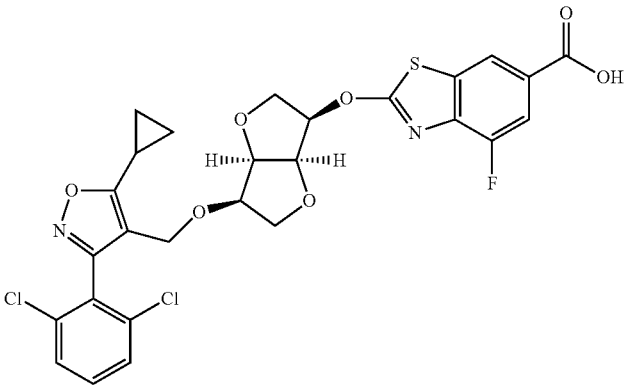 [SMILES: O=C(O)c1cc(F)c2nc(O[C@@H]3CO[C@H]4[C@@H]3OC[C@H]4OCc3c(-c4c(Cl)cccc4Cl)noc3C3CC3)sc2c1] |
| 6 | 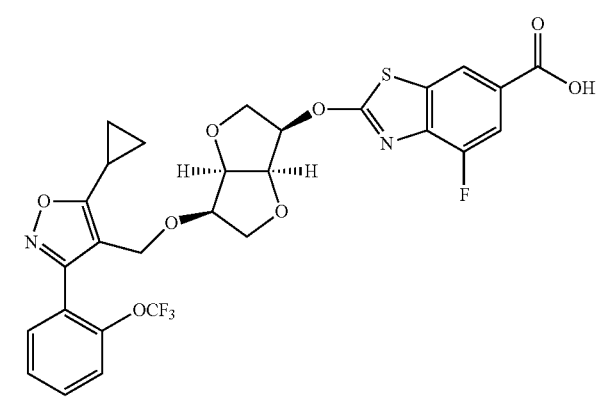 [SMILES: O=C(O)c1cc(F)c2nc(O[C@@H]3CO[C@H]4[C@@H]3OC[C@H]4OCc3c(-c4ccccc4OC(F)(F)F)noc3C3CC3)sc2c1] |
| 7 | 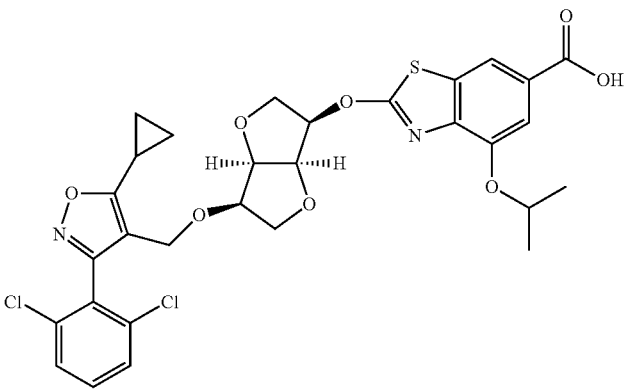 [SMILES: CC(C)Oc1cc(C(=O)O)cc2sc(O[C@@H]3CO[C@H]4[C@@H]3OC[C@H]4OCc3c(-c4c(Cl)cccc4Cl)noc3C3CC3)nc12] |

| Compound | Structure |
|---|---|
| 8 | 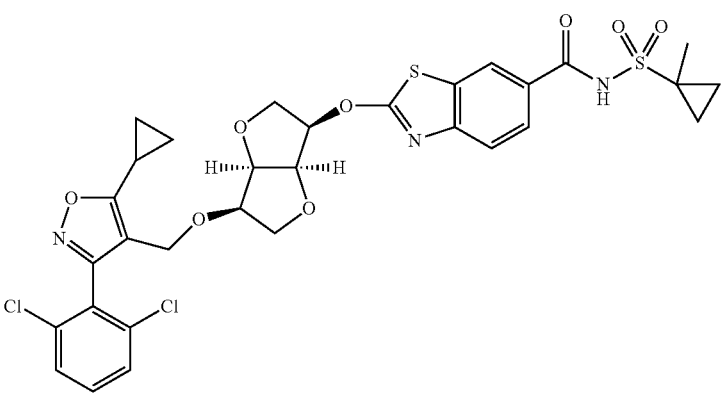 [SMILES: CC1(S(=O)(=O)NC(=O)c2ccc3nc(O[C@@H]4CO[C@H]5[C@@H]4OC[C@H]5OCc4c(-c5c(Cl)cccc5Cl)noc4C4CC4)sc3c2)CC1] |
| 9 | 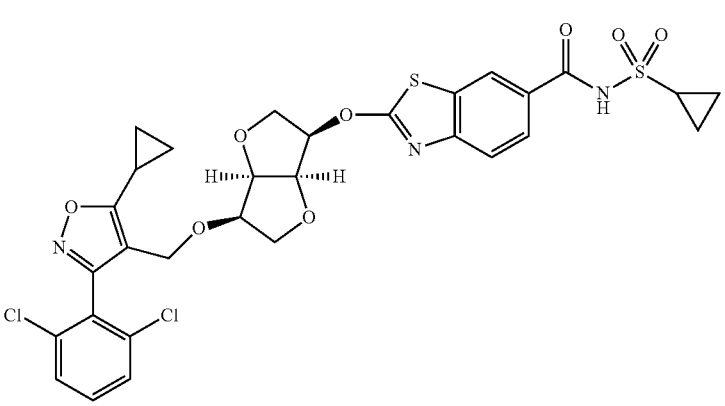 [SMILES: O=C(NS(=O)(=O)C1CC1)c1ccc2nc(O[C@@H]3CO[C@H]4[C@@H]3OC[C@H]4OCc3c(-c4c(Cl)cccc4Cl)noc3C3CC3)sc2c1] |
| 10 | 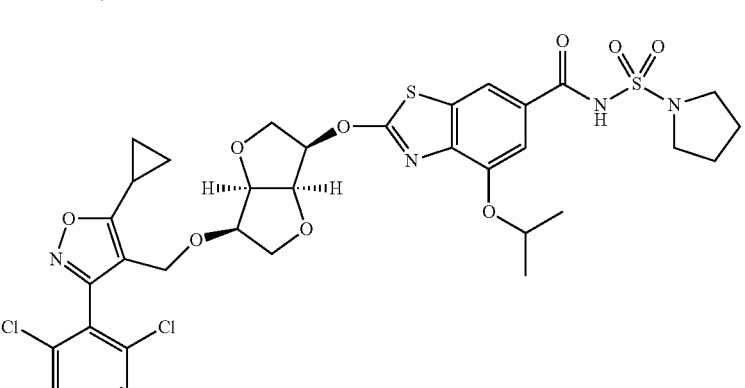 |
| 11 | 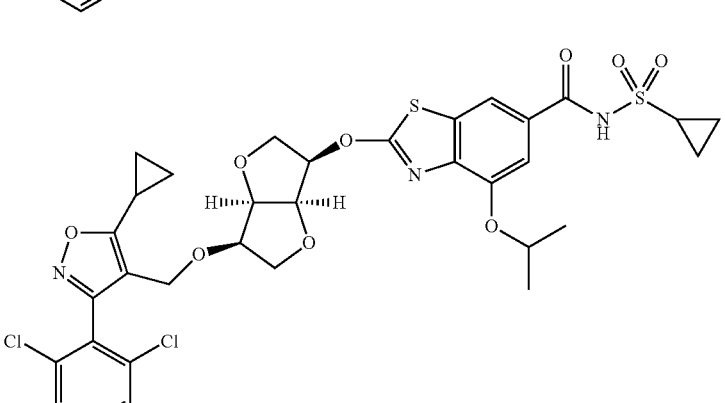 |

| Compound | Structure |
|---|---|
| 12 | 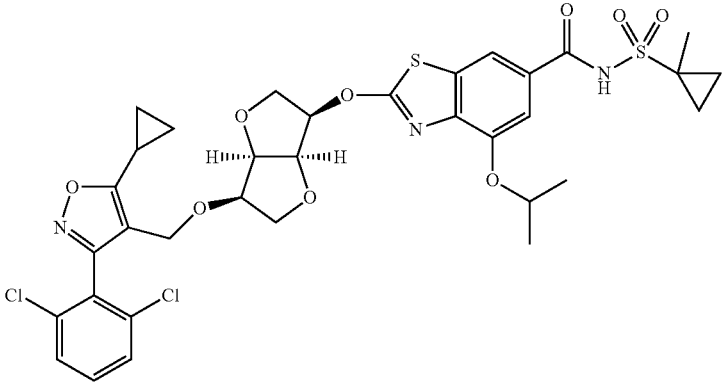 [SMILES: CC(C)Oc1cc(C(=O)NS(=O)(=O)C2(C)CC2)cc2sc(O[C@@H]3CO[C@H]4[C@@H]3OC[C@H]4OCc3c(-c4c(Cl)cccc4Cl)noc3C3CC3)nc12] |
| 13 | 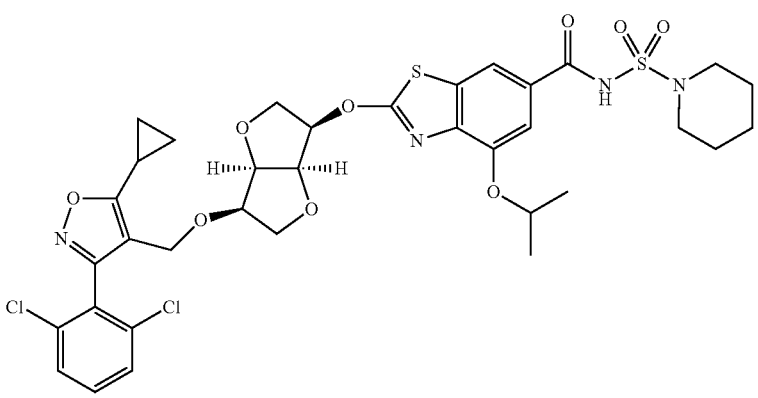 [SMILES: CC(C)Oc1cc(C(=O)NS(=O)(=O)N2CCCCC2)cc2sc(O[C@@H]3CO[C@H]4[C@@H]3OC[C@H]4OCc3c(-c4c(Cl)cccc4Cl)noc3C3CC3)nc12] |
| 14 | 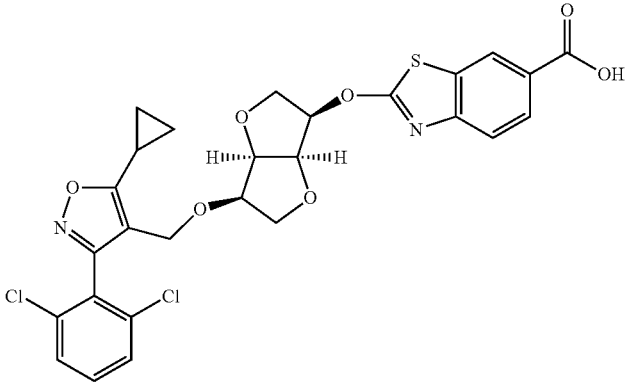 [SMILES: O=C(O)c1ccc2nc(O[C@@H]3CO[C@H]4[C@@H]3OC[C@H]4OCc3c(-c4c(Cl)cccc4Cl)noc3C3CC3)sc2c1] |
| 15 | 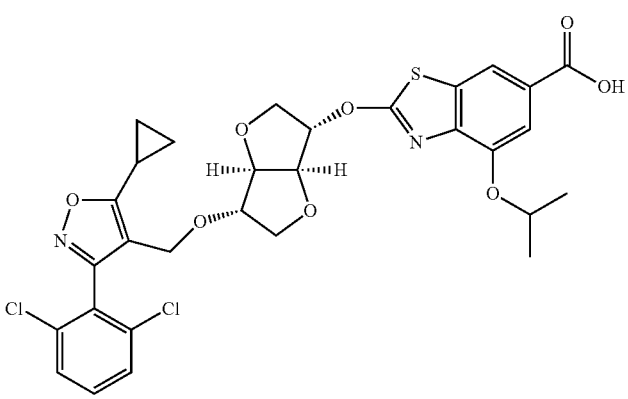 [SMILES: CC(C)Oc1cc(C(=O)O)cc2sc(O[C@H]3CO[C@H]4[C@@H]3OC[C@@H]4OCc3c(-c4c(Cl)cccc4Cl)noc3C3CC3)nc12] |

| Compound | Structure |
|---|---|
| 16 | 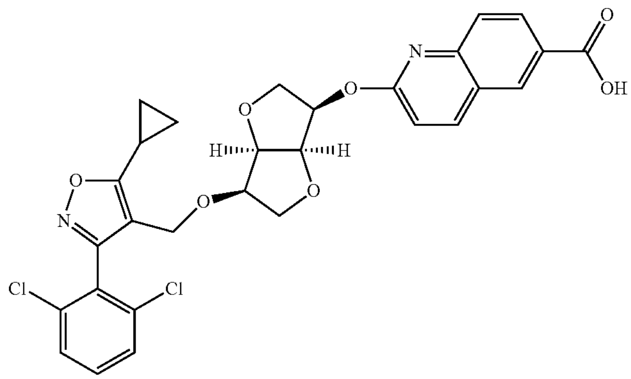 [SMILES: O=C(O)c1ccc2nc(O[C@@H]3CO[C@H]4[C@@H]3OC[C@H]4OCc3c(-c4c(Cl)cccc4Cl)noc3C3CC3)ccc2c1] |
| 17 | 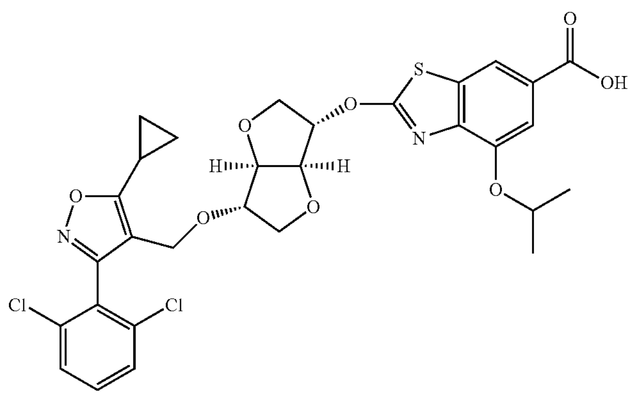 [SMILES: CC(C)Oc1cc(C(=O)O)cc2sc(O[C@H]3CO[C@H]4[C@@H]3OC[C@@H]4OCc3c(-c4c(Cl)cccc4Cl)noc3C3CC3)nc12] |
| 18 | 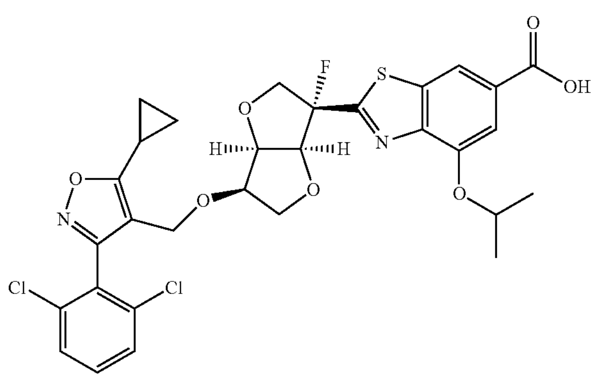 [SMILES: CC(C)Oc1cc(C(=O)O)cc2sc([C@]3(F)CO[C@@H]4[C@H](OCc5c(-c6c(Cl)cccc6Cl)noc5C5CC5)CO[C@@H]43)nc12] |
| 19 | 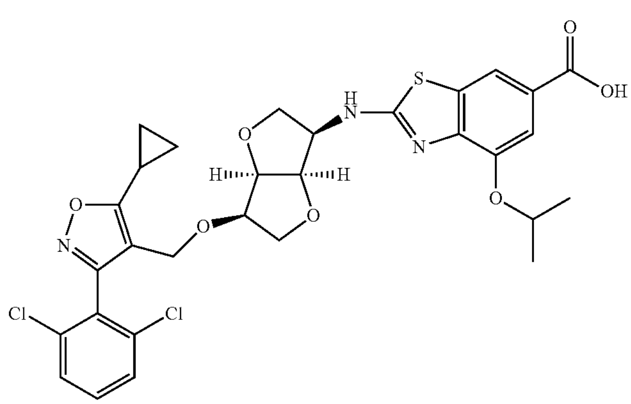 [SMILES: CC(C)Oc1cc(C(=O)O)cc2sc(N[C@@H]3CO[C@H]4[C@@H]3OC[C@H]4OCc3c(-c4c(Cl)cccc4Cl)noc3C3CC3)nc12] |

-continued
| Compound | Structure |
|---|---|
| 20 | 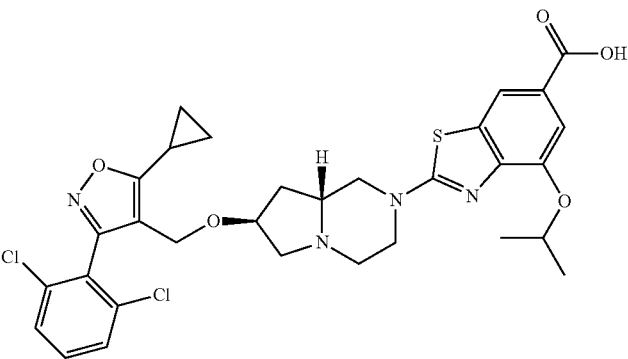 [SMILES: CC(C)Oc1cc(C(=O)O)cc2sc(N3CCN4C[C@@H](OCc5c(-c6c(Cl)cccc6Cl)noc5C5CC5)C[C@@H]4C3)nc12] |
| 21 | 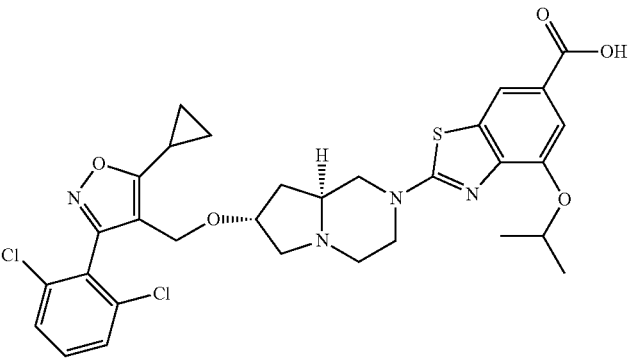 [SMILES: CC(C)Oc1cc(C(=O)O)cc2sc(N3CCN4C[C@H](OCc5c(-c6c(Cl)cccc6Cl)noc5C5CC5)C[C@H]4C3)nc12] |
| 22 | 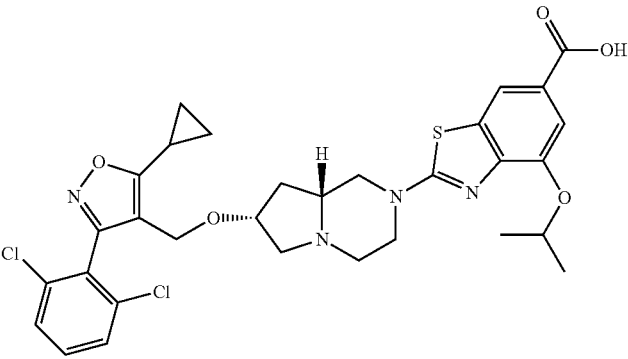 [SMILES: CC(C)Oc1cc(C(=O)O)cc2sc(N3CCN4C[C@H](OCc5c(-c6c(Cl)cccc6Cl)noc5C5CC5)C[C@@H]4C3)nc12] |
| 23 | 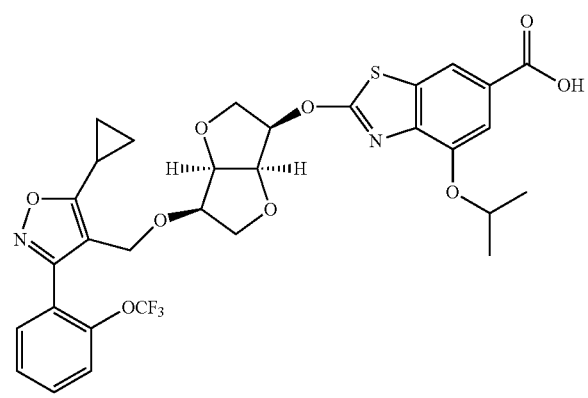 [SMILES: CC(C)Oc1cc(C(=O)O)cc2sc(O[C@@H]3CO[C@H]4[C@@H]3OC[C@H]4OCc3c(-c4ccccc4OC(F)(F)F)noc3C3CC3)nc12] |

| Compound | Structure |
|---|---|
| 24 | 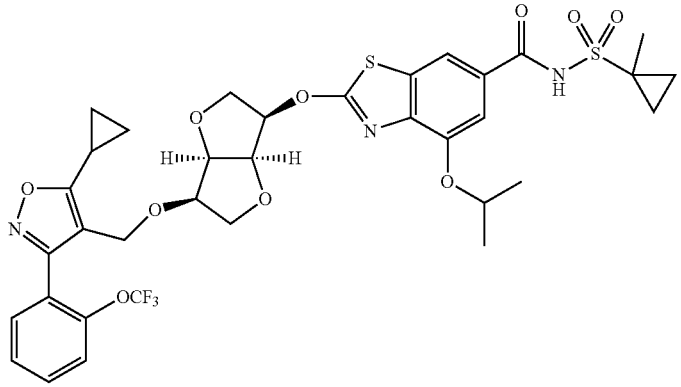 [SMILES: CC(C)Oc1cc(C(=O)NS(=O)(=O)C2(C)CC2)cc2sc(O[C@@H]3CO[C@H]4[C@@H]3OC[C@H]4OCc3c(-c4ccccc4OC(F)(F)F)noc3C3CC3)nc12] |
| 25 | 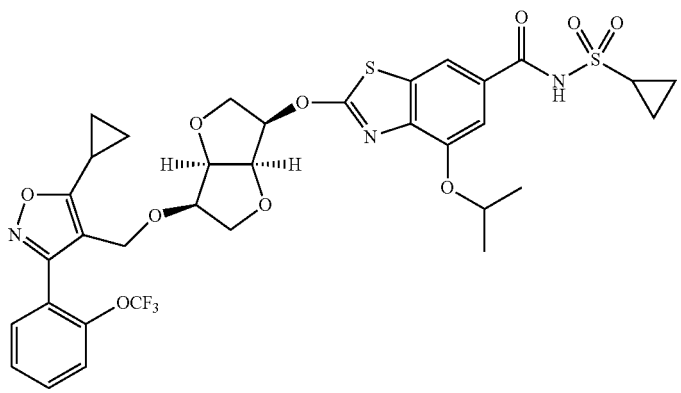 [SMILES: CC(C)Oc1cc(C(=O)NS(=O)(=O)C2CC2)cc2sc(O[C@@H]3CO[C@H]4[C@@H]3OC[C@H]4OCc3c(-c4ccccc4OC(F)(F)F)noc3C3CC3)nc12] |
| 26 | 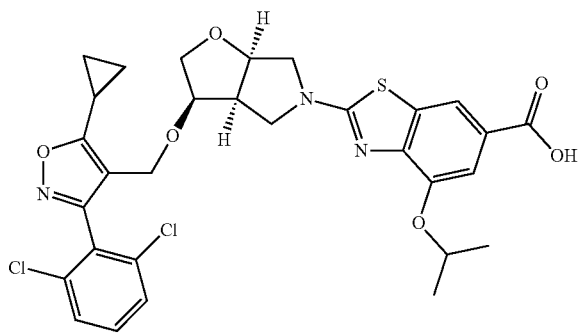 [SMILES: CC(C)Oc1cc(C(=O)O)cc2sc(N3C[C@H]4[C@@H](OCc5c(-c6c(Cl)cccc6Cl)noc5C5CC5)CO[C@H]4C3)nc12] |
| 27a | 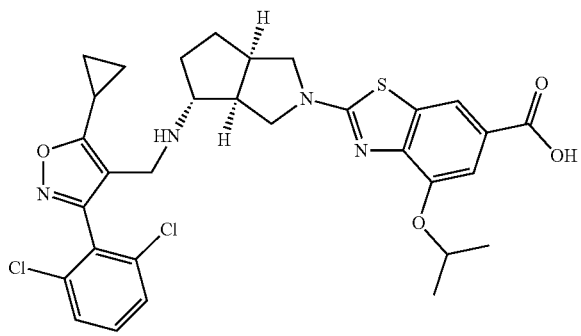 [SMILES: CC(C)Oc1cc(C(=O)O)cc2sc(N3C[C@@H]4CC[C@@H](NCc5c(-c6c(Cl)cccc6Cl)noc5C5CC5)[C@@H]4C3)nc12] |

| Compound | Structure |
|---|---|
| 27b | 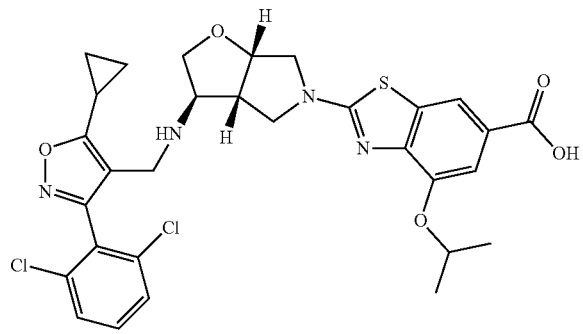 [SMILES: CC(C)Oc1cc(C(=O)O)cc2sc(N3C[C@@H]4[C@@H](NCc5c(-c6c(Cl)cccc6Cl)noc5C5CC5)CO[C@@H]4C3)nc12] |
| 28 | 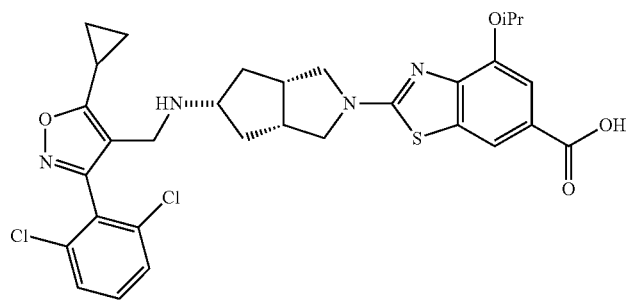 |
| 29 | 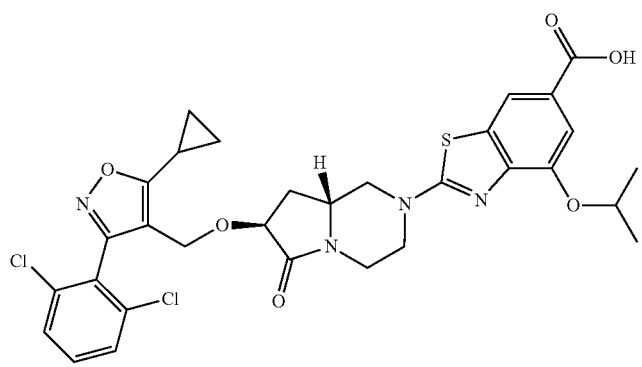 [SMILES: CC(C)Oc1cc(C(=O)O)cc2sc(N3CCN4C(=O)[C@@H](OCc5c(-c6c(Cl)cccc6Cl)noc5C5CC5)C[C@@H]4C3)nc12] |
| 30 | 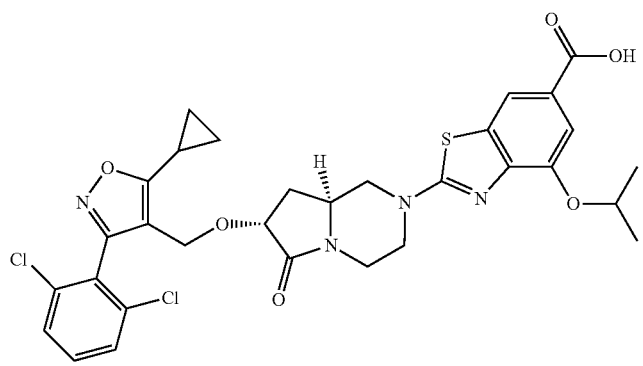 [SMILES: CC(C)Oc1cc(C(=O)O)cc2sc(N3CCN4C(=O)[C@H](OCc5c(-c6c(Cl)cccc6Cl)noc5C5CC5)C[C@H]4C3)nc12] |

| Compound | Structure |
|---|---|
| 31 | 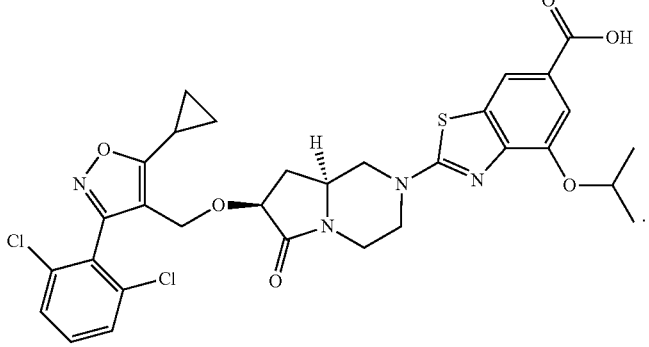 |

16. A method for treating an FXR-mediated disease or condition in a subject in need thereof, comprising administering to the subject a therapeutically effective amount of a compound according to claim 1, wherein the FXR-mediated disease or condition is selected from the group consisting of primary biliary cirrhosis, primary sclerosing cholangitis, pulmonary fibrosis, renal fibrosis, liver fibrosis, cerebrotendinous xanthomatosis, primary sclerosing cholangitis, drug induced cholestasis, intrahepatic cholestasis of pregnancy, parenteral nutrition associated cholestasis, bacterial overgrowth or sepsis associated cholestasis, autoimmune hepatitis, chronic viral hepatitis, alcoholic liver disease, nonalcoholic fatty liver disease, nonalcoholic steatohepatitis, liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, alpha 1-antitrypsin deficiency, diabetic nephropathy, focal segmental glomerulosclerosis, hypertensive nephrosclerosis, chronic glomerulonephritis, chronic transplant glomerulopathy, chronic interstitial nephritis, polycystic kidney disease, atherosclerosis, arteriosclerosis, dyslipidemia, hypercholesterolemia, hypertriglyceridemia, insulin resistance, Type I and Type II diabetes, and obesity.

17. The method according to claim 16, wherein the FXR-mediated disease or condition is selected from primary biliary cirrhosis, primary sclerosing cholangitis, pulmonary fibrosis, renal fibrosis, and liver fibrosis.

18. The method according to claim 16, wherein the FXR-mediated disease or condition is selected from the group consisting of primary biliary cirrhosis, cerebrotendinous xanthomatosis, primary sclerosing cholangitis, drug induced cholestasis, intrahepatic cholestasis of pregnancy, parenteral nutrition associated cholestasis, bacterial overgrowth or sepsis associated cholestasis, autoimmune hepatitis, chronic viral hepatitis, alcoholic liver disease, nonalcoholic fatty liver disease, nonalcoholic steatohepatitis, liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency.

19. The method according to claim 16, wherein the FXR-mediated disease or condition is selected from the group consisting of diabetic nephropathy, focal segmental glomerulosclerosis, hypertensive nephrosclerosis, chronic glomerulonephritis, chronic transplant glomerulopathy, chronic interstitial nephritis, and polycystic kidney disease.

20. The method according to claim 16, wherein the FXR-mediated disease or condition is selected from the group consisting of atherosclerosis, arteriosclerosis, dyslipidemia, hypercholesterolemia, and hypertriglyceridemia.

21. The method according to claim 16, wherein the FXR-mediated disease or condition is selected from the group consisting of insulin resistance, Type I and Type II diabetes, and obesity.

22. A pharmaceutical composition comprising a compound of claim 1 and a pharmaceutically acceptable carrier.

* * * * *

UNITED STATES PATENT AND TRADEMARK OFFICE
CERTIFICATE OF CORRECTION

PATENT NO. : 10,689,391 B2  
APPLICATION NO. : 16/217749  
DATED : June 23, 2020  
INVENTOR(S) : Yat Sun Or et al.

Page 1 of 4

It is certified that error appears in the above-identified patent and that said Letters Patent is hereby corrected as shown below:

In the Claims

At Column 319  
In Claim 4, Line 48, after Ⓑ, insert -- Z --.

At Column 358

In Claim 8, Compound 103 delete " 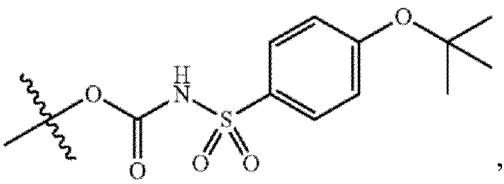 " and insert
-- 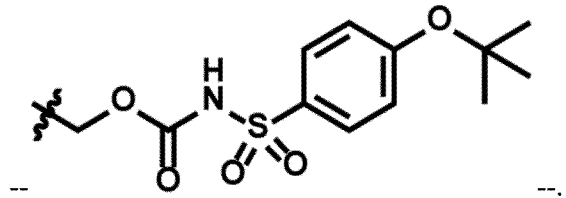 --.

At Column 373

In Claim 8, Compound 151 delete " 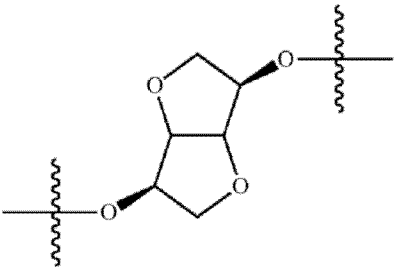 " and insert

Signed and Sealed this  
Twenty-fourth Day of November, 2020

Andrei Iancu  
*Director of the United States Patent and Trademark Office*

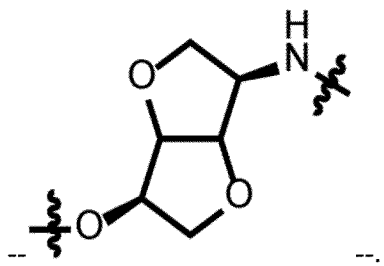
At Column 374
In Claim 8, Compound 147 delete " 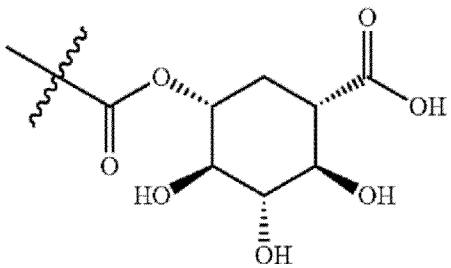 " and insert
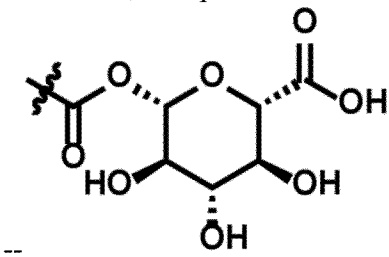 --;
In Claim 8, Compound 148 delete " 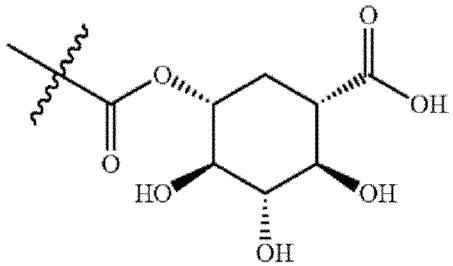 " and insert
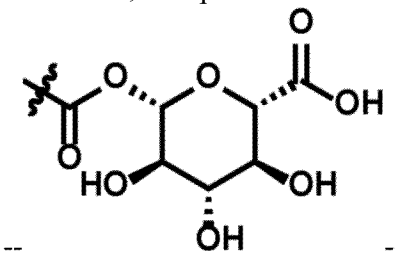 --;
In Claim 8, Compound 149 delete " 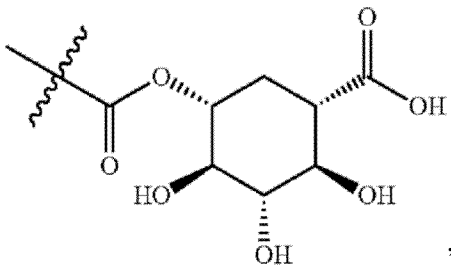 " and insert

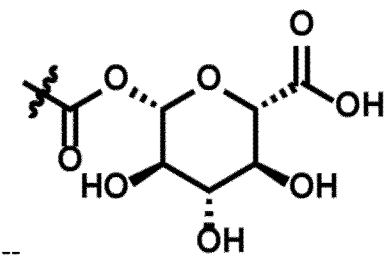
-- 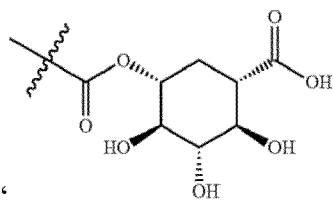 --; and
In Claim 8, Compound 150 delete " 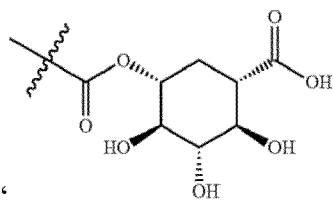 " and insert
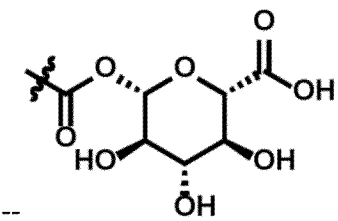
-- 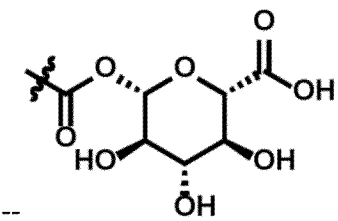 --.
At Column 387
In Claim 9, Line 17 delete "IC" and insert -- $R^7$ --; and
In Claim 10, Line 19 delete "IC" and insert -- $R^7$ --.
At Column 392
In Claim 10, Compound 214 delete " 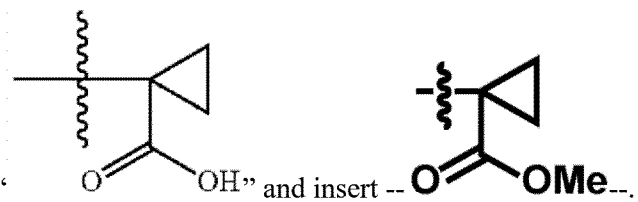 " and insert -- 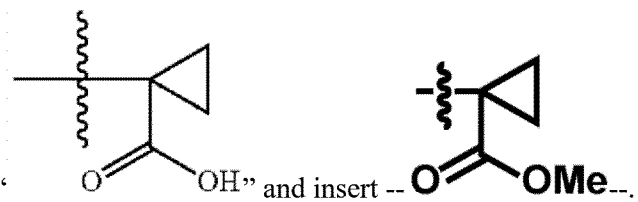 --.
At Column 478
In Claim 12, Compound 547 delete " 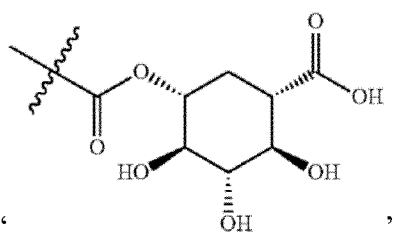 " and insert
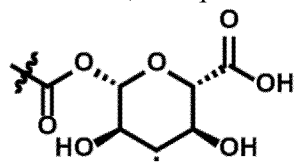
-- 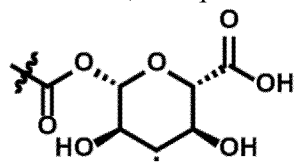 --; and In Claim 12, Compound 548 delete " 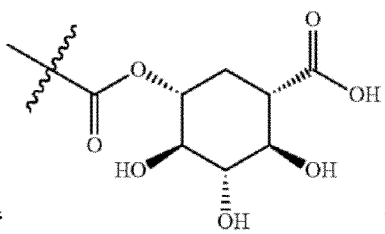 " and insert
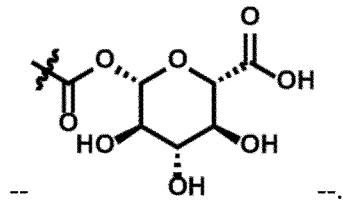 --.
At Column 480
In Claim 12, Compound 549 delete " 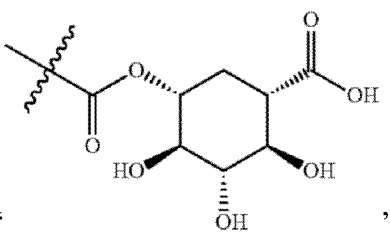 " and insert
-- 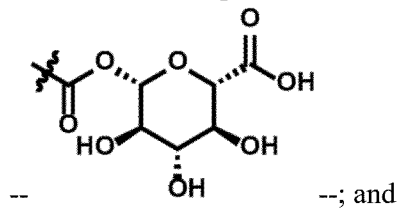 --; and
In Claim 12, Compound 550 delete " 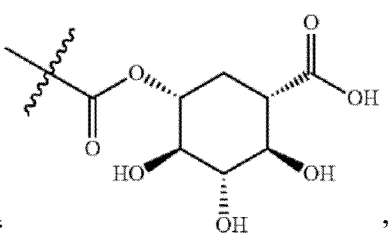 " and insert
-- 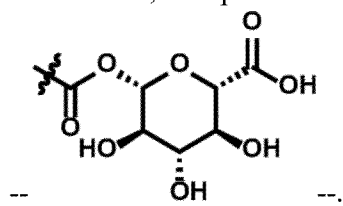 --.